United States Patent
Goldman et al.

(10) Patent No.: US 10,813,931 B2
(45) Date of Patent: Oct. 27, 2020

(54) METHODS AND COMPOSITIONS RELATING TO THE TREATMENT OF CANCER

(71) Applicant: THE BRIGHAM AND WOMEN'S HOSPITAL, INC., Boston, MA (US)

(72) Inventors: Aaron Goldman, Somerville, MA (US); Ashish Kulkarni, Cambridge, MA (US); Shiladitya Sengupta, Waltham, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 602 days.

(21) Appl. No.: 14/768,230

(22) PCT Filed: Feb. 12, 2014

(86) PCT No.: PCT/US2014/015957
§ 371 (c)(1),
(2) Date: Aug. 17, 2015

(87) PCT Pub. No.: WO2014/130313
PCT Pub. Date: Aug. 28, 2014

(65) Prior Publication Data
US 2015/0374692 A1   Dec. 31, 2015

Related U.S. Application Data

(60) Provisional application No. 61/766,325, filed on Feb. 19, 2013, provisional application No. 61/814,441, filed on Apr. 22, 2013.

(51) Int. Cl.
| | | |
|---|---|---|
| *A61K 31/506* | (2006.01) |
| *A61K 45/06* | (2006.01) |
| *A61K 31/7088* | (2006.01) |
| *A61K 31/337* | (2006.01) |
| *A61K 47/69* | (2017.01) |
| *A61P 35/00* | (2006.01) |
| *A61K 31/517* | (2006.01) |
| *C12N 15/113* | (2010.01) |
| *G01N 33/574* | (2006.01) |

(52) U.S. Cl.
CPC .......... *A61K 31/506* (2013.01); *A61K 31/337* (2013.01); *A61K 31/517* (2013.01); *A61K 31/7088* (2013.01); *A61K 45/06* (2013.01); *A61K 47/6907* (2017.08); *A61P 35/00* (2018.01); *C12N 15/1138* (2013.01); *G01N 33/57484* (2013.01); *C12N 2310/14* (2013.01); *G01N 2500/10* (2013.01); *G01N 2800/52* (2013.01)

(58) Field of Classification Search
CPC .. A61K 31/337; A61K 31/506; A61K 31/517; A61K 45/06; A61K 47/6907; A61K 31/7088; C12N 15/1138; C12N 2310/14; G01N 2500/10; G01N 2800/52; G01N 33/57484; A61P 35/00
USPC .......................................................... 514/449
See application file for complete search history.

(56) References Cited

U.S. PATENT DOCUMENTS

| | | | |
|---|---|---|---|
| 7,400,979 B2 * | 7/2008 | Borhani ............... | C12N 9/1205 435/15 |
| 10,525,060 B2 * | 1/2020 | Treon ................... | A61K 31/505 |
| 2011/0318336 A1 | 12/2011 | Petricoin et al. | |
| 2012/0165340 A1 | 6/2012 | Furnari et al. | |

FOREIGN PATENT DOCUMENTS

| | | |
|---|---|---|
| EP | 1391213 A1 | 2/2004 |
| WO | 2005046597 A2 | 5/2005 |
| WO | 2009002993 A1 | 12/2008 |
| WO | 2012075679 A1 | 6/2012 |

OTHER PUBLICATIONS

Boggon et al., "Structure and regulation of Src family kinases", 2004, Oncogene, 23(48), pp. 7918-7927. (Year: 2004).*
Koreckij et al., "Dasatinib inhibits the growth of prostate cancer in bone and provides additional protection from osteolysis", 2009, British Journal of Cancer, 101(2), 263-268. (Year: 2009).*
Montero et al., "Inhibition of Src Family Kinases and Receptor Tyrosine Kinases by Dasatinib: Possible Combinations in Solid Tumors", 2011, Clin. Cancer Res., 17(17), pp. 5546-5552. (Year: 2011).*
Pene-Dumitrescu et al., "An inhibitor-resistant mutant of Hck protects CML cells against the antiproliferative and apoptotic effects of the broad-spectrum Src family kinase inhibitor A-419259", 2008, Oncogene, 27(56), pp. 7055-7069. (Year: 2008).*
Fornier et al., "A phase I study of dasatinib and weekly paclitaxel for metastatic breast cancer", 2011, Annals of Oncology, 22(12), pp. 2575-2581. (Year: 2011).*

(Continued)

*Primary Examiner* — My-Chau T. Tran
(74) *Attorney, Agent, or Firm* — Nixon Peabody LLP; David S. Resnick; Nicole D. Kling

(57) ABSTRACT

The compositions and methods described herein relate to the treatment of cancer, e.g. by reducing the regression of cancer cells from regressing into cancer stem cell-like phenotypes and/or reducing the development of drug-resistant cancer cells. In some embodiments, the compositions and methods relate to inhibitors of PI3K pathway kinases and Src family kinases.

21 Claims, 48 Drawing Sheets
Specification includes a Sequence Listing.

(56) References Cited

OTHER PUBLICATIONS

Abrams et al., "Preclinical evaluation of the tyrosine kinase inhibitor SU11248 as a single agent and in combination with "standard of care" therapeutic agents for the treatment of breast cancer", 2003, Mol. Cancer Ther., 2(10), pp. 1011-1021. (Year: 2003).*

Ciardiello et al., "Phase II study of gefitinib in combination with docetaxel as first-line therapy in metastatic breast cancer", 2006, British Journal of Cancer, 94(11), pp. 1604-1609. (Year: 2006).*

Araujo et al., "Dasatinib combined with docetaxel for castration-resistant prostate cancer: results from a phase 1/2 study", Cancer, 118(1): 63-71 (2012).

Gong et al., "Markers of tumor-initiating cells predict chemoresistance in breast cancer" PLoS One, 5(12): 1-11 (2012).

Gupta et al., "Stochastic state transitions give rise to phenotypic equilibrium in populations of cancer cells", Cell, 146(4): 633-44 (2011).

Lee et al., "Sequential application of anti-cancer drugs enhances cell death by re-wiring apoptotic signaling networks", Cell, 149(4): 780-94 (2012).

Madhunapantula et al., "PRAS40 Deregulates Apoptosis in Malignant Melanoma", Cancer Res. 67(8): 3626-3636 (2007).

Goldman et al., "Chemotherapy-induced Akt survival signaling is regulated by CD44 Ezrin/Radaxin Moesin (ERM) scaffolding, dependent on EGFR activity", Supplement 72(8) Cancer Research (2012).

Hellqvist et al., "CD44 monoclonal Antibody-Enhanced Clearance of Chronic Myeloid Leukemia Stem Cells From the Malignant Niche", Blood 122:858 (2013).

Myssina et al., "Combined BCR-ABL inhibition with lentiviral-delivered shRNA and dasatinib augments induction of apoptosis in Philadelphia-positive cells", Experimental Hematology 37(2):206-214 (2009).

Padhye et al., "Sustained Expression of the RON Receptor Tyrosine Kinase by Pancreatic Cancer Stem Cells as a Potential Targeting Moiety for Antibody-Directed Chemotherapeutics", Molecular Pharmaceuticals 8:2310-2319 (2011).

\* cited by examiner

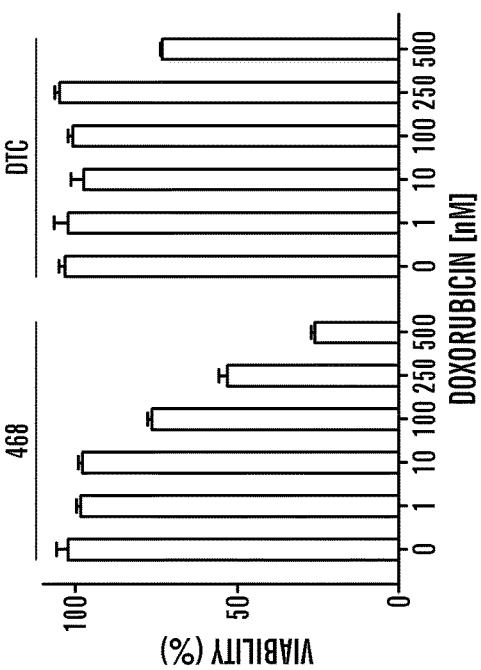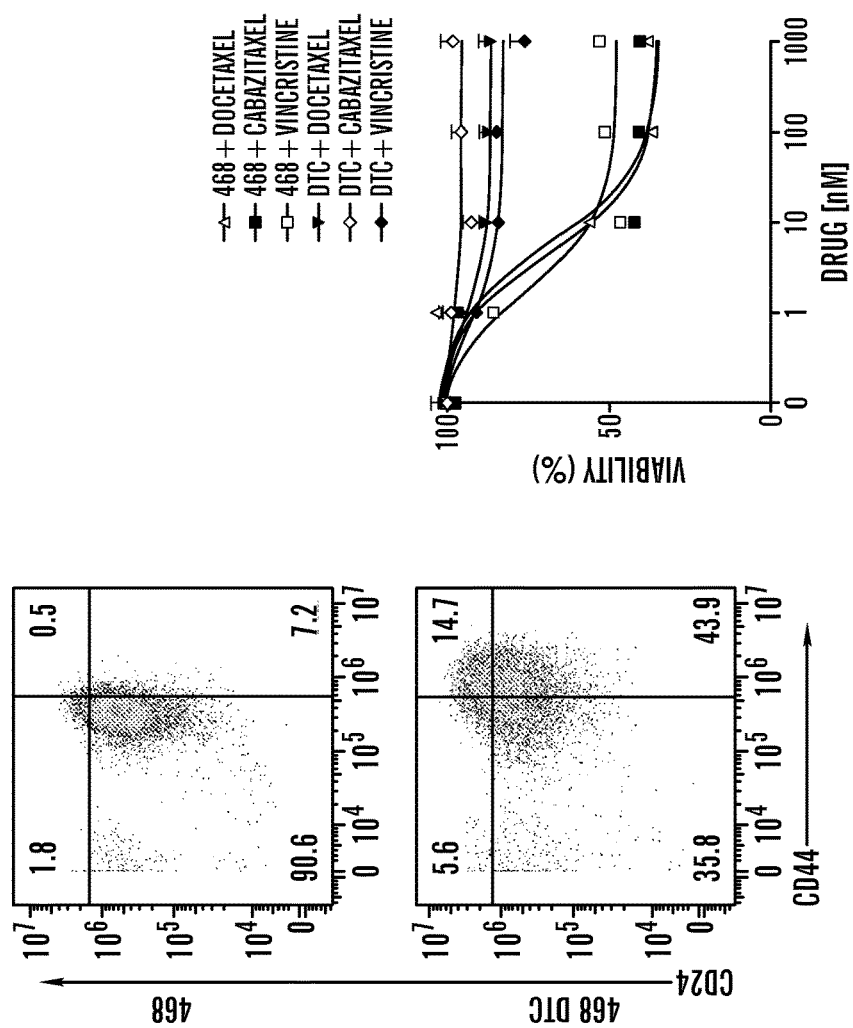
FIG. 1N
FIG. 1M
FIG. 1L

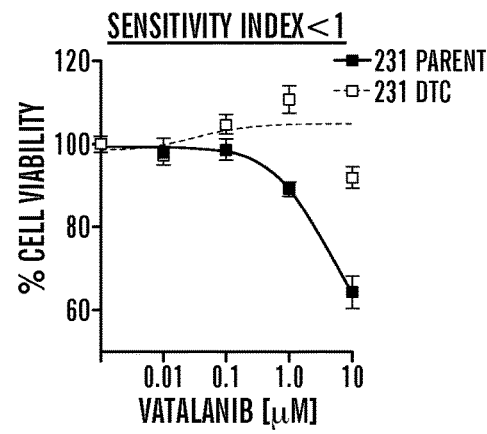
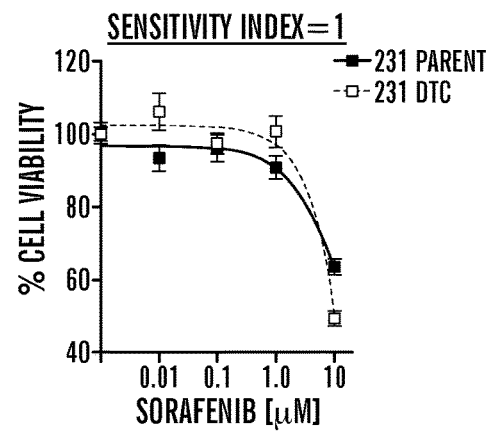
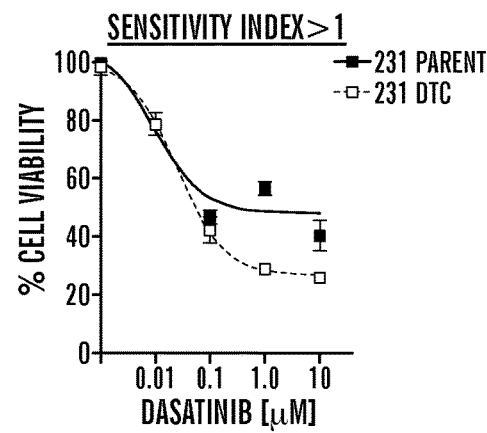
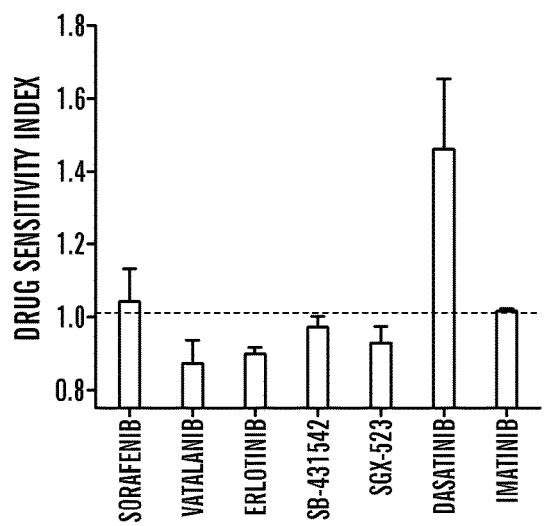
FIG. 5A

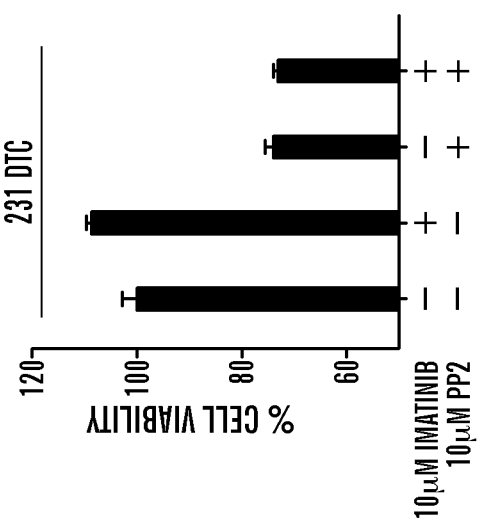
| KINASE | PHOSPHO RESIDUE |
|---|---|
| Hck | Y411 |
| Fyn | Y420 |
| Src | Y419 |
| Yes | Y426 |
| Lyn | Y397 |
| Fgr | Y412 |
| Lck | Y394 |
| Akt | T308 |
| P70S6K(1) | T389 |
| P70S6K(2) | T421/S424 |
| RSK1/2/3 | S380/S386/S377 |
| mTor | S2448 |
| PRAS40 | T246 |
FIG. 5E
FIG. 5B
FIG. 5C
FIG. 5D

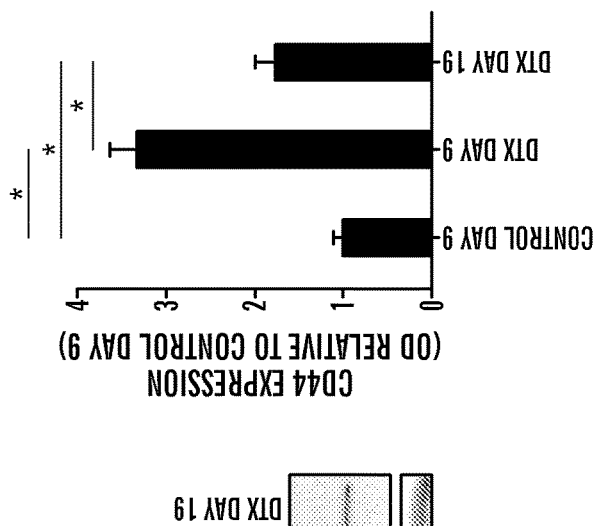
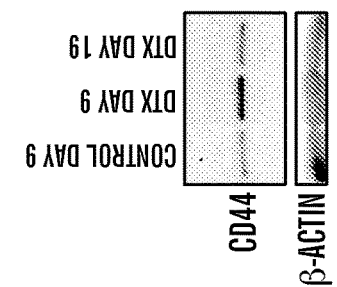
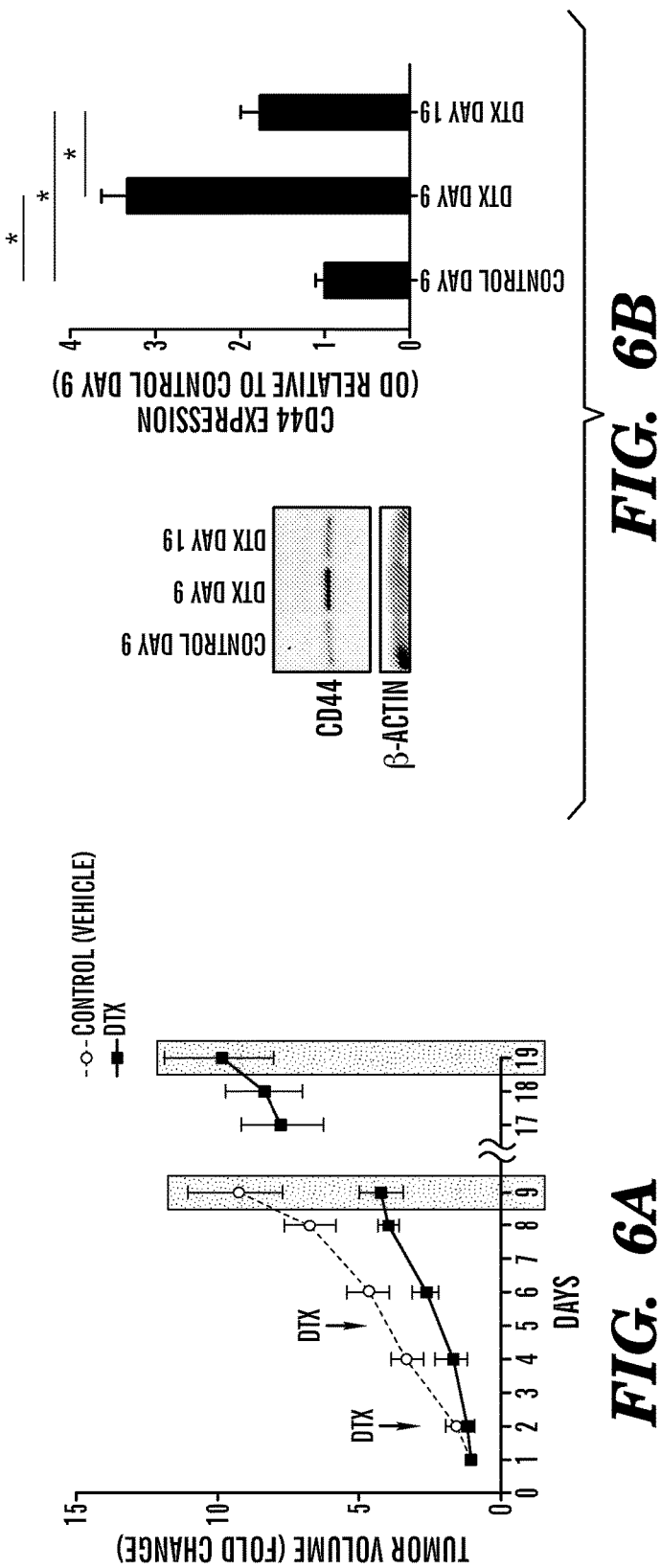
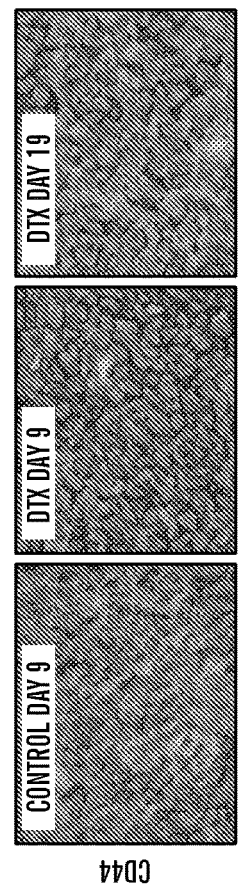
FIG. 6A
FIG. 6B
FIG. 6C

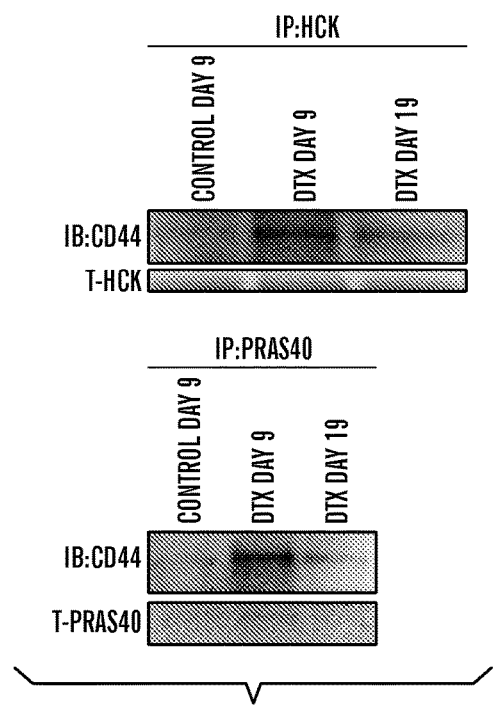
FIG. 6G
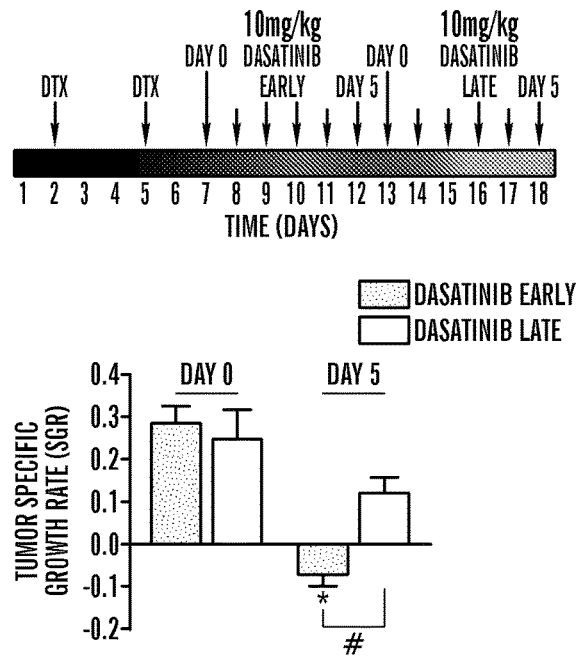
FIG. 6H
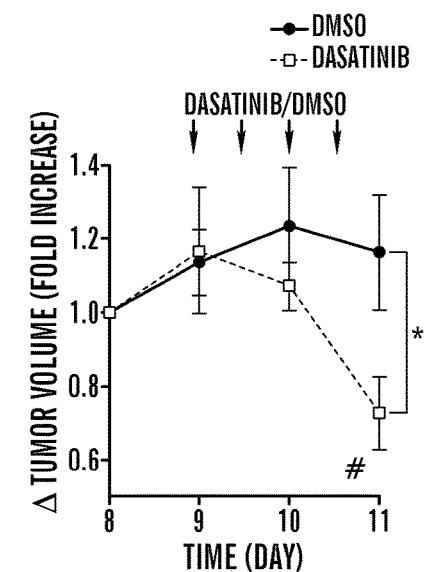
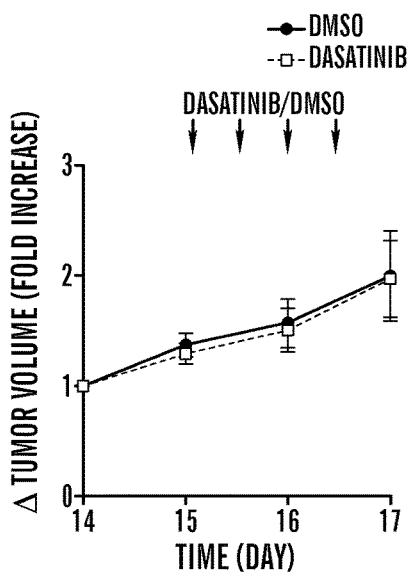
FIG. 6I

| Patient ID | Age/Sex | Tumor stage | Receptor Status | Treatment | Clinical Observation |
|---|---|---|---|---|---|
| MBT 295 | 33/F | T2N2 M0 | ER+PR+ HER2- | 4 cycles of *Adriamycin+Endoxcen+5 Fu 3 cycles of Taxole+Adriamycin+Endoxcen | Carcinoma(R) with axiillary LN Mets |
| MBT 308 | 35/F | T3N2M1 | ER+ PR+ HER2- | 6 cycles of Docetaxel+ Epirubicin+Endoxcen. 2 cycles Docetaxel+Zoledronic acid, 20 doses of Zoledronic acid | Ca Breast with axillary LN (L) and Bone Mets |
| MBT 651 | 51/F | Stage 4 | ER- PR- HER2+ | 6 cycles of Doxorubicin+Docetaxel+ Cyclophposphamide | Metastatic CaBr |
| MBT 680 | 37/F | Stage4 | N/A | 6 cycles of Docetaxel+pirubiucin +endaxecen | Ca Breast with chest wall and chest nodules recurrence |
| MBT 685 | 46/F | IV | N/A | 6 cycles of Docetaxel+cyclophospham ide+Adriamycin---→ MRM+Rad | CaBr with recurrence and lymph node metastasis |

FIG. 9

SEQUENCE LISTING

<160> NUMBER OF SEQ ID NOS: 39

<210> SEQ ID NO 1
<211> LENGTH: 5616
<212> TYPE: DNA
<213> ORGANISM: Homo sapiens

<400> SEQUENCE: 1

| | | | | | |
|---|---|---|---|---|---|
| ccccggcgca | gcgcggccgc | agcagcctcc | gcccccgca | cggtgtgagc | gcccgacgcg | 60 |
| gccgaggcgg | ccggagtccc | gagctagccc | cggcggccgc | cgccgcccag | accgacgac | 120 |
| aggccacctc | gtcggcgtcc | gcccgagtcc | ccgcctcgcc | gccaacgcca | caaccaccgc | 180 |
| gcacggcccc | ctgactccgt | ccagtattga | tcgggagagc | cggagcgagc | tcttcgggga | 240 |
| gcagcgatgc | gaccctccgg | gacggccggg | gcagcgctcc | tggcgctgct | ggctgcgctc | 300 |
| tgcccggcga | gtcgggctct | ggaggaaaag | aaagtttgcc | aaggcacgag | taacaagctc | 360 |
| acgcagttgg | gcacttttga | agatcatttt | ctcagcctcc | agaggatgtt | caataactgt | 420 |
| gaggtggtcc | ttgggaattt | ggaaattacc | tatgtgcaga | ggaattatga | tctttccttc | 480 |
| ttaaagacca | tccaggaggt | ggctggttat | gtcctcattg | ccctcaacac | agtggagcga | 540 |
| attcctttgg | aaaacctgca | gatcatcaga | ggaaatatgt | actacgaaaa | ttcctatgcc | 600 |
| ttagcagtct | tatctaacta | tgatgcaaat | aaaaccggac | tgaaggagct | gcccatgaga | 660 |
| aatttacagg | aaatcctgca | tggcgccgtg | cggttcagca | caaccctgc | cctgtgcaac | 720 |
| gtggagagca | tccagtggcg | ggacatagtc | agcagtgact | ttctcagcaa | catgtcgatg | 780 |
| gacttccaga | accacctggg | cagctgccaa | aagtgtgatc | caagctgtcc | caatgggagc | 840 |
| tgctggggtg | caggagagga | gaactgccag | aaactgacca | aaatcatctg | tgcccagcag | 900 |
| tgctccgggc | gctgccgtgg | caagtccccc | agtgactgct | gccacaacca | gtgtgctgca | 960 |
| ggctgcacag | gcccccggga | gagcgactgc | ctggtctgcc | gcaaattccg | agacgaagcc | 1020 |
| acgtgcaagg | acacctgccc | cccactcatg | ctctacaacc | ccaccacgta | ccagatggat | 1080 |
| gtgaaccccg | agggcaaata | cagctttggt | gccacctgcg | tgaagaagtg | tccccgtaat | 1140 |
| tatgtggtga | cagatcacgg | ctcgtgcgtc | cgagcctgtg | ggccgacag | ctatgagatg | 1200 |
| gaggaagacg | gcgtccgcaa | gtgtaagaag | tgcgaagggc | cttgccgcaa | agtgtgtaac | 1260 |
| ggaataggta | ttggtgaatt | taaagactca | ctctccataa | atgctacgaa | tattaaacac | 1320 |
| ttcaaaaact | gcacctccat | cagtggcgat | ctccacatcc | tgccggtggc | atttaggggt | 1380 |
| gactccttca | cacatactcc | tcctctggat | ccacaggaac | tggatattct | gaaaaccgta | 1440 |
| aaggaaatca | cagggttttt | gctgattcag | gcttggcctg | aaaacaggac | ggacctccat | 1500 |
| gcctttgaga | acctagaaat | catacgcggc | aggaccaagc | aacatggtca | gttttctctt | 1560 |
| gcagtcgtca | gcctgaacat | aacatccttg | ggattacgct | ccctcaagga | gataagtgat | 1620 |
| ggagatgtga | taatttcagg | aaacaaaaat | ttgtgctatg | caaatacaat | aaactggaaa | 1680 |
| aaactgtttg | ggacctccgg | tcagaaaacc | aaaattataa | gcaacagagg | tgaaaacagc | 1740 |
| tgcaaggcca | caggccaggt | ctgccatgcc | ttgtgctccc | ccgagggctg | ctggggcccg | 1800 |
| gagcccaggg | actgcgtctc | ttgccggaat | gtcagccgag | caggaatg | cgtggacaag | 1860 |
| tgcaaccttc | tggagggtga | gccaaggag | tttgtggaga | actctgagtg | catacagtgc | 1920 |
| cacccagagt | gcctgcctca | ggccatgaac | atcacctgca | caggacgggg | accagacaac | 1980 |

```
tgtatccagt gtgcccacta cattgacggc ccccactgcg tcaagacctg cccggcagga     2040
gtcatgggag aaaacaacac cctggtctgg aagtacgcag acgccggcca tgtgtgccac     2100
ctgtgccatc caaactgcac ctacggatgc actgggccag gtcttgaagg ctgtccaacg     2160
aatgggccta agatcccgtc catcgccact gggatggtgg gggccctcct cttgctgctg     2220
gtggtggccc tggggatcgg cctcttcatg cgaaggcgcc acatcgttcg gaagcgcacg     2280
ctgcggaggc tgctgcagga gagggagctt gtggagcctc ttacacccag tggagaagct     2340
cccaaccaag ctctcttgag gatcttgaag gaaactgaat tcaaaaagat caaagtgctg     2400
ggctccggtg cgttcggcac ggtgtataag ggactctgga tcccagaagg tgagaaagtt     2460
aaaattcccg tcgctatcaa ggaattaaga gaagcaacat ctccgaaagc caacaaggaa     2520
atcctcgatg aagcctacgt gatggccagc gtggacaacc cccacgtgtg ccgcctgctg     2580
ggcatctgcc tcacctccac cgtgcagctc atcacgcagc tcatgcccct cggctgcctc     2640
ctggactatg tccgggaaca caaagacaat attggctccc agtacctgct caactggtgt     2700
gtgcagatcg caaagggcat gaactacttg gaggaccgtc gcttggtgca ccgcgacctg     2760
gcagccagga acgtactggt gaaaacaccg cagcatgtca agatcacaga ttttgggctg     2820
gccaaactgc tgggtgcgga agagaaagaa taccatgcag aaggaggcaa agtgcctatc     2880
aagtggatgg cattggaatc aattttacac agaatctata cccaccagag tgatgtctgg     2940
agctacgggg tgaccgtttg ggagttgatg acctttggat ccaagccata tgacggaatc     3000
cctgccagcg agatctcctc catcctggag aaaggagaac gcctccctca gccacccata     3060
tgtaccatcg atgtctacat gatcatggtc aagtgctgga tgatagacgc agatagtcgc     3120
ccaaagttcc gtgagttgat catcgaattc tccaaaatgg cccgagaccc ccagcgctac     3180
cttgtcattc aggggatga agaatgcat ttgccaagtc ctacagactc caacttctac     3240
cgtgccctga tggatgaaga agacatggac gacgtggtgg atgccgacga gtacctcatc     3300
ccacagcagg gcttcttcag cagccctcc acgtcacgga ctcccctcct gagctctctg     3360
agtgcaacca gcaacaattc caccgtggct tgcattgata gaaatgggct gcaaagctgt     3420
cccatcaagg aagacagctt cttgcagcga tacagctcag accccacagg cgccttgact     3480
gaggacagca tagacgacac cttcctccca gtgcctgaat acataaacca gtccgttccc     3540
aaaaggcccg ctggctctgt gcagaatcct gtctatcaca atcagcctct gaaccccgcg     3600
cccagcagag acccacacta ccaggacccc cacagcactg cagtgggcaa ccccgagtat     3660
ctcaacactg tccagcccac ctgtgtcaac agcacattcg acagccctgc ccactgggcc     3720
cagaaaggca gccaccaaat tagcctggac aaccctgact accagcagga cttcttcccc     3780
aaggaagcca agccaaatgg catctttaag ggctccacag ctgaaaatgc agaataccta     3840
agggtcgcgc cacaaagcag tgaatttatt ggagcatgac cacggaggat agtatgagcc     3900
ctaaaaatcc agactctttc gatacccagg accaagccac agcaggtcct ccatcccaac     3960
agccatgccc gcattagctc ttagacccac agactggttt tgcaacgttt acaccgacta     4020
gccaggaagt acttccacct cgggcacatt tgggaagtt gcattccttt gtcttcaaac     4080
tgtgaagcat ttcagaaac gcatccagca agaatattgt ccctttgagc agaaatttat     4140
cttctcaaaga ggtatatttg aaaaaaaaaa aaagtatatg tgaggatttt tattgattgg     4200
ggatcttgga gttttttcatt gtcgctattg attttttactt caatgggctc ttccaacaag     4260
gaagaagctt gctggtagca cttgctaccc tgagttcatc caggcccaac tgtgagcaag     4320
gagcacaagc cacaagtctt ccagaggatg cttgattcca gtggttctgc ttcaaggctt     4380
```

-continued

```
ccactgcaaa acactaaaga tccaagaagg ccttcatggc cccagcaggc cggatcggta   4440
ctgtatcaag tcatggcagg tacagtagga taagccactc tgtcccttcc tgggcaaaga   4500
agaaacggag gggatggaat tcttccttag acttactttt gtaaaaatgt ccccacggta   4560
cttactcccc actgatggac cagtggtttc cagtcatgag cgttagactg acttgtttgt   4620
cttccattcc attgttttga aactcagtat gctgcccctg tcttgctgtc atgaaatcag   4680
caagagagga tgacacatca ataataact cggattccag cccacattgg attcatcagc    4740
atttggacca atagcccaca gctgagaatg tggaatacct aaggatagca ccgcttttgt   4800
tctcgcaaaa acgtatctcc taatttgagg ctcagatgaa atgcatcagg tcctttgggg   4860
catagatcag aagactacaa aaatgaagct gctctgaaat ctcctttagc catcacccca   4920 acccccaaa attagtttgt gttacttatg aagatagtt ttctcctttt acttcacttc     4980
aaaagctttt tactcaaaga gtatatgttc cctccaggtc agctgccccc aaaccccctc   5040
cttacgcttt gtcacacaaa aagtgtctct gccttgagtc atctattcaa gcacttacag   5100
ctctggccac aacagggcat tttacaggtg cgaatgacag tagcattatg agtagtgtgg   5160
aattcaggta gtaaatatga aactagggtt tgaaattgat aatgctttca caacatttgc   5220
agatgtttta gaaggaaaaa agttccttcc taaaataatt tctctacaat tggaagattg   5280
gaagattcag ctagttagga gcccacctttt tttcctaatc tgtgtgtgcc ctgtaacctg   5340
actggttaac agcagtcctt tgtaaacagt gttttaaact ctcctagtca atatccaccc   5400
catccaattt atcaaggaag aaatggttca gaaatatttt tcagcctaca gttatgttca   5460
gtcacacaca catacaaaat gttcctttg cttttaaagt aattttttgac tcccagatca   5520 gtcagagccc ctacagcatt gttaagaaag tatttgattt ttgtctcaat gaaaataaaa   5580
ctatattcat ttccactcta aaaaaaaaaa aaaaaa                              5616
```

<210> SEQ ID NO 2
<211> LENGTH: 1210
<212> TYPE: PRT
<213> ORGANISM: Homo sapiens

<400> SEQUENCE: 2

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
```

-continued

```
            145                 150                 155                 160
Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Asn Cys Gln
            195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
    355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
    420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
    515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575
```

-continued

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 3
<211> LENGTH: 4145
<212> TYPE: DNA
<213> ORGANISM: Homo sapiens

<400> SEQUENCE: 3
caaacaagtg cggccatttc accagcccag gctggcttct gctgttgact ggctgtggca      60
cctcaagcag ccccttccc ctctagcctc agtttatcac cgcaagagct accattcatc     120
tagcacaacc tgaccatcct cacactggtc agttccaacc ttcccaggaa tcttctgtgg     180
ccatgttcac tccggtttta cagaacagag aacagaagct cagagaagtg aagcaacttg     240
cccagctatg agagacagag ccaggatttg aaaccagatg aggacgctga ggcccagaga     300
gggaaagcca cttgcctagg gacacacagc ggggagaggt ggagcagggc ctctatttcg     360
agacccctga ctccacacct ggtgtttgtg ccaagacccc aggctgcctc ccaggtcctc     420
tgggacagcc cctgccttct accaggacca tgggtagcaa caagagcaag cccaaggatg     480
ccagccagcg cgcgccgcagc ctggagcccg ccgagaacgt gcacggcgct ggcggggggcg     540 ctttccccgc ctcgcagacc cccagcaagc cagcctcggc cgacgccac cgcggccccca     600 gcgcggccttt cgccccgcg gccgccgagc ccaagctgtt cggaggcttc aactcctcgg     660
acaccgtcac ctccccgcag agggcgggcc cgctggccgg tgagtgacc acctttgtgg     720 ccctctatga ctatgagtct aggacggaga cagacctgtc cttcaagaaa ggcgagcggc     780

```
tccagattgt caacaacaca gagggagact ggtggctggc ccactcgctc agcacaggac    840
agacaggcta catccccagc aactacgtgg cgccctccga ctccatccag gctgaggagt    900
ggtattttgg caagatcacc agacgggagt cagagcggtt actgctcaat gcagagaacc    960
cgagagggac cttcctcgtg cgagaaagtg agaccacgaa aggtgcctac tgcctctcag   1020
tgtctgactt cgacaacgcc aagggcctca acgtgaagca ctacaagatc cgcaagctgg   1080
acagcggcgg cttctacatc acctcccgca cccagttcaa cagcctgcag cagctggtgg   1140
cctactactc caaacacgcc gatggcctgt gccaccgcct caccaccgtg tgccccacgt   1200
ccaagccgca gactcagggc ctggccaagg atgcctggga gatccctcgg gagtcgctgc   1260
ggctggaggt caagctgggc cagggctgct ttggcgaggt gtggatgggg acctggaacg   1320
gtaccaccag ggtggccatc aaaaccctga agcctggcac gatgtctcca gaggccttcc   1380
tgcaggaggc ccaggtcatg aagaagctga ggcatgagaa gctggtgcag ttgtatgctg   1440
tggtttcaga ggagcccatt tacatcgtca cggagtacat gagcaagggg agtttgctgg   1500
actttctcaa gggggagaca ggcaagtacc tgcggctgcc tcagctggtg gacatggctg   1560
ctcagatcgc ctcaggcatg gcgtacgtgg agcggatgaa ctacgtccac cgggaccttc   1620
gtgcagccaa catcctggtg ggagagaacc tggtgtgcaa agtggccgac tttgggctgg   1680
ctcggctcat tgaagacaat gagtacacgg cgcggcaagg tgccaaattc cccatcaagt   1740
ggacggctcc agaagctgcc ctctatggcc gcttcaccat caagtcggac gtgtggtcct   1800
tcgggatcct gctgactgag ctcaccacaa agggacgggt gcctacccct gggatggtga   1860
accgcgaggt gctggaccag gtggagcggg gctaccggat gcctgcccg ccggagtgtc   1920
ccgagtccct gcacgacctc atgtgccagt gctggcggaa ggagcctgag gagcggccca   1980
ccttcgagta cctgcaggcc ttcctggagg actacttcac gtccaccgag ccccagtacc   2040
agcccgggga gaacctctag gcacaggcgg gcccagaccg gcttctcggc ttggatcctg   2100
ggctgggtgg cccctgtctc ggggcttgcc ccactctgcc tgcctgctgt tggtcctctc   2160
tctgtggggc tgaattgcca ggggcgaggc ccttcctctt tggtggcatg aagggcttt   2220
ctggacctag ggtggcctga gagggcggtg ggtatgcgag accagcacgg tgactctgtc   2280
cagctcccgc tgtggccgca cgcctctccc tgcactccct cctggagctc tgtgggtctc   2340
tggaagagga accaggagaa gggctggggc cgggctgag ggtgcccttt tccagcctca   2400
gcctactccg ctcactgaac tccttcccca cttctgtgcc accccggtc tatgtcgaga   2460
gctggccaaa gagcctttcc aaagaggagc gatgggcccc tggccccgcc tgcctgccac   2520
cctgccccctt gccatccatt ctggaaacac ctgtaggcag aggctgccga cagaccctt   2580
ctgccgctgc ttccaggctg ggcagcacaa ggccttgcct ggcctgatga tggtgggtgg   2640
gtgggatgag taccccctca aaccctgccc tccttagacc tgagggaccc ttcgagatca   2700
tcacttcctt gcccccattt cacccatggg gagacagttg agagcgggga tgtgacatgc   2760
ccaaggccac ggagcagttc agagtggagg cgggcttgga acccggtgct ccctctgtca   2820
tcctcaggaa ccaacaattc gtcggaggca tcatggaaag actgggacag cccaggaaac   2880
aaggggtctg aggatgcatt cgagatggca gattcccact gccgctgccc gctcagccca   2940
gctgttggga acagcatgga ggcagatgtg gggctgagct ggggaatcag ggtaaaaggt   3000
gcaggtgtgg agagagaggc ttcaatcggc ttgtgggtga tgtttgacct tcagagccag   3060
ccggctatga aagggagcga gccctcggc tctggaggca atcaagcaga catagaagag   3120
ccaagagtcc aggaggccct ggtcctggcc tccttccccg tactttgtcc cgtggcattt   3180
```

-continued

```
caattcctgg ccctgttctc ctccccaagt cggcacccct taactcatga ggagggaaaa    3240
gagtgcctaa gcgggggtga aagaggacgt gttacccact gccatgcacc aggactggct    3300
gtgtaacctt gggtggcccc tgctgtctct ctgggctgca gagtctgccc cacatgtggc    3360
catggcctct gcaactgctc agctctggtc caggccctgt ggcaggacac acatggtgag    3420
cctagccctg ggacatcagg agactgggct ctggctctgt tcggccttg ggtgtgtggt    3480 ggattctccc tgggcctcag tgtgcccatc tgtaaagggg cagctgacag tttgtggcat    3540
cttgccaagg gtccctgtgt gtgtgtatgt gtgtgcatgt gtgcgtgtct ccatgtgcgt    3600
ccatatttaa catgtaaaaa tgtccccccc gctccgtccc ccaaacatgt tgtacatttc    3660
accatggccc cctcatcata gcaataacat tcccactgcc aggggttctt gagccagcca    3720
ggccctgcca gtggggaagg aggccaagca gtgcctgcct atgaaatttc aacttttcct    3780
ttcatacgtc tttattaccc aagtcttctc ccgtccattc cagtcaaatc tgggctcact    3840
caccccagcg agctctcaaa tccctctcca actgcctaag gcccttgtg taaggtgtct    3900 taatactgtc cttttttttt ttttaacagt gttttgtaga tttcagatga ctatgcagag    3960 gcctgggga cccctggctc tgggccgggc ctggggctcc gaaattccaa ggcccagact    4020
tgcggggggt gggggggtat ccagaattgg ttgtaaatac tttgcatatt gtctgattaa    4080
acacaaacag acctcagaaa aaaaaaaaa aaaaaaaaa aaaaaaaaaa aaaaaaaaaa    4140
aaaaa                                                                4145
```

<210> SEQ ID NO 4
<211> LENGTH: 536
<212> TYPE: PRT
<213> ORGANISM: Homo sapiens

<400> SEQUENCE: 4

```
Met Gly Ser Asn Lys Ser Lys Pro Lys Asp Ala Ser Gln Arg Arg Arg
1               5                   10                  15

Ser Leu Glu Pro Ala Glu Asn Val His Gly Ala Gly Gly Gly Ala Phe
            20                  25                  30

Pro Ala Ser Gln Thr Pro Ser Lys Pro Ala Ser Ala Asp Gly His Arg
        35                  40                  45

Gly Pro Ser Ala Ala Phe Ala Pro Ala Ala Glu Pro Lys Leu Phe
    50                  55                  60

Gly Gly Phe Asn Ser Ser Asp Thr Val Thr Ser Pro Gln Arg Ala Gly
65                  70                  75                  80

Pro Leu Ala Gly Gly Val Thr Thr Phe Val Ala Leu Tyr Asp Tyr Glu
                85                  90                  95

Ser Arg Thr Glu Thr Asp Leu Ser Phe Lys Lys Gly Glu Arg Leu Gln
            100                 105                 110

Ile Val Asn Asn Thr Glu Gly Asp Trp Trp Leu Ala His Ser Leu Ser
        115                 120                 125

Thr Gly Gln Thr Gly Tyr Ile Pro Ser Asn Tyr Val Ala Pro Ser Asp
    130                 135                 140

Ser Ile Gln Ala Glu Glu Trp Tyr Phe Gly Lys Ile Thr Arg Arg Glu
145                 150                 155                 160

Ser Glu Arg Leu Leu Leu Asn Ala Glu Asn Pro Arg Gly Thr Phe Leu
                165                 170                 175

Val Arg Glu Ser Glu Thr Thr Lys Gly Ala Tyr Cys Leu Ser Val Ser
            180                 185                 190
```

| | | | | | | | | | | | | |
|---|---|---|---|---|---|---|---|---|---|---|---|---|
|Asp|Phe|Asp|Asn|Ala|Lys|Gly|Leu|Asn|Val|Lys|His|Tyr|Lys|Ile|Arg|
| |195| | | |200| | | |205| | | | |

Asp Phe Asp Asn Ala Lys Gly Leu Asn Val Lys His Tyr Lys Ile Arg
                195                 200                 205

Lys Leu Asp Ser Gly Gly Phe Tyr Ile Thr Ser Arg Thr Gln Phe Asn
            210                 215                 220

Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
                245                 250                 255

Gly Leu Ala Lys Asp Ala Trp Glu Ile Pro Arg Glu Ser Leu Arg Leu
            260                 265                 270

Glu Val Lys Leu Gly Gln Gly Cys Phe Gly Glu Val Trp Met Gly Thr
        275                 280                 285

Trp Asn Gly Thr Thr Arg Val Ala Ile Lys Thr Leu Lys Pro Gly Thr
        290                 295                 300

Met Ser Pro Glu Ala Phe Leu Gln Glu Ala Gln Val Met Lys Lys Leu
305                 310                 315                 320

Arg His Glu Lys Leu Val Gln Leu Tyr Ala Val Val Ser Glu Glu Pro
                325                 330                 335

Ile Tyr Ile Val Thr Glu Tyr Met Ser Lys Gly Ser Leu Leu Asp Phe
            340                 345                 350

Leu Lys Gly Glu Thr Gly Lys Tyr Leu Arg Leu Pro Gln Leu Val Asp
        355                 360                 365

Met Ala Ala Gln Ile Ala Ser Gly Met Ala Tyr Val Glu Arg Met Asn
        370                 375                 380

Tyr Val His Arg Asp Leu Arg Ala Ala Asn Ile Leu Val Gly Glu Asn
385                 390                 395                 400

Leu Val Cys Lys Val Ala Asp Phe Gly Leu Ala Arg Leu Ile Glu Asp
                405                 410                 415

Asn Glu Tyr Thr Ala Arg Gln Gly Ala Lys Phe Pro Ile Lys Trp Thr
            420                 425                 430

Ala Pro Glu Ala Ala Leu Tyr Gly Arg Phe Thr Ile Lys Ser Asp Val
        435                 440                 445

Trp Ser Phe Gly Ile Leu Leu Thr Glu Leu Thr Thr Lys Gly Arg Val
450                 455                 460

Pro Tyr Pro Gly Met Val Asn Arg Glu Val Leu Asp Gln Val Glu Arg
465                 470                 475                 480

Gly Tyr Arg Met Pro Cys Pro Pro Glu Cys Pro Glu Ser Leu His Asp
                485                 490                 495

Leu Met Cys Gln Cys Trp Arg Lys Glu Pro Glu Glu Arg Pro Thr Phe
            500                 505                 510

Glu Tyr Leu Gln Ala Phe Leu Glu Asp Tyr Phe Thr Ser Thr Glu Pro
        515                 520                 525

Gln Tyr Gln Pro Gly Glu Asn Leu
530                 535

<210> SEQ ID NO 5
<211> LENGTH: 4685
<212> TYPE: DNA
<213> ORGANISM: Homo sapiens

<400> SEQUENCE: 5
ggaggaggtg gagagtgagg ccgaggcgtg gggagcccgg gaactccctc ctcctgaagt    60
aacgcgtccc gggccggctc tgccgtcgtt gctgccgccg ggcgcccggg acgaggagg    120 tggaggaggg agagggcccg cgggcctcgc ctccgccctc cgccacctcg agctgcggta   180

```
gcagcgactc atgagagcgc ggccggagga cagatttgat aatgggctgc attaaaagta      240
aagaaaacaa aagtccagcc attaaataca gacctgaaaa tactccagag cctgtcagta      300
caagtgtgag ccattatgga gcagaaccca ctacagtgtc accatgtccg tcatcttcag      360
caaagggaac agcagttaat ttcagcagtc tttccatgac accatttgga ggatcctcag      420
gggtaacgcc ttttggaggt gcatcttcct cattttcagt ggtgccaagt tcatatcctg      480
ctggtttaac aggtggtgtt actatatttg tggccttata tgattatgaa gctagaacta      540
cagaagacct ttcatttaag aagggtgaaa gatttcaaat aattaacaat acggaaggag      600
attggtggga agcaagatca atcgctacag gaaagaatgg ttatatcccg agcaattatg      660
tagcgcctgc agattccatt caggcagaag aatggtattt tggcaaaatg gggagaaaag      720
atgctgaaag attactttg aatcctggaa atcaacgagg tattttctta gtaagagaga       780
gtgaaacaac taaggtgct tattcccttt ctattcgtga ttgggatgag ataaggggtg        840
acaatgtgaa acactacaaa attaggaaac ttgacaatgg tggatactat atcacaacca      900
gagcacaatt tgatactctg cagaaattgg tgaaacacta cacagaacat gctgatggtt      960
tatgccacaa gttgacaact gtgtgtccaa ctgtgaaacc tcagactcaa ggtctagcaa     1020
aagatgcttg ggaaatccct cgagaatctt tgcgactaga ggttaaacta ggacaaggat     1080
gtttcggcga agtgtggatg ggaacatgga atggaaccac gaaagtagca atcaaaacac     1140
taaaaccagg tacaatgatg ccagaagctt tccttcaaga agctcagata atgaaaaaat     1200
taagacatga taaacttgtt ccactatatg ctgttgtttc tgaagaacca atttacattg     1260
tcactgaatt tatgtcaaaa ggaagcttat tagatttcct taaggaagga gatggaaagt     1320
atttgaagct tccacagctg gttgatatgg ctgctcagat tgctgatggt atggcatata     1380
ttgaaagaat gaactatatt caccgagatc ttcgggctgc taatattctt gtaggagaaa     1440
atcttgtgtg caaatagca gactttggtt tagcaaggtt aattgaagac aatgaataca      1500
cagcaagaca aggtgcaaaa tttccaatca aatggacagc tcctgaagct gcactgtatg     1560
gtcggtttac aataaagtct gatgtctggt catttggaat tctgcaaaca gaactagtaa     1620
caaagggccg agtgccatat ccaggtatgg tgaaccgtga agtactagaa caagtggagc     1680
gaggatacag gatgccgtgc cctcagggct gtccagaatc cctccatgaa ttgatgaatc     1740
tgtgttggaa gaaggaccct gatgaaagac caacatttga atatattcag tccttcttgg     1800
aagactactt cactgctaca gagccacagt accagccagg agaaaattta taattcaagt     1860
agcctatttt atatgcacaa atctgccaaa atataaagaa cttgtgtaga tttcctacag     1920
gaatcaaaag aagaaaatct tctttactct gcatgttttt aatggtaaac tggaatccca     1980
gatatggttg cacaaaacca cttttttttc cccaagtatt aaactctaat gtaccaatga     2040
tgaatttatc agcgtatttc agggtccaaa caaaatagag ctaagatact gatgacagtg     2100
tgggtgacag catggtaatg aaggacagtg aggctcctgc ttatttataa atcatttcct     2160
ttcttttttt ccccaaagtc agaattgctc aaagaaaatt atttattgtt acagataaaa     2220
cttgagagat aaaaagctat accataataa aatctaaaat taaggaatat catgggacca     2280
aataattcca ttccagtttt ttaaagtttc ttgcatttat tattctcaaa agttttttct     2340
aagttaaaca gtcagtatgc aatcttaata tatgctttct tttgcatgga catgggccag     2400 gttttttcaaa aggaatataa acaggatctc aaacttgatt aaatgttaga ccacagaagt     2460
ggaatttgaa agtataatgc agtacattaa tattcatgtt catggaactg aaagaataag     2520
```

| | |
|---|---|
| aacttttttca cttcagtcct tttctgaaga gtttgactta gaataatgaa ggtaactaga | 2580 |
| aagtgagtta atcttgtatg aggttgcatt gattttttaa ggcaatatat aattgaaact | 2640 |
| actgtccaat caaaggggaa atgttttgat ctttagatag catgcaaagt aagacccagc | 2700 |
| attttaaaag ccctttttaa aaactagact tcgtactgtg agtattgctt atatgtcctt | 2760 |
| atggggatgg gtgccacaaa tagaaaatat gaccagatca gggacttgaa tgcacttttg | 2820 |
| ctcatggtga atatagatga acagagagga aaatgtattt aaaagaaata cgagaaaaga | 2880 |
| aagtgaaagt tttacaagtt agagggatgg aaggtaatgt ttaatgttga tgtcatggag | 2940 |
| tgacagaatg gctttgctgg cactcagagc tcctcactta gctatattct gagactttga | 3000 |
| agagttataa agtataacta taaaactaat ttttcttaca cactaaatgg gtatttgttc | 3060 |
| aaaataatga agttatggct tcacattcat tgcagtggga tatggttttt atgtaaaaca | 3120 |
| ttttttagaac tccagttttc aaatcatgtt tgaatctaca ttcacttttt tttgttttct | 3180 |
| tttttgagac ggagtctcgc tctgtcgccc aggctggagt gcagtggcgc gatctcggct | 3240 |
| cactgcaagc tctgcctccc aggttcacac cattctcctg cctcagcctc ccagtagcct | 3300 |
| gggactacag gtgcccacca ccacgcctgg ctagtttttt gtattttttag tagagacgca | 3360 |
| gtttcaccgt gttagccagg atggtctcga tctcctgacc ttgtgatctg cccgcctcgg | 3420 |
| cctcccaaag tgctgggatt acaggcgtga gccaccgcgc ccagcctaca ttcacttcta | 3480 |
| aagtctatgt aatggtggtc atttttttccc ttttagaata cattaaatgg ttgatttggg | 3540 |
| gaggaaaact tattctgaat attaacggtg gtgaaaaggg gacagttttt accctaaagt | 3600 |
| gcaaaagtga aacatacaaa ataagactaa tttttaagag taactcagta atttcaaaat | 3660 |
| acagatttga atagcagcat tagtggtttg agtgtctagc aaaggaaaaa ttgatgaata | 3720 |
| aaatgaaggt ctggtgtata tgttttaaaa tactctcata tagtcacact ttaaattaag | 3780 |
| ccttatatta ggcccctcta ttttcaggat ataattctta actatcatta tttacctgat | 3840 |
| tttaatcatc agattcgaaa ttctgtgcca tggcatatat gttcaaattc aaaccatttt | 3900 |
| taaaatgtga agatggactt catgcaagtt ggcagtggtt ctggtactaa aaattgtggt | 3960 |
| tgttttttct gtttacgtaa cctgcttagt attgacactc tctaccaaga gggtcttcct | 4020 |
| aagaagagtg ctgtcattat ttcctcttat caacaacttg tgacatgaga ttttttaagg | 4080 |
| gctttatgtg aactatgata ttgtaatttt tctaagcata ttcaaagggg tgacaaaatt | 4140 |
| acgtttatgt actaaatcta atcaggaaag taaggcagga aaagttgatg gtattcatta | 4200 |
| ggttttaact gaatggagca gttccttata taataacaat tgtatagtag ggataaaaca | 4260 |
| ctaacttaat gtgtattcat tttaaattgt tctgtatttt taaattgcca agaaaaacaa | 4320 |
| ctttgtaaat ttggagatat tttccaacag cttttcgtct tcagtgtctt aatgtggaag | 4380 |
| ttaaccctta ccaaaaaagg aagttggcaa aaacagcctt ctagcacact ttttttaaatg | 4440 |
| aataatggta gcctaaactt aatatttta taaagtattg taatattgtt ttgtggataa | 4500 |
| ttgaaataaa aagttctcat tgaatgcacc tattaatcgt tttagttgct attcatattc | 4560 |
| tcattcgttt tttaaaaact gatatattct gaatttattc ttccattgag aaaaaaatgt | 4620 |
| tcagttactt gtaactactg agcagaattt aatcaatcct ttattaaatt cagaacatta | 4680 |
| ttgaa | 4685 |

<210> SEQ ID NO 6
<211> LENGTH: 543
<212> TYPE: PRT
<213> ORGANISM: Homo sapiens

<400> SEQUENCE: 6

```
Met Gly Cys Ile Lys Ser Lys Glu Asn Lys Ser Pro Ala Ile Lys Tyr
1               5                   10                  15

Arg Pro Glu Asn Thr Pro Glu Pro Val Ser Thr Ser Val Ser His Tyr
            20                  25                  30

Gly Ala Glu Pro Thr Thr Val Ser Pro Cys Pro Ser Ser Ser Ala Lys
            35                  40                  45

Gly Thr Ala Val Asn Phe Ser Ser Leu Ser Met Thr Pro Phe Gly Gly
    50                  55                  60

Ser Ser Gly Val Thr Pro Phe Gly Gly Ala Ser Ser Ser Phe Ser Val
65                  70                  75                  80

Val Pro Ser Ser Tyr Pro Ala Gly Leu Thr Gly Gly Val Thr Ile Phe
                85                  90                  95

Val Ala Leu Tyr Asp Tyr Glu Ala Arg Thr Thr Glu Asp Leu Ser Phe
            100                 105                 110

Lys Lys Gly Glu Arg Phe Gln Ile Ile Asn Asn Thr Glu Gly Asp Trp
            115                 120                 125

Trp Glu Ala Arg Ser Ile Ala Thr Gly Lys Asn Gly Tyr Ile Pro Ser
130                 135                 140

Asn Tyr Val Ala Pro Ala Asp Ser Ile Gln Ala Glu Glu Trp Tyr Phe
145                 150                 155                 160

Gly Lys Met Gly Arg Lys Asp Ala Glu Arg Leu Leu Leu Asn Pro Gly
                165                 170                 175

Asn Gln Arg Gly Ile Phe Leu Val Arg Glu Ser Glu Thr Thr Lys Gly
            180                 185                 190

Ala Tyr Ser Leu Ser Ile Arg Asp Trp Asp Glu Ile Arg Gly Asp Asn
            195                 200                 205

Val Lys His Tyr Lys Ile Arg Lys Leu Asp Asn Gly Gly Tyr Tyr Ile
210                 215                 220

Thr Thr Arg Ala Gln Phe Asp Thr Leu Gln Lys Leu Val Lys His Tyr
225                 230                 235                 240

Thr Glu His Ala Asp Gly Leu Cys His Lys Leu Thr Thr Val Cys Pro
                245                 250                 255

Thr Val Lys Pro Gln Thr Gln Gly Leu Ala Lys Asp Ala Trp Glu Ile
            260                 265                 270

Pro Arg Glu Ser Leu Arg Leu Glu Val Lys Leu Gly Gln Gly Cys Phe
            275                 280                 285

Gly Glu Val Trp Met Gly Thr Trp Asn Gly Thr Thr Lys Val Ala Ile
290                 295                 300

Lys Thr Leu Lys Pro Gly Thr Met Met Pro Glu Ala Phe Leu Gln Glu
305                 310                 315                 320

Ala Gln Ile Met Lys Lys Leu Arg His Asp Lys Leu Val Pro Leu Tyr
                325                 330                 335

Ala Val Val Ser Glu Glu Pro Ile Tyr Ile Val Thr Glu Phe Met Ser
            340                 345                 350

Lys Gly Ser Leu Leu Asp Phe Leu Lys Glu Gly Asp Gly Lys Tyr Leu
            355                 360                 365

Lys Leu Pro Gln Leu Val Asp Met Ala Ala Gln Ile Ala Asp Gly Met
            370                 375                 380

Ala Tyr Ile Glu Arg Met Asn Tyr Ile His Arg Asp Leu Arg Ala Ala
385                 390                 395                 400

Asn Ile Leu Val Gly Glu Asn Leu Val Cys Lys Ile Ala Asp Phe Gly
```

```
                405                410                415
Leu Ala Arg Leu Ile Glu Asp Asn Glu Tyr Thr Ala Arg Gln Gly Ala
            420                425                430

Lys Phe Pro Ile Lys Trp Thr Ala Pro Glu Ala Ala Leu Tyr Gly Arg
            435                440                445

Phe Thr Ile Lys Ser Asp Val Trp Ser Phe Gly Ile Leu Gln Thr Glu
            450                455                460

Leu Val Thr Lys Gly Arg Val Pro Tyr Pro Gly Met Val Asn Arg Glu
465                470                475                480

Val Leu Glu Gln Val Glu Arg Gly Tyr Arg Met Pro Cys Pro Gln Gly
                485                490                495

Cys Pro Glu Ser Leu His Glu Leu Met Asn Leu Cys Trp Lys Lys Asp
            500                505                510

Pro Asp Glu Arg Pro Thr Phe Glu Tyr Ile Gln Ser Phe Leu Glu Asp
            515                520                525

Tyr Phe Thr Ala Thr Glu Pro Gln Tyr Gln Pro Gly Glu Asn Leu
            530                535                540

<210> SEQ ID NO 7
<211> LENGTH: 3628
<212> TYPE: DNA
<213> ORGANISM: Homo sapiens

<400> SEQUENCE: 7
agagcatcag caagagtagc agcgagcagc cgcgctggtg gcggcggcgc gtcgttgcag     60
ttgcgccatc tgtcaggagc ggagccggcg aggaggggc tgccgcgggc gaggaggag     120 ggtcgccgcg agccgaaggc cttcgagacc cgcccgccgc ccggcggcga gagtagaggc   180
gaggttgttg tgcgagcggc gcgtcctctc ccgcccgggc gcgccgcgct tctcccagcg   240
caccgaggac cgcccgggcg cacacaaagc cgccgcccgc gccgcaccgc ccggcggccg   300
ccgcccgcgc cagggaggga ttcggccgcc gggccgggga caccccggcg ccgcccctc    360 ggtgctctcg gaaggcccac cggctcccgg gcccgccggg gacccccgg agccgcctcg    420 gccgcgccgg aggagggcgg ggagaggacc atgtgagtgg gctccggagc ctcagcgccg   480
cgcagttttt ttgaagaagc aggatgctga tctaaacgtg gaaaagacc agtcctgcct    540 ctgttgtaga agacatgtgg tgtatataaa gtttgtgatc gttggcggac attttggaat   600
ttagataatg ggctgtgtgc aatgtaagga taaagaagca acaaaactga cggaggagag   660
ggacggcagc ctgaaccaga gctctgggta ccgctatggc acagacccca cccctcagca   720
ctaccccagc ttcggtgtga cctccatccc caactacaac aacttccacg cagccggggg   780
ccaaggactc accgtctttg gaggtgtgaa ctcttcgtct catacgggga ccttgcgtac   840
gagaggagga acaggagtga cactctttgt ggcccttat gactatgaag cacggacaga    900
agatgacctg agttttcaca aggagaaaa atttcaaata ttgaacagct cggaaggaga    960
ttggtgggaa gcccgctcct tgacaactgg agagacaggt acattccca gcaattatgt   1020 ggctccagtt gactctatcc aggcagaaga gtggtacttt ggaaaacttg gccgaaaaga  1080
tgctgagcga cagctattgt cctttggaaa cccaagaggg acctttctta tccgcgagag  1140
tgaaaccacc aaaggtgcct attcactttc tatccgtgat tgggatgata tgaaaggaga  1200
ccatgtcaaa cattataaaa ttcgcaaact tgacaatggt ggatactaca ttaccacccg  1260
ggcccagttt gaaacacttc agcagcttgt acaacattac tcagagagag ctgcaggtct  1320
ctgctgccgc ctagtagttc cctgtcacaa agggatgcca aggcttaccg atctgtctgt  1380
```

```
caaaaccaaa gatgtctggg aaatccctcg agaatccctg cagttgatca agagactggg     1440
aaatgggcag tttggggaag tatggatggg tacctggaat ggaaacacaa aagtagccat     1500
aaagactctt aaaccaggca caatgtcccc cgaatcattc cttgaggaag cgcagatcat     1560
gaagaagctg aagcacgaca agctggtcca gctctatgca gtggtgtctg aggagcccat     1620
ctacatcgtc accgagtata tgaacaaagg aagtttactg gatttcttaa aagatggaga     1680
aggaagagct ctgaaattac caaatcttgt ggacatggca gcacaggtgg ctgcaggaat     1740
ggcttacatc gagcgcatga attatatcca tagagatctg cgatcagcaa acattctagt     1800
ggggaatgga ctcatatgca agattgctga cttcggattg gcccgattga tagaagacaa     1860
tgagtacaca gcaagacaag gtgcaaagtt ccccatcaag tggacggccc ccgaggcagc     1920
cctgtacgga aggttcacaa tcaagtctga cgtgtggtct tttggaatct tactcacaga     1980
gctggtcacc aaaggaagag tgccataccc aggcatgaac aaccgggagg tgctggagca     2040
ggtggagcga ggctacagga tgcccctgcc gcaggactgc cccatctctc tgcatgagct     2100
catgatccac tgctggaaaa aggaccctga agaacgcccc acttttgagt acttgcagag     2160
cttcctggaa gactacttta ccgcgacaga gccccagtac caacctggtg aaaacctgta     2220
aggcccgggt ctgcggagag aggccttgtc ccagaggctg ccccacccct ccccattagc     2280
tttcaattcc gtagccagct gctcccagc agcggaaccg cccaggatca gattgcatgt      2340
gactctgaag ctgacgaact tccatggccc tcattaatga cacttgtccc caaatccgaa     2400
cctcctctgt gaagcattcg agacagaacc ttgttatttc tcagactttg gaaaatgcat     2460
tgtatcgatg ttatgtaaaa ggccaaacct ctgttcagtg taaatagtta ctccagtgcc     2520
aacaatccta gtgctttcct ttttttaaaaa tgcaaatcct atgtgatttt aactctgtct    2580
tcacctgatt caactaaaaa aaaaaaagta ttattttcca aaagtggcct ctttgtctaa     2640
aacaataaaa tttttttttca tgttttaaca aaaaccaatc aggacaggtg tttgttttttg    2700 ttttcttttt tataaatatg aatatatata atatatatgt ccctgtacat atacaatgtg     2760
ggtgctaatg tggagactgt ggccggcctg agccaccaag ctgcgggacc cagagggagg    2820 atttttactgc aagtcagcat caaagcaccg gtgttattct gaaaacacca gtggcctcat    2880 tttttggcttt tgcaaagcat gaattttttc atttggattg cactttcctg gttcatgact    2940
gtacctgtag gtggttgtta cttgactct tttcaggaac cacccccaa gctgaattta       3000 caagttctgt tagcactatt tgcttcaact tactgcgatt tgttctcaaa acttaaaaat     3060
aagcaagcaa atggctgata ctaccaagag aactggaaga tggataccac acaaacttct    3120
tgtataaaaa tatgaatgct gaaatgtttc agacatttttt aatttaataa acctgtaacc   3180
acatttaagt gatctaaaac ccatagcatt gtagtcatgg caaccgcta aacttctca      3240 tgcaactaaa atttctgggg gaaatgaggg tggggttgt acatttccca ttgtaaaata      3300
agtgttttaa atgtcctgta ctgctaacga atgactttct atatgtccag gagttctcca    3360
gtggaataac tatgcactac tttacatttc atggggatgc acaaaaacaa aaagtatta     3420 cattttttagt tgctgtttgt accaaccta aattacatat gtttaacaac aacaaatcaa    3480
aaatcctatt tctattgagt ttttaatact gactagcaac tctgaagtct taattccttt    3540
tttgttatga tttatttgtg agtttacatt tttaaattgt ttaactttct taatttagta   3600
attaaaaaga gagcattttta catttgaa                                         3628
```

<210> SEQ ID NO 8

<211> LENGTH: 537
<212> TYPE: PRT
<213> ORGANISM: Homo sapiens

<400> SEQUENCE: 8

```
Met Gly Cys Val Gln Cys Lys Asp Lys Glu Ala Thr Lys Leu Thr Glu
1               5                   10                  15

Glu Arg Asp Gly Ser Leu Asn Gln Ser Ser Gly Tyr Arg Tyr Gly Thr
            20                  25                  30

Asp Pro Thr Pro Gln His Tyr Pro Ser Phe Gly Val Thr Ser Ile Pro
        35                  40                  45

Asn Tyr Asn Asn Phe His Ala Ala Gly Gly Gln Gly Leu Thr Val Phe
    50                  55                  60

Gly Gly Val Asn Ser Ser Ser His Thr Gly Thr Leu Arg Thr Arg Gly
65                  70                  75                  80

Gly Thr Gly Val Thr Leu Phe Val Ala Leu Tyr Asp Tyr Glu Ala Arg
                85                  90                  95

Thr Glu Asp Asp Leu Ser Phe His Lys Gly Glu Lys Phe Gln Ile Leu
            100                 105                 110

Asn Ser Ser Glu Gly Asp Trp Trp Glu Ala Arg Ser Leu Thr Thr Gly
        115                 120                 125

Glu Thr Gly Tyr Ile Pro Ser Asn Tyr Val Ala Pro Val Asp Ser Ile
    130                 135                 140

Gln Ala Glu Glu Trp Tyr Phe Gly Lys Leu Gly Arg Lys Asp Ala Glu
145                 150                 155                 160

Arg Gln Leu Leu Ser Phe Gly Asn Pro Arg Gly Thr Phe Leu Ile Arg
                165                 170                 175

Glu Ser Glu Thr Thr Lys Gly Ala Tyr Ser Leu Ser Ile Arg Asp Trp
            180                 185                 190

Asp Asp Met Lys Gly Asp His Val Lys His Tyr Lys Ile Arg Lys Leu
        195                 200                 205

Asp Asn Gly Gly Tyr Tyr Ile Thr Thr Arg Ala Gln Phe Glu Thr Leu
    210                 215                 220

Gln Gln Leu Val Gln His Tyr Ser Glu Arg Ala Ala Gly Leu Cys Cys
225                 230                 235                 240

Arg Leu Val Val Pro Cys His Lys Gly Met Pro Arg Leu Thr Asp Leu
                245                 250                 255

Ser Val Lys Thr Lys Asp Val Trp Glu Ile Pro Arg Glu Ser Leu Gln
            260                 265                 270

Leu Ile Lys Arg Leu Gly Asn Gly Gln Phe Gly Glu Val Trp Met Gly
        275                 280                 285

Thr Trp Asn Gly Asn Thr Lys Val Ala Ile Lys Thr Leu Lys Pro Gly
    290                 295                 300

Thr Met Ser Pro Glu Ser Phe Leu Glu Glu Ala Gln Ile Met Lys Lys
305                 310                 315                 320

Leu Lys His Asp Lys Leu Val Gln Leu Tyr Ala Val Val Ser Glu Glu
                325                 330                 335

Pro Ile Tyr Ile Val Thr Glu Tyr Met Asn Lys Gly Ser Leu Leu Asp
            340                 345                 350

Phe Leu Lys Asp Gly Glu Gly Arg Ala Leu Lys Leu Pro Asn Leu Val
        355                 360                 365

Asp Met Ala Ala Gln Val Ala Ala Gly Met Ala Tyr Ile Glu Arg Met
    370                 375                 380

Asn Tyr Ile His Arg Asp Leu Arg Ser Ala Asn Ile Leu Val Gly Asn
```

```
                385                 390                 395                 400
        Gly Leu Ile Cys Lys Ile Ala Asp Phe Gly Leu Ala Arg Leu Ile Glu
                            405                 410                 415

Asp Asn Glu Tyr Thr Ala Arg Gln Gly Ala Lys Phe Pro Ile Lys Trp
                        420                 425                 430

Thr Ala Pro Glu Ala Ala Leu Tyr Gly Arg Phe Thr Ile Lys Ser Asp
                    435                 440                 445

Val Trp Ser Phe Gly Ile Leu Leu Thr Glu Leu Val Thr Lys Gly Arg
                450                 455                 460

Val Pro Tyr Pro Gly Met Asn Asn Arg Glu Val Leu Glu Gln Val Glu
        465                 470                 475                 480

Arg Gly Tyr Arg Met Pro Cys Pro Gln Asp Cys Pro Ile Ser Leu His
                            485                 490                 495

Glu Leu Met Ile His Cys Trp Lys Lys Asp Pro Glu Glu Arg Pro Thr
                        500                 505                 510

Phe Glu Tyr Leu Gln Ser Phe Leu Glu Asp Tyr Phe Thr Ala Thr Glu
                    515                 520                 525

Pro Gln Tyr Gln Pro Gly Glu Asn Leu
                530                 535

<210> SEQ ID NO 9
<211> LENGTH: 2442
<212> TYPE: DNA
<213> ORGANISM: Homo sapiens

<400> SEQUENCE: 9
tacacacatg agagatcact tagagcaaag ggtgagaggg gcaggtgggg ctagggtgga      60
gaccaaagca ctgatgtgac ggaaccatca gccaggcaac tggacctggt ggatccagga    120
agactttctg gaagaggtct ctgaccccctc ccaaggatca tgccgcagcc ccactgaccc   180
aggagtaggg gcctaagggc agggaacctg gaatgggctg tgtgttctgc aagaaattgg    240
agccggtggc cacggccaag gaggatgctg gcctggaagg ggacttcaga agctacgggg   300
cagcagacca ctatgggcct gaccccacta aggcccggcc tgcatcctca tttgcccaca    360
tccccaacta cagcaacttc tcctctcagg ccatcaaccc tggcttcctt gatagtggca    420
ccatcagggg tgtgtcaggg attggggtga ccctgttcat tgccctgtat gactatgagg    480
ctcgaactga ggatgacctc accttcacca agggcgagag gttccacatc ctgaacaata    540
ctgaaggtga ctggtgggag gctcggtctc tcagctccgg aaaaactggc tgcattccca    600
gcaactacgt ggccctgtt gactcaatcc aagctgaaga gtggtacttt ggaaagattg    660
ggagaaagga tgcagagagg cagctgcttt caccaggcaa ccccaggggg cctttctca    720 ttcgggaaag cgagaccacc aaaggtgcct actccctgtc catccgggac tgggatcaga    780
ccagaggcga tcatgtgaag cattacaaga tccgcaaact ggacatgggc ggctactaca    840
tcaccacacg ggttcagttc aactcggtgc aggagctggt gcagcactac atggaggtga    900
atgacgggct gtgcaacctg ctcatcgcgc cctgcaccat catgaagccg cagacgctgg    960
gcctggccaa ggacgcctgg gagatcagcc gcagctccat cacgctggag cgccggctgg   1020
gcaccggctg cttcggggat gtgtggctgg cacgtggaa cggcagcact aaggtggcg   1080 tgaagacgct gaagccgggc accatgtccc cgaaggcctt cctggaggag cgcaggtca   1140 tgaagctgct gcggcacgac aagctggtgc agctgtacgc cgtggtgtcg gaggagccca   1200
tctacatcgt gaccgagttc atgtgtcacg gcagcttgct ggattttctc aagaacccag   1260
```

-continued

```
agggccagga tttgaggctg ccccaattgg tggacatggc agcccaggta gctgagggca    1320
tggcctacat ggaacgcatg aactacattc accgcgacct gagggcagcc aacatcctgg    1380
ttggggagcg gctggcgtgc aagatcgcag actttggctt ggcgcgtctc atcaaggacg    1440
atgagtacaa cccctgccaa ggttccaagt tccccatcaa gtggacagcc ccagaagctg    1500
ccctctttgg cagattcacc atcaagtcag acgtgtggtc ctttgggatc ctgctcactg    1560
agctcatcac caagggccga atcccctacc caggcatgaa taaacgggaa gtgttggaac    1620
aggtggagca gggctaccac atgccgtgcc ctccaggctg cccagcatcc ctgtacgagg    1680
ccatggaaca gacctggcgt ctggacccgg aggagaggcc taccttcgag tacctgcagt    1740
ccttcctgga ggactacttc acctccgctg aaccacagta ccagcccggg gatcagacat    1800
agcctgtccg gcatcaacc ctctctggcg gtggccacca gtccttgcca atccccagag    1860
ctgttcttcc aaagccccca ggctggctta gaaccccata gagtcctagc atcaccgagg    1920
acgtggctgc tctgacacca cctagggcaa cctacttgtt ttacagatgg ggcaaaagga    1980
ggcccagagc tgatctctca tccgctctgg ccccaagcac tatttcttcc ttttccactt    2040
aggcccctac atgcctgtag cctttctcac tccatcccca cccaaagtgc tcagaccttg    2100
tctagttatt tataaaactg tatgtacctc cctcacttct ctcctatcac tgctttccta    2160
ctctcctttt atctcactct agtccaggtg ccaagaattt cccttctacc ctctattctc    2220
ttgtgtctgt aagttacaaa gtcaggaaaa gtcttggctg gaccccttc ctgctgggtg    2280 gatgcagtgg tccaggactg gggtctgggc ccaggtttga gggagaaggt tgcagagcac    2340
ttcccacctc tctgaatagt gtgtatgtgt tggtttattg attctgtaaa taagtaaaat    2400
gacaatatga atcctcaaac catgaaaaaa aaaaaaaaaa aa                       2442
```

<210> SEQ ID NO 10
<211> LENGTH: 529
<212> TYPE: PRT
<213> ORGANISM: Homo sapiens

<400> SEQUENCE: 10

```
Met Gly Cys Val Phe Cys Lys Lys Leu Glu Pro Val Ala Thr Ala Lys
1               5                   10                  15

Glu Asp Ala Gly Leu Glu Gly Asp Phe Arg Ser Tyr Gly Ala Ala Asp
            20                  25                  30

His Tyr Gly Pro Asp Pro Thr Lys Ala Arg Pro Ala Ser Ser Phe Ala
        35                  40                  45

His Ile Pro Asn Tyr Ser Asn Phe Ser Ser Gln Ala Ile Asn Pro Gly
    50                  55                  60

Phe Leu Asp Ser Gly Thr Ile Arg Gly Val Ser Gly Ile Gly Val Thr
65                  70                  75                  80

Leu Phe Ile Ala Leu Tyr Asp Tyr Glu Ala Arg Thr Glu Asp Asp Leu
                85                  90                  95

Thr Phe Thr Lys Gly Glu Lys Phe His Ile Leu Asn Asn Thr Glu Gly
            100                 105                 110

Asp Trp Trp Glu Ala Arg Ser Leu Ser Ser Gly Lys Thr Gly Cys Ile
        115                 120                 125

Pro Ser Asn Tyr Val Ala Pro Val Asp Ser Ile Gln Ala Glu Glu Trp
    130                 135                 140

Tyr Phe Gly Lys Ile Gly Arg Lys Asp Ala Glu Arg Gln Leu Leu Ser
145                 150                 155                 160

Pro Gly Asn Pro Gln Gly Ala Phe Leu Ile Arg Glu Ser Glu Thr Thr
```

```
                    165                 170                 175
Lys Gly Ala Tyr Ser Leu Ser Ile Arg Asp Trp Asp Gln Thr Arg Gly
                180                 185                 190

Asp His Val Lys His Tyr Lys Ile Arg Lys Leu Asp Met Gly Gly Tyr
            195                 200                 205

Tyr Ile Thr Thr Arg Val Gln Phe Asn Ser Val Gln Glu Leu Val Gln
        210                 215                 220

His Tyr Met Glu Val Asn Asp Gly Leu Cys Asn Leu Leu Ile Ala Pro
225                 230                 235                 240

Cys Thr Ile Met Lys Pro Gln Thr Leu Gly Leu Ala Lys Asp Ala Trp
                245                 250                 255

Glu Ile Ser Arg Ser Ser Ile Thr Leu Glu Arg Arg Leu Gly Thr Gly
                260                 265                 270

Cys Phe Gly Asp Val Trp Leu Gly Thr Trp Asn Gly Ser Thr Lys Val
                275                 280                 285

Ala Val Lys Thr Leu Lys Pro Gly Thr Met Ser Pro Lys Ala Phe Leu
            290                 295                 300

Glu Glu Ala Gln Val Met Lys Leu Leu Arg His Asp Lys Leu Val Gln
305                 310                 315                 320

Leu Tyr Ala Val Val Ser Glu Glu Pro Ile Tyr Ile Val Thr Glu Phe
                325                 330                 335

Met Cys His Gly Ser Leu Leu Asp Phe Leu Lys Asn Pro Glu Gly Gln
                340                 345                 350

Asp Leu Arg Leu Pro Gln Leu Val Asp Met Ala Ala Gln Val Ala Glu
            355                 360                 365

Gly Met Ala Tyr Met Glu Arg Met Asn Tyr Ile His Arg Asp Leu Arg
370                 375                 380

Ala Ala Asn Ile Leu Val Gly Glu Arg Leu Ala Cys Lys Ile Ala Asp
385                 390                 395                 400

Phe Gly Leu Ala Arg Leu Ile Lys Asp Asp Glu Tyr Asn Pro Cys Gln
                405                 410                 415

Gly Ser Lys Phe Pro Ile Lys Trp Thr Ala Pro Glu Ala Ala Leu Phe
                420                 425                 430

Gly Arg Phe Thr Ile Lys Ser Asp Val Trp Ser Phe Gly Ile Leu Leu
            435                 440                 445

Thr Glu Leu Ile Thr Lys Gly Arg Ile Pro Tyr Pro Gly Met Asn Lys
        450                 455                 460

Arg Glu Val Leu Glu Gln Val Glu Gln Gly Tyr His Met Pro Cys Pro
465                 470                 475                 480

Pro Gly Cys Pro Ala Ser Leu Tyr Glu Ala Met Glu Gln Thr Trp Arg
                485                 490                 495

Leu Asp Pro Glu Glu Arg Pro Thr Phe Glu Tyr Leu Gln Ser Phe Leu
                500                 505                 510

Glu Asp Tyr Phe Thr Ser Ala Glu Pro Gln Tyr Gln Pro Gly Asp Gln
            515                 520                 525

Thr

<210> SEQ ID NO 11
<211> LENGTH: 2118
<212> TYPE: DNA
<213> ORGANISM: Homo sapiens

<400> SEQUENCE: 11
gtgtgaattt acttgtagcc tgagggctca gagggagcac cggtttggag ctgggacccc    60
```

```
ctatttttagc ttttctgtgg ctggtgaatg gggatcccag gatctcacaa tctcagggac    120
catgggctgt ggctgcagct cacacccgga agatgactgg atggaaaaca tcgatgtgtg    180
tgagaactgc cattatccca tagtcccact ggatggcaag ggcacgctgc tcatccgaaa    240
tggctctgag gtgcgggacc cactggttac ctacgaaggc tccaatccgc cggcttcccc    300
actgcaagac aacctggtta tcgctctgca cagctatgag ccctctcacg acggagatct    360
gggctttgag aaggggggaac agctccgcat cctggagcag agcggcgagt ggtggaaggc    420
gcagtccctg accacgggcc aggaaggctt catccccttc aatttttgtgg ccaaagcgaa    480 cagcctggag cccgaacccct ggttcttcaa gaacctgagc cgcaaggacg cggagcggca    540
gctcctggcg cccgggaaca ctcacggctc cttcctcatc cgggagagcg agagcaccgc    600
gggatcgttt tcactgtcgg tccgggactt cgaccagaac cagggagagg tggtgaaaca    660
ttacaagatc cgtaatctgg acaacggtgg cttctacatc tcccctcgaa tcacttttcc    720
cggcctgcat gaactggtcc gccattacac caatgcttca gatgggctgt gcacacggtt    780
gagccgcccc tgccagaccc agaagcccca gaagccgtgg tgggaggacg agtgggaggt    840
tcccagggag acgctgaagc tggtggagcg gctgggggct ggacagttcg gggaggtgtg    900
gatggggtac tacaacgggc acacgaaggt ggcggtgaag agcctgaagc agggcagcat    960
gtccccggac gccttcctgg ccgaggccaa cctcatgaag cagctgcaac accagcggct   1020
ggttcggctc tacgctgtgg tcacccagga gcccatctac atcatcactg aatacatgga   1080
gaatgggagt ctagtggatt ttctcaagac cccttcaggc atcaagttga ccatcaacaa   1140
actcctggac atggcagccc aaattgcaga aggcatggca ttcattgaag agcggaatta   1200
tattcatcgt gaccttcggg ctgccaacat tctggtgtct gacaccctga gctgcaagat   1260
tgcagacttt ggcctagcac gcctcattga ggacaacgag tacacagcca gggaggggc   1320 caagtttccc attaagtgga cagcgccaga agccattaac tacgggacat tcaccatcaa   1380
gtcagatgtg tggtcttttg gatcctgct gacggaaatt gtcacccacg gccgcatccc   1440
ttacccaggg atgaccaacc cggaggtgat tcagaacctg gagcgaggct accgcatggt   1500
gcgccctgac aactgtccag aggagctgta ccaactcatg aggctgtgct ggaaggagcg   1560
cccagaggac cggcccacct ttgactacct gcgcagtgtg ctggaggact cttcacggc   1620 cacagagggc cagtaccagc ctcagccttg agaggccttg agaggccctg ggttctcccc   1680
cctttctctc cagcctgact tggggagatg gagttcttgt gccatagtca catggcctat   1740
gcacatatgg actctgcaca tgaatcccac ccacatgtga cacatatgca ccttgtgtct   1800
gtacacgtgt cctgtagttg cgtggactct gcacatgtct tgtacatgtg tagcctgtgc   1860
atgtatgtct tggacactgt acaaggtacc cctttctggc tctcccattt cctgagacca   1920
cagagagagg ggagaagcct gggattgaca gaagcttctg cccacctact tttctttcct   1980
cagatcatcc agaagttcct caaggccag gactttatct aatacctctg tgtgctcctc   2040
cttggtgcct ggcctggcac acatcaggag ttcaataaat gtctgttgat gactgttgta   2100
aaaaaaaaaa aaaaaaaa                                                  2118
```

<210> SEQ ID NO 12
<211> LENGTH: 509
<212> TYPE: PRT
<213> ORGANISM: Homo sapiens

<400> SEQUENCE: 12

```
Met Gly Cys Gly Cys Ser Ser His Pro Glu Asp Trp Met Glu Asn
1               5                   10                  15

Ile Asp Val Cys Glu Asn Cys His Tyr Pro Ile Val Pro Leu Asp Gly
            20                  25                  30

Lys Gly Thr Leu Leu Ile Arg Asn Gly Ser Glu Val Arg Asp Pro Leu
            35                  40                  45

Val Thr Tyr Glu Gly Ser Asn Pro Pro Ala Ser Pro Leu Gln Asp Asn
50                      55                  60

Leu Val Ile Ala Leu His Ser Tyr Glu Pro Ser His Asp Gly Asp Leu
65                      70                  75                  80

Gly Phe Glu Lys Gly Glu Gln Leu Arg Ile Leu Glu Gln Ser Gly Glu
                85                  90                  95

Trp Trp Lys Ala Gln Ser Leu Thr Thr Gly Gln Glu Gly Phe Ile Pro
                100                 105                 110

Phe Asn Phe Val Ala Lys Ala Asn Ser Leu Glu Pro Glu Pro Trp Phe
                115                 120                 125

Phe Lys Asn Leu Ser Arg Lys Asp Ala Glu Arg Gln Leu Leu Ala Pro
            130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
                165                 170                 175

Val Val Lys His Tyr Lys Ile Arg Asn Leu Asp Asn Gly Gly Phe Tyr
                180                 185                 190

Ile Ser Pro Arg Ile Thr Phe Pro Gly Leu His Glu Leu Val Arg His
                195                 200                 205

Tyr Thr Asn Ala Ser Asp Gly Leu Cys Thr Arg Leu Ser Arg Pro Cys
210                 215                 220

Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
                245                 250                 255

Gly Glu Val Trp Met Gly Tyr Tyr Asn Gly His Thr Lys Val Ala Val
                260                 265                 270

Lys Ser Leu Lys Gln Gly Ser Met Ser Pro Asp Ala Phe Leu Ala Glu
            275                 280                 285

Ala Asn Leu Met Lys Gln Leu Gln His Gln Arg Leu Val Arg Leu Tyr
            290                 295                 300

Ala Val Val Thr Gln Glu Pro Ile Tyr Ile Ile Thr Glu Tyr Met Glu
305                 310                 315                 320

Asn Gly Ser Leu Val Asp Phe Leu Lys Thr Pro Ser Gly Ile Lys Leu
                325                 330                 335

Thr Ile Asn Lys Leu Leu Asp Met Ala Ala Gln Ile Ala Glu Gly Met
            340                 345                 350

Ala Phe Ile Glu Glu Arg Asn Tyr Ile His Arg Asp Leu Arg Ala Ala
            355                 360                 365

Asn Ile Leu Val Ser Asp Thr Leu Ser Cys Lys Ile Ala Asp Phe Gly
370                 375                 380

Leu Ala Arg Leu Ile Glu Asp Asn Glu Tyr Thr Ala Arg Glu Gly Ala
385                 390                 395                 400

Lys Phe Pro Ile Lys Trp Thr Ala Pro Glu Ala Ile Asn Tyr Gly Thr
            405                 410                 415

Phe Thr Ile Lys Ser Asp Val Trp Ser Phe Gly Ile Leu Leu Thr Glu
```

```
              420                 425                 430
Ile Val Thr His Gly Arg Ile Pro Tyr Pro Gly Met Thr Asn Pro Glu
                435                 440                 445

Val Ile Gln Asn Leu Glu Arg Gly Tyr Arg Met Val Arg Pro Asp Asn
        450                 455                 460

Cys Pro Glu Glu Leu Tyr Gln Leu Met Arg Leu Cys Trp Lys Glu Arg
465                 470                 475                 480

Pro Glu Asp Arg Pro Thr Phe Asp Tyr Leu Arg Ser Val Leu Glu Asp
                485                 490                 495

Phe Phe Thr Ala Thr Glu Gly Gln Tyr Gln Pro Gln Pro
                500                 505

<210> SEQ ID NO 13
<211> LENGTH: 2168
<212> TYPE: DNA
<213> ORGANISM: Homo sapiens

<400> SEQUENCE: 13
ggagttagcc tcgctcaggg cgcggctaag gcgcccagat ggcctgcggg cgccaccacg      60
tccctggtcc cagctcggga gcacatcaga ggcttagagg cgagtgggaa gggactcaga    120
cagtgcagga cgagaaacgc ccgcggcacc aaagcccctc agagcgtcgc ccccgcctct    180
agttctagaa agtcagtttc ccggcactgg caccccggaa cctcagggc  tgccgagctg    240 gggggcgct  caagctgcga ggatccgggc tgcccgcgag acgaggagcg gcgcccagg     300 atggggtgca tgaagtccaa gttcctccag gtcggaggca atacattctc aaaaactgaa    360
accagcgcca gcccacactg tcctgtgtac gtgccggatc ccacatccac catcaagccg    420
gggcctaata gccacaacag caacacacca ggaatcaggg aggcaggctc tgaggacatc    480
atcgtggttg ccctgtatga ttacgaggcc attcaccacg aagacctcag cttccagaag    540
ggggaccaga tggtggtcct agaggaatcc ggggagtggt ggaaggctcg atccctggcc    600
acccggaagg agggctacat cccaagcaac tatgtcgccc gcgttgactc tctggagaca    660
gaggagtggt ttttcaaggg catcagccgg aaggacgcag agcgccaact gctggctccc    720
ggcaacatgc tgggctcctt catgatccgg gatagcgaga ccactaaagg aagctactct    780
ttgtccgtgc gagactacga ccctcggcag ggagataccg tgaaacatta caagatccgg    840
accctggaca acgggggctt ctacatatcc ccccgaagca ccttcagcac tctgcaggag    900
ctggtggacc actacaagaa ggggaacgac gggctctgcc agaaactgtc ggtgccctgc    960
atgtcttcca gccccagaa  gccttgggag aaagatgcct gggagatccc tcgggaatcc   1020
ctcaagctgg agaagaaact tggagctggg cagtttgggg aagtctggat ggccacctac   1080
aacaagcaca ccaaggtggc agtgaagacg atgaagccag gagcatgtc  ggtggaggcc   1140 ttcctggcag aggccaacgt gatgaaaact ctgcagcatg acaagctggt caaacttcat   1200
gcggtggtca ccaaggagcc catctacatc atcacggagt tcatggccaa ggaagcttg    1260 ctggactttc tgaaaagtga tgagggcagc aagcagccat gccaaaact  cattgacttc   1320 tcagcccaga ttgcagaagg catggccttc atcgagcaga ggaactacat ccaccgagac   1380
ctccgagctg ccaacatctt ggtctctgca tccctggtgt gtaagattgc tgactttggc   1440 ctggccccggg tcattgagga caacgagtac acggctcggg aaggggccaa gttccccatc   1500
aagtggacag ctcctgaagc catcaacttt ggctccttca ccatcaagtc agacgtctgg   1560
tcctttggta tcctgctgat ggagatcgtc acctacgggc ggatccctta cccagggatg   1620
```

```
tcaaaccctg aagtgatccg agctctggag cgtggatacc ggatgcctcg cccagagaac    1680
tgcccagagg agctctacaa catcatgatg cgctgctgga aaaaccgtcc ggaggagcgg    1740
ccgaccttcg aatacatcca gagtgtgctg gatgacttct acacggccac agagagccag    1800
taccaacagc agccatgata gggaggacca gggcagggcc aggggggtgcc caggtggtgg   1860 ctgcaaggtg gctccagcac catccgccag ggcccacacc cccttcctac tcccagacac    1920
ccaccctcgc ttcagccaca gtttcctcat ctgtccagtg ggtaggttgg actggaaaat    1980 ctcttttga ctcttgcaat ccacaatctg acattctcag gaagccccca agttgatatt     2040
tctatttcct ggaatggttg gattttagtt acagctgtga tttggaaggg aaactttcaa    2100
aatagtgaaa tgaatattta aataaaagat ataaatgcca aagtctttac caaaaaaaaa    2160
aaaaaaaa                                                              2168

<210> SEQ ID NO 14
<211> LENGTH: 505
<212> TYPE: PRT
<213> ORGANISM: Homo sapiens

<400> SEQUENCE: 14

Met Gly Cys Met Lys Ser Lys Phe Leu Gln Val Gly Gly Asn Thr Phe
1               5                   10                  15

Ser Lys Thr Glu Thr Ser Ala Ser Pro His Cys Pro Val Tyr Val Pro
            20                  25                  30

Asp Pro Thr Ser Thr Ile Lys Pro Gly Pro Asn Ser His Asn Ser Asn
        35                  40                  45

Thr Pro Gly Ile Arg Glu Ala Gly Ser Glu Asp Ile Ile Val Val Ala
    50                  55                  60

Leu Tyr Asp Tyr Glu Ala Ile His His Glu Asp Leu Ser Phe Gln Lys
65                  70                  75                  80

Gly Asp Gln Met Val Val Leu Glu Glu Ser Gly Glu Trp Trp Lys Ala
                85                  90                  95

Arg Ser Leu Ala Thr Arg Lys Glu Gly Tyr Ile Pro Ser Asn Tyr Val
            100                 105                 110

Ala Arg Val Asp Ser Leu Glu Thr Glu Glu Trp Phe Phe Lys Gly Ile
        115                 120                 125

Ser Arg Lys Asp Ala Glu Arg Gln Leu Leu Ala Pro Gly Asn Met Leu
    130                 135                 140

Gly Ser Phe Met Ile Arg Asp Ser Glu Thr Thr Lys Gly Ser Tyr Ser
145                 150                 155                 160

Leu Ser Val Arg Asp Tyr Asp Pro Arg Gln Gly Asp Thr Val Lys His
                165                 170                 175

Tyr Lys Ile Arg Thr Leu Asp Asn Gly Gly Phe Tyr Ile Ser Pro Arg
            180                 185                 190

Ser Thr Phe Ser Thr Leu Gln Glu Leu Val Asp His Tyr Lys Lys Gly
        195                 200                 205

Asn Asp Gly Leu Cys Gln Lys Leu Ser Val Pro Cys Met Ser Ser Lys
    210                 215                 220

Pro Gln Lys Pro Trp Glu Lys Asp Ala Trp Glu Ile Pro Arg Glu Ser
225                 230                 235                 240

Leu Lys Leu Glu Lys Lys Leu Gly Ala Gly Gln Phe Gly Glu Val Trp
                245                 250                 255

Met Ala Thr Tyr Asn Lys His Thr Lys Val Ala Val Lys Thr Met Lys
            260                 265                 270
```

```
Pro Gly Ser Met Ser Val Glu Ala Phe Leu Ala Glu Ala Asn Val Met
            275                 280                 285
Lys Thr Leu Gln His Asp Lys Leu Val Lys Leu His Ala Val Val Thr
    290                 295                 300
Lys Glu Pro Ile Tyr Ile Ile Thr Glu Phe Met Ala Lys Gly Ser Leu
305                 310                 315                 320
Leu Asp Phe Leu Lys Ser Asp Glu Gly Ser Lys Gln Pro Leu Pro Lys
                325                 330                 335
Leu Ile Asp Phe Ser Ala Gln Ile Ala Glu Gly Met Ala Phe Ile Glu
            340                 345                 350
Gln Arg Asn Tyr Ile His Arg Asp Leu Arg Ala Ala Asn Ile Leu Val
        355                 360                 365
Ser Ala Ser Leu Val Cys Lys Ile Ala Asp Phe Gly Leu Ala Arg Val
    370                 375                 380
Ile Glu Asp Asn Glu Tyr Thr Ala Arg Glu Gly Ala Lys Phe Pro Ile
385                 390                 395                 400
Lys Trp Thr Ala Pro Glu Ala Ile Asn Phe Gly Ser Phe Thr Ile Lys
                405                 410                 415
Ser Asp Val Trp Ser Phe Gly Ile Leu Leu Met Glu Ile Val Thr Tyr
            420                 425                 430
Gly Arg Ile Pro Tyr Pro Gly Met Ser Asn Pro Glu Val Ile Arg Ala
        435                 440                 445
Leu Glu Arg Gly Tyr Arg Met Pro Arg Pro Glu Asn Cys Pro Glu Glu
    450                 455                 460
Leu Tyr Asn Ile Met Met Arg Cys Trp Lys Asn Arg Pro Glu Glu Arg
465                 470                 475                 480
Pro Thr Phe Glu Tyr Ile Gln Ser Val Leu Asp Asp Phe Tyr Thr Ala
                485                 490                 495
Thr Glu Ser Gln Tyr Gln Gln Pro
            500                 505

<210> SEQ ID NO 15
<211> LENGTH: 2642
<212> TYPE: DNA
<213> ORGANISM: Homo sapiens

<400> SEQUENCE: 15
cacacagatg gcacatggca gagcccaagc cctctccatg agatctgcag cgtttgtcca    60
cacggcaggg caaattacct tgtagagtca gcatggaggt ttgctaactc tgccggactt   120
ggtgcagaaa aaataccagc cgtgctgtta accaaaaacc ccaggagaaa actttctggt   180
gacagaaggg cattgtgacc cacgttgccc agggccaggg acaggcagc  tgctcatggt   240 ccttcctcac gagttttcct ggagcagagg ataccccca  aacccaggga gcccacagga   300
gcttcagaag ggctcggctg gagggcgggg cccctgttgc acttgctcac tggggactgg   360
ggaggctctg atcgcagacc gggggtgctg ccacctctgt ctgctgccgg cagaaagcca   420
caagccatga aaactgattg agatgagaag aattcatctg ggactggctt ttgctttagg   480
atggtgttgg aagttgctcg ttgtcgctag gagcctgctc cactgtaagg gtgtcaggat   540
ctgaagagct atggtgaaac accactgaag cattgccaag gatggggctg gtaagtagca   600
aaaagccgga caaggaaaag ccgatcaaag agaaggacaa gggccaatgg agccccctga   660
aggtcagcgc ccaagacaag gacgccccgc cactgccgcc cctggttgtc ttcaaccacc   720
ttactcctcc accgcccgat gaacacctgg atgaagacaa gcatttcgtg gtggctctgt   780
```

| | |
|---|---|
| atgactacac cgctatgaat gatcgggacc tgcagatgct gaaggggggag aagctacagg | 840 |
| tcctgaaggg aactggagac tggtggctgg ccaggtcact cgtcacagga agagaaggct | 900 |
| atgtgcccag taactttgtg gcccgagtgg agagcctgga atggaaagg tggttcttta | 960 |
| gatcacaggg tcggaaggag gctgagaggc agcttcttgc tccaatcaac aaggccggct | 1020 |
| cctttcttat cagagagagt gaaaccaaca aggtgccttc tccctgtct gtgaaggatg | 1080 |
| tcaccaccca gggggagctg atcaagcact ataagatccg ctgcctggat gaaggggct | 1140 |
| actacatctc ccccggatc accttcccct cgctccaggc cctggtgcag cactattcta | 1200 |
| agaagggga tggtctatgc cagaggctga ccctgccctg tgtgcgcccg ccccgcaga | 1260 |
| atccctgggc ccaggatgaa tgggagatcc cccggcagtc tctcaggctg tcaggaaac | 1320 |
| tcgggtctgg acaattcggc gaagtctgga tgggttacta caaaaacaac atgaaggtgg | 1380 |
| ccattaagac gctgaaggag ggaaccatgt ctccagaagc ctttctgggt gaggccaacg | 1440 |
| tgatgaaggc tctgcagcac gagcggctgg tccgactcta cgcagtggtc accaaggagc | 1500 |
| ccatctacat tgtcaccgag tacatggcca gaggatgcct gctggatttc ctgaagacag | 1560 |
| atgaagggag cagattgtca ctcccaaggc tgattgacat gtcggcgcag attgctgaag | 1620 |
| ggatggcata cattgagcgc atgaattcca tccaccgcga cctgcgggcg ccaacatcc | 1680 |
| tggtgtctga ggccttgtgc tgcaaaattg ctgattttgg cttggctcga atcatcgaca | 1740 |
| gtgaatacac ggcccaagag ggggccaagt cccccatcaa gtgacagcc ccggaagcca | 1800 |
| tccacttcgg ggtcttcacc atcaaagcag acgtgtggtc gtttggagtc ctcctgatgg | 1860 |
| aagttgtcac ttatgggcgg gtgccatacc cagggatgag caaccccgag gtcatccgca | 1920 |
| acctggagcg cggctaccgc atgccgcgcc ccgacacctg cccgcccgag ctgtaccgcg | 1980 |
| gcgtcatcgc cgagtgctgg cgcagccggc ccgaggagcg gcccaccttc gagttcctgc | 2040 |
| agtcggtgct ggaggacttc tacacggcca ccgagcggca gtacgagctg cagccctagc | 2100 |
| cggccgcgcc cgcctgcgcc ccgtgcccac ctctgcgcgg acgaccccga cttccgtgcc | 2160 |
| atcccagacg ggccgcgaag gcggggtgtc gcctgtgccc ttttctcaga cccggaatcc | 2220 |
| agtgggcaga ggcagcttcg caggggggtcc ccggacggac tccttcaccg actgcacccc | 2280 |
| cgggcgagtt acgcggcctc tctgtgccgc ttcatttgta gagggctgta acagtgacct | 2340 |
| cgcacggtca tccggagtac taagcccag taaggtgttc aggactggta agcgactgtc | 2400 |
| atcaagtaag gcccccgtgc tggcacccc ccgtgctggc cgcgtccccg cctctgcgcc | 2460 |
| ctgcgtggac cccgccctgc cccgctacag aagccagact gggtcccgcg gacgccagca | 2520 |
| ggggcagccc cagcctaggc tgcgctccag cactgcgggg cttttctgca ataaagtcac | 2580 |
| gagcgttcga aaaaaaaaa aaaaaaaaa aaaaaaaaa aaaaaaaaa aaaaaaaaa | 2640 |
| aa | 2642 |

<210> SEQ ID NO 16
<211> LENGTH: 505
<212> TYPE: PRT
<213> ORGANISM: Homo sapiens

<400> SEQUENCE: 16

Met Gly Leu Val Ser Ser Lys Lys Pro Asp Lys Glu Lys Pro Ile Lys
1               5                   10                  15

Glu Lys Asp Lys Gly Gln Trp Ser Pro Leu Lys Val Ser Ala Gln Asp
            20                  25                  30

Lys Asp Ala Pro Pro Leu Pro Pro Leu Val Val Phe Asn His Leu Thr

```
                35                  40                  45
Pro Pro Pro Pro Asp Glu His Leu Asp Glu Asp Lys His Phe Val Val
 50                  55                  60
Ala Leu Tyr Asp Tyr Thr Ala Met Asn Asp Arg Asp Leu Gln Met Leu
 65                  70                  75                  80
Lys Gly Glu Lys Leu Gln Val Leu Lys Gly Thr Gly Asp Trp Trp Leu
                 85                  90                  95
Ala Arg Ser Leu Val Thr Gly Arg Glu Gly Tyr Val Pro Ser Asn Phe
                100                 105                 110
Val Ala Arg Val Glu Ser Leu Glu Met Glu Arg Trp Phe Phe Arg Ser
                115                 120                 125
Gln Gly Arg Lys Glu Ala Glu Arg Gln Leu Leu Ala Pro Ile Asn Lys
                130                 135                 140
Ala Gly Ser Phe Leu Ile Arg Glu Ser Glu Thr Asn Lys Gly Ala Phe
145                 150                 155                 160
Ser Leu Ser Val Lys Asp Val Thr Thr Gln Gly Glu Leu Ile Lys His
                165                 170                 175
Tyr Lys Ile Arg Cys Leu Asp Glu Gly Gly Tyr Tyr Ile Ser Pro Arg
                180                 185                 190
Ile Thr Phe Pro Ser Leu Gln Ala Leu Val Gln His Tyr Ser Lys Lys
                195                 200                 205
Gly Asp Gly Leu Cys Gln Arg Leu Thr Leu Pro Cys Val Arg Pro Ala
                210                 215                 220
Pro Gln Asn Pro Trp Ala Gln Asp Glu Trp Glu Ile Pro Arg Gln Ser
225                 230                 235                 240
Leu Arg Leu Val Arg Lys Leu Gly Ser Gly Gln Phe Gly Glu Val Trp
                245                 250                 255
Met Gly Tyr Tyr Lys Asn Asn Met Lys Val Ala Ile Lys Thr Leu Lys
                260                 265                 270
Glu Gly Thr Met Ser Pro Glu Ala Phe Leu Gly Glu Ala Asn Val Met
                275                 280                 285
Lys Ala Leu Gln His Glu Arg Leu Val Arg Leu Tyr Ala Val Val Thr
                290                 295                 300
Lys Glu Pro Ile Tyr Ile Val Thr Glu Tyr Met Ala Arg Gly Cys Leu
305                 310                 315                 320
Leu Asp Phe Leu Lys Thr Asp Glu Gly Ser Arg Leu Ser Leu Pro Arg
                325                 330                 335
Leu Ile Asp Met Ser Ala Gln Ile Ala Glu Gly Met Ala Tyr Ile Glu
                340                 345                 350
Arg Met Asn Ser Ile His Arg Asp Leu Arg Ala Ala Asn Ile Leu Val
                355                 360                 365
Ser Glu Ala Leu Cys Cys Lys Ile Ala Asp Phe Gly Leu Ala Arg Ile
                370                 375                 380
Ile Asp Ser Glu Tyr Thr Ala Gln Glu Gly Ala Lys Phe Pro Ile Lys
385                 390                 395                 400
Trp Thr Ala Pro Glu Ala Ile His Phe Gly Val Phe Thr Ile Lys Ala
                405                 410                 415
Asp Val Trp Ser Phe Gly Val Leu Leu Met Glu Val Val Thr Tyr Gly
                420                 425                 430
Arg Val Pro Tyr Pro Gly Met Ser Asn Pro Glu Val Ile Arg Asn Leu
                435                 440                 445
Glu Arg Gly Tyr Arg Met Pro Arg Pro Asp Thr Cys Pro Pro Glu Leu
                450                 455                 460
```

```
        Tyr Arg Gly Val Ile Ala Glu Cys Trp Arg Ser Arg Pro Glu Glu Arg
        465                 470                 475                 480

Pro Thr Phe Glu Phe Leu Gln Ser Val Leu Glu Asp Phe Tyr Thr Ala
                        485                 490                 495

Thr Glu Arg Gln Tyr Glu Leu Gln Pro
                    500                 505

<210> SEQ ID NO 17
<211> LENGTH: 4095
<212> TYPE: DNA
<213> ORGANISM: Homo sapiens

<400> SEQUENCE: 17
agacagccag ttcctctccc gccgcgccgg gccgcgctgc cgctcgctcc ccggccgtgg      60
cgcctccggg ccagacgcgc tgcagcctcc agcccgcggc aagcggggcg gccgcgccac     120
ccccggcccc gcgccagcag cccctcgccg cgcgtccagc gttcccggcc agcagcctcc     180
ccatacgcag gtcctgctgg gccgcccgt cgcgcccccc actctgaact caagtcaccg      240
tggagctccg ccgccccgaa actttcaccg cgagcgggaa atatgggatg tataaaatca     300
aaagggaaag acagcttgag tgacgatgga gtagatttga agactcaacc agttccagaa     360
tctcagcttt tacctggaca gaggtttcaa actaaagatc cagaggaaca aggagacatt     420
gtggtagcct tgtaccccta tgatggcatc cacccgacg acttgtcttt caagaaagga     480
gagaagatga aagtcctgga ggagcatgga gaatggtgga agcaaagtc ccttttaaca      540 aaaaaagaag gcttcatccc cagcaactat gtggccaaac tcaacacctt agaaacagaa     600
gagtggtttt tcaaggatat aaccaggaag gacgcagaaa ggcagctttt ggcaccagga     660
aatagcgctg gagctttcct tattagagaa agtgaaacat aaaaggaag cttctctctg      720 tctgtcagag actttgaccc tgtgcatggt gatgttatta agcactacaa aattagaagt     780
ctggataatg ggggctatta catctctcca cgaatcactt ttccctgtat cagcgacatg     840
attaaacatt accaaaagca ggcagatggc ttgtgcagaa gattggagaa ggcttgtatt     900
agtcccaagc cacagaagcc atgggataaa gatgcctggg agatccccg ggagtccatc      960 aagttggtga aaaggcttgg cgctgggcag tttggggaag tctggatggg ttactataac    1020
aacagtacca aggtggctgt gaaaaccctg aagccaggaa ctatgtctgt gcaagccttc    1080
ctggaagaag ccaacctcat gaagaccctg cagcatgaca agctcgtgag gctctacgct    1140
gtggtcacca gggaggagcc catttacatc atcaccgagt acatggccaa gggcagtttg    1200
ctggatttcc tgaagagcga tgaaggtggc aaagtgctgc ttccaaagct cattgacttt    1260
tctgctcaga ttgcagaggg aatggcatac atcgagcgga gaactacat tcaccgggac    1320 ctgcgagcag ctaatgttct ggtctccgag tcactcatgt gcaaaattgc agattttggc    1380
cttgctagag taattgaaga taatgagtac acagcaaggg aaggtgctaa gttccctatt    1440
aagtggacgg ctccagaagc aatcaacttt ggatgtttca ctattaagtc tgatgtgtgg    1500
tcctttggaa tcctcctata cgaaattgtc acctatggga aaattcccta cccagggaga    1560
actaatgccg acgtgatgac cgccctgtcc cagggctaca gatgccccg tgtgagaac     1620 tgcccagatg agctctatga cattatgaaa atgtgctgga agaaaggc agaagagaga     1680 ccaacgtttg actacttaca gagcgtcctg gatgatttct acacagccac ggaagggcaa    1740
taccagcagc agccttagag cacagggaga cccgtccatt tggcagggt ggctgcctca    1800 tttagagagg aaaagtaacc atcactggtt gcacttatga tttcatgtgc ggggatcatc    1860
```

```
tgccgtgcct ggatcctgaa atagaggcta aattactcag gaagaacacc ctctaaatgg    1920
gaaagtattc tgtactctta gatggattct ccactcagtt gcaacttgga cttgtcctca    1980
gcagctggta atcttgctct gcttgacaac atctgagtgc agccgtttga aagaaaaca    2040
tctattctct ccaaaaatgc acccaactag ctctatgttt acaaatggac ataggactca    2100
aagtttcaga gaccattgca atgaatcccc aataattgca gaactaaact catttataaa    2160
gctaaaataa ccggatatat acatagcatg acatttcttt gtgctttggc ttacttgttt    2220
aaaaaaaaaa aaaaactaat ccaacctgtt agattttgca ggtgaagtca gcagcttaaa    2280
aatgtctttc ccagatttca atgattttt tcccctacc tcccaaaatc tgagactgtt     2340
aaaacatttt tcttctatga acactgctca gacctgctag acatgccata ggagtggcgt    2400
gcacatctct ctctcttcca gcaggaggag cccgtgagca cgcacagctg ccctgtctgc    2460
tcacccgaag gcaccgggct cacctggacc tcccaggaaa gggagaagag cctcagaaac    2520
tgctctgtgt ttagaaggaa tattttaag agtccagctt tttcatttcc acaatttcct    2580
atatccagat ttgttttgac aatgtagttt ggaagaacta agattctaat ctctgaagaa    2640
ccttataggg ccttctaaaa cataagagtt tcctttgttg cttcaaatat ttgaacatta    2700
tgttaaagat caagtattaa ttttagttgt actctagaaa gctaaagtgc cacattcggg    2760
gctatttta tgattcagca atcttttcta aattgtgtag catgtgtatg agactattta    2820
tacccaagga tatgaaggaa cataagtgac tacaaggctc taataagcca cggtggcagg    2880
aggttcaagc ggttctgttc actaaatttt tctcctgtaa gctttgaatg gaaacttctg    2940
tatcacatga tgtgtttcac ttatgctgtt gtgtatatac ctaatatttc tattttgat    3000
tttatttaa tacacctcgt ccaataacat ctcaagcttt ttatttgcat ttacattttc    3060
agctgtggtc agtgtaaaaa ttggtcatca gctgggggcg gggtggttag aagtgattca    3120
acagagctac atgctttaaa cttgcccaag ttctacctcc ttcctttgaa catttcagat    3180
tggagaacca aggagttgat tgcctgaaca cctgaacatc cgtttatggg ggccagatag    3240
aatttgtttt caaataggct taacaggcat cattaaaatt tcattctgtg tgttttgttt    3300
aggcttgagg tgcttagaag atgggataaa atattctact ttttctaaa ttttaacttt    3360
gtttcctatg tgattttttt aaatgtcctt tctaaaatat tctaaaatta ttgattcaca    3420
agtgccatgt tcagaactat agaatattac tgttacataa tgtctgcaca gctggtccct    3480
tgattcagtg gtaaggtttt tgtgtacacc ccctgcttg cattttattt cagaaccaca    3540
agtattaccc aatatgttac atggagagga actataaaga atccctaagg caaaagaag    3600
tctctagaaa atgactagag gttttttttt tagcataaca aatttattta agaaaatta    3660
ttaaatttat cttcgccttg ttttgcttct cccagttcct cctcttcttg ccattttcca    3720
cttgtctttc cctcccaatc aagcctgtga tccttacctc catgtgggcc cttcaccagc    3780
ttgggcctca tctctggtgt ccagcatgtg tggaagtcac acgttccctt gatgaacagc    3840
acacacagtc tccttactta gctataggtt tccagcctcc ctgtgacaga caggcataat    3900
gagggggctga ataggtgttt gtagcatttt cgggtatcca gtggtgtgca aaatggctca    3960
tgtcatcaca cctcaggtta ttgtagagaa ctggaaagac agaatccata ctccctaccg    4020
ccaagattct gacttagctg ttgtgcagcg ggagatgtat gtcagtctat tttaaaagct    4080
tctccagtca gctag                                                    4095
```

<210> SEQ ID NO 18

```
<211> LENGTH: 491
<212> TYPE: PRT
<213> ORGANISM: Homo sapiens

<400> SEQUENCE: 18

Met Gly Cys Ile Lys Ser Lys Gly Lys Asp Ser Leu Ser Asp Asp Gly
1               5                   10                  15

Val Asp Leu Lys Thr Gln Pro Val Pro Glu Ser Gln Leu Leu Pro Gly
            20                  25                  30

Gln Arg Phe Gln Thr Lys Asp Pro Glu Glu Gln Gly Asp Ile Val Val
        35                  40                  45

Ala Leu Tyr Pro Tyr Asp Gly Ile His Pro Asp Leu Ser Phe Lys
    50                  55                  60

Lys Gly Glu Lys Met Lys Val Leu Glu His Gly Glu Trp Trp Lys
65                  70                  75                  80

Ala Lys Ser Leu Leu Thr Lys Lys Glu Gly Phe Ile Pro Ser Asn Tyr
                85                  90                  95

Val Ala Lys Leu Asn Thr Leu Glu Thr Glu Trp Phe Phe Lys Asp
            100                 105                 110

Ile Thr Arg Lys Asp Ala Glu Arg Gln Leu Leu Ala Pro Gly Asn Ser
            115                 120                 125

Ala Gly Ala Phe Leu Ile Arg Glu Ser Glu Thr Leu Lys Gly Ser Phe
    130                 135                 140

Ser Leu Ser Val Arg Asp Phe Asp Pro Val His Gly Asp Val Ile Lys
145                 150                 155                 160

His Tyr Lys Ile Arg Ser Leu Asp Asn Gly Gly Tyr Tyr Ile Ser Pro
                165                 170                 175

Arg Ile Thr Phe Pro Cys Ile Ser Asp Met Ile Lys His Tyr Gln Lys
            180                 185                 190

Gln Ala Asp Gly Leu Cys Arg Arg Leu Glu Lys Ala Cys Ile Ser Pro
        195                 200                 205

Lys Pro Gln Lys Pro Trp Asp Lys Asp Ala Trp Glu Ile Pro Arg Glu
    210                 215                 220

Ser Ile Lys Leu Val Lys Arg Leu Gly Ala Gly Gln Phe Gly Glu Val
225                 230                 235                 240

Trp Met Gly Tyr Tyr Asn Asn Ser Thr Lys Val Ala Val Lys Thr Leu
                245                 250                 255

Lys Pro Gly Thr Met Ser Val Gln Ala Phe Leu Glu Glu Ala Asn Leu
            260                 265                 270

Met Lys Thr Leu Gln His Asp Lys Leu Val Arg Leu Tyr Ala Val Val
        275                 280                 285

Thr Arg Glu Glu Pro Ile Tyr Ile Ile Thr Glu Tyr Met Ala Lys Gly
    290                 295                 300

Ser Leu Leu Asp Phe Leu Lys Ser Asp Glu Gly Gly Lys Val Leu Leu
305                 310                 315                 320

Pro Lys Leu Ile Asp Phe Ser Ala Gln Ile Ala Glu Gly Met Ala Tyr
                325                 330                 335

Ile Glu Arg Lys Asn Tyr Ile His Arg Asp Leu Arg Ala Ala Asn Val
            340                 345                 350

Leu Val Ser Glu Ser Leu Met Cys Lys Ile Ala Asp Phe Gly Leu Ala
        355                 360                 365

Arg Val Ile Glu Asp Asn Glu Tyr Thr Ala Arg Glu Gly Ala Lys Phe
    370                 375                 380

Pro Ile Lys Trp Thr Ala Pro Glu Ala Ile Asn Phe Gly Cys Phe Thr
```

```
                385                 390                 395                 400
        Ile Lys Ser Asp Val Trp Ser Phe Gly Ile Leu Leu Tyr Glu Ile Val
                        405                 410                 415

Thr Tyr Gly Lys Ile Pro Tyr Pro Gly Arg Thr Asn Ala Asp Val Met
                        420                 425                 430

Thr Ala Leu Ser Gln Gly Tyr Arg Met Pro Arg Val Glu Asn Cys Pro
                        435                 440                 445

Asp Glu Leu Tyr Asp Ile Met Lys Met Cys Trp Lys Glu Lys Ala Glu
                    450                 455                 460

Glu Arg Pro Thr Phe Asp Tyr Leu Gln Ser Val Leu Asp Asp Phe Tyr
        465                 470                 475                 480

Thr Ala Thr Glu Gly Gln Tyr Gln Gln Gln Pro
                        485                 490

<210> SEQ ID NO 19
<211> LENGTH: 2864
<212> TYPE: DNA
<213> ORGANISM: Homo sapiens

<400> SEQUENCE: 19
```

| | | | | | |
|---|---|---|---|---|---|
| cctggcgaaa | gcaagacgtg | gaggttttac | caggggttag | tagcttcctc | ttgctaactt      60 |
| tttattggga | caaaaggcaa | gatggcacca | ttctgttctc | agatatttgt | ctaaataaag     120 |
| ccctttttaat | tttatttat | ttttgttgtg | ggattcttaa | gcagataaga | agaaaagaca     180 |
| ccttcctagt | gagcagctgc | ccagctcctg | ctcagttttg | cctcggggta | gcacctccag     240 |
| ccacagaaag | caagccggta | agtctctcca | ggtaggactt | gctgcaaccc | agctgctgga     300 |
| ctgatctgaa | acgggacttt | gcatactctc | cgaagtatgg | tgagttggtg | ctgacttcaa     360 |
| agttgcctgg | tgaaggaaga | taaggtggat | cgcagagact | aagggagag | ggagaagccc     420 |
| tgctcctctt | ctccccacca | aggcacaatg | agcaacatct | gtcagaggct | ctgggagtac     480 |
| ctagaaccct | atctccctg | tttgtccacg | gaggcagaca | agtcaaccgt | gattgaaaat     540 |
| ccaggggccc | tttgctctcc | ccagtcacag | aggcatggcc | actactttgt | ggctttgttt     600 |
| gattaccagg | ctcggactgc | tgaggacttg | agcttccgag | caggtgacaa | acttcaagtt     660 |
| ctggacactt | tgcatgaggg | ctggtggttt | gccagacact | tggagaaaag | acgagatggc     720 |
| tccagtcagc | aactacaagg | ctatattcct | tctaactacg | tggctgagga | cagaagccta     780 |
| caggcagagc | cgtggttctt | tggagcaatc | ggaagatcag | atgcagagaa | acaactatta     840 |
| tattcagaaa | acaagaccgg | ttcctttcta | atcagagaaa | gtgaaagcca | aaaggagaa     900 |
| ttctctcttt | cagttttaga | tggagcagtt | gtaaaacact | acagaattaa | aagactggat     960 |
| gaaggggat | ttttctcac | gcgaagaaga | atcttttcaa | cactgaacga | atttgtgagc    1020 |
| cactacacca | agacaagtga | cggcctgtgt | gtcaagctgg | ggaaaccatg | cttaaagatc    1080 |
| caggtcccag | ctccatttga | tttgtcgtat | aaaaccgtgg | accaatggga | gatagaccgc    1140 |
| aactccatac | agcttctgaa | gcgattggga | tctggtcagt | ttggcgaagt | atgggaaggt    1200 |
| ctgtggaaca | ataccactcc | agtagcagtg | aaaacattaa | aaccaggttc | aatggatcca    1260 |
| aatgacttcc | tgagggaggc | acagataatg | aagaacctaa | gacatccaaa | gcttatccag    1320 |
| ctttatgctg | tttgcacttt | agaagatcca | atttatatta | ttacagagtt | gatgagacat    1380 |
| ggaagtctgc | aagaatatct | ccaaaatgac | actggatcaa | aaatccatct | gactcaacag    1440 |
| gtagacatgg | cggcacaggt | tgcctctgga | atggcctatc | tggagtctcg | gaactacatt    1500 |
| cacagagatc | tggctgccag | aaatgtcctc | gttggtgaac | ataatatcta | caaagtagca    1560 |

```
gattttggac ttgccagagt ttttaaggta gataatgaag acatctatga atctagacac   1620
gaaataaagc tgccggtgaa gtggactgcg cccgaagcca ttcgtagtaa taaattcagc   1680
attaagtccg atgtatggtc atttggaatc cttctttatg aaatcattac ttatggcaaa   1740
atgccttaca gtggtatgac aggtgcccag gtaatccaga tgttggctca aaactataga   1800
cttccgcaac catccaactg tccacagcaa ttttacaaca tcatgttgga gtgctggaat   1860
gcagagccta aggaacgacc tacatttgag acactgcgtt ggaaacttga agactatttt   1920
gaaacagact cttcatattc agatgcaaat aacttcataa gatgaacact ggagaagaat   1980
atcaaataat aaagtagcaa aacaaattca ataatccat tccaaaatac aatgttatca   2040
accaactgca caatcagttt atcctgacat attcaagtga taggataaag ttggccatgt   2100
attatgaaaa agattatttg tgcattttat tgactgggca acactgcagg acagtcaagg   2160
tgatatataa tttcctcact gcctggtaaa attaagcaca ctaaaccaag ttatttttct   2220
ttttaagaga tacttacatt tccatttatt gtttgaaatg tcgatcaaga gaatcaacag   2280
atgatagtcc aattttttact cagtgactgt tgtagcattt tcctgtttac tgattagagt   2340
ggttattcat tattcctcag attgctgaat cccatcaggc tgttattatg aaggaatttg   2400
attgctttgc tgcacagcag gacctgtgct ttgagatttt tttttctctt ttaaaatatc   2460
ctgtaactac aatgatggta aagccatgtt aaatgacttg attgtacttg gagtaattgc   2520
acattttttt ctatgcataa aaaatgatg cagctgttga gaaaacgaag tcttttttcat   2580 tttgcagaag gaaatgatgg aattttttctg tacttcagta tgtgtcaact gagagtcata   2640
tacattagtt ttaatctctt aatattgaga atcaggttgc aaaacggatg agttattatc   2700 tatgaaatg tgagaaatgt ctaatagccc ataaagtctg agaaataggt atcaaaatag   2760
tttaggaaaa tgagaggaga acagtaggat tgctgtggcc tagacttctg agtaattaat   2820
aaagaaaaag aagtacccctt tggcctacaa aaaaaaaaa aaaa                    2864
```

<210> SEQ ID NO 20
<211> LENGTH: 505
<212> TYPE: PRT
<213> ORGANISM: Homo sapiens

<400> SEQUENCE: 20

```
Met Ser Asn Ile Cys Gln Arg Leu Trp Glu Tyr Leu Glu Pro Tyr Leu
1               5                   10                  15

Pro Cys Leu Ser Thr Glu Ala Asp Lys Ser Thr Val Ile Glu Asn Pro
            20                  25                  30

Gly Ala Leu Cys Ser Pro Gln Ser Gln Arg His Gly His Tyr Phe Val
        35                  40                  45

Ala Leu Phe Asp Tyr Gln Ala Arg Thr Ala Glu Asp Leu Ser Phe Arg
    50                  55                  60

Ala Gly Asp Lys Leu Gln Val Leu Asp Thr Leu His Glu Gly Trp Trp
65                  70                  75                  80

Phe Ala Arg His Leu Glu Lys Arg Arg Asp Gly Ser Ser Gln Gln Leu
                85                  90                  95

Gln Gly Tyr Ile Pro Ser Asn Tyr Val Ala Glu Asp Arg Ser Leu Gln
            100                 105                 110

Ala Glu Pro Trp Phe Phe Gly Ala Ile Gly Arg Ser Asp Ala Glu Lys
        115                 120                 125

Gln Leu Leu Tyr Ser Glu Asn Lys Thr Gly Ser Phe Leu Ile Arg Glu
    130                 135                 140
```

Ser Glu Ser Gln Lys Gly Glu Phe Ser Leu Ser Val Leu Asp Gly Ala
145                 150                 155                 160

Val Val Lys His Tyr Arg Ile Lys Arg Leu Asp Glu Gly Gly Phe Phe
                165                 170                 175

Leu Thr Arg Arg Arg Ile Phe Ser Thr Leu Asn Glu Phe Val Ser His
            180                 185                 190

Tyr Thr Lys Thr Ser Asp Gly Leu Cys Val Lys Leu Gly Lys Pro Cys
        195                 200                 205

Leu Lys Ile Gln Val Pro Ala Pro Phe Asp Leu Ser Tyr Lys Thr Val
210                 215                 220

Asp Gln Trp Glu Ile Asp Arg Asn Ser Ile Gln Leu Leu Lys Arg Leu
225                 230                 235                 240

Gly Ser Gly Gln Phe Gly Glu Val Trp Glu Gly Leu Trp Asn Asn Thr
                245                 250                 255

Thr Pro Val Ala Val Lys Thr Leu Lys Pro Gly Ser Met Asp Pro Asn
            260                 265                 270

Asp Phe Leu Arg Glu Ala Gln Ile Met Lys Asn Leu Arg His Pro Lys
        275                 280                 285

Leu Ile Gln Leu Tyr Ala Val Cys Thr Leu Glu Asp Pro Ile Tyr Ile
290                 295                 300

Ile Thr Glu Leu Met Arg His Gly Ser Leu Gln Glu Tyr Leu Gln Asn
305                 310                 315                 320

Asp Thr Gly Ser Lys Ile His Leu Thr Gln Gln Val Asp Met Ala Ala
                325                 330                 335

Gln Val Ala Ser Gly Met Ala Tyr Leu Glu Ser Arg Asn Tyr Ile His
            340                 345                 350

Arg Asp Leu Ala Ala Arg Asn Val Leu Val Gly Glu His Asn Ile Tyr
        355                 360                 365

Lys Val Ala Asp Phe Gly Leu Ala Arg Val Phe Lys Val Asp Asn Glu
370                 375                 380

Asp Ile Tyr Glu Ser Arg His Glu Ile Lys Leu Pro Val Lys Trp Thr
385                 390                 395                 400

Ala Pro Glu Ala Ile Arg Ser Asn Lys Phe Ser Ile Lys Ser Asp Val
                405                 410                 415

Trp Ser Phe Gly Ile Leu Leu Tyr Glu Ile Ile Thr Tyr Gly Lys Met
            420                 425                 430

Pro Tyr Ser Gly Met Thr Gly Ala Gln Val Ile Gln Met Leu Ala Gln
        435                 440                 445

Asn Tyr Arg Leu Pro Gln Pro Ser Asn Cys Pro Gln Gln Phe Tyr Asn
450                 455                 460

Ile Met Leu Glu Cys Trp Asn Ala Glu Pro Lys Glu Arg Pro Thr Phe
465                 470                 475                 480

Glu Thr Leu Arg Trp Lys Leu Glu Asp Tyr Phe Glu Thr Asp Ser Ser
                485                 490                 495

Tyr Ser Asp Ala Asn Asn Phe Ile Arg
            500                 505

<210> SEQ ID NO 21
<211> LENGTH: 2794
<212> TYPE: DNA
<213> ORGANISM: Homo sapiens

<400> SEQUENCE: 21
cggcaggacc gagcgcggca ggcggctggc ccagcgcagc cagcgcggcc cgaaggacgg     60

| | |
|---|---|
| gagcaggcgg ccgagcaccg agcgctgggc accgggcacc gagcggcggc ggcacgcgag | 120 |
| gcccggcccc gagcagcgcc cccgcccgcc gcggcctcca gcccggcccc gcccagcgcc | 180 |
| ggcccgcggg gatgcggagc ggcgggcgcc ggaggccgcg gcccggctag gcccgcgctc | 240 |
| gcgcccggac gcggcggccc gaggctgtgg ccaggccagc tgggctcggg gagcgccagc | 300 |
| ctgagaggag cgcgtgagcg tcgcgggagc ctcgggcacc atgagcgacg tggctattgt | 360 |
| gaaggagggt tggctgcaca acgaggggga gtacatcaag acctggcggc acgctactt | 420 |
| cctcctcaag aatgatggca ccttcattgg ctacaaggag cggccgcagg atgtggacca | 480 |
| acgtgaggct cccctcaaca acttctctgt ggcgcagtgc cagctgatga agacggagcg | 540 |
| gccccggccc aacaccttca tcatccgctg cctgcagtgg accactgtca tcgaacgcac | 600 |
| cttccatgtg gagactcctg aggagcggga ggagtggaca accgccatcc agactgtggc | 660 |
| tgacggcctc aagaagcagg aggaggagga gatggacttc cggtcgggct cacccagtga | 720 |
| caactcaggg gctgaagaga tggaggtgtc cctggccaag cccaagcacc gcgtgaccat | 780 |
| gaacgagttt gagtacctga agctgctggg caagggcact ttcggcaagg tgatcctggt | 840 |
| gaaggagaag gccacaggcc gctactacgc catgaagatc ctcaagaagg aagtcatcgt | 900 |
| ggccaaggac gaggtggccc acacactcac cgagaaccgc gtcctgcaga actccaggca | 960 |
| ccccttcctc acagccctga gtactctttt ccagacccac gaccgcctct gctttgtcat | 1020 |
| ggagtacgcc aacggggggcg agctgttctt ccacctgtcc cgggagcgtg tgttctccga | 1080 |
| ggaccggggc cgcttctatg cgctgagat tgtgtcagcc ctggactacc tgcactcgga | 1140 |
| gaagaacgtg gtgtaccggg acctcaagct ggagaacctc atgctggaca aggacgggca | 1200 |
| cattaagatc acagacttcg ggctgtgcaa ggaggggatc aaggacgtg ccaccatgaa | 1260 |
| gacccttttgc ggcacacctg agtacctggc ccccgaggtg ctggaggaca atgactacgg | 1320 |
| ccgtgcagtg gactggtggg ggctgggcgt ggtcatgtac gagatgatgt gcggtcgcct | 1380 |
| gcccttctac aaccaggacc atgagaagct tttttgagctc atcctcatgg aggagatccg | 1440 |
| cttcccgcgc acgcttggtc ccgaggccaa gtccttgctt tcagggctgc tcaagaagga | 1500 |
| ccccaagcag aggcttggcg ggggctccga ggacgccaag gagatcatgc agcatcgctt | 1560 |
| cttttgccggt atcgtgtggc agcacgtgta cgagaagaag ctcagcccac ccttcaagcc | 1620 |
| ccaggtcacg tcggagactg acaccaggta ttttgatgag gagttcacgg cccagatgat | 1680 |
| caccatcaca ccacctgacc aagatgacag catggagtgt gtggacagcg agcgcaggcc | 1740 |
| ccacttcccc cagttctcct actcggccag cggcacggcc tgaggcggcg gtggactgcg | 1800 |
| ctggacgata gcttggaggg atggagaggc ggcctcgtgc catgatctgt atttaatggt | 1860 |
| ttttatttct cgggtgcatt tgagagaagc cacgctgtcc tctcgagccc agatggaaag | 1920 |
| acgttttttgt gctgtgggca gcaccctccc ccgcagcggg gtaggaagaa aaactatcct | 1980 |
| gcgggttttta atttatttca tccagtttgt tctccgggtg tggcctcagc cctcagaaca | 2040 |
| atccgattca cgtagggaaa tgttaaggac ttctgcagct atgcgcaatg tggcattggg | 2100 |
| gggccgggca ggtcctgccc atgtgtcccc tcactctgtc agccagccgc cctgggctgt | 2160 |
| ctgtcaccag ctatctgtca tctctctggg gccctgggcc tcagttcaac ctggtggcac | 2220 |
| cagatgcaac ctcactatgg tatgctggcc agcaccctct cctgggggtg gcaggcacac | 2280 |
| agcagccccc cagcactaag gccgtgtctc tgaggacgtc atcggaggct gggccctgg | 2340 |
| gatgggacca gggatggggg atgggccagg gtttacccag tgggacagag gagcaaggtt | 2400 |

-continued

```
taaatttgtt attgtgtatt atgttgttca aatgcatttt gggggttttt aatctttgtg    2460
acaggaaagc cctcccccttt cccttctgt gtcacagttc ttggtgactg tcccaccggg    2520
agcctccccc tcagatgatc tctccacggt agcacttgac cttttcgacg cttaaccttt    2580
ccgctgtcgc cccaggccct ccctgactcc ctgtggggggt ggccatccct gggcccctcc   2640
acgcctcctg gccagacgct gccgctgccg ctgcaccacg gcgtttttttt acaacattca   2700 actttagtat ttttactatt ataatataat atggaacctt ccctccaaat tcttcaataa    2760
aagttgcttt tcaaaaaaaa aaaaaaaaaa aaaa                                2794
```

<210> SEQ ID NO 22
<211> LENGTH: 480
<212> TYPE: PRT
<213> ORGANISM: Homo sapiens

<400> SEQUENCE: 22

```
Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300
```

```
Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
450                 455                 460

Arg Arg Pro His Phe Pro Gln Phe Ser Tyr Ser Ala Ser Gly Thr Ala
465                 470                 475                 480

<210> SEQ ID NO 23
<211> LENGTH: 5388
<212> TYPE: DNA
<213> ORGANISM: Homo sapiens

<400> SEQUENCE: 23
aaaatgttgg agatctgcct gaagctggtg ggctgcaaat ccaagaaggg gctgtcctcg      60
tcctccagct gttatctgga agaagccctt cagcggccag tagcatctga ctttgagcct     120
cagggtctga gtgaagccgc tcgttggaac tccaaggaaa accttctcgc tggacccagt     180
gaaaatgacc ccaacctttt cgttgcactg tatgattttg tggccagtgg agataacact     240
ctaagcataa ctaaaggtga aaagctccgg gtcttaggct ataatcacaa tggggaatgg     300
tgtgaagccc aaaccaaaaa tggccaaggc tgggtcccaa gcaactacat cacgccagtc     360
aacagtctgg agaaacactc ctggtaccat gggcctgtgt cccgcaatgc cgctgagtat     420
ctgctgagca gcgggatcaa tgcagcttc ttggtgcgtg agagtgagag cagtcctggc     480
cagaggtcca tctcgctgag atacgaaggg agggtgtacc attacaggat caacactgct     540
tctgatggca agctctacgt ctcctccgag agccgcttca cacccctggc cgagttggtt     600
catcatcatt caacggtggc cgacgggctc atcaccacgc tccattatcc agccccaaag     660
cgcaacaagc ccactgtcta tggtgtgtcc cccaactacg acaagtggga gatggaacgc     720
acggacatca ccatgaagca caagctgggc gggggccagt acgggaggt gtacgagggc     780 gtgtggaaga atacagcct gacggtggcc gtgaagacct tgaaggagga caccatggag     840
gtggaagagt tcttgaaaga agctgcagtc atgaaagaga tcaaacaccc taacctggtg     900
cagctccttg gggtctgcac ccgggagccc cgttctata tcatcactga gttcatgacc     960
tacgggaacc tcctggacta cctgagggag tgcaaccggc aggaggtgaa cgccgtggtg    1020
ctgctgtaca tggccactca gatctcgtca gccatggagt acctggagaa gaaaaacttc    1080
atccacagag atcttgctgc ccgaaactgc ctggtagggg agaaccactt ggtgaaggta    1140
```

```
gctgattttg gcctgagcag gttgatgaca gggacacct acacagccca tgctggagcc    1200
aagttcccca tcaaatggac tgcacccgag agcctggcct acaacaagtt ctccatcaag    1260
tccgacgtct gggcatttgg agtattgctt tgggaaattg ctacctatgg catgtcccct    1320
tacccgggaa ttgacctgtc ccaggtgtat gagctgctag agaaggacta ccgcatggag    1380
cgcccagaag gctgcccaga gaaggtctat gaactcatgc gagcatgttg gcagtggaat    1440
ccctctgacc ggccctcctt tgctgaaatc caccaagcct ttgaaacaat gttccaggaa    1500
tccagtatct cagacgaagt ggaaaggag ctggggaaac aaggcgtccg tggggctgtg    1560
agtaccttgc tgcaggcccc agagctgccc accaagacga ggacctccag gagagctgca    1620
gagcacagag acaccactga cgtgcctgag atgcctcact ccaagggcca gggagagagc    1680
gatcctctgg accatgagcc tgccgtgtct ccattgctcc ctcgaaaaga gcgaggtccc    1740
ccggagggcg gcctgaatga agatgagcgc cttctcccca aagacaaaaa gaccaacttg    1800
ttcagcgcct tgatcaagaa gaagaagaag acagccccaa ccctcccaa acgcagcagc    1860 tccttccggg agatggacgg ccagccgag cgcagagggg ccggcgagga agagggccga    1920
gacatcagca acgggcact ggctttcacc cccttggaca cagctgaccc agccaagtcc    1980
ccaaagccca gcaatgggc tggggtcccc aatggagccc tccgggagtc cggggcctca    2040
ggcttccggt ctccccacct gtggaagaag tccagcacgc tgaccagcag ccgcctagcc    2100
accggcgagg aggagggcgg tggcagctcc agcaagcgct tcctgcgctc ttgctccgcc    2160
tcctgcgttc cccatggggc caaggacacg gagtggaggt cagtcacgct gcctcgggac    2220
ttgcagtcca cggaagaca gtttgactcg tccacatttg gagggcacaa aagtgagaag    2280
ccggctctgc ctcggaagag ggcaggggag aacaggtctg accaggtgac ccgaggcaca    2340
gtaacgcctc cccccaggct ggtgaaaaag aatgaggaag ctgctgatga ggtcttcaaa    2400
gacatcatgg agtccagccc gggctccagc ccgcccaacc tgactccaaa accctccgg    2460 cggcaggtca ccgtggcccc tgcctcgggc ctcccccaca aggaagaagc tggaaagggc    2520
agtgccttag ggaccctgc tgcagctgag ccagtgaccc ccaccagcaa agcaggctca    2580
ggtgcaccag ggggcaccag caagggcccc gccgaggagt ccagagtgag gaggcacaag    2640
cactcctctg agtcgccagg gagggacaag gggaaattgt ccaggctcaa acctgccccg    2700
ccgcccccac cagcagcctc tgcagggaag ctggaggaa agccctcgca gagcccgagc    2760
caggaggcgg ccggggaggc agtcctgggc gcaaagacaa aagccacgag tctggttgat    2820
gctgtgaaca gtgacgctgc caagcccagc cagccgggag agggcctcaa aaagcccgtg    2880 ctccccggcca ctccaaagcc acagtccgcc aagccgtcgg ggaccccat cagcccagcc    2940 cccgttccct ccacgttgcc atcagcatcc tcggccctgg caggggacca gccgtcttcc    3000
accgccttca tccctctcat atcaacccga gtgtctcttc ggaaaacccg ccagcctcca    3060
gagcggatcg ccagcggcgc catcaccaag ggcgtggtcc tggacagcac cgaggcgctg    3120
tgcctcgcca tctctaggaa ctccgagcag atggccagcc acagcgcagt gctggaggcc    3180
ggcaaaaacc tctacacgtt ctgcgtgagc tatgtggatt ccatccagca aatgaggaac    3240
aagtttgcct tccgagaggc catcaacaaa ctggagaata tctccgggga gcttcagatc    3300
tgcccggcga cagcaggcag tggtccagcg gccactcagg acttcagcaa gctcctcagt    3360
tcggtgaagg aaatcagtga catagtgcag aggtagcagc agtcaggggt caggtgtcag    3420
gcccgtcgga gctgcctgca gcacatgcgg gctcgcccat accgtgaca gtggctgaca    3480 agggactagt gagtcagcac cttggcccag gagctctgcg ccaggcagag ctgagggccc    3540
```

```
tgtggagtcc agctctacta cctacgtttg caccgcctgc cctcccgcac cttcctcctc    3600
cccgctccgt ctctgtcctc gaattttatc tgtggagttc ctgctccgtg gactgcagtc    3660
ggcatgccag gacccgccag ccccgctccc acctagtgcc ccagactgag ctctccaggc    3720
caggtgggaa cggctgatgt ggactgtctt tttcattttt ttctctctgg agcccctcct    3780
cccccggctg ggcctccttc ttccacttct ccaagaatgg aagcctgaac tgaggccttg    3840
tgtgtcaggc cctctgcctg cactccctgg ccttgcccgt cgtgtgctga agacatgttt    3900
caagaaccgc atttcgggaa gggcatgcac gggcatgcac acggctggtc actctgccct    3960
ctgctgctgc ccggggtggg gtgcactcgc catttcctca cgtgcaggac agctcttgat    4020
ttgggtggaa aacagggtgc taaagccaac cagcctttgg gtcctgggca ggtgggagct    4080
gaaaaggatc gaggcatggg gcatgtcctt tccatctgtc cacatcccca gagcccagct    4140
cttgctctct tgtgacgtgc actgtgaatc ctggcaagaa agcttgagtc tcaagggtgg    4200
caggtcactg tcactgccga catccctccc ccagcagaat ggaggcaggg gacaaggggag   4260
gcagtggcta gtggggtgaa cagctggtgc caaatagccc cagactgggc ccaggcaggt    4320
ctgcaagggc ccagagtgaa ccgtcctttc acacatctgg gtgccctgaa agggcccttc    4380
ccctccccca ctcctctaag acaaagtaga ttcttacaag gcccttttcct ttggaacaag   4440
acagccttca cttttctgag ttcttgaagc atttcaaagc cctgcctctg tgtagccgcc    4500
ctgagagaga atagagctgc cactgggcac ctgcgcacag gtgggaggaa agggcctggc    4560
cagtcctggt cctggctgca ctcttgaact gggcgaatgt cttatttaat taccgtgagt    4620
gacatagcct catgttctgt gggggtcatc agggagggtt aggaaaacca caaacggagc    4680
ccctgaaagc ctcacgtatt tcacagagca cgcctgccat cttctccccg aggctgcccc    4740
aggccggagc ccagatacgg gggctgtgac tctgggcagg gaccccgggt ctcctggacc    4800
ttgacagagc agctaactcc gagagcagtg ggcaggtggc cgccccctgag gcttcacgcc   4860
gggagaagcc accttcccac cccttcatac cgcctcgtgc cagcagcctc gcacaggccc    4920
tagctttacg ctcatcacct aaacttgtac tttatttttc tgatagaaat ggtttcctct    4980
ggatcgtttt atgcggttct tacagcacat cacctctttg cccccgacgg ctgtgacgca    5040
gccggaggga ggcactagtc accgacagcg gccttgaaga cagagcaaag cgcccaccca    5100
ggtcccccga ctgcctgtct ccatgaggta ctggtcccttt ccttttgtta acgtgatgtg    5160
ccactatatt ttacacgtat ctcttggtat gcatctttta tagacgctct tttctaagtg    5220
gcgtgtgcat agcgtcctgc cctgcccct cgggggcctg tggtggctcc ccctctgctt    5280
ctcggggtcc agtgcatttt gtttctgtat atgattctct gtggtttttt ttgaatccaa    5340
atctgtcctc tgtagtattt tttaaataaa tcagtgttta cattagaa                 5388
```

<210> SEQ ID NO 24
<211> LENGTH: 1130
<212> TYPE: PRT
<213> ORGANISM: Homo sapiens

<400> SEQUENCE: 24

Met Leu Glu Ile Cys Leu Lys Leu Val Gly Cys Lys Ser Lys Lys Gly
1               5                   10                  15

Leu Ser Ser Ser Ser Cys Tyr Leu Glu Glu Ala Leu Gln Arg Pro
            20                  25                  30

Val Ala Ser Asp Phe Glu Pro Gln Gly Leu Ser Glu Ala Ala Arg Trp
        35                  40                  45

```
Asn Ser Lys Glu Asn Leu Leu Ala Gly Pro Ser Glu Asn Asp Pro Asn
    50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
            100                 105                 110

Ser Asn Tyr Ile Thr Pro Val Asn Ser Leu Glu Lys His Ser Trp Tyr
        115                 120                 125

His Gly Pro Val Ser Arg Asn Ala Ala Glu Tyr Leu Leu Ser Ser Gly
    130                 135                 140

Ile Asn Gly Ser Phe Leu Val Arg Glu Ser Glu Ser Ser Pro Gly Gln
145                 150                 155                 160

Arg Ser Ile Ser Leu Arg Tyr Glu Gly Arg Val Tyr His Tyr Arg Ile
                165                 170                 175

Asn Thr Ala Ser Asp Gly Lys Leu Tyr Val Ser Ser Glu Ser Arg Phe
            180                 185                 190

Asn Thr Leu Ala Glu Leu Val His His Ser Thr Val Ala Asp Gly
        195                 200                 205

Leu Ile Thr Thr Leu His Tyr Pro Ala Pro Lys Arg Asn Lys Pro Thr
    210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gly Gln Tyr Gly Glu Val
                245                 250                 255

Tyr Glu Gly Val Trp Lys Lys Tyr Ser Leu Thr Val Ala Val Lys Thr
            260                 265                 270

Leu Lys Glu Asp Thr Met Glu Val Glu Glu Phe Leu Lys Glu Ala Ala
        275                 280                 285

Val Met Lys Glu Ile Lys His Pro Asn Leu Val Gln Leu Leu Gly Val
    290                 295                 300

Cys Thr Arg Glu Pro Pro Phe Tyr Ile Ile Thr Glu Phe Met Thr Tyr
305                 310                 315                 320

Gly Asn Leu Leu Asp Tyr Leu Arg Glu Cys Asn Arg Gln Glu Val Asn
                325                 330                 335

Ala Val Val Leu Leu Tyr Met Ala Thr Gln Ile Ser Ser Ala Met Glu
            340                 345                 350

Tyr Leu Glu Lys Lys Asn Phe Ile His Arg Asp Leu Ala Ala Arg Asn
        355                 360                 365

Cys Leu Val Gly Glu Asn His Leu Val Lys Val Ala Asp Phe Gly Leu
    370                 375                 380

Ser Arg Leu Met Thr Gly Asp Thr Tyr Thr Ala His Ala Gly Ala Lys
385                 390                 395                 400

Phe Pro Ile Lys Trp Thr Ala Pro Glu Ser Leu Ala Tyr Asn Lys Phe
                405                 410                 415

Ser Ile Lys Ser Asp Val Trp Ala Phe Gly Val Leu Leu Trp Glu Ile
            420                 425                 430

Ala Thr Tyr Gly Met Ser Pro Tyr Pro Gly Ile Asp Leu Ser Gln Val
        435                 440                 445

Tyr Glu Leu Leu Glu Lys Asp Tyr Arg Met Glu Arg Pro Glu Gly Cys
    450                 455                 460
```

```
Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
            485                 490                 495

Phe Gln Glu Ser Ser Ile Ser Asp Glu Val Glu Lys Glu Leu Gly Lys
        500                 505                 510

Gln Gly Val Arg Gly Ala Val Ser Thr Leu Leu Gln Ala Pro Glu Leu
    515                 520                 525

Pro Thr Lys Thr Arg Thr Ser Arg Arg Ala Ala Glu His Arg Asp Thr
530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
                565                 570                 575

Arg Gly Pro Pro Glu Gly Leu Asn Glu Asp Glu Arg Leu Leu Pro
            580                 585                 590

Lys Asp Lys Lys Thr Asn Leu Phe Ser Ala Leu Ile Lys Lys Lys
        595                 600                 605

Lys Thr Ala Pro Thr Pro Pro Lys Arg Ser Ser Ser Phe Arg Glu Met
    610                 615                 620

Asp Gly Gln Pro Glu Arg Arg Gly Ala Gly Glu Glu Glu Gly Arg Asp
625                 630                 635                 640

Ile Ser Asn Gly Ala Leu Ala Phe Thr Pro Leu Asp Thr Ala Asp Pro
                645                 650                 655

Ala Lys Ser Pro Lys Pro Ser Asn Gly Ala Gly Val Pro Asn Gly Ala
            660                 665                 670

Leu Arg Glu Ser Gly Gly Ser Gly Phe Arg Ser Pro His Leu Trp Lys
        675                 680                 685

Lys Ser Ser Thr Leu Thr Ser Ser Arg Leu Ala Thr Gly Glu Glu Glu
    690                 695                 700

Gly Gly Gly Ser Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
                725                 730                 735

Pro Arg Asp Leu Gln Ser Thr Gly Arg Gln Phe Asp Ser Ser Thr Phe
            740                 745                 750

Gly Gly His Lys Ser Glu Lys Pro Ala Leu Pro Arg Lys Arg Ala Gly
        755                 760                 765

Glu Asn Arg Ser Asp Gln Val Thr Arg Gly Thr Val Thr Pro Pro
    770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Ser Pro Pro Asn Leu Thr Pro Lys
                805                 810                 815

Pro Leu Arg Arg Gln Val Thr Val Ala Pro Ala Ser Gly Leu Pro His
            820                 825                 830

Lys Glu Glu Ala Gly Lys Gly Ser Ala Leu Gly Thr Pro Ala Ala Ala
        835                 840                 845

Glu Pro Val Thr Pro Thr Ser Lys Ala Gly Ser Gly Ala Pro Gly Gly
    850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Arg Leu Lys
```

```
                885                890                895
Pro Ala Pro Pro Pro Pro Ala Ala Ser Ala Gly Lys Ala Gly Gly
            900                905                910
Lys Pro Ser Gln Ser Pro Ser Gln Glu Ala Ala Gly Glu Ala Val Leu
            915                920                925
Gly Ala Lys Thr Lys Ala Thr Ser Leu Val Asp Ala Val Asn Ser Asp
        930                935                940
Ala Ala Lys Pro Ser Gln Pro Gly Glu Gly Leu Lys Lys Pro Val Leu
945                950                955                960
Pro Ala Thr Pro Lys Pro Gln Ser Ala Lys Pro Ser Gly Thr Pro Ile
                965                970                975
Ser Pro Ala Pro Val Pro Ser Thr Leu Pro Ser Ala Ser Ala Leu
            980                985                990
Ala Gly Asp Gln Pro Ser Ser Thr Ala Phe Ile Pro Leu Ile Ser Thr
            995                1000               1005
Arg Val Ser Leu Arg Lys Thr Arg Gln Pro Pro Glu Arg Ile Ala
        1010               1015               1020
Ser Gly Ala Ile Thr Lys Gly Val Val Leu Asp Ser Thr Glu Ala
        1025               1030               1035
Leu Cys Leu Ala Ile Ser Arg Asn Ser Glu Gln Met Ala Ser His
        1040               1045               1050
Ser Ala Val Leu Glu Ala Gly Lys Asn Leu Tyr Thr Phe Cys Val
        1055               1060               1065
Ser Tyr Val Asp Ser Ile Gln Gln Met Arg Asn Lys Phe Ala Phe
        1070               1075               1080
Arg Glu Ala Ile Asn Lys Leu Glu Asn Asn Leu Arg Glu Leu Gln
        1085               1090               1095
Ile Cys Pro Ala Thr Ala Gly Ser Gly Pro Ala Ala Thr Gln Asp
        1100               1105               1110
Phe Ser Lys Leu Leu Ser Ser Val Lys Glu Ile Ser Asp Ile Val
        1115               1120               1125
Gln Arg
1130

<210> SEQ ID NO 25
<211> LENGTH: 2033
<212> TYPE: DNA
<213> ORGANISM: Homo sapiens

<400> SEQUENCE: 25
atattgtata ctggaattga agccaaggag gtaccatttt gctcgagggc atggcctaag      60
ccggtcagct aaggccatgt taatacgggg ctgtcccatc tctctgcggg gcgcgacagc     120
tggaagagcc gaacggataa gaagaggag gtgagagga gctgtacacc acaagaggca      180
ctgagggact caggataacg ggatgaagcc gtcagtgccc ccagaaacga agcgccccg      240 gacgaatttc tgagtcaccg tcgcgagaaa gcgggctgag ccgccatttt gaagcctggc      300
aaaccgaagc aagaaatgct gccgtgttgg atctttgcca gccttcgtgc gaatgggag      360 cagggcgcgg atggcgtcgg ggcgccccga ggagctgtgg gaggccgtgg tgggggccgc      420
tgagcgcttc cgggcccgga ctggcacgga gctggtgctg ctgaccgcgg ccccgccgcc      480 accacccgc ccgggcccct gtgcctatgc tgcccatggt cgaggagccc tggcggaggc      540
agcgcgccgt tgcctccacg acatcgcact ggcccacagg gctgccactg ctgctcggcc      600
tcctgcgccc ccaccagcac cacagccacc cagtcccaca cccagcccac cccggcctac      660
```

```
cctggccaga gaggacaacg aggaggacga ggatgagccc acagagacag agacctccgg    720
ggagcagctg ggcattagtg ataatggagg gctctttgtg atggatgagg acgccaccct    780
ccaggacctt ccccccttct gtgagtcaga ccccgagagt acagatgatg cagcctgag     840 cgaggagacc cccgccggcc ccccacctg ctcagtgccc ccagcctcag ccctacccac     900
acagcagtac gccaagtccc tgcctgtgtc tgtgcccgtc tggggcttca aggagaagag    960
gacagaggcg cggtcatcag atgaggagaa tgggccgccc tcttcgcccg acctggaccg   1020
catcgcggcg agcatgcgcg cgctggtgct gcgagaggcc gaggacaccc aggtcttcgg   1080
ggacctgcca cggccgcggc ttaacaccag cgacttccag aagctgaagc ggaaatattg   1140
aagtccaggg agggagcgcc ccgggccgcg tccgccccgt ccacactac gccccgccc    1200 cactcccggg gcctgctaat ctgaggccga tccgggaccg gcctccttgc gtctcccatt   1260
cccaagattg tcccgcctct gccaatcccc gccgtccttc cagcccacga cctgccgcgc   1320
cgaggagcgc atctgtcccc gtttcccgat tgggtctgtc gtctctctcc gcctagcgac   1380
agattccttc tattaaggga ttggctcgct gagttctaag ctctaaatgg gtcaactcct   1440
ttgttttccg cctagcgaca agggatttgc tcgcacggca ttggctccat ccctagtcg   1500 ctggacagct cttttttga ttggctcaaa tcctgtaaag ggcttgacca gtctctacat   1560
agtcaccgtc cgcttttcct gagttctccc tcccaattgg ctccagcttc ctggggcgt   1620 ggccaagccc tcctcttccc agaattggcc cggggccttc aatttacgtt ctttacacta   1680
cggggactgg ggtcgtcttt gcccacgtcc cgacaacttg ttccctgacc ccctcaggga   1740
tggccccaaa ctgtccctgc ctctggcacc ccctttcatt ggttccatcc atccccacaa   1800
cagcctgcca atcgaagccc gtccctgcat ccaggatggt accagctccc gcccctcgcc   1860
ccccacctcc acaggtgcct taagggccc tcgtccaccc aaggtggggg gcaggggccc    1920
tcactctccg gccctggtgt ggggagaga gtgaggggtt gggggatcgg cagttgggag    1980
gggcgctctg agattaaaga gttttacctc tgagataaaa aaaaaaaaaa aaa          2033

<210> SEQ ID NO 26
<211> LENGTH: 256
<212> TYPE: PRT
<213> ORGANISM: Homo sapiens

<400> SEQUENCE: 26

Met Ala Ser Gly Arg Pro Glu Glu Leu Trp Glu Ala Val Val Gly Ala
1               5                   10                  15

Ala Glu Arg Phe Arg Ala Arg Thr Gly Thr Glu Leu Val Leu Leu Thr
                20                  25                  30

Ala Ala Pro Pro Pro Pro Arg Pro Gly Pro Cys Ala Tyr Ala Ala
            35                  40                  45

His Gly Arg Gly Ala Leu Ala Glu Ala Ala Arg Arg Cys Leu His Asp
        50                  55                  60

Ile Ala Leu Ala His Arg Ala Ala Thr Ala Ala Arg Pro Pro Ala Pro
65                  70                  75                  80

Pro Pro Ala Pro Gln Pro Pro Ser Pro Thr Pro Ser Pro Pro Arg Pro
                85                  90                  95

Thr Leu Ala Arg Glu Asp Asn Glu Glu Asp Glu Asp Glu Pro Thr Glu
                100                 105                 110

Thr Glu Thr Ser Gly Glu Gln Leu Gly Ile Ser Asp Asn Gly Gly Leu
            115                 120                 125
```

```
Phe Val Met Asp Glu Asp Ala Thr Leu Gln Asp Leu Pro Pro Phe Cys
        130                 135                 140

Glu Ser Asp Pro Glu Ser Thr Asp Asp Gly Ser Leu Ser Glu Glu Thr
145                 150                 155                 160

Pro Ala Gly Pro Pro Thr Cys Ser Val Pro Ala Ser Ala Leu Pro
                165                 170                 175

Thr Gln Gln Tyr Ala Lys Ser Leu Pro Val Ser Val Pro Val Trp Gly
            180                 185                 190

Phe Lys Glu Lys Arg Thr Glu Ala Arg Ser Ser Asp Glu Glu Asn Gly
        195                 200                 205

Pro Pro Ser Ser Pro Asp Leu Asp Arg Ile Ala Ala Ser Met Arg Ala
210                 215                 220

Leu Val Leu Arg Glu Ala Glu Asp Thr Gln Val Phe Gly Asp Leu Pro
225                 230                 235                 240

Arg Pro Arg Leu Asn Thr Ser Asp Phe Gln Lys Leu Lys Arg Lys Tyr
                245                 250                 255

<210> SEQ ID NO 27
<211> LENGTH: 8733
<212> TYPE: DNA
<213> ORGANISM: Homo sapiens

<400> SEQUENCE: 27
gctcccggct tagaggacag cggggaaggc gggcggtggg gcaggggggcc tgaagcggcg      60 gtaccggtgc tggcggcggc agctgaggcc ttggccgaag ccgcgcgaac ctcagggcaa     120
gatgcttgga accggacctg ccgccgccac caccgctgcc accacatcta gcaatgtgag     180
cgtcctgcag cagtttgcca gtggcctaaa gagccggaat gaggaaacca gggccaaagc     240
cgccaaggag ctccagcact atgtcaccat ggaactccga gagatgagtc aagaggagtc     300
tactcgcttc tatgaccaac tgaaccatca cattttgaa ttggtttcca gctcagatgc      360
caatgagagg aaaggtggca tcttggccat agctagcctc ataggagtgg aaggtgggaa     420
tgccacccga attggcagat tgccaactta tcttcggaac ctcctcccct ccaatgaccc     480
agttgtcatg gaaatggcat ccaaggccat tggccgtctt gccatggcag ggacacttt      540 taccgctgag tacgtggaat tgaggtgaa gcgagccctg aatggctgg gtgctgaccg      600 caatgagggc cggagacatg cagctgtcct ggttctccgt gagctggcca tcagcgtccc     660
taccttcttc ttccagcaag tgcaaccctt ctttgacaac atttttgtgg ccgtgtggga     720
ccccaaacag gccatccgtg agggagctgt agccgccctt cgtgcctgtc tgattctcac     780
aacccagcgt gagccgaagg agatgcagaa gcctcagtgg tacaggcaca catttgaaga     840
agcagagaag ggatttgatg agaccttggc caaagagaag ggcatgaatc gggatgatcg     900
gatccatgga gccttgttga tccttaacga gctggtccga atcagcagca tggagggaga     960
gcgtctgaga gaagaaatgg aagaaatcac acagcagcag ctggtacacg acaagtactg    1020
caaagatctc atgggcttcg gaacaaaacc tcgtcacatt ccccccttca ccagtttcca    1080
ggctgtacag ccccagcagt caaatgcctt ggtggggctg ctggggtaca gctctcacca    1140
aggcctcatg ggatttggga cctccccag tccagctaag tccaccctgg tggagagccg     1200
gtgttgcaga gacttgatgg aggagaaatt tgatcaggtg tgccagtggg tgctgaaatg    1260
caggaatagc aagaactcgc tgatccaaat gacaatcctt aatttgttgc ccgcttggc     1320 tgcattccga ccttctgcct tcacagatac ccagtatctc caagatacca tgaaccatgt    1380
cctaagctgt gtcaagaagg agaaggaacg tacagcggcc ttccaagccc tggggctact    1440
```

```
ttctgtggct gtgaggtctg agtttaaggt ctatttgcct cgcgtgctgg acatcatccg   1500
agcggccctg cccccaaagg acttcgccca taagaggcag aaggcaatgc aggtggatgc   1560
cacagtcttc acttgcatca gcatgctggc tcgagcaatg gggccaggca tccagcagga   1620
tatcaaggag ctgctggagc ccatgctggc agtgggacta agccctgccc tcactgcagt   1680
gctctacgac ctgagccgtc agattccaca gctaaagaag gacattcaag atgggctact   1740
gaaaatgctg tccctggtcc ttatgcacaa accccttcgc cacccaggca tgcccaaggg   1800
cctggcccat cagctggcct ctcctggcct cacgaccctc cctgaggcca gcgatgtggg   1860
cagcatcact cttgccctcc gaacgcttgg cagctttgaa tttgaaggcc actctctgac   1920
ccaatttgtt cgccactgtg cggatcattt cctgaacagt gagcacaagg agatccgcat   1980
ggaggctgcc cgcacctgct cccgcctgct cacaccctcc atccacctca tcagtggcca   2040
tgctcatgtg gttagccaga ccgcagtgca agtggtggca gatgtgctta gcaaactgct   2100
cgtagttggg ataacagatc ctgaccctga cattcgctac tgtgtcttgg cgtccctgga   2160
cgagcgcttt gatgcacacc tggcccaggc ggagaacttg caggccttgt tgtggctct    2220 gaatgaccag gtgtttgaga tccgggagct ggccatctgc actgtgggcc gactcagtag   2280
catgaaccct gcctttgtca tgcctttcct gcgcaagatg ctcatccaga ttttgacaga   2340
gttggagcac agtgggattg gaagaatcaa agagcagagt gcccgcatgc tggggcacct   2400
ggtctccaat gccccccgac tcatccgccc ctacatggag cctattctga aggcattaat   2460
tttgaaactg aaagatccag accctgatcc aaacccaggt gtgatcaata atgtcctggc   2520
aacaatagga gaattggcac aggttagtgg cctggaaatg aggaaatggg ttgatgaact   2580
ttttattatc atcatggaca tgctccagga ttcctctttg ttggccaaaa ggcaggtggc   2640
tctgtggacc ctgggacagt tggtggccag cactggctat gtagtagagc cctacaggaa   2700
gtacccatct ttgcttgagg tgctactgaa ttttctgaag actgagcaga accagggtac   2760
acgcagagag gccatccgtg tgttagggct tttagggct ttggatcctt acaagcacaa    2820
agtgaacatt ggcatgatag accagtcccg ggatgcctct gctgtcagcc tgtcagaatc   2880
caagtcaagt caggattcct ctgactatag cactagtgaa atgctggtca acatgggaaa   2940
cttgcctctg gatgagttct acccagctgt gtccatggtg gccctgatgc ggatcttccg   3000
agaccagtca ctctctcatc atcacaccat ggttgtccag gccatcacct tcatcttcaa   3060
gtccctggga ctcaaatgtg tgcagttcct gccccaggtc atgcccacgt tccttaacgt   3120
cattcgagtc tgtgatgggg ccatccggga attttgttc cagcagctgg gaatgttggt    3180
gtcctttgtg aagagccaca tcagacctta tatggatgaa atagtcaccc tcatgagaga   3240
attctgggtc atgaacacct caattcagag cacgatcatt cttctcattg agcaaattgt   3300
ggtagctctt gggggtgaat ttaagctcta cctgccccag ctgatcccac acatgctgcg   3360
tgtcttcatg catgacaaca gcccaggccg cattgtctct atcaagttac tggctgcaat   3420
ccagctgttt ggcgccaacc tggatgacta cctgcattta ctgctgcctc ctattgttaa   3480
gttgtttgat gcccctgaag ctccactgcc atctcgaaag gcagcgctag agactgtgga   3540
ccgcctgacg gagtccctgg atttcactga ctatgcctcc cggatcattc accctattgt   3600
tcgaacactg gaccagagcc cagaactgcg ctccacagcc atggacacgc tgtcttcact   3660 tgttttttcag ctggggaaga agtaccaaat tttcattcca atggtgaata agttctctgg   3720
gcgacaccga atcaatcatc agcgctatga tgtgctcatc tgcagaattg tcaagggata   3780
```

```
cacacttgct gatgaagagg aggatccttt gatttaccag catcggatgc ttaggagtgg    3840
ccaaggggat gcattggcta gtggaccagt ggaaacagga cccatgaaga aactgcacgt    3900
cagcaccatc aacctccaaa aggcctgggg cgctgccagg agggtctcca agatgactg     3960 gctggaatgg ctgagacggc tgagcctgga gctgctgaag gactcatcat cgccctccct   4020
gcgctcctgc tgggccctgg cacaggccta aacccgatg gccagggatc tcttcaatgc     4080
tgcatttgtg tcctgctggt ctgaactgaa tgaagatcaa caggatgagc tcatcagaag    4140
catcgagttg gccctcacct cacaagacat cgctgaagtc acacagaccc tcttaaactt    4200
ggctgaattc atggaacaca gtgacaaggg ccccctgcca ctgagagatg acaatggcat    4260
tgttctgctg ggtgagagag ctgccaagtg ccgagcatat gccaaagcac tacactacaa    4320
agaactggag ttccagaaag gccccacccc tgccattcta gaatctctca tcagcattaa    4380
taataagcta cagcagccgg aggcagcggc cggagtgtta aatatgcca tgaaacactt     4440 tggagagctg gagatccagg ctacctggta tgagaaactg cacgagtggg aggatgccct    4500
tgtggcctat gacaagaaaa tggacaccaa caaggacgac ccagagctga tgctgggccg    4560
catgcgctgc ctcgaggcct tggggaatg gggtcaactc caccagcagt gctgtgaaaa     4620
gtggaccctg gttaatgatg agacccaagc caagatggcc cggatggctg ctgcagctgc    4680
atggggttta ggtcagtggg acagcatgga agaatacacc tgtatgatcc ctcgggacac    4740
ccatgatggg gcattttata gagctgtgct ggcactgcat caggacctct tctccttggc    4800
acaacagtgc attgacaagg ccagggacct gctggatgct gaattaactg cgatggcagg    4860
agagagttac agtcgggcat atggggccat ggtttcttgc cacatgctgt ccgagctgga    4920
ggaggttatc cagtacaaac ttgtccccga gcgacgagag atcatccgcc agatctggtg    4980
ggagagactg cagggctgcc agcgtatcgt agaggactgg cagaaaatcc ttatggtgcg    5040
gtcccttgtg gtcagccctc atgaagacat gagaacctgg ctcaagtatg caagcctgtg    5100
cggcaagagt ggcaggctgg ctcttgctca taaaacttta gtgttgctcc tgggagttga    5160
tccgtctcgg caacttgacc atcctctgcc aacagttcac cctcaggtga cctatgccta    5220
catgaaaaac atgtggaaga gtgcccgcaa gatcgatgcc ttccagcaca tgcagcattt    5280
tgtccagacc atgcagcaac aggcccagca tgccatcgct actgaggacc agcagcataa    5340
gcaggaactg cacaagctca tggcccgatg cttcctgaaa cttggagagt ggcagctgaa    5400
tctacagggc atcaatgaga gcacaatccc caaagtgctg cagtactaca gcgccgccac    5460
agagcacgac cgcagctggt acaaggcctg catgcgtgg gcagtgatga acttcgaagc     5520
tgtgctacac tacaaacatc agaaccaagc ccgcgatgag aagaagaaac tgcgtcatgc    5580
cagcggggcc aacatcacca acgccaccac tgccgccacc acggccgcca ctgccaccac    5640
cactgccagc accgagggca gcaacagtga gagcgaggcc gagagcaccg agaacagccc    5700
caccccatcg ccgctgcaga agaaggtcac tgaggatctg tccaaaaccc tcctgatgta    5760
cacggtgcct gccgtccagg gcttcttccg ttccatctcc ttgtcacgag caacaacct     5820 ccaggataca ctcagagttc tcaccttatg gtttgattat ggtcactggc cagatgtcaa    5880
tgaggcctta gtgaggggg tgaaagccat ccagattgat acctggctac aggttatacc     5940
tcagctcatt gcaagaattg atacgcccag acccttggtg ggacgtctca ttcaccagct    6000
tctcacagac attggtcggt accaccccca ggccctcatc tacccactga cagtggcttc    6060
taagtctacc acgacagccc ggcacaatgc agccaacaag attctgaaga acatgtgtga    6120
gcacagcaac ccctggtcc agcaggccat gatggtgagc gaggagctga tccgagtggc     6180
```

```
catcctctgg catgagatgt ggcatgaagg cctggaagag gcatctcgtt tgtactttgg    6240
ggaaaggaac gtgaaaggca tgtttgaggt gctggagccc ttgcatgcta tgatggaacg    6300
gggcccccag actctgaagg aaacatcctt taatcaggcc tatggtcgag atttaatgga    6360
ggcccaagag tggtgcagga agtacatgaa atcaggaat gtcaaggacc tcacccaagc     6420
ctgggacctc tattatcatg tgttccgacg aatctcaaag cagctgcctc agctcacatc    6480
cttagagctg caatatgttt ccccaaaact tctgatgtgc cgggaccttg aattggctgt    6540
gccaggaaca tatgaccca accagccaat cattcgcatt cagtccatag caccgtcttt     6600
gcaagtcatc acatccaagc agaggccccg gaaattgaca cttatgggca gcaacggaca    6660
tgagtttgtt ttccttctaa aaggccatga agatctgcgc caggatgagc gtgtgatgca    6720
gctcttcggc ctggttaaca cccttctggc caatgaccca acatctcttc ggaaaaacct    6780
cagcatccag agatacgctg tcatccctt atcgaccaac tcgggcctca ttggctgggt     6840
tccccactgt gacacactgc acgccctcat ccgggactac agggagaaga agaagatcct    6900
tctcaacatc gagcatcgca tcatgttgcg gatggctccg gactatgacc acttgactct    6960
gatgcagaag gtgaggtgt ttgagcatgc cgtcaataat acagctgggg acgacctggc     7020
caagctgctg tggctgaaaa gccccagctc cgaggtgtgg tttgaccgaa gaaccaatta    7080
tacccgttct ttagcggtca tgtcaatggt tgggtatatt ttaggcctgg gagatagaca    7140
cccatccaac ctgatgctgg accgtctgag tgggaagatc ctgcacattg actttgggga    7200
ctgctttgag gttgctatga cccgagagaa gtttccagag aagattccat ttagactaac    7260
aagaatgttg accaatgcta tggaggttac aggcctggat ggcaactaca gaatcacatg    7320
ccacacagtg atggaggtgc tgcgagagca caaggacagt gtcatggccg tgctggaagc    7380 cttttgtctat gaccccttgc tgaactggag gctgatggac acaaatacca aaggcaacaa    7440
gcgatcccga acgaggacgg attcctactc tgctggccag tcagtcgaaa ttttggacgg    7500
tgtggaactt ggagagccag cccataagaa aacgggggacc acagtgccag aatctattca    7560
ttctttcatt ggagacggtt tggtgaaacc agaggcccta aataagaag ctatccagat     7620 tattaacagg gttcgagata agctcactgg tcgggacttc tctcatgatg acactttgga    7680
tgttccaacg caagttgagc tgctcatcaa acaagcgaca tcccatgaaa acctctgcca    7740
gtgctatatt ggctggtgcc cttctggta actggaggcc cagatgtgcc catcacgttt     7800
tttctgaggc ttttgtactt tagtaaatgc ttccactaaa ctgaaaccat ggtgagaaag    7860
tttgactttg ttaaatattt tgaaatgtaa atgaaaagaa ctactgtata ttaaaagttg    7920
gtttgaacca actttctagc tgctgttgaa gaatatattg tcagaaacac aaggcttgat    7980
ttggttccca ggacagtgaa acatagtaat accacgtaaa tcaagccatt cattttgggg    8040
aacagaagat ccataacttt agaaatacgg gttttgactt aactcacaag agaactcatc    8100
ataagtactt gctgatggaa gaatgaccta gttgctcctc tcaacatggg tacagcaaac    8160
tcagcacagc caagaagcct caggtcgtgg agaacatgga ttaggatcct agactgtaaa    8220
gacacagaag atgctgacct cacccctgcc acctatccca agacctcact ggtctgtgga    8280
cagcagcaga aatgtttgca agataggcca aaatgagtac aaaaggtctg tcttccatca    8340
gacccagtga tgctgcgact cacacgcttc aattcaagac ctgaccgcta gtagggaggt    8400
ttattcagat cgctggcagc ctcggctgag cagatgcaca gagggatca ctgtgcagtg     8460 ggaccaccct cactggcctt ctgcagcagg gttctgggat gttttcagtg gtcaaaatac    8520
```

```
tctgtttaga gcaagggctc agaaaacaga aatactgtca tggaggtgct gaacacaggg    8580
aaggtctggt acatattgga aattatgagc agaacaaata ctcaactaaa tgcacaaagt    8640
ataaagtgta gccatgtcta gacaccatgt tgtatcagaa taattttgt gccaataaat     8700 gacatcagaa ttttaaacat atgtaaaaaa aaa                                 8733
```

<210> SEQ ID NO 28
<211> LENGTH: 2549
<212> TYPE: PRT
<213> ORGANISM: Homo sapiens

<400> SEQUENCE: 28

```
Met Leu Gly Thr Gly Pro Ala Ala Thr Thr Ala Ala Thr Thr Ser
1               5                   10                  15

Ser Asn Val Ser Val Leu Gln Gln Phe Ala Ser Gly Leu Lys Ser Arg
                20                  25                  30

Asn Glu Glu Thr Arg Ala Lys Ala Ala Lys Glu Leu Gln His Tyr Val
            35                  40                  45

Thr Met Glu Leu Arg Glu Met Ser Gln Glu Glu Ser Thr Arg Phe Tyr
        50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Glu Met Glu Glu
        275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Gly Tyr
                325                 330                 335
```

-continued

```
Ser Ser His Gln Gly Leu Met Gly Phe Gly Thr Ser Pro Ser Pro Ala
            340                 345                 350
Lys Ser Thr Leu Val Glu Ser Arg Cys Cys Arg Asp Leu Met Glu Glu
        355                 360                 365
Lys Phe Asp Gln Val Cys Gln Trp Val Leu Lys Cys Arg Asn Ser Lys
    370                 375                 380
Asn Ser Leu Ile Gln Met Thr Ile Leu Asn Leu Leu Pro Arg Leu Ala
385                 390                 395                 400
Ala Phe Arg Pro Ser Ala Phe Thr Asp Thr Gln Tyr Leu Gln Asp Thr
                405                 410                 415
Met Asn His Val Leu Ser Cys Val Lys Lys Glu Lys Glu Arg Thr Ala
            420                 425                 430
Ala Phe Gln Ala Leu Gly Leu Leu Ser Val Ala Val Arg Ser Glu Phe
        435                 440                 445
Lys Val Tyr Leu Pro Arg Val Leu Asp Ile Ile Arg Ala Ala Leu Pro
    450                 455                 460
Pro Lys Asp Phe Ala His Lys Arg Gln Lys Ala Met Gln Val Asp Ala
465                 470                 475                 480
Thr Val Phe Thr Cys Ile Ser Met Leu Ala Arg Ala Met Gly Pro Gly
                485                 490                 495
Ile Gln Gln Asp Ile Lys Glu Leu Leu Glu Pro Met Leu Ala Val Gly
            500                 505                 510
Leu Ser Pro Ala Leu Thr Ala Val Leu Tyr Asp Leu Ser Arg Gln Ile
        515                 520                 525
Pro Gln Leu Lys Lys Asp Ile Gln Asp Gly Leu Leu Lys Met Leu Ser
    530                 535                 540
Leu Val Leu Met His Lys Pro Leu Arg His Pro Gly Met Pro Lys Gly
545                 550                 555                 560
Leu Ala His Gln Leu Ala Ser Pro Gly Leu Thr Thr Leu Pro Glu Ala
                565                 570                 575
Ser Asp Val Gly Ser Ile Thr Leu Ala Leu Arg Thr Leu Gly Ser Phe
            580                 585                 590
Glu Phe Glu Gly His Ser Leu Thr Gln Phe Val Arg His Cys Ala Asp
        595                 600                 605
His Phe Leu Asn Ser Glu His Lys Glu Ile Arg Met Glu Ala Ala Arg
    610                 615                 620
Thr Cys Ser Arg Leu Leu Thr Pro Ser Ile His Leu Ile Ser Gly His
625                 630                 635                 640
Ala His Val Val Ser Gln Thr Ala Val Gln Val Val Ala Asp Val Leu
                645                 650                 655
Ser Lys Leu Leu Val Val Gly Ile Thr Asp Pro Asp Pro Asp Ile Arg
            660                 665                 670
Tyr Cys Val Leu Ala Ser Leu Asp Glu Arg Phe Asp Ala His Leu Ala
        675                 680                 685
Gln Ala Glu Asn Leu Gln Ala Leu Phe Val Ala Leu Asn Asp Gln Val
    690                 695                 700
Phe Glu Ile Arg Glu Leu Ala Ile Cys Thr Val Gly Arg Leu Ser Ser
705                 710                 715                 720
Met Asn Pro Ala Phe Val Met Pro Phe Leu Arg Lys Met Leu Ile Gln
                725                 730                 735
Ile Leu Thr Glu Leu Glu His Ser Gly Ile Gly Arg Ile Lys Glu Gln
            740                 745                 750
Ser Ala Arg Met Leu Gly His Leu Val Ser Asn Ala Pro Arg Leu Ile
```

```
            755                 760                 765
Arg Pro Tyr Met Glu Pro Ile Leu Lys Ala Leu Ile Leu Lys Leu Lys
770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Ile Met Asp Met Leu Gln Asp Ser Ser
                820                 825                 830

Leu Leu Ala Lys Arg Gln Val Ala Leu Trp Thr Leu Gly Gln Leu Val
                835                 840                 845

Ala Ser Thr Gly Tyr Val Val Glu Pro Tyr Arg Lys Tyr Pro Thr Leu
850                 855                 860

Leu Glu Val Leu Leu Asn Phe Leu Lys Thr Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
                900                 905                 910

Ser Ala Val Ser Leu Ser Glu Ser Lys Ser Ser Gln Asp Ser Ser Asp
                915                 920                 925

Tyr Ser Thr Ser Glu Met Leu Val Asn Met Gly Asn Leu Pro Leu Asp
930                 935                 940

Glu Phe Tyr Pro Ala Val Ser Met Val Ala Leu Met Arg Ile Phe Arg
945                 950                 955                 960

Asp Gln Ser Leu Ser His His Thr Met Val Val Gln Ala Ile Thr
                965                 970                 975

Phe Ile Phe Lys Ser Leu Gly Leu Lys Cys Val Gln Phe Leu Pro Gln
                980                 985                 990

Val Met Pro Thr Phe Leu Asn Val Ile Arg Val Cys Asp Gly Ala Ile
                995                 1000                1005

Arg Glu Phe Leu Phe Gln Gln Leu Gly Met Leu Val Ser Phe Val
        1010                1015                1020

Lys Ser His Ile Arg Pro Tyr Met Asp Glu Ile Val Thr Leu Met
        1025                1030                1035

Arg Glu Phe Trp Val Met Asn Thr Ser Ile Gln Ser Thr Ile Ile
        1040                1045                1050

Leu Leu Ile Glu Gln Ile Val Ala Leu Gly Gly Glu Phe Lys
        1055                1060                1065

Leu Tyr Leu Pro Gln Leu Ile Pro His Met Leu Arg Val Phe Met
        1070                1075                1080

His Asp Asn Ser Pro Gly Arg Ile Val Ser Ile Lys Leu Leu Ala
        1085                1090                1095

Ala Ile Gln Leu Phe Gly Ala Asn Leu Asp Asp Tyr Leu His Leu
        1100                1105                1110

Leu Leu Pro Pro Ile Val Lys Leu Phe Asp Ala Pro Glu Ala Pro
        1115                1120                1125

Leu Pro Ser Arg Lys Ala Ala Leu Glu Thr Val Asp Arg Leu Thr
        1130                1135                1140

Glu Ser Leu Asp Phe Thr Asp Tyr Ala Ser Arg Ile Ile His Pro
        1145                1150                1155

Ile Val Arg Thr Leu Asp Gln Ser Pro Glu Leu Arg Ser Thr Ala
        1160                1165                1170
```

```
Met Asp Thr Leu Ser Ser Leu Val Phe Gln Leu Gly Lys Lys Tyr
    1175            1180                1185

Gln Ile Phe Ile Pro Met Val Asn Lys Val Leu Val Arg His Arg
    1190            1195                1200

Ile Asn His Gln Arg Tyr Asp Val Leu Ile Cys Arg Ile Val Lys
    1205            1210                1215

Gly Tyr Thr Leu Ala Asp Glu Glu Asp Pro Leu Ile Tyr Gln
    1220            1225                1230

His Arg Met Leu Arg Ser Gly Gln Gly Asp Ala Leu Ala Ser Gly
    1235            1240                1245

Pro Val Glu Thr Gly Pro Met Lys Lys Leu His Val Ser Thr Ile
    1250            1255                1260

Asn Leu Gln Lys Ala Trp Gly Ala Ala Arg Arg Val Ser Lys Asp
    1265            1270                1275

Asp Trp Leu Glu Trp Leu Arg Arg Leu Ser Leu Glu Leu Leu Lys
    1280            1285                1290

Asp Ser Ser Pro Ser Leu Arg Ser Cys Trp Ala Leu Ala Gln
    1295            1300                1305

Ala Tyr Asn Pro Met Ala Arg Asp Leu Phe Asn Ala Ala Phe Val
    1310            1315                1320

Ser Cys Trp Ser Glu Leu Asn Glu Asp Gln Gln Asp Glu Leu Ile
    1325            1330                1335

Arg Ser Ile Glu Leu Ala Leu Thr Ser Gln Asp Ile Ala Glu Val
    1340            1345                1350

Thr Gln Thr Leu Leu Asn Leu Ala Glu Phe Met Glu His Ser Asp
    1355            1360                1365

Lys Gly Pro Leu Pro Leu Arg Asp Asp Asn Gly Ile Val Leu Leu
    1370            1375                1380

Gly Glu Arg Ala Ala Lys Cys Arg Ala Tyr Ala Lys Ala Leu His
    1385            1390                1395

Tyr Lys Glu Leu Glu Phe Gln Lys Gly Pro Thr Pro Ala Ile Leu
    1400            1405                1410

Glu Ser Leu Ile Ser Ile Asn Asn Lys Leu Gln Gln Pro Glu Ala
    1415            1420                1425

Ala Ala Gly Val Leu Glu Tyr Ala Met Lys His Phe Gly Glu Leu
    1430            1435                1440

Glu Ile Gln Ala Thr Trp Tyr Glu Lys Leu His Glu Trp Glu Asp
    1445            1450                1455

Ala Leu Val Ala Tyr Asp Lys Lys Met Asp Thr Asn Lys Asp Asp
    1460            1465                1470

Pro Glu Leu Met Leu Gly Arg Met Arg Cys Leu Glu Ala Leu Gly
    1475            1480                1485

Glu Trp Gly Gln Leu His Gln Gln Cys Cys Glu Lys Trp Thr Leu
    1490            1495                1500

Val Asn Asp Glu Thr Gln Ala Lys Met Ala Arg Met Ala Ala Ala
    1505            1510                1515

Ala Ala Trp Gly Leu Gly Gln Trp Asp Ser Met Glu Glu Tyr Thr
    1520            1525                1530

Cys Met Ile Pro Arg Asp Thr His Asp Gly Ala Phe Tyr Arg Ala
    1535            1540                1545

Val Leu Ala Leu His Gln Asp Leu Phe Ser Leu Ala Gln Gln Cys
    1550            1555                1560
```

```
Ile Asp Lys Ala Arg Asp Leu Leu Asp Ala Glu Leu Thr Ala Met
1565                1570                1575

Ala Gly Glu Ser Tyr Ser Arg Ala Tyr Gly Ala Met Val Ser Cys
1580                1585                1590

His Met Leu Ser Glu Leu Glu Glu Val Ile Gln Tyr Lys Leu Val
1595                1600                1605

Pro Glu Arg Arg Glu Ile Ile Arg Gln Ile Trp Trp Glu Arg Leu
1610                1615                1620

Gln Gly Cys Gln Arg Ile Val Glu Asp Trp Gln Lys Ile Leu Met
1625                1630                1635

Val Arg Ser Leu Val Val Ser Pro His Glu Asp Met Arg Thr Trp
1640                1645                1650

Leu Lys Tyr Ala Ser Leu Cys Gly Lys Ser Gly Arg Leu Ala Leu
1655                1660                1665

Ala His Lys Thr Leu Val Leu Leu Leu Gly Val Asp Pro Ser Arg
1670                1675                1680

Gln Leu Asp His Pro Leu Pro Thr Val His Pro Gln Val Thr Tyr
1685                1690                1695

Ala Tyr Met Lys Asn Met Trp Lys Ser Ala Arg Lys Ile Asp Ala
1700                1705                1710

Phe Gln His Met Gln His Phe Val Gln Thr Met Gln Gln Gln Ala
1715                1720                1725

Gln His Ala Ile Ala Thr Glu Asp Gln Gln His Lys Gln Glu Leu
1730                1735                1740

His Lys Leu Met Ala Arg Cys Phe Leu Lys Leu Gly Glu Trp Gln
1745                1750                1755

Leu Asn Leu Gln Gly Ile Asn Glu Ser Thr Ile Pro Lys Val Leu
1760                1765                1770

Gln Tyr Tyr Ser Ala Ala Thr Glu His Asp Arg Ser Trp Tyr Lys
1775                1780                1785

Ala Trp His Ala Trp Ala Val Met Asn Phe Glu Ala Val Leu His
1790                1795                1800

Tyr Lys His Gln Asn Gln Ala Arg Asp Glu Lys Lys Lys Leu Arg
1805                1810                1815

His Ala Ser Gly Ala Asn Ile Thr Asn Ala Thr Thr Ala Ala Thr
1820                1825                1830

Thr Ala Ala Thr Ala Thr Thr Thr Ala Ser Thr Glu Gly Ser Asn
1835                1840                1845

Ser Glu Ser Glu Ala Glu Ser Thr Glu Asn Ser Pro Thr Pro Ser
1850                1855                1860

Pro Leu Gln Lys Lys Val Thr Glu Asp Leu Ser Lys Thr Leu Leu
1865                1870                1875

Met Tyr Thr Val Pro Ala Val Gln Gly Phe Phe Arg Ser Ile Ser
1880                1885                1890

Leu Ser Arg Gly Asn Asn Leu Gln Asp Thr Leu Arg Val Leu Thr
1895                1900                1905

Leu Trp Phe Asp Tyr Gly His Trp Pro Asp Val Asn Glu Ala Leu
1910                1915                1920

Val Glu Gly Val Lys Ala Ile Gln Ile Asp Thr Trp Leu Gln Val
1925                1930                1935

Ile Pro Gln Leu Ile Ala Arg Ile Asp Thr Pro Arg Pro Leu Val
1940                1945                1950

Gly Arg Leu Ile His Gln Leu Leu Thr Asp Ile Gly Arg Tyr His
```

-continued

```
            1955                1960                1965
Pro Gln Ala Leu Ile Tyr Pro Leu Thr Val Ala Ser Lys Ser Thr
            1970                1975                1980

Thr Thr Ala Arg His Asn Ala Ala Asn Lys Ile Leu Lys Asn Met
            1985                1990                1995

Cys Glu His Ser Asn Thr Leu Val Gln Gln Ala Met Met Val Ser
            2000                2005                2010

Glu Glu Leu Ile Arg Val Ala Ile Leu Trp His Glu Met Trp His
            2015                2020                2025

Glu Gly Leu Glu Glu Ala Ser Arg Leu Tyr Phe Gly Glu Arg Asn
            2030                2035                2040

Val Lys Gly Met Phe Glu Val Leu Glu Pro Leu His Ala Met Met
            2045                2050                2055

Glu Arg Gly Pro Gln Thr Leu Lys Glu Thr Ser Phe Asn Gln Ala
            2060                2065                2070

Tyr Gly Arg Asp Leu Met Glu Ala Gln Glu Trp Cys Arg Lys Tyr
            2075                2080                2085

Met Lys Ser Gly Asn Val Lys Asp Leu Thr Gln Ala Trp Asp Leu
            2090                2095                2100

Tyr Tyr His Val Phe Arg Arg Ile Ser Lys Gln Leu Pro Gln Leu
            2105                2110                2115

Thr Ser Leu Glu Leu Gln Tyr Val Ser Pro Lys Leu Leu Met Cys
            2120                2125                2130

Arg Asp Leu Glu Leu Ala Val Pro Gly Thr Tyr Asp Pro Asn Gln
            2135                2140                2145

Pro Ile Ile Arg Ile Gln Ser Ile Ala Pro Ser Leu Gln Val Ile
            2150                2155                2160

Thr Ser Lys Gln Arg Pro Arg Lys Leu Thr Leu Met Gly Ser Asn
            2165                2170                2175

Gly His Glu Phe Val Phe Leu Leu Lys Gly His Glu Asp Leu Arg
            2180                2185                2190

Gln Asp Glu Arg Val Met Gln Leu Phe Gly Leu Val Asn Thr Leu
            2195                2200                2205

Leu Ala Asn Asp Pro Thr Ser Leu Arg Lys Asn Leu Ser Ile Gln
            2210                2215                2220

Arg Tyr Ala Val Ile Pro Leu Ser Thr Asn Ser Gly Leu Ile Gly
            2225                2230                2235

Trp Val Pro His Cys Asp Thr Leu His Ala Leu Ile Arg Asp Tyr
            2240                2245                2250

Arg Glu Lys Lys Lys Ile Leu Leu Asn Ile Glu His Arg Ile Met
            2255                2260                2265

Leu Arg Met Ala Pro Asp Tyr Asp His Leu Thr Leu Met Gln Lys
            2270                2275                2280

Val Glu Val Phe Glu His Ala Val Asn Asn Thr Ala Gly Asp Asp
            2285                2290                2295

Leu Ala Lys Leu Leu Trp Leu Lys Ser Pro Ser Ser Glu Val Trp
            2300                2305                2310

Phe Asp Arg Arg Thr Asn Tyr Thr Arg Ser Leu Ala Val Met Ser
            2315                2320                2325

Met Val Gly Tyr Ile Leu Gly Leu Gly Asp Arg His Pro Ser Asn
            2330                2335                2340

Leu Met Leu Asp Arg Leu Ser Gly Lys Ile Leu His Ile Asp Phe
            2345                2350                2355
```

Gly Asp Cys Phe Glu Val Ala Met Thr Arg Lys Phe Pro Glu
          2360                2365                2370

Lys Ile Pro Phe Arg Leu Thr Arg Met Leu Thr Asn Ala Met Glu
     2375                2380                2385

Val Thr Gly Leu Asp Gly Asn Tyr Arg Ile Thr Cys His Thr Val
 2390                2395                2400

Met Glu Val Leu Arg Glu His Lys Asp Ser Val Met Ala Val Leu
 2405                2410                2415

Glu Ala Phe Val Tyr Asp Pro Leu Leu Asn Trp Arg Leu Met Asp
 2420                2425                2430

Thr Asn Thr Lys Gly Asn Lys Arg Ser Arg Thr Arg Thr Asp Ser
 2435                2440                2445

Tyr Ser Ala Gly Gln Ser Val Glu Ile Leu Asp Gly Val Glu Leu
 2450                2455                2460

Gly Glu Pro Ala His Lys Lys Thr Gly Thr Thr Val Pro Glu Ser
 2465                2470                2475

Ile His Ser Phe Ile Gly Asp Gly Leu Val Lys Pro Glu Ala Leu
 2480                2485                2490

Asn Lys Lys Ala Ile Gln Ile Ile Asn Arg Val Arg Asp Lys Leu
 2495                2500                2505

Thr Gly Arg Asp Phe Ser His Asp Asp Thr Leu Asp Val Pro Thr
 2510                2515                2520

Gln Val Glu Leu Leu Ile Lys Gln Ala Thr Ser His Glu Asn Leu
 2525                2530                2535

Cys Gln Cys Tyr Ile Gly Trp Cys Pro Phe Trp
 2540                2545

<210> SEQ ID NO 29
<211> LENGTH: 5299
<212> TYPE: DNA
<213> ORGANISM: Homo sapiens

<400> SEQUENCE: 29
gtttggcttc acggaaccct gtacgcatgc tcctacgctg aactttagga gccagtctaa      60
ggcctaggcg cagacgcact gagcctaagc agccggtgat ggcggcagcg gctgtggtgg     120
ctgcggcggg tccgggccca tgaggcgacg aaggaggcgg gacggctttt acccagcccc     180
ggacttccga gacagggaag ctgaggacat ggcaggagtg tttgacatag acctggacca     240
gccagaggac gcgggctctg aggatgagct ggaggagggg ggtcagttaa atgaaagcat     300
ggaccatggg ggagttggac catatgaact tggcatggaa cattgtgaga aatttgaaat     360
ctcagaaact agtgtgaaca gagggccaga aaaaatcaga ccagaatgtt ttgagctact     420
tcgggtactt ggtaaagggg gctatggaaa ggcaatgata gtaagaaatg ctaaagatac     480
agctcataca aaagcagaac ggaatattct ggaggaagta aagcatccct tcatcgtgga     540
tttaatttat gcctttcaga ctggtggaaa actctacctc atccttgagt atctcagtgg     600
aggagaacta tttatgcagt tagaaagaga gggaatattt atggaagaca ctgcctgctt     660
ttacttggca gaaatctcca tggcttgggg gcatttacat caaaagggga tcatctacag     720
agacctgaag ccggagaata tcatgcttaa tcaccaaggt catgtgaaac taacagactt     780
tggactatgc aaagaatcta ttcatgatgg aacagtcaca cacacatttt gtggaacaat     840
agaatacatg gcccctgaaa tcttgatgag aagtggccac aatcgtgctg tggattggtg     900
gagtttggga gcattaatgt atgacatgct gactggagca ccccattca ctggggagaa     960

-continued

```
tagaaagaaa acaattgaca aaatcctcaa atgtaaactc aatttgcctc cctacctcac    1020
acaagaagcc agagatctgc ttaaaaagct gctgaaaaga aatgctgctt ctcgtctggg    1080
agctggtcct ggggacgctg gagaagttca agctcatcca ttctttagac acattaactg    1140
ggaagaactt ctggctcgaa aggtggagcc cccctttaaa cctctgttgc aatctgaaga    1200
ggatgtaagt cagtttgatt ccaagtttac acgtcagaca cctgtcgaca gcccagatga    1260
ctcaactctc agtgaaagtg ccaatcaggt ctttctgggt tttacatatg tggctccatc    1320
tgtacttgaa agtgtgaaag aaaagttttc ctttgaacca aaaatccgat cacctcgaag    1380
atttattggc agcccacgaa cacctgtcag cccagtcaaa ttttctcctg gggatttctg    1440
gggaagaggt gcttcggcca gcacagcaaa tcctcagaca cctgtggaat acccaatgga    1500
aacaagtggc atagagcaga tggatgtgac aatgagtggg gaagcatcgg caccacttcc    1560
aatacgacag ccgaactctg ggccatacaa aaaacaagct tttcccatga tctccaaacg    1620
gccagagcac ctgcgtatga atctatgaca gagcaatgct tttaatgaat ttaaggcaaa    1680
aaaggtggag agggagatgt gtgagcatcc tgcaaggtga aacgactcaa aatgacagtt    1740
tcagagagtc aatgtcatta catagaacac ttcagacaca ggaaaaataa acgtggattt    1800
taaaaaatca atcaatggtg caaaaaaaaa cttaaagcaa aatagtattg ctgaactctt    1860
aggcacatca attaattgat tcctcgcgac atcttctcaa ccttatcaag gattttcatg    1920
ttgatgactc gaaactgaca gtattaaggg taggatgttg cttctgaatc actgttgagt    1980
tctgattgtg ttgaagaagg gttatccttt cattaggcaa agtacaaaat tgcctataat    2040
acttgcaact aaggacaaat tagcatgcaa gcttggtcaa acttttccca gcaaaatgga    2100
agcaaagaca aaagaaactt accaattgat gttttacgtg caaacaacct gaatcttttt    2160
tttatataaa tatatatttt tcaaatagat ttttgattca gctcattatg aaaaacatcc    2220
caaactttaa aatgcgaaat tattggttgg tgtgaagaaa gccagacaac ttctgtttct    2280
tctcttggtg aaataataaa atgcaaatga atcattgtta accacagctg tggctcgttt    2340
gagggattgg ggtggacctg gggtttattt tcagtaaccc agctgcaata cctgtctgta    2400
atatgagaaa aaaaaaatga atctatttaa tcatttctac ttgcagtact gctatgtgct    2460
aagcttaact ggaagccttg gaatgggcat aagttgtatg tcctacattt catcattgtc    2520
ccgggcctgc attgcactgg aaaaaaaaat cgccacctgt tcttacacca gtatttggtt    2580
caagacacca aatgtcttca gcccatggct gaagaacaac agaagagagt caggataaaa    2640
aatacatact gtggtcggca aggtgaggga gatagggata tccaggggaa gagggtgttg    2700
ctgtggccca ctctctgtct aatctcttta cagcaaattg gtaagatttt cagttttact    2760
tctttctact gtttctgctg tctaccttcc ttatattttt ttcctcaaca gttttaaaaa    2820
gaaaaaaagg tctatttttt tttctcctat acttgggcta catttttga ttgtaaaaat     2880 atttgatggc cttttgatga atgtcttcca cagtaaagaa aacttagtgg cttaatttag    2940
gaaacatgtt aacaggacac tatgtttttg aaattgtaac aaaatctaca taaatgattt    3000
acaggttaaa agaataaaaa taaggtaac tttacctttc ttaaatattt cctgccttaa     3060
agagagcatt tccatgactt tagctggtga aagggtttaa tatctgcaga gctttataaa    3120
aatatatttc agtgcatact ggtataatag atgatcatgc agttgcagtt gagttgtatc    3180 acctttttttg tttgtctttt ataatgtctt cagtctgagt gtgcaaagtc aatttgtaat    3240
attttgcaac cctaggattt ttttaaatag atgctgcttg ctatgttttc aaaccttttt    3300
```

```
gagccatagg atccaagcca taaaattctt tatgcatgtt gaattcagtc agaaaagagc    3360
aaggctttgc ttttgaaat tgcaactcaa atgagatggg atgaaatcct atgcagtaa      3420 gcaaaaacag aaccatgaaa atgattgga catacacctt ttcaattgtg caataattg      3480 aaagaatcga taaagttca tctttggaca gaaagccttt aaaaaaaaa tcactccctc     3540 ttccccctcc tcccttattg cagcagccta ctgagaactt tgactgttgc tggtaaatta    3600
gaagctacaa taataattaa gggcagaaat tatacttaaa aagtgcagat ccttgttctt    3660
tgacaatttg tgatgtctga aaaaacagaa cccgaaaagc tatggtgata tgtacaggca    3720
ttatttcaga ctgtaaatgg cttgtgatac tcttgatact tgttttcaaa tatgtttact    3780
aactgtagtg ttgactgcct gaccaaattc cagtgaaact tatacaccaa atattcttc    3840 ctaggtccta tttgctagta acatgagcac tgtgattggc tggctataac caccccagtt    3900
aaaccatttt cataattagt agtgccagca atagtggcaa acactgcaac ttttctgcat    3960
aaaaagcatt aattgcacag ctaccatcca cacaaataca tagttttct gacttcacat     4020 ttattaagtg aaatttattt cccatgctgt ggaaagttta ttgagaactt gtttcataaa    4080
tggatatccc tactatgact gtgaaaacat gtcaagtgtc acattagtgt cacagacaga    4140
aagcacacac ctatgcaata tggcttatct atatttattt gtaaaaatcc aagcatagtt    4200
taaaatatga tgtcgatatt actagtcttg agtttctaag agggttcttt atgttatacc    4260
aggtaagtgt ataaaagaga ttaagtgctt tttttcatc acttgattat tttcttaaa     4320 atcagctatt acaggatatt tttttatttt atacatgctg ttttttaatt aaaatataat    4380
cactgaagtt tactaatttg attttataag gtttgtagca ttacagaata actaaactgg    4440
gatttataaa ccagctgtga ttaacaatgt aaagtattaa ttattgaact ttgaaccaga    4500 ttttaggaa aattatgttc ttttccccc tttatggtct taactaattt gaatccttca     4560
agaaggattt ttccatacta ttttttaaga tagaagataa tttgtgggca ggggtggagg    4620
atgcatgtat gatactccat aaattcaaca ttctttacta taggtaatga atgattataa    4680
acaagatgca tcttagatag tattaatata ctgagccttg gattatatat ttaatatagg    4740
acctattttg aatattcagt taatcatatg gttcctagct tacaagggct agatctaaga    4800
ttattcccat gagaaatgtt gaatttatga agaatagatt ttaaggcttt gaaaatggtt    4860
aatttctcaa aaacatcaat gtccaaacat ctacctttt tcataggagt agacactagc     4920
aagctggaca aactatcaca aaagtatttg tcacacataa cctgtggtct gttgctgatt    4980
aatacagtac ttttcttgt gtgattctta acattatagc acaagtatta tctcagtgga    5040
ttatccggaa taacatctga aagatgggtt catctatgtt tgtgtttgct ctttaaacta    5100
ttgtttctcc tatcccaagt tcgctttgca tctatcagta aataaaattc ttcagctgcc    5160
ttattaggag tgctatgagg gtaacacctg ttctgctttt catcttgtat ttagttgact    5220
gtattatttg atttcggatt gaatgaatgt aaatagaaat taaatgcaaa tttgaatgaa    5280 cataaaaaa aaaaaaaa                                                    5299
```

<210> SEQ ID NO 30
<211> LENGTH: 502
<212> TYPE: PRT
<213> ORGANISM: Homo sapiens
<400> SEQUENCE: 30

```
Met Arg Arg Arg Arg Arg Arg Asp Gly Phe Tyr Pro Ala Pro Asp Phe
1               5                   10                  15
```

```
Arg Asp Arg Glu Ala Glu Asp Met Ala Gly Val Phe Asp Ile Asp Leu
            20                  25                  30

Asp Gln Pro Glu Asp Ala Gly Ser Glu Asp Glu Leu Glu Glu Gly Gly
            35                  40                  45

Gln Leu Asn Glu Ser Met Asp His Gly Gly Val Gly Pro Tyr Glu Leu
 50                  55                  60

Gly Met Glu His Cys Glu Lys Phe Glu Ile Ser Glu Thr Ser Val Asn
 65                  70                  75                  80

Arg Gly Pro Glu Lys Ile Arg Pro Glu Cys Phe Glu Leu Leu Arg Val
            85                  90                  95

Leu Gly Lys Gly Gly Tyr Gly Lys Ala Met Ile Val Arg Asn Ala Lys
            100                 105                 110

Asp Thr Ala His Thr Lys Ala Glu Arg Asn Ile Leu Glu Glu Val Lys
            115                 120                 125

His Pro Phe Ile Val Asp Leu Ile Tyr Ala Phe Gln Thr Gly Gly Lys
            130                 135                 140

Leu Tyr Leu Ile Leu Glu Tyr Leu Ser Gly Gly Glu Leu Phe Met Gln
145                 150                 155                 160

Leu Glu Arg Glu Gly Ile Phe Met Glu Asp Thr Ala Cys Phe Tyr Leu
                    165                 170                 175

Ala Glu Ile Ser Met Ala Leu Gly His Leu His Gln Lys Gly Ile Ile
                    180                 185                 190

Tyr Arg Asp Leu Lys Pro Glu Asn Ile Met Leu Asn His Gln Gly His
            195                 200                 205

Val Lys Leu Thr Asp Phe Gly Leu Cys Lys Glu Ser Ile His Asp Gly
 210                 215                 220

Thr Val Thr His Thr Phe Cys Gly Thr Ile Glu Tyr Met Ala Pro Glu
225                 230                 235                 240

Ile Leu Met Arg Ser Gly His Asn Arg Ala Val Asp Trp Trp Ser Leu
                    245                 250                 255

Gly Ala Leu Met Tyr Asp Met Leu Thr Gly Ala Pro Pro Phe Thr Gly
                    260                 265                 270

Glu Asn Arg Lys Lys Thr Ile Asp Lys Ile Leu Lys Cys Lys Leu Asn
            275                 280                 285

Leu Pro Pro Tyr Leu Thr Gln Glu Ala Arg Asp Leu Leu Lys Lys Leu
 290                 295                 300

Leu Lys Arg Asn Ala Ala Ser Arg Leu Gly Ala Gly Pro Gly Asp Ala
305                 310                 315                 320

Gly Glu Val Gln Ala His Pro Phe Phe Arg His Ile Asn Trp Glu Glu
                    325                 330                 335

Leu Leu Ala Arg Lys Val Glu Pro Pro Phe Lys Pro Leu Leu Gln Ser
                    340                 345                 350

Glu Glu Asp Val Ser Gln Phe Asp Ser Lys Phe Thr Arg Gln Thr Pro
            355                 360                 365

Val Asp Ser Pro Asp Asp Ser Thr Leu Ser Glu Ser Ala Asn Gln Val
 370                 375                 380

Phe Leu Gly Phe Thr Tyr Val Ala Pro Ser Val Leu Glu Ser Val Lys
385                 390                 395                 400

Glu Lys Phe Ser Phe Glu Pro Lys Ile Arg Ser Pro Arg Arg Phe Ile
                    405                 410                 415

Gly Ser Pro Arg Thr Pro Val Ser Pro Val Lys Phe Ser Pro Gly Asp
                    420                 425                 430

Phe Trp Gly Arg Gly Ala Ser Ala Ser Thr Ala Asn Pro Gln Thr Pro
```

|     |     |     |     | 435 |     |     |     | 440 |     |     |     | 445 |     |
| --- | --- | --- | --- | --- | --- | --- | --- | --- | --- | --- | --- | --- | --- |
| Val | Glu | Tyr | Pro | Met | Glu | Thr | Ser | Gly | Ile | Glu | Gln | Met | Asp | Val | Thr |
|     | 450 |     |     |     |     | 455 |     |     |     |     | 460 |     |     |

Met Ser Gly Glu Ala Ser Ala Pro Leu Pro Ile Arg Gln Pro Asn Ser
465                 470                 475                 480

Gly Pro Tyr Lys Lys Gln Ala Phe Pro Met Ile Ser Lys Arg Pro Glu
                485                 490                 495

His Leu Arg Met Asn Leu
            500

<210> SEQ ID NO 31
<211> LENGTH: 3112
<212> TYPE: DNA
<213> ORGANISM: Homo sapiens

<400> SEQUENCE: 31

```
ccccggactc tgcctgctcc tgccatggtg ccgtggccct gctgggcgga tggagcagga     60
tcccaagccg ccccgtctgc ggctctgggc cctgatcccc tggcttccca ggaagcagcg    120
gcccaggatc agccagacct ctctgcctgt ccctggccct ggctctggcc cccagcggga    180
ctcggatgag ggcgtcctca aggagatctc catcacgcac cacgtcaagg ctggctctga    240
gaaggctgat ccatcccatt tcgagctcct caaggttctg ggccagggat cctttggcaa    300
agtcttcctg gtgcggaaag tcaccccgcc tgacagtggg cacctgtatg ctatgaaggt    360
gctgaagaag gcaacgctga agtacgtgga ccgcgtccgg accaagatgg agagagacat    420
cctggctgat gtaaatcacc cattcgtggt gaagctgcac tatgccttcc agaccgaggg    480
caagctctat ctcattctgg acttcctgcg tggtgggac  tcttcacccc ggctctcaaa    540
agaggtgatg ttcacggagg aggatgtgaa gttttacctg ccgagctggc tctgggcct    600
ggatcacctg cacagcctgg gtatcattta cagagacctc aagcctgaga catccttct    660
ggatgaggag ggccacatca aactcactga ctttggcctg agcaaagagg ccattgacca    720
cgagaagaag gcctattctt tctgcgggac agtggagtac atggcccctg aggtcgtcaa    780
ccgccagggc cactcccata gtgcggactg gtggtcctat ggggtgttga tgtttgagat    840
gctgacgggc tccctgccct tcagggggaa ggaccggaag gagaccatga cactgattct    900
gaaggcgaag ctaggcatgc ccagtttct gagcactgaa gcccagagcc tcttgcgggc    960
cctgttcaag cggaatcctg ccaaccggct cggctccggc cctgatgggg cagaggaaat   1020
caagcggcat gtcttctact ccaccattga ctggaataag ctataccgtc gtgagatcaa   1080
gccacccttc aagccagcag tggctcagcc tgatgacacc ttctactttg acaccgagtt   1140
cacgtcccgc acacccaagg attcccccag catcccccc agcgctgggg cccatcagct   1200
gttccggggc ttcagcttcg tggccaccgg cctgatggaa gacgacggca gcctcgtgc   1260
cccgcaggca cccctgcact cggtggtaca gcaactccat gggaagaacc tggttttag   1320
tgacggctac gtggtaaagg agacaattgg tgtgggctcc tactctgagt gcaagcgctg   1380
tgtccacaag gccaccaaca tggagtatgc tgtcaaggtc attgataaga gcaagcggga   1440
tccttcagaa gagattgaga ttcttctgcg gtatggccag cacccccaaca tcatcactct   1500
gaaagatgtg tatgatgatg caaacacgt gtacctggtg acagagctga tgcggggtgg   1560
ggagctgctg acaagatcc tgcggcagaa gttcttctca gagcgggagg ccagctttgt   1620
cctgcacacc attggcaaaa ctgtggagta tctgcactca cagggggttg tgcacaggga   1680
cctgaagccc agcaacatcc tgtatgtgga cgagtccggg aatcccgagt gcctgcgcat   1740
```

```
ctgtgacttt ggttttgcca aacagctgcg ggctgagaat gggctcctca tgacaccttg    1800
ctacacagcc aactttgtgg cgcctgaggt gctgaagcgc cagggctacg atgaaggctg    1860
cgacatctgg agcctgggca ttctgctgta caccatgctg gcaggatata ctccatttgc    1920
caacggtccc agtgacacac cagaggaaat cctaacccgg atcggcagtg ggaagtttac    1980
cctcagtggg ggaaattgga acacagtttc agagacagcc aaggacctgg tgtccaagat    2040
gctacacgtg gatccccacc agcgcctcac agctaagcag gttctgcagc atccatgggt    2100
cacccagaaa gacaagcttc cccaaagcca gctgtcccac caggacctac agcttgtgaa    2160
gggagccatg gctgccacgt actccgcact caacagctcc aagcccaccc ccagctgaa    2220 gcccatcgag tcatccatcc tggcccagcg gcgagtgagg aagttgccat ccaccaccct    2280
gtgaggcacc agggcattcg ggccacaggg cggtgctagc ttgacacagt cagcatgctt    2340
cccagaggga gcaggccgga accacagggc cagagggagc tggaacccga ggggccgggg    2400
aagctgccag cccagaacac ccctaatgag ggtgtgagaa gtgccttctc cttccccagg    2460
atggactctt ctcggctcag gctctgctgg tggaaagcga ttcactgtat aaactttttt    2520
ttatgaaaaa aatggcatca accaccatgg attttttacaa gatccatttg cctttctggg    2580
agcagaaaca gccattgcgg ccccaggagg ggaactgagt cacgctgggg ctctctgaga    2640
ctctttagag cagctttggg atcccaccct ggggacccce acgattggcc acctgtagcc    2700
atctgcacac acctccgaga cagtccagtg tcacctctct cagagcatct ggctgtttag    2760
cagaactcat tctatccca atcagctcct tttccgttct gttctgctgg gagttctaga    2820
accacttcct gctacaggag gggtctcatg tcctgctggc ttccagcttc aggcaccagc    2880
atccaccttg gctctgccag tggatcccct gcggtcaggc tgggcagccc cagagagagg    2940
atgtggaaag cacttttttgg ctgacttcat ctggggttgg caacaggaca gagttcacag    3000
gaggccagtg ggcgggccat gagggacagg gtcttttttc atttcttcct cagctggtta    3060
ctcagggttc atctgtccat ggcctttcta ataaactgtt gagttgaagc ac            3112
```

<210> SEQ ID NO 32
<211> LENGTH: 744
<212> TYPE: PRT
<213> ORGANISM: Homo sapiens

<400> SEQUENCE: 32

```
Met Glu Gln Asp Pro Lys Pro Pro Arg Leu Arg Leu Trp Ala Leu Ile
1               5                   10                  15

Pro Trp Leu Pro Arg Lys Gln Arg Pro Arg Ile Ser Gln Thr Ser Leu
            20                  25                  30

Pro Val Pro Gly Pro Gly Ser Gly Pro Gln Arg Asp Ser Asp Glu Gly
        35                  40                  45

Val Leu Lys Glu Ile Ser Ile Thr His His Val Lys Ala Gly Ser Glu
    50                  55                  60

Lys Ala Asp Pro Ser His Phe Glu Leu Leu Lys Val Leu Gly Gln Gly
65                  70                  75                  80

Ser Phe Gly Lys Val Phe Leu Val Arg Lys Val Thr Arg Pro Asp Ser
                85                  90                  95

Gly His Leu Tyr Ala Met Lys Val Leu Lys Lys Ala Thr Leu Lys Val
            100                 105                 110

Arg Asp Arg Val Arg Thr Lys Met Glu Arg Asp Ile Leu Ala Asp Val
        115                 120                 125
```

```
Asn His Pro Phe Val Val Lys Leu His Tyr Ala Phe Gln Thr Glu Gly
    130                 135                 140

Lys Leu Tyr Leu Ile Leu Asp Phe Leu Arg Gly Gly Asp Leu Phe Thr
145                 150                 155                 160

Arg Leu Ser Lys Glu Val Met Phe Thr Glu Glu Asp Val Lys Phe Tyr
                165                 170                 175

Leu Ala Glu Leu Ala Leu Gly Leu Asp His Leu His Ser Leu Gly Ile
            180                 185                 190

Ile Tyr Arg Asp Leu Lys Pro Glu Asn Ile Leu Leu Asp Glu Glu Gly
        195                 200                 205

His Ile Lys Leu Thr Asp Phe Gly Leu Ser Lys Glu Ala Ile Asp His
    210                 215                 220

Glu Lys Lys Ala Tyr Ser Phe Cys Gly Thr Val Glu Tyr Met Ala Pro
225                 230                 235                 240

Glu Val Val Asn Arg Gln Gly His Ser His Ser Ala Asp Trp Trp Ser
                245                 250                 255

Tyr Gly Val Leu Met Phe Glu Met Leu Thr Gly Ser Leu Pro Phe Gln
            260                 265                 270

Gly Lys Asp Arg Lys Glu Thr Met Thr Leu Ile Leu Lys Ala Lys Leu
        275                 280                 285

Gly Met Pro Gln Phe Leu Ser Thr Glu Ala Gln Ser Leu Leu Arg Ala
    290                 295                 300

Leu Phe Lys Arg Asn Pro Ala Asn Arg Leu Gly Ser Gly Pro Asp Gly
305                 310                 315                 320

Ala Glu Glu Ile Lys Arg His Val Phe Tyr Ser Thr Ile Asp Trp Asn
                325                 330                 335

Lys Leu Tyr Arg Arg Glu Ile Lys Pro Pro Phe Lys Pro Ala Val Ala
            340                 345                 350

Gln Pro Asp Asp Thr Phe Tyr Phe Asp Thr Glu Phe Thr Ser Arg Thr
        355                 360                 365

Pro Lys Asp Ser Pro Gly Ile Pro Pro Ser Ala Gly Ala His Gln Leu
    370                 375                 380

Phe Arg Gly Phe Ser Phe Val Ala Thr Gly Leu Met Glu Asp Asp Gly
385                 390                 395                 400

Lys Pro Arg Ala Pro Gln Ala Pro Leu His Ser Val Val Gln Gln Leu
                405                 410                 415

His Gly Lys Asn Leu Val Phe Ser Asp Gly Tyr Val Val Lys Glu Thr
            420                 425                 430

Ile Gly Val Gly Ser Tyr Ser Glu Cys Lys Arg Cys Val His Lys Ala
        435                 440                 445

Thr Asn Met Glu Tyr Ala Val Lys Val Ile Asp Lys Ser Lys Arg Asp
    450                 455                 460

Pro Ser Glu Glu Ile Glu Ile Leu Leu Arg Tyr Gly Gln His Pro Asn
465                 470                 475                 480

Ile Ile Thr Leu Lys Asp Val Tyr Asp Asp Gly Lys His Val Tyr Leu
                485                 490                 495

Val Thr Glu Leu Met Arg Gly Gly Glu Leu Leu Asp Lys Ile Leu Arg
            500                 505                 510

Gln Lys Phe Phe Ser Glu Arg Glu Ala Ser Phe Val Leu His Thr Ile
        515                 520                 525

Gly Lys Thr Val Glu Tyr Leu His Ser Gln Gly Val Val His Arg Asp
    530                 535                 540

Leu Lys Pro Ser Asn Ile Leu Tyr Val Asp Glu Ser Gly Asn Pro Glu
```

```
                    545                 550                 555                 560
Cys Leu Arg Ile Cys Asp Phe Gly Phe Ala Lys Gln Leu Arg Ala Glu
                565                 570                 575
Asn Gly Leu Leu Met Thr Pro Cys Tyr Thr Ala Asn Phe Val Ala Pro
                580                 585                 590
Glu Val Leu Lys Arg Gln Gly Tyr Asp Glu Gly Cys Asp Ile Trp Ser
                595                 600                 605
Leu Gly Ile Leu Leu Tyr Thr Met Leu Ala Gly Tyr Thr Pro Phe Ala
                610                 615                 620
Asn Gly Pro Ser Asp Thr Pro Glu Glu Ile Leu Thr Arg Ile Gly Ser
625                 630                 635                 640
Gly Lys Phe Thr Leu Ser Gly Gly Asn Trp Asn Thr Val Ser Glu Thr
                645                 650                 655
Ala Lys Asp Leu Val Ser Lys Met Leu His Val Asp Pro His Gln Arg
                660                 665                 670
Leu Thr Ala Lys Gln Val Leu Gln His Pro Trp Val Thr Gln Lys Asp
                675                 680                 685
Lys Leu Pro Gln Ser Gln Leu Ser His Gln Asp Leu Gln Leu Val Lys
                690                 695                 700
Gly Ala Met Ala Ala Thr Tyr Ser Ala Leu Asn Ser Ser Lys Pro Thr
705                 710                 715                 720
Pro Gln Leu Lys Pro Ile Glu Ser Ser Ile Leu Ala Gln Arg Arg Val
                725                 730                 735
Arg Lys Leu Pro Ser Thr Thr Leu
                740

<210> SEQ ID NO 33
<211> LENGTH: 7723
<212> TYPE: DNA
<213> ORGANISM: Homo sapiens

<400> SEQUENCE: 33
atgccgctgg cgcagctggc ggacccgtgg cagaagatgg ctgtggagag cccgtccgac      60
agcgctgaga atggacagca aattatggat gaacctatgg agaggaggga gattaaccca     120
caaactgaag aagtcagtat caaagaaatt gcaatcacac atcatgtaaa ggaaggacat     180
gaaaaggcag atccttccca gtttgaactt ttaaaagtat tagggcaggg atcatttgga     240
aaggttttct tagttaaaaa aatctcaggc tctgatgcta ggcagcttta tgccatgaag     300
gtattgaaga aggccacact gaaagttcga gaccgagttc ggacaaaaat ggaacgtgat     360
atcttggtag aggttaatca tccttttatt gtcaagttgc attatgcttt tcaaactgaa     420
gggaagttgt atcttatttt ggattttctc agggaggag aatttgtttac acgcttatcc     480 aaagaggtga tgttcacaga agaagatgtc aaattctact ggctgaact tgcacttgct     540 ttagaccatc tacatagcct gggaataatt tatagagact aaaaccaga aaatatactt     600 cttgatgaag aaggtcacat caagttaaca gatttcggcc taagtaaaga gtctattgac     660
catgaaaaga aggcatattc tttttgtgga actgtggagt atatggctcc agaagtagtt     720
aatcgtcgag gtcatactca gagtgctgac tggtggtctt ttggtgtgtt aatgtttgaa     780
atgcttactg gtacactccc tttccaagga aaagatcgaa agaaacaat gactatgatt     840 cttaaagcca aacttggaat gccacagttt tgagtcctg aagcgcagag tcttttacga     900
atgcttttca agcgaaatcc tgcaaacaga ttaggtgcag gaccagatgg agttgaagaa     960
attaaaagac attcattttt ctcaacgata gactggaata aactgtatag aagagaaatt    1020
```

```
catccgccat ttaaacctgc aacgggcagg cctgaagata cattctatt  tgatcctgag    1080
tttactgcaa aaactcccaa agattcacct ggcattccac ctagtgctaa tgcacatcag    1140
cttttcggg  ggtttagttt tgttgctatt acctcagatg atgaaagcca agctatgcag    1200
acagttggtg tacattcaat tgttcagcag ttacacagga acagtattca gtttactgat    1260
ggatatgaag taaaagaaga tattggagtt ggctcctact ctgtttgcaa gagatgtata    1320
cataaagcta caaacatgga gtttgcagtg aagattattg ataaaagcaa gagagaccca    1380
acagaagaaa ttgaaattct tcttcgttat ggacagcatc caaacattat cactctaaag    1440
gatgtatatg atgatggaaa gtatgtgtat gtagtaacag aacttatgaa aggaggtgaa    1500
ttgctggata aaattcttag acaaaaattt ttctctgaac gagaggccag tgctgtcctg    1560
ttcactataa ctaaaaccgt tgaatatctt cacgcacaag gggtggttca tagagacttg    1620
aaacctagca acattcttta tgtggatgaa tctggtaatc cggaatctat tcgaatttgt    1680
gattttggct ttgcaaaaca gctgagagcg gaaaatggtc ttctcatgac tccttgttac    1740
actgcaaatt ttgttgcacc agaggtttta aaaagacaag gctatgatgc tgcttgtgat    1800
atatggagtc ttggtgtcct actctataca atgcttaccg gttacactcc atttgcaaat    1860
ggtcctgatg atacaccaga ggaaatattg gcacgaatag gtagcggaaa attctcactc    1920
agtggtggtt actggaattc tgtttcagac acagcaaagg acctggtgtc aaagatgctt    1980
catgtagacc ctcatcagag actgactgct gctcttgtgc tcagacatcc ttggatcgtc    2040
cactgggacc aactgccaca ataccaacta acagacagg  atgcaccaca tctagtaaag    2100
ggtgccatgg cagctacata ttctgctttg aaccgtaatc agtcaccagt tttggaacca    2160
gtaggccgct ctactcttgc tcagcggaga ggtattaaaa aaatcacctc aacagccctg    2220
tgaagtgacc tcagtgagat atttggtacc atggtgtaag ctgatagcac aagttctggc    2280
gacaggtagc acgtatctga gagacacctg caagcacaca ctgtcccagc tggtacccat    2340
aatgctgctg ttcctgctgc tgctcctgct ttcctctctt ctcgctttaa atgattgtta    2400
gcaagttaga ttttcctgga gcttcggaag aaatgaaaat ggaaacatga tgaagatata    2460
gtcactgaat caatgagaaa aataatgaac atatgaatac cacctaaaaa tacactgaat    2520
aaagtacacc atatagcatt attttatag gaaatatttc atgtcccta aatattcttt     2580
gttagttata gggatggaca gtttatgtta agcacttagc ttaaacaatc cgtttatatt    2640
agcactgtat cccttgtgcc atccaacatt ttgtatgttt ttgtaaacag ttcatataca    2700
gtacatttct gtactgcttt cttaatgta tacatgcctt gtttaacttg gaatctatta     2760
ttattaatca attgactatt aaatctggtt aaatagttca cctggattaa cagtattgtt    2820
ggacagtcct aaaaatggcc agattgtgga acagctgttg aatgtaatac ttccaaaatg    2880
tacatatctt tccccacgtc tgtttcactg gttcgttcat ttgtttgttt cttaaagtca    2940
ggtgctctgt cagactaacc tagagagctg ttatggtaga gaaagttatc atatgtgtgt    3000
ggcatgaaat caagaataca cctatgaagt tagtccatat actttgcaac tccttagagt    3060
actttttcc  ttaattaagg aagtagtcct tgcacttcta atcttacata gcatccatac    3120
ttagaatttg gcatatcatc tgggattttg ccaatatacg tcaaagccct ttaagagtca    3180
tggtaaggag atgggtgaag gaaaatttag caacaggtaa ttgaagtcct attggatatt    3240
tcatgtttaa atagatattc tatattaaac actaatttaa atgtaataaa ggccaaaggc    3300
ctctgtatga aattggattt aaactttctt attttaggga ataaaacatt attgatcaaa    3360
```

```
cagtatctgt tctaacctaa aattataggt agggcaggct aagtgaacag cattgagtat    3420
tttctgaatc cctcatgata atttatagcc acatactgct tcctttgact tcaggaatga    3480
tcagttttca taatggccac tgggcctgct tagattgcag tattcattat ctgcatctaa    3540
tttggtagtt tccacaatcg tatttgatga aagaaacttc agtccccatt attacctgtg    3600
tctttgccaa gctgcctagc atacatcagt atgtaatgta aaagacatat gagcaagaaa    3660
aaagtgattt aacttacctc atcaagaatg tgcccctaca ggccgggcgc agtggctcac    3720
gcctgtaatc ccagcatttt gggaggccga ggcaggtgga tcacctgagg tcaggagttt    3780
gagaccagcc tggccaacat ggtgaaaccc cgtctctact aaaaaataca aaaattagct    3840
gggcatggtg gcgtgcacct gtaatcctag ctactcagga ggctgaggca ggagaatcgc    3900
ttgaacctgg gaggtggtgg ttgcagtgag ccaagatcac accattgcac tccagcctgg    3960
gtgacagagt gagactctgt ctcaagaagg aaaaaaaaaa aaagaatgt actcatacag     4020 attttttgtta gtcatcatgt aataagccat ttatatcaga aacctttttt cctgccacag    4080
aagctttaaa ttttccccta agagtacaaa gccaagagag tgtggtttat ctaaatgtcc    4140
tgaaatccac ttgtcattcc ttaatttctc ctctatgcaa ttaaagagaa aggggaaatc    4200
tataacattt cttttgccca gtgacacaa aaatgattac tgcatagaaa tcaaatgtaa     4260
gtttagcttc taaatgaaat aatatatagg agggatatca gaatgtctag atagagaaag    4320
tattttcaaa ttcttgaata tatggatgct attaaaagct gctttccatt gcctggaaag    4380
agagcttttt tccctcctct attcagtgtt tcaaactttg gtcatctcaa attattgtca    4440
cttttaaaat gttaatgtca ttctgagcag aaatagatat attttcagat tttttacac    4500 tgatgctact ccgtaattgc ttaggagtat tgtccatcat agtattttag aactagaagt    4560
aaacacataa atccttataa attacccaat ccaactttct catattgcat gtagagaacc    4620
tgagacacat atcaaagtct agaatcctta acttctcccc attttgtttt tttccgcctc    4680
atcacaccat gctgcctttc cctcatatga tcaccaacca gtagctgagt tcaaaaacta    4740
catatttctt gggcagtcct ctactggtat gtgatgccaa cttttatttc tttcgaagat    4800
aattgccttc tttgcctagc caagcagcca atttttattgg agaaaagcaa gttatatgtt    4860
cacaaaatgg aaggctttct acctaaattt atttcatctg tggtcctctt attctcttcc    4920
attgcttttg acatacagtg gaaaaacttg gccaacgatg tgctctaaat atagtgcttg    4980
tgttgggtta acttttccat taatttctca acatcaatta ttcaggcccc tacagttgtg    5040
gtattgaggc ccctaaaggc ttctgccttt caccaattag tgctgccagt tactgaggct    5100
tctcccaaaa ggtatcagtc cagtcttaaa gatatttcat tgtgaaagaa gaaactaaac    5160
tatcaggcct cttttacaaa atgagagatt gaatttaagc ttgtcaagca cgtactggaa    5220
ggtatgaatt acactaccat gtgttttgta tcttcccttt caagtgatga tgttaaatga    5280
aggtaagttt ttcatccttt tttaattttt gttttttata aatcatttca gcttttctg    5340 gtttatagag gtgtcttatt tctaatgcaa cagaccccca actttaacag atttgatatg    5400
gatgcattta ttcacaagca accccaaaag tccaaaatg taataatttt gacaaggccc     5460
aaagttgaga tgctatgaag cttgtgtgtg tgaaagtca gttatgattg tctgagaga     5520 agctgtggtg tgtatgctgt agagtttcca catttcacat gcagtgtact ccaaaaagcg    5580
ggtttgggtc aaccatttcc catctctttt taagaagtga ctgctgttgg ggccagggga    5640
catcatggga ggtggggctg tccagttagc tgtgccctgc accttcagcc caggaaagat    5700
ttgaacagag caaaggcttc aagagagggc agaatgtatt cggcagaaaa gggactcagg    5760
```

```
taagcccagc ctgggatgag agcagaaaag cattcaagat ttgcaggcct tgctatggat    5820
gcgcttaatc accatggagg ccagcaatac ccatctcagc atggctttga tattctctac    5880
ttcctggcct ttaaaaatga cctataattt ttcagtttgc tttactatat tttataaaga    5940
aaattctatc ttatggttga ttgagcattg agacttatga aggcattagg atagatagct    6000
caggaatgta aaggttcaga aaaggtctgt tttctcagat taacaaatat gatggattcc    6060
atggctgacc ttggtgctta accaggagg tttcaatcta gtcctagagt tgtgtccctc      6120
tgaaaggccc aatgccatgt aactaacttt aaactggata tatactttga gccttactta    6180
attcacagat aagttgactt aactcagtat ttttatttca attaatgaaa acagtcctct    6240
tttcaacccc aggttgctta cattttgctg gtctccccaa gtgaccattg gtggagacca    6300
attaatgaag gaatgaaatt cactttattg ggactgtggt attcaacaga gccacactta    6360
accacttttt ccaatgaaga atctccagaa tgataatgcc caaatatgga tggccaagaa    6420
gaatttgtat ctacggtgtg ctttatgtgt ttttgacact gctgtattct gtgtgatcaa    6480
gtgatttgca gctggttcca atgtgactga gtgttctcaa agatttctag taactaagtc    6540
aacttaattt tcttaagcct ggtattacta tcagcctcac atttaccact ttgattctag    6600
tttttttaact gttcataaca gggcataccg agggttggga tgagagccta cttcctacct    6660
cttaaggcac tttcctcatt attttgccat ataatcttga actgcatgat aagctgttta    6720
aatgtccatg acttctccca gagcaactag caaagtatat gacattttga atagagatta    6780
gtggaaagga aaatgtagag atttaagttc agaggtacaa acctcaataa aacctcctta    6840
gagcacatac catgagtaga gtatatgtaa acgtatatga aagagagtc gctataatag      6900
tcctctctaa gtagattagt tcattgtcta atggaagtga acatctttac tcctgttatc    6960
accatagtac tgaatgaact gtataatgag ttttttcaaac aagtatttaa aatagaactt    7020
tcacgtacaa agcaagggca taaagatttt ggtttgtgtt tctgtaagtg tagtttacca    7080
tctaaagctt tggtttttaa ttttaaaaaa agcttcaagg tattgccatt ccttagcatc    7140
cttattgatt atgggtgatg agttttaac tcttaaaatc atatacgtgt attagtttat      7200
cttaactgtt gccctaagca aaagggaagg tatacaccta agggatgtac ttattttgca    7260
ttttggtca tgggtgggaa tggggtgggt gcctacttaa atagttttta aaaagaaaa      7320
aaatcacaaa tattttccta ctgttatata tgatcttcct ttatactagt ttctctctag    7380
taaggcatgc cagaagccca agataccata tcatgaattc ttacatattg tacctttgt      7440
tggtggttaa atcgcatcag atgcttggca ttgctgccat aattataaaa tgcttgtaaa    7500
ggatcaaata tcactaaata ctttaaattg ttttacttaa gagtctaatc tgggaagttt    7560
tcaaatcata ctattaatgt gtaatctaag ctcttcagat gtatccatga ataatcctgg    7620
aacaatattg cttgtattcc tgtcatagaa caggttttgt aatctttaaa agaaatgaaa    7680
atttatataa taaagtttca aatcaatgca aaaaaaaaa aaa                        7723
```

<210> SEQ ID NO 34
<211> LENGTH: 740
<212> TYPE: PRT
<213> ORGANISM: Homo sapiens

<400> SEQUENCE: 34

Met Pro Leu Ala Gln Leu Ala Asp Pro Trp Gln Lys Met Ala Val Glu
1               5                   10                  15

Ser Pro Ser Asp Ser Ala Glu Asn Gly Gln Gln Ile Met Asp Glu Pro

-continued

```
                20                  25                  30
Met Gly Glu Glu Glu Ile Asn Pro Gln Thr Glu Glu Val Ser Ile Lys
            35                  40                  45
Glu Ile Ala Ile Thr His His Val Lys Glu Gly His Glu Lys Ala Asp
        50                  55                  60
Pro Ser Gln Phe Glu Leu Leu Lys Val Leu Gly Gln Gly Ser Phe Gly
65                  70                  75                  80
Lys Val Phe Leu Val Lys Lys Ile Ser Gly Ser Asp Ala Arg Gln Leu
                85                  90                  95
Tyr Ala Met Lys Val Leu Lys Lys Ala Thr Leu Lys Val Arg Asp Arg
            100                 105                 110
Val Arg Thr Lys Met Glu Arg Asp Ile Leu Val Glu Val Asn His Pro
        115                 120                 125
Phe Ile Val Lys Leu His Tyr Ala Phe Gln Thr Glu Gly Lys Leu Tyr
        130                 135                 140
Leu Ile Leu Asp Phe Leu Arg Gly Gly Asp Leu Phe Thr Arg Leu Ser
145                 150                 155                 160
Lys Glu Val Met Phe Thr Glu Glu Asp Val Lys Phe Tyr Leu Ala Glu
                165                 170                 175
Leu Ala Leu Ala Leu Asp His Leu His Ser Leu Gly Ile Ile Tyr Arg
            180                 185                 190
Asp Leu Lys Pro Glu Asn Ile Leu Leu Asp Glu Glu Gly His Ile Lys
        195                 200                 205
Leu Thr Asp Phe Gly Leu Ser Lys Glu Ser Ile Asp His Glu Lys Lys
        210                 215                 220
Ala Tyr Ser Phe Cys Gly Thr Val Glu Tyr Met Ala Pro Glu Val Val
225                 230                 235                 240
Asn Arg Arg Gly His Thr Gln Ser Ala Asp Trp Trp Ser Phe Gly Val
                245                 250                 255
Leu Met Phe Glu Met Leu Thr Gly Thr Leu Pro Phe Gln Gly Lys Asp
            260                 265                 270
Arg Lys Glu Thr Met Thr Met Ile Leu Lys Ala Lys Leu Gly Met Pro
        275                 280                 285
Gln Phe Leu Ser Pro Glu Ala Gln Ser Leu Leu Arg Met Leu Phe Lys
        290                 295                 300
Arg Asn Pro Ala Asn Arg Leu Gly Ala Gly Pro Asp Gly Val Glu Glu
305                 310                 315                 320
Ile Lys Arg His Ser Phe Phe Ser Thr Ile Asp Trp Asn Lys Leu Tyr
                325                 330                 335
Arg Arg Glu Ile His Pro Pro Phe Lys Pro Ala Thr Gly Arg Pro Glu
            340                 345                 350
Asp Thr Phe Tyr Phe Asp Pro Glu Phe Thr Ala Lys Thr Pro Lys Asp
        355                 360                 365
Ser Pro Gly Ile Pro Pro Ser Ala Asn Ala His Gln Leu Phe Arg Gly
        370                 375                 380
Phe Ser Phe Val Ala Ile Thr Ser Asp Asp Glu Ser Gln Ala Met Gln
385                 390                 395                 400
Thr Val Gly Val His Ser Ile Val Gln Gln Leu His Arg Asn Ser Ile
                405                 410                 415
Gln Phe Thr Asp Gly Tyr Glu Val Lys Glu Asp Ile Gly Val Gly Ser
            420                 425                 430
Tyr Ser Val Cys Lys Arg Cys Ile His Lys Ala Thr Asn Met Glu Phe
        435                 440                 445
```

```
Ala Val Lys Ile Ile Asp Lys Ser Lys Arg Asp Pro Thr Glu Glu Ile
            450                 455                 460
Glu Ile Leu Leu Arg Tyr Gly Gln His Pro Asn Ile Ile Thr Leu Lys
465                 470                 475                 480
Asp Val Tyr Asp Asp Gly Lys Tyr Val Tyr Val Thr Glu Leu Met
                485                 490                 495
Lys Gly Gly Glu Leu Leu Asp Lys Ile Leu Arg Gln Lys Phe Phe Ser
                500                 505                 510
Glu Arg Glu Ala Ser Ala Val Leu Phe Thr Ile Thr Lys Thr Val Glu
            515                 520                 525
Tyr Leu His Ala Gln Gly Val Val His Arg Asp Leu Lys Pro Ser Asn
            530                 535                 540
Ile Leu Tyr Val Asp Glu Ser Gly Asn Pro Glu Ser Ile Arg Ile Cys
545                 550                 555                 560
Asp Phe Gly Phe Ala Lys Gln Leu Arg Ala Glu Asn Gly Leu Leu Met
                565                 570                 575
Thr Pro Cys Tyr Thr Ala Asn Phe Val Ala Pro Glu Val Leu Lys Arg
            580                 585                 590
Gln Gly Tyr Asp Ala Ala Cys Asp Ile Trp Ser Leu Gly Val Leu Leu
            595                 600                 605
Tyr Thr Met Leu Thr Gly Tyr Thr Pro Phe Ala Asn Gly Pro Asp Asp
610                 615                 620
Thr Pro Glu Glu Ile Leu Ala Arg Ile Gly Ser Gly Lys Phe Ser Leu
625                 630                 635                 640
Ser Gly Gly Tyr Trp Asn Ser Val Ser Asp Thr Ala Lys Asp Leu Val
                645                 650                 655
Ser Lys Met Leu His Val Asp Pro His Gln Arg Leu Thr Ala Ala Leu
                660                 665                 670
Val Leu Arg His Pro Trp Ile Val His Trp Asp Gln Leu Pro Gln Tyr
            675                 680                 685
Gln Leu Asn Arg Gln Asp Ala Pro His Leu Val Lys Gly Ala Met Ala
            690                 695                 700
Ala Thr Tyr Ser Ala Leu Asn Arg Asn Gln Ser Pro Val Leu Glu Pro
705                 710                 715                 720
Val Gly Arg Ser Thr Leu Ala Gln Arg Arg Gly Ile Lys Lys Ile Thr
                725                 730                 735
Ser Thr Ala Leu
            740

<210> SEQ ID NO 35
<211> LENGTH: 5735
<212> TYPE: DNA
<213> ORGANISM: Homo sapiens

<400> SEQUENCE: 35
gcgtcccttg gcttccgaca tcccgtctgg ccgtccccct gtgccggtcc gagcctctgt      60
ttatttcctt tcctactatc aatactcgac cagcagaaaa ggaaagttta aaaatgccaa     120
tcgcacagtt gctggaacta tggaaaaaga tcgaggtgga gcctatggaa atagagacca     180
cagaggagga tctcaacctg gatgtggagc ccaccacaga agacactgca gaagaagaag     240
aaggcgtcgt gaaggagata gacatcagcc atcatgtgaa ggagggcttt gagaaggcag     300
atccttccca gtttgagctg ctgaaggttt aggacaagg atcctatgga aaggtgttcc     360
tggtgaggaa ggtgaagggg tccgacgctg ggcagctcta cgccatgaag gtccttaaga     420
```

| | |
|---|---|
| aagccaccct aaaagttcgg gaccgagtga gatcgaagat ggagagagac atcttggcag | 480 |
| aagtgaatca ccccttcatt gtgaagcttc attatgcctt tcagacggaa ggaaagctct | 540 |
| acctgatcct ggacttcctg cggggagggg acctcttcac ccggctctcc aaagaggtca | 600 |
| tgttcacgga ggaggatgtc aagttctacc tggctgagct ggccttggct ttagaccatc | 660 |
| tccacagcct ggggatcatc tacagagatc tgaagcctga aacatcctc ctggatgaag | 720 |
| aggggcacat taagatcaca gatttcggcc tgagtaagga ggccattgac cacgacaaga | 780 |
| gagcgtactc cttctgcggg acgatcgagt acatggcgcc cgaggtggtg aaccggcgag | 840 |
| gacacacgca gagtgccgac tggtggtcct tcggcgtgct catgtttgag atgctcacgg | 900 |
| ggtccctgcc gttccagggg aaggacagga aggagaccat ggctctcatc ctcaaagcca | 960 |
| agctggggat gccgcagttc ctcagtgggg aggcacagag tttgctgcga gctctcttca | 1020 |
| aacggaaccc ctgcaaccgg ctgggtgctg gcattgacgg agtggaggaa attaagcgcc | 1080 |
| atcccttctt tgtgaccata gactggaaca cgctgtaccg gaaggagatc aagccaccgt | 1140 |
| tcaaaccagc agtgggcagg cctgaggaca ccttccactt tgaccccgag ttcacagcgc | 1200 |
| ggacgcccac agactctcct ggcgtccccc cgagtgcaaa cgctcatcac ctgtttagag | 1260 |
| gattcagctt tgtggcctca agcctgatcc aggagccctc acagcaagat ctgcacaaag | 1320 |
| tcccagttca cccaatcgtg cagcagttac acgggaacaa catccacttc accgatggct | 1380 |
| acgagatcaa ggaggacatc ggggtgggct cctactcagt gtgcaagcga tgtgtgcata | 1440 |
| aagccacaga caccgagtat gccgtgaaga tcattgataa gagcaagaga gacccctcgg | 1500 |
| aagagattga gatcctcctg cggtacggcc agcacccgaa catcatcacc ctcaaggatg | 1560 |
| tctatgatga tggcaagttt gtgtacctgg taatggagct gatgcgtggt ggggagctcc | 1620 |
| tggaccgcat cctccggcag agatacttct cggagcgcga agccagtgac gtcctgtgca | 1680 |
| ccatcaccaa gaccatggac tacctccatt cccaggggt tgttcatcga gacctgaagc | 1740 |
| cgagtaacat cctgtacagg gatgagtcgg ggagcccaga atccatccga gtctgcgact | 1800 |
| tcggctttgc caagcagctg cgcgcgggga acgggctgct catgacaccc tgctacacgg | 1860 |
| ccaatttcgt ggccccggag gtcctgaagc gtcaaggcta tgatgcggcg tgtgacatct | 1920 |
| ggagtttggg gatcctgttg tacaccatgc tggcaggatt tacccctttt gcaaatgggc | 1980 |
| cagacgatac ccctgaggag attctggcgc ggatcggcag tgggaagtat gccctttctg | 2040 |
| ggggaaactg ggactcgata tctgacgcag ctaaagacgt cgtgtccaag atgctccacg | 2100 |
| tggaccctca tcagcgcctg acggcgatgc aagtgctcaa acaccgtgg gtggtcaaca | 2160 |
| gagagtacct gtccccaaac cagctcagcc gacaggacgt gcacctggtg aagggcgcga | 2220 |
| tggccgccac ctactttgct ctaaacagaa cacctcaggc cccgcggctg gagcccgtgc | 2280 |
| tgtcatccaa cctggctcag cgcagaggca tgaagagact cacgtccacg cggctgtagc | 2340 |
| gggtgggacc ctggccccag cgtcccctgc cagcatcctc gtgggctcac agaccccggc | 2400 |
| ctcggagccc gtctggcacc cagagtgacc acaagtccag cagggaggcg cgcccgccc | 2460 |
| tcgccgtgtc cgtgttttct ttttcagccc cggagagggt cctgacctgg ggcttctcc | 2520 |
| aagcctcact gcgccagcct ccccgcccgc tctcttttct cccaagcgaa accaaatgcg | 2580 |
| cccccttcacc tcgcgtgccc gtgcgaggcc gggggcttct ttcagagccc gcgggtcctc | 2640 |
| tcatacatgg cttctgtttc tgccgagaga tctgttttcc aattatgaag ccggtcggtt | 2700 |
| tggtcagact cccgacaccc acgtcccagg taccggtgg gaaagtggca gtgcgagggc | 2760 |

```
gcagccattg gtggttgcag ggccccagag ggctggggtg acctggcatc ccggggctcc    2820
ccacgggctg gatgacgggg ttggcactgt ggcgtccagg aggagatgcc tggttctgcc    2880
caaaataatc caaagagccg tttcctcctc gcccttcagt ttttgcctga ggtgctgggt    2940
agcccatcct ttcctctgtc ccagattcaa atgaggagta agagcccaga cgagaggaag    3000
gcaggctgga tctttgcctt gagagctccg tgtcaccagg atggaagggg gtgcctctcg    3060
gaggagcctg tgtccacctc cagtctcggc tttccccggg gggccaagcg cactgggctg    3120
ccgtctgtcc ccagctcccg tggccacaca gctatctgga ggctttgcag ggagtcgtgg    3180
gttctcgcac ctgctcagcc ctgtgtcggc ttcctgtgtg ctcacctaaa gctgtggttt    3240
tgctgtgttc acttcgattt ttctggtctg tggagaaact gtgaattgga gaaatggagc    3300
tctgtggctt cccacccaaa ccttctcagt ccagctggag ctggaggga  gacacaggcc    3360 ccacccagca gactgagggg cagaggcaca ggtgggaggg cagcggagat cagcgtggac    3420
aggagcgatg cactttgtag atgctgtggc tttgtgttgc gttttgtgtc tctgttgcac    3480
agatctgttt tttcacactg atccgtattc ccctgggtgt gcacacaggg cgggtgtggg    3540
gcatttaggc catgctgtgc tctacttcat tgagtaaaat cgagtgagag gttccgggca    3600
gcaggatcga cgcccagtcc agccggcaga gggaacacac gggtccttca ttgtcctgta    3660
agggtgttga agatgctccc tggcggcccc caagcagact agatgggagg aggcgccgct    3720
cagcccctca ccctgcatca ctgaagagcg gcgcctctgc agcaagcagg gcttcaggag    3780
gtgcccgctg ccacagcca  ggttttccct aagaagatgt tattttgttg ggttttgttc    3840
cccctccatc tcgattctcg tacccaacta aaaaaaaaaa aataaagaaa aaatgtgctg    3900
cgttctgaaa ataactcct  tagcttggtc tgattgtttt cagaccttaa aatataaact    3960
tgtttcacaa gctttaatcc atgtggattt tttttttctt agagaaccac aaaacataaa    4020
aggagcaagt cggactgaat acctgtttcc atagtgccca cagggtattc ctcacatttt    4080
ctccatagaa gatgcttttt cccaaggcta gaacgacttc caccatgatg aatttgcttt    4140
ttaggtctta attatttcac ttcttttag  aaacttagga agaagtggat aatcctgagg    4200
tcacacaatc tgtcctccca gaaatgaaca aaagtcatca cctttctgc  ttgctacaca    4260 ggcaacgatt cccccatcag ctgcccggac cctttggcct ggcttggtgt gcaggcctgt    4320
ctgtttgctt aaagtcagtg ggttctggtg caggagtga  gaagtggggg aagtgaaagg    4380
gaaagcatcc gtgagaaagc ggccacggtt ttccctcctt gtgtgcccat ggggcaccag    4440
ctcatggtct ttttcagtca tcccagtttg tacagactta gcttctgaac tctaagaatg    4500
ccaaagggac cgacgagact ccccatcaca gcgagctctg tccttacatg tatttgatgt    4560
gcatcagcgg aggagaacac tggcttggcc ctgctccgct gagtgtctgt gaaataacctc   4620 tactttccct cccatatcca gaacaaaatg atacttgaca tccttccaca aaagtcagcc    4680
taaagaagtt atggtatcat atgttaaact aagctttcaa aaaccttagt gaaatagcaa    4740
gtgactgctt tcaagcagca gtcgacatgt aaatgaaggt gttcttagaa ttcgcatttt    4800
gccagctcag cgcacctcca caacgaatga aatgctccgt atgatttgca caaatgacat    4860
agacctcccc aaaagttaac tggctctcct tcctcacaca gttcatcata acccaacccc    4920 ccaccccgg  gtcatgaaaa tcacagaact tataaacaca ttgaacccta gatctcaggc    4980
ttcctgacct accgccagtg gccccttgct ggccacccta tagggtcctc cttccctggc    5040 agcccccat  gtgggagaaa tacctgattc tcccaatctg cagtgggaga gctttgctga    5100
attccatccc aaagtcaaac atgggcaaga ggtgaggatt tcacttttac cctcaagtcc    5160
```

```
gatttgtctg tgattttaaa ctaactgtgt atgtattgat gtttggaaga ttgtttgaat    5220
tttaaagtga taatagtact taatgttatc cagtattgtt cattaaatgg tgttatccta    5280
aagctgcact tgggattttt acctaacgct ttactgattc tctcaagcac atggcaaagt    5340
ttgatttgca ctccgttcat ttctgacacg ttttgctgcc tcctaccttt ctaagcgtca    5400
tgcaaattcg agaatggaga aggacgctgc cggtccctga gcggtgtgga gagggcggaa    5460
ggtggactcc agcgcagctt gaggggctga ggacggaggc tgcagcatct gtgtcgttct    5520
actgagcacg cttctctgcc tcgctcctga ctcagcactt tgttcactgg ctcagcagtt    5580
atgtttacac atcatttta tgttcctgct ttgtaattca tgtttgagat gggtggccac    5640
tgtacagata tttattacgc tttccagact ttctgaatag attttttttga ataaacatgg    5700 ttttatgaag tgtaatcttt ttctagccta acaat                               5735
```

<210> SEQ ID NO 36
<211> LENGTH: 741
<212> TYPE: PRT
<213> ORGANISM: Homo sapiens

<400> SEQUENCE: 36

```
Met Pro Ile Ala Gln Leu Leu Glu Leu Trp Lys Lys Ile Glu Val Glu
1               5                   10                  15

Pro Met Glu Ile Glu Thr Thr Glu Glu Asp Leu Asn Leu Asp Val Glu
            20                  25                  30

Pro Thr Thr Glu Asp Thr Ala Glu Glu Glu Gly Val Val Lys Glu
        35                  40                  45

Ile Asp Ile Ser His His Val Lys Glu Gly Phe Glu Lys Ala Asp Pro
    50                  55                  60

Ser Gln Phe Glu Leu Leu Lys Val Leu Gly Gln Gly Ser Tyr Gly Lys
65                  70                  75                  80

Val Phe Leu Val Arg Lys Val Lys Gly Ser Asp Ala Gly Gln Leu Tyr
                85                  90                  95

Ala Met Lys Val Leu Lys Lys Ala Thr Leu Lys Val Arg Asp Arg Val
            100                 105                 110

Arg Ser Lys Met Glu Arg Asp Ile Leu Ala Glu Val Asn His Pro Phe
        115                 120                 125

Ile Val Lys Leu His Tyr Ala Phe Gln Thr Glu Gly Lys Leu Tyr Leu
    130                 135                 140

Ile Leu Asp Phe Leu Arg Gly Gly Asp Leu Phe Thr Arg Leu Ser Lys
145                 150                 155                 160

Glu Val Met Phe Thr Glu Glu Asp Val Lys Phe Tyr Leu Ala Glu Leu
                165                 170                 175

Ala Leu Ala Leu Asp His Leu His Ser Leu Gly Ile Ile Tyr Arg Asp
            180                 185                 190

Leu Lys Pro Glu Asn Ile Leu Leu Asp Glu Glu Gly His Ile Lys Ile
        195                 200                 205

Thr Asp Phe Gly Leu Ser Lys Glu Ala Ile Asp His Asp Lys Arg Ala
    210                 215                 220

Tyr Ser Phe Cys Gly Thr Ile Glu Tyr Met Ala Pro Glu Val Val Asn
225                 230                 235                 240

Arg Arg Gly His Thr Gln Ser Ala Asp Trp Trp Ser Phe Gly Val Leu
                245                 250                 255

Met Phe Glu Met Leu Thr Gly Ser Leu Pro Phe Gln Gly Lys Asp Arg
            260                 265                 270
```

```
Lys Glu Thr Met Ala Leu Ile Leu Lys Ala Lys Leu Gly Met Pro Gln
            275                 280                 285

Phe Leu Ser Gly Glu Ala Gln Ser Leu Leu Arg Ala Leu Phe Lys Arg
        290                 295                 300

Asn Pro Cys Asn Arg Leu Gly Ala Gly Ile Asp Gly Val Glu Ile
305                 310                 315                 320

Lys Arg His Pro Phe Phe Val Thr Ile Asp Trp Asn Thr Leu Tyr Arg
                    325                 330                 335

Lys Glu Ile Lys Pro Pro Phe Lys Pro Ala Val Gly Arg Pro Glu Asp
                340                 345                 350

Thr Phe His Phe Asp Pro Glu Phe Thr Ala Arg Thr Pro Thr Asp Ser
            355                 360                 365

Pro Gly Val Pro Pro Ser Ala Asn Ala His His Leu Phe Arg Gly Phe
        370                 375                 380

Ser Phe Val Ala Ser Ser Leu Ile Gln Glu Pro Ser Gln Gln Asp Leu
385                 390                 395                 400

His Lys Val Pro Val His Pro Ile Val Gln Gln Leu His Gly Asn Asn
                    405                 410                 415

Ile His Phe Thr Asp Gly Tyr Glu Ile Lys Glu Asp Ile Gly Val Gly
                420                 425                 430

Ser Tyr Ser Val Cys Lys Arg Cys Val His Lys Ala Thr Asp Thr Glu
            435                 440                 445

Tyr Ala Val Lys Ile Ile Asp Lys Ser Lys Arg Asp Pro Ser Glu Glu
        450                 455                 460

Ile Glu Ile Leu Leu Arg Tyr Gly Gln His Pro Asn Ile Ile Thr Leu
465                 470                 475                 480

Lys Asp Val Tyr Asp Asp Gly Lys Phe Val Tyr Leu Val Met Glu Leu
                    485                 490                 495

Met Arg Gly Gly Glu Leu Leu Asp Arg Ile Leu Arg Gln Arg Tyr Phe
                500                 505                 510

Ser Glu Arg Glu Ala Ser Asp Val Leu Cys Thr Ile Thr Lys Thr Met
            515                 520                 525

Asp Tyr Leu His Ser Gln Gly Val Val His Arg Asp Leu Lys Pro Ser
        530                 535                 540

Asn Ile Leu Tyr Arg Asp Glu Ser Gly Ser Pro Glu Ser Ile Arg Val
545                 550                 555                 560

Cys Asp Phe Gly Phe Ala Lys Gln Leu Arg Ala Gly Asn Gly Leu Leu
                    565                 570                 575

Met Thr Pro Cys Tyr Thr Ala Asn Phe Val Ala Pro Glu Val Leu Lys
                580                 585                 590

Arg Gln Gly Tyr Asp Ala Ala Cys Asp Ile Trp Ser Leu Gly Ile Leu
            595                 600                 605

Leu Tyr Thr Met Leu Ala Gly Phe Thr Pro Phe Ala Asn Gly Pro Asp
        610                 615                 620

Asp Thr Pro Glu Glu Ile Leu Ala Arg Ile Gly Ser Gly Lys Tyr Ala
625                 630                 635                 640

Leu Ser Gly Gly Asn Trp Asp Ser Ile Ser Asp Ala Ala Lys Asp Val
                    645                 650                 655

Val Ser Lys Met Leu His Val Asp Pro His Gln Arg Leu Thr Ala Met
                660                 665                 670

Gln Val Leu Lys His Pro Trp Val Val Asn Arg Glu Tyr Leu Ser Pro
            675                 680                 685
```

-continued

```
Asn Gln Leu Ser Arg Gln Asp Val His Leu Val Lys Gly Ala Met Ala
    690                 695                 700
Ala Thr Tyr Phe Ala Leu Asn Arg Thr Pro Gln Ala Pro Arg Leu Glu
705                 710                 715                 720
Pro Val Leu Ser Ser Asn Leu Ala Gln Arg Arg Gly Met Lys Arg Leu
                725                 730                 735
Thr Ser Thr Arg Leu
            740

<210> SEQ ID NO 37
<211> LENGTH: 742
<212> TYPE: PRT
<213> ORGANISM: Homo sapiens

<400> SEQUENCE: 37

Met Asp Lys Phe Trp Trp His Ala Ala Trp Gly Leu Cys Leu Val Pro
1               5                   10                  15
Leu Ser Leu Ala Gln Ile Asp Leu Asn Ile Thr Cys Arg Phe Ala Gly
                20                  25                  30
Val Phe His Val Glu Lys Asn Gly Arg Tyr Ser Ile Ser Arg Thr Glu
            35                  40                  45
Ala Ala Asp Leu Cys Lys Ala Phe Asn Ser Thr Leu Pro Thr Met Ala
    50                  55                  60
Gln Met Glu Lys Ala Leu Ser Ile Gly Phe Glu Thr Cys Arg Tyr Gly
65                  70                  75                  80
Phe Ile Glu Gly His Val Val Ile Pro Arg Ile His Pro Asn Ser Ile
                85                  90                  95
Cys Ala Ala Asn Asn Thr Gly Val Tyr Ile Leu Thr Ser Asn Thr Ser
                100                 105                 110
Gln Tyr Asp Thr Tyr Cys Phe Asn Ala Ser Ala Pro Pro Glu Glu Asp
            115                 120                 125
Cys Thr Ser Val Thr Asp Leu Pro Asn Ala Phe Asp Gly Pro Ile Thr
    130                 135                 140
Ile Thr Ile Val Asn Arg Asp Gly Thr Arg Tyr Val Gln Lys Gly Glu
145                 150                 155                 160
Tyr Arg Thr Asn Pro Glu Asp Ile Tyr Pro Ser Asn Pro Thr Asp Asp
                165                 170                 175
Asp Val Ser Ser Gly Ser Ser Glu Arg Ser Ser Thr Ser Gly Gly
                180                 185                 190
Tyr Ile Phe Tyr Thr Phe Ser Thr Val His Pro Ile Pro Asp Glu Asp
            195                 200                 205
Ser Pro Trp Ile Thr Asp Ser Thr Asp Arg Ile Pro Ala Thr Thr Leu
    210                 215                 220
Met Ser Thr Ser Ala Thr Ala Thr Glu Thr Ala Thr Lys Arg Gln Glu
225                 230                 235                 240
Thr Trp Asp Trp Phe Ser Trp Leu Phe Leu Pro Ser Glu Ser Lys Asn
                245                 250                 255
His Leu His Thr Thr Thr Gln Met Ala Gly Thr Ser Ser Asn Thr Ile
            260                 265                 270
Ser Ala Gly Trp Glu Pro Asn Glu Glu Asn Glu Asp Glu Arg Asp Arg
    275                 280                 285
His Leu Ser Phe Ser Gly Ser Gly Ile Asp Asp Asp Glu Asp Phe Ile
    290                 295                 300
Ser Ser Thr Ile Ser Thr Thr Pro Arg Ala Phe Asp His Thr Lys Gln
305                 310                 315                 320
```

```
Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
                340                 345                 350

Thr Ala Tyr Glu Gly Asn Trp Asn Pro Glu Ala His Pro Pro Leu Ile
            355                 360                 365

His His Glu His His Glu Glu Glu Thr Pro His Ser Thr Ser Thr
        370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Lys Glu Asp Ser His Ser Thr Thr Gly Thr Ala Ala Ser Ala His
                420                 425                 430

Thr Ser His Pro Met Gln Gly Arg Thr Thr Pro Ser Pro Glu Asp Ser
            435                 440                 445

Ser Trp Thr Asp Phe Phe Asn Pro Ile Ser His Pro Met Gly Arg Gly
        450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
                500                 505                 510

Phe Ser Thr Ser His Glu Gly Leu Glu Glu Asp Lys Asp His Pro Thr
                515                 520                 525

Thr Ser Thr Leu Thr Ser Ser Asn Arg Asn Asp Val Thr Gly Gly Arg
                530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
                580                 585                 590

Asp Ser Asn Ser Asn Val Asn Arg Ser Leu Ser Gly Asp Gln Asp Thr
                595                 600                 605

Phe His Pro Ser Gly Gly Ser His Thr Thr His Gly Ser Glu Ser Asp
            610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
                660                 665                 670

Arg Arg Arg Cys Gly Gln Lys Lys Leu Val Ile Asn Ser Gly Asn
                675                 680                 685

Gly Ala Val Glu Asp Arg Lys Pro Ser Gly Leu Asn Gly Glu Ala Ser
            690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735
```

```
Asp Met Lys Ile Gly Val
            740

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
uauuccacgu ggagaaaaat t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
cgugggaugc ucaaagauat t                                              21
```

METHODS AND COMPOSITIONS RELATING TO THE TREATMENT OF CANCER

CROSS-REFERENCE TO RELATED APPLICATIONS

This application is a 35 U.S.C. § 371 National Phase Entry Application of International Application No. PCT/US2014/015957 filed Feb. 12, 2014, which designates the U.S., and which claims benefit under 35 U.S.C. § 119(e) of U.S. Provisional Application Nos. 61/766,325 filed Feb. 19, 2013 and 61/814,441 filed Apr. 22, 2013, the contents of which are incorporated herein by reference in their entirety.

GOVERNMENT SUPPORT

This invention was made with federal funding under Grant No. 1RO1CA135242-01A2 awarded by the National Institutes of Health and Grant Nos. W81XWH-07-1-0482 and W81XWH-09-1-0700 awarded by the Department of Defense. The U.S. government has certain rights in the invention.

SEQUENCE LISTING

The instant application contains a Sequence Listing which has been submitted electronically in ASCII format and is hereby incorporated by reference in its entirety. Said ASCII copy, created on Jan. 21, 2014, is named 043214-076692-PCT_SL.txt and is 219,710 bytes in size.

TECHNICAL FIELD

The technology described herein relates to methods and compositions of treating cancer.

BACKGROUND

Acquired resistance to chemotherapy is a key obstacle to successful cancer treatment. Often, a course of treatment with chemotherapy does not result in the death of all cancer cells present in a subject. The surviving cells can cause the subject to relapse. The existence of cancer cells resistant to chemotherapeutics was originally explained by the presence of mutations in the DNA of a subset of cancer cells which conferred resistance to treatment (Cairns, 1975). However, chemotherapeutic resistance has been observed in tumor cells which do not have such mutations (Marusyk et al. 2012; Okabe et al. 2008; Berrieman et al. 2004; and Talpaz et al. 2002), indicating that this explanation is incomplete.

A more recently developed theory to explain non-genetic resistance to chemotherapeutics has revolved around "cancer stem cells" (CSCs). CSCs are believed to be static population of cells that have phenotypes which make them instrinically resistant to chemotherapeutics. According to this theory, while fully mature cancer cells are killed by the chemotherapy, the CSCs survive and produce new mature cancer cells, leading to tumor regrowth and relapse (Dean et al. 2005; Shackleton et al. 2009). However, recent experimental evidence demonstrates that instead of a static population of CSCs, there are individual cancer cells which can transition to CSC-like phenotypes and subsequently return to their original phenotype (Gupta et al., 2011).

SUMMARY

Provided herein are novel compositions and methods for the treatment of cancer. Specifically, the novel compositions are directed to preventing cancer cells from regressing into cancer stem cell-like phenotypes, a mechanism that has been identified by the inventors as important in development of resistance to cytotoxic cancer treatments. Accordingly, the invention provides novel compositions incorporating a cancer cell targeting moiety with kinase inhibitors that are directed to inhibit two important pathways for cancer cell regression that the inventors have discovered, namely, PI3K pathway kinases and Src family kinases.

The novel compositions specifically target cancer cells that can escape the chemotherapy by regressing into stem cell-like state that can escape cancer treatment. Thus, the compositions significantly reduce or prevent development of drug resistant cancer cells.

The invention is based, at least in part, on the discovery that tumor cells can be induced to temporarily acquire chemoresistant phenotypes, i.e., they become transiently tolerant. These cells can acquire stemlike properties, induce expression and functional activity of CSC biomarkers, and reorganize a redundant kinase-signaling network to persist and re-emerge from drug treatments. Also demonstrated herein is that this chemoresistant behavior can be prevented by a combination treatment of kinase inhibitors. Accordingly, provided herein are methods and compositions relating to the treatment of cancer, e.g. preventing the emergence of chemoresistant cancer cells.

In one aspect, described herein is a composition comprising a combination of a binding reagent specific for a transiently tolerant cancer cell and/or a cancer stem cell; and a kinase inhibitor, capable of inhibiting the activity of at least one PI3K pathway kinase and at least one Src family kinase. In some embodiments, the PI3K pathway kinase is selected from the group consisting of Akt; BCR-Abl; PRAS40; mTOR; S6K; Rsk1; Rsk2; and Rsk3. In some embodiments, the PI3K pathway kinase is BCR-Abl. In some embodiments, the kinase inhibitor comprises a dual kinase inhibitor. In some embodiments, the dual kinase inhibitor is dasatinib. In some embodiments, the kinase inhibitor comprises a mixture of at least two kinase inhibitors.

In one aspect, described herein is a composition comprising a combination of a binding reagent specific for a transiently tolerant cancer cell and/or a cancer stem cell; a kinase inhibitor capable of inhibiting the activity at least one Src family kinase; and an EGFR inhibitor.

In some embodiments of any of the foregoing aspects, the Src family kinase is selected from the group consisting of Src; Yes; Fyn; Fgr; Lck; Hck; Blk; Lyn; and Frk. In some embodiments of any of the foregoing aspects, the Src family kinase is selected from the group consisting of Src; Yes; Fyn; and Fgr. In some embodiments of any of the foregoing aspects, the Src family kinase is Src.

In one aspect, described herein is a composition comprising a binding reagent specific for a transiently tolerant cancer cell and/or a cancer stem cell; and dasatinib.

In some embodiments of any of the foregoing aspects, the binding reagent specific for a transiently tolerant cancer cell and/or a cancer stem cell is an antibody or antigen-binding portion of an antibody. In some embodiments of any of the foregoing aspects, the binding reagent specific for a transiently tolerant cancer cell and/or a cancer stem cell is an aptamer. In some embodiments of any of the foregoing aspects, the binding reagent is conjugated to the dual kinase inhibitor. In some embodiments of any of the foregoing aspects, the dual kinase inhibitor is selected from Formula I and Formula II,

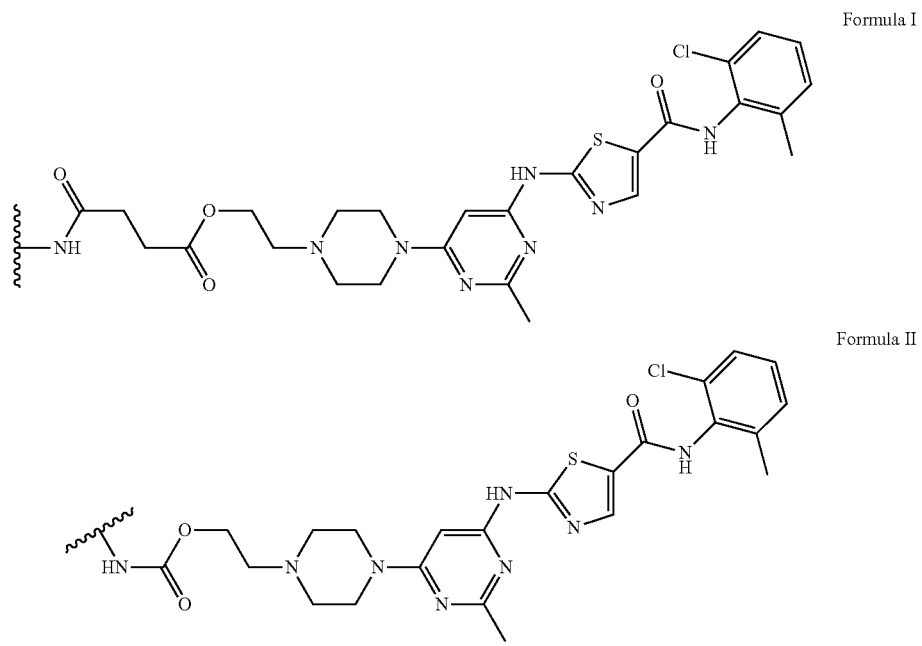

Formula I

Formula II wherein the structure of Formula I or Formula II is conjugated to a binding reagent specific for a transiently tolerant cancer cell and/or a cancer stem cell.

In some embodiments of any of the foregoing aspects, the binding reagent specific for a transiently tolerant cancer cell and/or a cancer stem cell binds specifically to a cell surface protein selected from the group consisting of: CD44; and isoforms thereof; cluster of differentiation protein family polypeptides; CD24; EpCAM; CD133; ganglioside GD2; epithelial specific antigen (ESA); Pgp; BCRP; MDR; ABC transport protein family polypeptides; EGFR; HER-2; ER; PR; IGF1R; insulin receptor; and EGFR-IGFR heterodimers.

In some embodiments of any of the foregoing aspects, the composition further comprises a scaffold material. In some embodiments, the scaffold material is selected from the group consisting of a nanoparticle; a matrix; a hydrogel; and a biodegradable scaffold material.

In some embodiments of any of the foregoing aspects, the composition further comprises an EGFR inhibitor. In some embodiments, the EGFR inhibitor is selected from the group consisting of erlotinib; cetuximab; gefitinib; panitumumab; zaltuumumab; nimotuzmab; matuzaumab; and lapatinib. In some embodiments, the EGFR inhibitor is erlotinib.

In some embodiments of any of the foregoing aspects, the composition further comprises a pharmaceutically acceptable carrier.

In one aspect, described herein is a method for treating cancer in a subject in need thereof comprising administering to the subject in need of treatment for cancer a combination of a cytotoxic chemotherapy agent and dasatinib or a composition as described herein. In some embodiments, the cytotoxic chemotherapy agent is selected from the group consisting of: doxorubicin; taxanes; cabazitaxel; vincristine; anti-tubulin chemotherapies; and vinblastine. In some embodiments, the composition as described herein is administered after the administration of the cytotoxic chemotherapy agent. In some embodiments, the composition as described herein is administered during a period in which at least a subpopulation of cancer cells in the subject display increased levels of CD44 on the cell surface. In some embodiments, the composition as described herein is administered during a period in which tumor growth plateaus. In some embodiments, the composition as described herein is administered at least 4 hours after the administration of the cytotoxic chemotherapy agent. In some embodiments, the composition as described herein is administered no more than about 216 hours after the administration of the cytotoxic chemotherapy agent. In some embodiments, the composition as described herein is administered from about 4 hours to about 216 hours after the administration of the cytotoxic chemotherapy agent. In some embodiments, the composition as described herein is administered from about 4 hours to about 96 hours after the administration of the cytotoxic chemotherapy agent. In some embodiments, the composition as described herein is administered from about 12 hours to about 96 hours after the administration of the cytotoxic chemotherapy. In some embodiments, the composition as described herein is administered about 72 hours after the administration of the cytotoxic chemotherapy. In some embodiments, the composition as described herein is administered within 10 days after the administration of the cytotoxic chemotherapy. In some embodiments, the composition as described herein is administered within 7 days after the administration of the cytotoxic chemotherapy. In some embodiments, the subject is further administered an EGFR inhibitor. In some embodiments, the EGFR inhibitor is selected from the group consisting of erlotinib; cetuximab; gefitinib; panitumumab; zaltuumumab; nimotuzmab; matuzaumab; and lapatinib. In some embodiments, the EGFR inhibitor is erlotinib.

In one aspect, described herein is a method of identifying a chemotherapy tolerant cancer cell, the method comprising detecting, in a cancer cell, the phosphorylation level of at least one gene selected from the group consisting of PRAS40, Src and Hck; wherein increased phosphorylation of the Y411 residue of Hck, decreased phosphorylation of the Tyr527 residue of Src; or increased phosphorylation of T246 residue of PRAS40 indicates the cancer cell is a chemotherapy tolerant cancer cell. In some embodiments, the method further comprises detecting the expression level of CD44, wherein increased expression of CD44 indicates the cancer cell is a chemotherapy tolerant cancer cell.

In one aspect, described herein is a method of treatment of a cancer in a subject in need thereof comprising detecting, in a cancer cell, the phosphorylation level of at least one gene selected from the group consisting of PRAS40, Src and Hck; and administering a composition as described herein to the subject when increased phosphorylation of the Y411 residue of Hck, decreased phosphorylation of the Tyr527 residue of Src; or increased phosphorylation of T246 residue of PRAS40 is detected. In some embodiments, the method further comprises detecting the expression level of CD44, and administering the composition as described herein to the subject when increased expression of CD44 is detected.

BRIEF DESCRIPTION OF THE DRAWINGS

FIG. 1A depicts a graph of CD44 expression. Human breast cancer tissue was obtained from taxane-refractory patients and thin biopsies were subsequently utilized for an explant model and either left untreated (time 0), treated with a taxane-containing regimen or DMSO control (72 h). CD44 expression was quantified visually for intensity of staining and proportion of cells positive for CD44 (N=7, FIG. 9 shows patient history). FIG. 11K depicts FAC analysis results. 468 parent cells and a subset of DTC were incubated with fluorescently conjugated antibody detecting EpCAM and analyzed by FACS. FIG. 1N depicts the survival curve of 468 and a subset of DTC following 48 h exposure to Doxorubicin at indicated concentrations. Data points indicate values from 3 separate samples. Similar results identified from other cell lines (data not shown).

FIG. 2A depicts FAC analysis results. Parent cells or DTC subsets isolated from 231 and 468 cells were analyzed for size based on three dimensional light scattering during flow cytometry. Note the tight correlation between parent and DTC within circumscribed gate indicating largest 20% of parent cells (FSC:A vs. SSC:A). FIG. 2B depicts graphs of parent or DTC subsets isolated from 231 and 468 cells and analyzed for cell diameter (μm) post-trypsinization. Translucent box indicates approximate largest 20% of parent cells; note that the majority of DTC exist in this constraint. FIG. 2D depicts FAC analysis results. Parent cells were isolated by cell sorting utilizing three-dimensional light scattering parameters to capture the 20% largest (large) and 20% smallest (small) cells following doublet discrimination. Image depicts example of cell sorting analysis. Enrichment of ~60-70% could be achieved and in some cases were enriched—for several times. FIG. 2E depicts graphs of fold change diameter. Following isolation of cells based on size (FIG. 2D), cells which adhered to culture plates were analyzed based on cell diameter (μm) and quantified as fold change diameter from the 'small' subset determined from >150 individual cells each (*p<0.05, error bars indicate SEM). FIG. 2F depicts graphs of cell survival. Cell survival was determined following incubation of 468Large/Small and 231 Large/Small with DTX or doxorubicin (48 h) at indicated concentrations. Histogram shows fold change viability. (*p<0.05, error bars indicate SEM). FIG. 11C shows example of full cytotoxicity curve with multiple concentrations of chemotherapy in the 231Large/Small cells. FIG. 2G depicts graphs of cell cycle. 231 and 468 parent cells were analyzed for cell cycle by propidium iodide solution and FACS. Cells were gated based on the 20% largest or 20% smallest (FSCA: vs. SSC:A) following doublet discrimination. Histogram shows % of cells in the indicated cell cycle, error bars indicate SEM. FIG. 2H depicts graphs of cell cycle. 231 parent cells or the DTC subset were analyzed by cell cycle utilizing a propidium iodide solution. Histogram shows % of cells in the indicated cell cycle, error bars indicate SEM. Similar analysis was performed in the 468 and DTC subset (FIG. 11D). FIG. 2I depicts FACS analysis results. 231 and 468 parent cells were incubated with fluorescently conjugated antibody detecting CD44 and analyzed by FACS. Cells were gated based on the 20% largest or 20% smallest (FSCA: vs. SSC:A) following doublet discrimination. Cell extract from equal number of cells obtained from cell sorting Large and Small populations was analyzed by western blot for CD44 expression.

FIG. 3A depicts FAC analysis results. Parent 468 cells or DTC were labeled with fluorescent CD44 antibody and analyzed by FACS. Circumscribed gate indicates equivalent size cells between cell lines (FSC:A vs. SSC:A), CD44 mean fluorescent intensity (CD44 per cell) was quantified within this gate and expressed as fold change from parent cells (error bars indicate SEM, $*p<0.05$). FIG. 3B depicts FAC analysis results. Parent cells or DTC from each cell line were incubated with fluorescently conjugated antibody detecting CD44 and analyzed by FACS. Gating indicates highest fluorescence of CD44 in parental cells. Note the 'generation' of CD44High cells detected within the DTC subsets not originally detected in the parent cell lines. FIG. 3C depicts FAC analysis results. 231 parent and DTC cells were incubated with fluorescently conjugated antibody detecting CD44 and analyzed by FACS. Schematic illustrates FACS isolation of DTC cells which express more CD44 than any cells from the parent population (3.5%+/−1.1%) and define these as CD44New. Expansion of CD44New in culture was performed with serum-containing medium requiring passaging before regaining proliferative capacity at day ~23 and full confluency by day ~35 (ParentPhenocopy). FIG. 3D depicts 231, DTC or 231Phenocopy cells visualized by brightfield microscopy (20×). Note regain of parental morphology in the DTCPhenocopy. FIG. 3E depicts FAC analysis results. 231, DTC or 231Phenocopy were labeled with fluorescently conjugated antibody detecting CD44 and analyzed by FACS. Note the re-equilibration of CD44 expression in 231Phenocopy indicated by gate. FIG. 3F depicts graphs of 231, DTC or 231Phenocopy analyzed utilizing propidium iodide solution and FACS to determine cell cycle status. FIG. 3G depicts a graph of 231, DTC or 231Phenocopy survival curves, indicating % viability of control in response to increasing concentrations of DTX chemotherapy (48 h).

FIG. 4A depicts western blot analysis. Cell extract from 468 parent and DTC were analyzed by western blot analysis for phosphorylated and total ERM and AKT. 13-Actin used as loading control. FIG. 4B depicts graphs of cell survival curve indicating % viability of control in 468 parent cells and DTC (left panel) or 231 parent cells and DTC (right panel) following incubation (48 h) with indicated concentrations of the PI3K/Akt inhibitors LY294002 or PI-103, respectively. Data points indicate values obtained from triplicate experiments (error bars indicate SEM). FIG. 4C depicts graphs and images of western blots. 468 cells were transfected with siRNA targeting ezrin and subsequently incubated with DTX (10 nM) or Vincristine (5 nM). Western blot analysis indicates phosphorylated residues and total protein levels, 13-Actin loading control. (Upper panel) Values obtained from triplicate experiments were quantified by protein band optical density and expressed as fold change from control of siScrambled or siEzrin transfections (error bars indicate SEM). FIG. 4D depicts graphs of 468 cells transfected with siEzrin incubated with indicated concentrations of chemotherapy and analyzed for viability (48 h). Each data point was obtained from triplicate experiment (data expressed as % viability of control, $*p<0.05$, error bars indicate SEM). FIG. 4E depicts images of western blots. Cell extract from 468 parent cells treated with 10 nM DTX+/−1 tM erlotinib (24 h) was analyzed by western blot for phosphorylated and total ERM and AKT protein. 13-Actin used as loading control. Note the inability of erlotinib to prevent ERM-complex activation. FIG. 4F depicts images of western blots. 468 cells were transfected with siRNA targeting CD44 or scrambled control and incubated with DTX (5 nM or 10 nM) for 24 h. Cell extract was analyzed by western blot. Note the increase of Akt, ezrin and ERM-complex signaling are attenuated when CD44 is silenced. 13-Actin used as loading control. FIG. 4G depicts images of western blots. 468 cells were transfected with siRNA targeting CD44 or scrambled control. Following incubation with indicated doses of vincristine or DTX, monoclonal antibody targeting Akt was immunoprecipitated from cell extract and applied to western blot analysis. Note the inability of Akt-ERM-EGFR to complex in the absence of CD44 expression. Total Akt used as loading control. FIG. 4H depicts images of western blots. 468 cells were incubated with DTX (10 nM)+/−erlotininb (1 tM) for 24 h. Following immunoprecipitation (IP) with monoclonal antibody targeting EGFR, cell extract was applied to western blot (WB) analysis to detect total CD44 protein. Major band was detected at 97kd (arrow). Lower panel indicates similar treatments performed western blot (WB) for CD44v6 identified at a similar molecular weight as pan-CD44 (97kd). Supplemental FIG. 4C shows similar analysis in 231 cells. Total EGFR used as loading control. FIG. 4I depicts images of western blots. Cell extract from 468 parent cells or DTC was incubated with monoclonal antibody detecting EGFR. Following immunoprecipitation (IP) Western blot (WB) was performed to detect total CD44 or CD44v6. Similar findings were observed in 231 and DTC cells (FIG. 12D). Total EGFR used as loading control.

FIGS. 5A-5H demonstrate that Akt and Src family kinase (SFK) survival signaling is functionally tied to CSC mimicry, which can be blocked using molecularly-targeted agents. FIG. 5A depicts graphs of the responses of cells to various drugs. Right panels indicate examples of cell viability assays performed in 231 parent and DTC incubated (48 h) with indicated concentrations of kinase inhibitors (table). Lower left panel shows drug sensitivity index (SI) calculated as the average cell viability across 4 drug concentrations: 10 nM, 100 nM, 1000 nM and 10 μM and expressed as fold change DTC:parent; SI<1 indicates drug resistance of DTC compared to parent; SI=1 indicates parental drug sensitivity; SI>1 indicates greater sensitivity of drug in DTC. FIG. 5B depicts a graph of drug sensitivity index (SI) of dasatinib determined in DTC isolated from multiple cell lines. SI>1 indicates greater sensitivity of DTC compared to parent in response to dasatinib (48 h). FIG. 5C depicts a graph of drug sensitivity index (SI) of dasatinib determined in 231 parent, DTC and 231Phenocopy. Note re-equilibrated, parental SI in the 231Phenocopy indicating temporal constraint of DTC dasatinib sensitivity. FIG. 5D depicts a graph of a cell viability assay performed in 231 DTC cells incubated with BCR/Abl kinase inhibitor, imatinib+/−Src Family kinase (SFK) inhibitor PP2. Note, combination of inhibitors does not further attenuate survival of DTC indicating BCR/Abl is not a key pathway of survival beyond SFK in DTC subset. FIG. 5E depicts a table showing kinases and phosphorylated residues from Akt-family and Src-family kinases analyzed in phosphorylation arrays found in FIG. 5F. FIG. 5F depicts phosphorylation assay membranes and a graph. Cell extract from 231 parent and DTC was applied to a phosphorylation array. Far right western blot indicates phosphorylated Src inhibitory residue (Y527) and shows β-Actin loading control. Optical density of phosphorylation array performed from 231 parent and DTC indicates Akt-family and SFK residues increased in DTC compared to parent cells, quantified and expressed as fold change. Values were determined from quadruplicate spots per phosphorylated residue determined from 2 independent experiments (*p<0.05, **p<0.01, error bars indicate SEM). FIG. 5G depicts phorphorylation array membranes. CD44 was immunoprecipitated from 231DTC and 468DTC cell extract and applied to a phosphorylation array. PBS control spots indicate exposure control of correlative arrays. Note: optical density of spots indicate enhanced physical association of phosphorylated protein with CD44 in the DTC subset. FIG. 5H depicts western blot images and a graph of the results. 231 DTC cells were incubated with dasatinib at indicated concentrations (4 h) and cell extract was applied to western blot analysis to detect phosphorylated and total Akt. Optical density of protein bands were quantified from three independent experiments and expressed as fold change from control. β-Actin used as loading control (*p<0.05, error bars indicate SEM).

FIGS. 6A-6I demonstrate the role of chemotherapy-induced CD44 expression in activation of adaptive resistance response in vivo. FIG. 6A depicts a graph of relative tumor volume expressed as fold increase from day 1 following DTX treatment on days 2 and 5 at 10 mg/kg i.v. and 15 mg/kg i.p., respectively, or vehicle control at similar time points. Box indicates time points when tumor tissue was harvested for subsequent experiments. FIG. 6B depicts a image of a representative western blot of mouse-specific CD44 (ABIN135065) from combined tumor tissue homogenate from at least 3 mice of each control day 9, DTX-treated day 9 or 19 and a graph of optical density of the results. Optical density of CD44 protein expression was determined from western blots performed on 3 separate tissue homogenates and expressed as fold change from control day 9. (*p<0.05 between indicated groups, error bars indicate SEM). FIG. 6C depicts images of representative IHC of CD44 (IM7) evaluated from tumors harvested from control day 9, DTX-treated day 9 or 19 (20×). FIG. 6D depicts a graph of the quantitation of CD44 expression from IHC of in vivo tumor tissue from at least 3 mice per group was determined by multiplying intensity of staining at the cellular level (1-4) with percentage of cells stained from at least 25 independent fields per group in a blinded fashion. FIG. 6E depicts a graph of kinase activity determined by optical density of protein bands obtained from western blot of phosphorylated PRAS40 and SrcY527 from tumor tissue of at least 3 mice from each group. Data are expressed as the difference in fold change from control day 9 of phosphorylated residue:total protein and normalized to 13-Actin. (*p<0.05, error bars indicate SEM). FIG. 6F depicts representative IHC images of phosphorylated Hck (Y410) from tumors of at least 3 mice per group harvested from control day 9, DTX-treated day 9 or 19. Note enhanced nuclear localization of signal at DTX day 9 with variable enhanced cytoplasmic staining compared to control day 9 and DTX day 19. FIG. 6G depicts western blots of combined lysate of tumor homogenate of at least 3 mice per group incubated with antibody detecting total Hck or PRAS40. Following immunoprecipitation (IP) eluent was applied to immunoblots (IB) to detect CD44 physical co-localization (ABIN135065). Total protein of each target used as loading control. FIG. 6H depicts a graph of tumor response. Tumors treated with DTX on days 2 and 5 were followed-up with adjuvant dasatinib in two schedules 1. Day 8 post tumor burden defined as 'early dasatinib' or 2. Day 14 post tumor burden defined as 'late dasatinib'. Histogram shows specific growth rate calculated by the formula (ln [V2/V1]/[t2−t1]) where V2 and t2=Day 5 and V1 and t1=Day 0. (*p<0.05 compared to day 0, #p<0.05 between indicated groups. Error bars indicate SEM) N=4 per group. FIG. 6I depicts graphs of relative tumor volume fold-change from Day 0 (1 day prior to initiation of dasatinib treatment). Left panel shows tumor volumes from 'early dasatinib', right panel shows tumor volumes from 'late dasatinib'. (#p<0.05 compared to day 0, *p<0.05 between indicated groups on day 5).

FIG. 7A depicts a 3-dimensional schematic of PI103-dasatinib chimeric nanoparticle (DPNP). PI103 conjugated to cholesterol stabilizes the lipid membrane while dasatinib is encapsulated within the nanoparticle decorated with polyethylene glycol (PEG). FIG. 7B depicts western blots images. Cell extract from 231 DTC treated with indicated drugs for 24 h was applied to western blot analysis for indicated phosphorylated residues. 13-Actin used as loading control. FIG. 7C depicts graphs of cell viability analysis of 231 DTC (left panel) and 468DTC (right panel) following incubation with dasatinib or DPNP (48 h). FIG. 7D depicts a graph of relative change in tumor volume following DTX pre-treatment or vehicle control with sequential addition of individual kinase inhibitors or DPNP administered at low dose on 3 independent occasions. N=4 per group (*p<0.05 between indicated groups on final day). Note DPNP treatment in DTX-naïve cells is insignificant compared to untreated vehicle control emphasizing the requirement for sequential addition of cytotoxics and kinase-inhibiting drugs. FIG. 7E depicts images of tissue obtained from a stage IV metastatic breast cancer patient, cut into thin slices and treated with the indicated drug regimens for 48 h as described in methods. Paraffin-embedded tissue was analyzed by H&E (top panels) or IHC for active apoptosis (cleaved caspase-3). FIG. 7F depicts a graph of activation of cleaved caspase-3 and caspase-8 determined from the refractory breast cancer explant shown in FIG. 7E. FIG. 7G depicts a schematic of the generation of CSC mimicry. Induction of CD44 expression as a consequence of phenotypic plasticity re-organizes a survival-signaling kinase network which exposes a therapeutic vulnerability. CSC mimicry, if left untreated, will re-assume a heterogeneous landscape. FIG. 7H depicts a schematic summarizing the temporal window to exploit for kinase therapy when the frequency of CSC mimicry peaks and vulnerability to secondary kinase inhibitors is maximal.

FIG. 9 depicts a table of human refractory explant patient information.

FIG. 10A depicts a graph of cell viability analysis of 468 parent cells following short-burst (24 h) treatment with 5 nM and 10 nM doses of DTX. Histogram indicates % cell viability of control obtained from triplicate experiments (error bars indicate SEM). Note preservation of viability between treated and untreated control groups indicating no selection of viable subsets. FIG. 10B depicts FACS analysis of 231 cells treated with increasing doses of DTX for 4 hours, fixed and stained with fluorescently-conjugated CD44 antibody. Quantification of CD44 mean fluorescent intensity was determined from 3 independent experiments (error bars indicate SEM, **$p<0.01$). FIG. 10C depicts FACS analysis and a graph of 468 parent cells incubated with 10 nM docetaxel at 75% confluency for 24 h and analyzed by flow cytometry for surface protein expression of CD24 and CD44 expression. Note the induction of both CD44 and CD24 in response to chemotherapy. FIG. 10D depicts FACS analysis of 231 parent cells or a subset of DTC incubated with fluorescently conjugated antibody detecting EpCAM. Cells were processed by flow cytometry and represented as FSC:A vs. EpCAM fluorescence. FIG. 10E depicts a graph of 231 DTC isolated as described, following fixation in formalin cells were labeled with fluorescently-tagged CD24 and analyzed by flow cytometry. Histogram graph indicates up regulation of CD24 in the DTC subset. FIG. 10F depicts a graph of the cell viability curve of 231 or a subset of DTC incubated with increasing doses of docetaxel or doxorubicin in the presence or absence of the drug-efflux inhibitor, elacridar.

FIGS. 11A-11E demonstrate the characterization of cancer stem cell mimicry. FIG. 11A depicts FACS analysis. (Left two panels) Parent cells or a DTC subset isolated from multiple cell lines were analyzed by flow cytometry to demonstrate size of cells based on 3-dimensional light-scattering parameters. Note correlation between parent and DTC within circumscribed gate indicating largest 20% of parent cells (FSC:A vs. SSC:A). (Right panel) 231 or a subset of Dox-TC isolated following the protocol outlined in FIG. 1D and utilizing 500 nM doxorubicin was analyzed by flow cytometry. Note correlation between parent and Dox-TC within the circumscribed gate indicating 20% largest parent cells. FIG. 11B depicts graphs of 231 cells treated with increasing doses of docetaxel for 4 hours and processed by a cell counter to determine cell diameter in microns. Note the increase in size can be observed after only 4 hours treatment, an effect which appeared to be dose-dependent. FIG. 11C depicts a graph of the viability curve of 231 parent cells sorted based on size, as described in methods. Cells were immediately plated into 96 well plates and treated with indicated concentrations of chemotherapy for 48 hours. Data points were averaged from triplicate experiments. Similar results were observed in 468 cells (data not shown). Fold increase of cell viability can be found in FIG. 3C. FIG. 11D depicts a graph of cell cycle analysis utilizing a propidium iodide solution processed by flow cytometry was performed in 468 parent cells or a DTC subset. Histogram shows % of cells in the indicated cell cycle, error bars indicate SEM. Results correlate to FIG. 2H of similar analysis performed in 231 parent cells and DTC. FIG. 11E depicts graphs of FACS analysis. Parent 231 cells were processed by FACS to isolate CD44High cells. Note: the proportion of CD44High (depicted as black dots) correlates to the largest population of cells determined by three dimensional light scattering parameters, an effect in contrast to CD44Low (grey dots).

FIG. 12A depicts a graph of Parent 468 and DTC cells analyzed by an EGFR phosphorylation array (RayBiotech). Histogram analysis represents the fold change of phosphorylated EGFR residues in DTC compared to 468 parent. Values were determined from normalized array membranes according to manufacturers instructions. Array was performed on at least 3 independent cell lysate extracts. Error bars indicate standard error from the mean (SEM) (*$p<0.05$, $p<0.01$, *$p<0.001$). Upper panel shows Co-immunoprecipitation of EGFR from unstimulated 468 and DTC cell lysate. Western analysis was performed using antibodies targeting phosphorylated tyrosine or EGFR as loading control. FIG. 12B depicts a graph of cell survival analysis of Ezrin-knockdown 468 parental cells or a scrambled control treated with docetaxel chemotherapy at the indicated concentrations for 48 hours+/−the EGFR kinase inhibitor erlotinib (1 μM). Values are expressed as % of the respective control. All error bars indicate standard error from the mean (SEM). (n.s.=not statistically significant) FIG. 12C depicts the results of EGFR immunoprecipitation (IP) performed using cell extract from MDA-MB-231 cells incubated with docetaxel (10 nM) in the presence or absence of erlotinib (1 μM) for 24 hours. Western blotting (WB) was performed using antibodies targeting total CD44 or EGFR as loading control. Indicated CD44 band appeared at 97kd (arrow). FIG. 12D depicts the results of immunoprecipitation. DTC were generated from MDA-MB-231 cells as described previously Immunoprecipitation (IP) from cell extract was performed using monoclonal antibody targeting EGFR. Western blot (WB) analysis was performed using antibodies targeting CD44v6 (clone VFF18) or EGFR as loading control.

FIG. 13A depicts images of immunohistochemistry. Balb/C Mice were injected with 4T-1 mouse mammary carcinoma cells per left flank and once tumors were palpable, injected with docetaxel (DTX) or vehicle control on day 2 and 5 and tumors were harvested on day 9 (control and DTX) and day 19 (DTX). Images are representative of immunohistochemistry of Phosphorylated PRAS40 was analyzed from tissue, note the increase in nuclear staining of p-PRAS40 increased from DTX-treated day 9, compared to control and reduced by day 19. FIG. 13B depicts graph of cell viability. DTC were generated from 231 or 468 cells as described previously. Cells were subsequently treated for 48 h with indicated concentrations of dasatinib, PI103 or a 1:1 combination of both inhibitors. Note synergy of combination therapy.

FIG. 16A depicts graphs of FACs analysis, demonstrating that Akt inhibitors prevent the accumulation of "large" DTC cells in culture. FIG. 16B depicts a graph demonstrating that inhibition of DNA accumulation and progression through the cell cycle is prevented by Akt inhibitors.

DETAILED DESCRIPTION

Figure 1B:
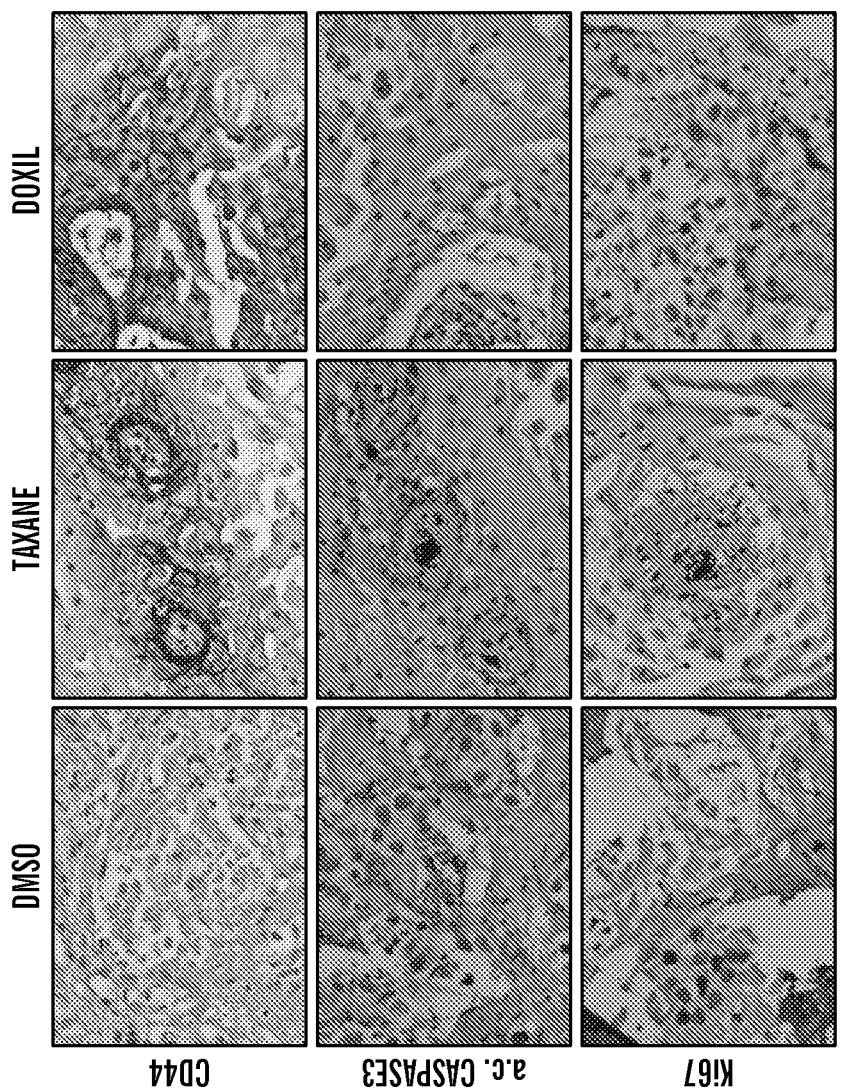
FIG. 1B depicts representative immunohistochemistry images of human explant studies following incubation with indicated chemotherapeutic regimens or control vehicles (72 h). Panels indicate CD44 expression, activated caspase-3 (apoptosis) and ki-67 proliferative marker performed on serial sections (N=7).

The technology described herein relates to the inventors' characterization of transiently tolerant cancer cells which display chemoresistance. As used herein, the term "transiently tolerant cancer cell" refers to a cell which is genetically identical to chemosensitive cancer cells but due to changes in subcellular organization, gene expression, and/or signaling activity has acquired chemoresistance and/or other stem-like properties, e.g. pluripotency, multipotency, and/or self-renewal. In some embodiments, the conversion to a chemoresistant phenotype can be temporary. In some embodiments, the conversion to a chemoresistant phenotype can be reversible. In some embodiments, the development of chemoresistance follows the expression of transiently tolerant cancer cell markers (e.g. CD44 and others described below herein), e.g. the development of measureable chemoresistance can be a later step in the conversion to a transiently tolerant cancer cell phenotype. In some embodiments, chemoresistance (e.g. the acquisition of transiently tolerant phenotypes) can be induced by exposure to a chemotherapeutic agent (e.g. a cytotoxic chemotherapeutic).

As described herein, the development of a chemoresistant phenotype can be prevented by inhibiting redundant kinase pathways. Specifically, inhibition of the PI3K kinase pathway and/or EGFR in combination with inhibition of a Src family kinase can prevent the development of a chemoresistant phenotype. An "inhibitor" of a given pathway and/or enzyme is a molecule and/or composition that interferes with or inhibits the activity of the pathway and/or enzyme, e.g. at least 10% inhibition, 20% inhibition, 30% inhibition, 40% inhibition, 50% inhibition, 75% inhibition, 80% inhibition, 90% inhibition, 95% inhibition, 98% inhibition, or greater inhibition Inhibitors of a given pathway and/or group of enzymes can inhibit one member of that pathway and/or group or multiple members of the pathway and/or group, e.g. 1 member, 2 members, 3 members, 4 members, or more members Inhibitors can encompass numerous classes of chemical molecules, e.g., small organic or inorganic molecules, polysaccharides, biological macromolecules, e.g., peptides, proteins, peptide analogs and derivatives, peptidomimetics, antibodies, antibody fragments, nucleic acids, nucleic acid analogs and derivatives, an extract made from biological materials such as bacteria, plants, fungi, or animal cells or tissues, naturally occurring or synthetic compositions.

As used herein, the "PI3K kinase pathway" (also referred to herein as the "Akt/BCR-Abl pathway") refers to a signaling pathway beginning with the interaction of PI3K with an activated receptor, resulting in the phosphorylation of the 3 position hydroxyl group of the inositol ring of phosphatidylinositols. The pathway then cascades through a branched series of signaling molecules, ultimately regulating apoptosis. When the PI3K kinase pathway is overactive, as in many cancers, apoptosis is suppressed, thereby allowing abnormally high levels of proliferation. In some embodiments, an inhibitor of the PI3K pathway can be an inhibitor of a PI3K pathway kinase. Non-limiting examples of PI3K pathways kinases can include Akt, BCR-Abl, PRAS40, mTOR, S6K, Rsk1, Rsk2, and/or Rsk3. In some embodiments, a PI3K pathway kinase can be BCR-Abl. The sequences of PI3K pathway kinases are well known in the art, eg. human Akt (NCBI Gene ID:207) (SEQ ID NO: 21 (mRNA) and SEQ ID NO: 22 (polypeptide)); human BCR-Abl (NCBI Gene ID:25) (SEQ ID NO: 23 (mRNA) and SEQ ID NO: 24 (polypeptide)); human PRAS40 (NCBI Gene ID:84335) (SEQ ID NO: 25 (mRNA) and SEQ ID NO: 26 (polypeptide)); human mTOR (NCBI Gene ID:2475) (SEQ ID NO: 27 (mRNA) and SEQ ID NO: 28 (polypeptide)); human S6K (NCBI Gene ID:6198) (SEQ ID NO: 29 (mRNA) and SEQ ID NO: 30 (polypeptide)); human Rsk1 (NCBI Gene ID:6195) (SEQ ID NO: 31 (mRNA) and SEQ ID NO: 32 (polypeptide)); human Rsk2 (NCBI Gene ID:6197) (SEQ ID NO: 33 (mRNA) and SEQ ID NO: 34 (polypeptide)); and human Rsk3 (NCBI Gene ID:6196) (SEQ ID NO: 35 (mRNA) and SEQ ID NO: 36 (polypeptide)).

Inhibitors of PI3K pathway kinases can include but are not limited to e.g. A-674563, AT7867, AT9283, AZD8055, BEZ235, BI-D1870, CCT128930, danusertib (PHA-739358), dasatinib (BMS-354825), deforolimus (Ridaforolimus), everolimus (RAD001), fingolimod (FTY720), GSK690693, H 89, imatinib, Ku-0063794, MK-2206, nilotinib, perifosine, PF-04691502, PHT-427, PI-103, ponatinib, PP242, rapamycin (sirolimus), rebastinib (DCC-2036), saracatinib (AZD0530), temsirolimus (Torisel), ticribine, WP1130, and XL765 Inhibitors of PI3K include, but are not limited to, BGT226 and BEZ235. Inhibitors of Akt include, but are not limited to, perifosine Inhibitors of mTOR include, but are not limited to, rapamycin, temsirolimus, and everolimus Inhibition of a PI3K pathway kinase can be determined, e.g. by in vitro assays to determine the activity of a PI3K pathway kinase, e.g. the ability to phosphorylate a target polypeptide. Such assays are readily understood by one of skill in the art.

As used herein, the term "EGFR" or "Epidermal Growth Factor Receptor" refers to a transmembrane receptor that binds to ligands including epidemeral growth factor "EGF" and TGFα. Ligand recognition causes autophosphorylation of EGFR and activates the MAPK, Akt, and/or JNK pathways, leading to cellular proliferation. The sequences of EGFR are well known in the art, eg. human EGFR (NCBI Gene ID:1956) (SEQ ID NO: 1 (mRNA) and SEQ ID NO: 2 (polypeptide)).

Inhibitors of EGFR can include but are not limited to aeroplysinin, afatinib, AG 1478, AG-490, AG-494, AG 555, AG 825, ARRY334543, AST 1306, AZD8931, BDPQ, BIBU 1361, BIBX 1382, BPIQ-I, BPIQ-II, butein, canertinib, cetuximab; CGP-74514A, CL-387,785, CUDC101, dacomitinib, DAPH, daphnetin, erbstatin analog, erlotinib; gefitinib, GW 583340, GW2974, HDS 029, hypericin, lapatinib, lavendustin A, lavendustin C, LFM-A12, matuzaumab; neratinib, nimotuzmab, panitumumab, PD 153035, PD 168393, pelitinib, PP 3, RG-13022, TAK 165, TAK 285, tyrphostin 47, tyrphostin 51, tyrphostin AG1478, tyrphostin AG183 tyrphostin AG 528, tyrphostin B44, tyrphostin RG 14620, vatalinib, WZ 4002, WZ8040, XL657, and zaltuumumab. In some embodiments, the EGFR inhibitor can be erlotinib; cetuximab; gefitinib; panitumumab; zaltuumumab; nimotuzmab; matuzaumab; or lapatinib. In some embodiments, the EGFR inhibitor can be erlotinib. Inhibition of EGFR can be determined, e.g. by assays to determine the level of phosphorylated EGFR, e.g. using phosphor-specific anti-EGFR antibodies (e.g. Cat. No. 1727-1;

Abcam: Cambridge, Mass.). Such assays are readily understood by one of skill in the art.

As used herein, the term "Src kinase family" refers to a family of non-receptor tyrosine kinases, encompassing the SrcA subfamily (Src, Yes, Fyn, and Fgr), the SrcB subfamily (Lck, Hck, Blk, and Lyn) and Frk. Non-limiting examples of Src family kinase can include Src, Yes, Fyn, Fgr, Lck, Hck, Blk, Lyn, and/or Frk. In some embodiments, a Src family kinase can be Src, Yes, Fyn, and Fgr. In some embodiments, a Src family kinase can be Src. The sequences of Src kinase family members are well known in the art, eg. human Src (NCBI Gene ID:6714) (SEQ ID NO: 3 (mRNA) and SEQ ID NO: 4 (polypeptide)); human Yes (NCBI Gene ID:7525) (SEQ ID NO: 5 (mRNA) and SEQ ID NO: 6 (polypeptide)); human Fyn (NCBI Gene ID:2534) (SEQ ID NO: 7 (mRNA) and SEQ ID NO: 8 (polypeptide)); human Fgr (NCBI Gene ID:2268) (SEQ ID NO: 9 (mRNA) and SEQ ID NO: 10 (polypeptide)); human Lck (NCBI Gene ID:3932) (SEQ ID NO: 11 (mRNA) and SEQ ID NO: 12 (polypeptide)); human Hck (NCBI Gene ID:3055) (SEQ ID NO: 13 (mRNA) and SEQ ID NO: 14 (polypeptide)); human Blk (NCBI Gene ID:640) (SEQ ID NO: 15 (mRNA) and SEQ ID NO: 16 (polypeptide)); human Lyn (NCBI Gene ID:4067) (SEQ ID NO: 17 (mRNA) and SEQ ID NO: 18 (polypeptide)) and human Frk (NCBI Gene ID:2444) (SEQ ID NO: 19 (mRNA) and SEQ ID NO: 20 (polypeptide)).

Inhibitors of Src family kinases can include but are not limited to 1-Naphthyl PP1, A 419259, AP23846, AZM 475271, bosutinib, dasatinib, DCC-2036, herbimycin A, ibrutinib (PCI-32765), KX2-391, MNS, NVP-BHG712, PD 166285, piceatannol, ponatinib (AP24534), PP1, PP2, saracatinib, SrcI1, TG100435 and XL228. Inhibition of a Src family kinase can be determined, e.g. by in vitro assays to determine the activity of a Src kinase, e.g. the ability to phosphorylate a target polypeptide. Such assays are readily understood by one of skill in the art.

In one aspect, the technology described herein relates to a composition comprising a binding reagent specific for a transiently tolerant cancer cell and/or a cancer stem cell and a kinase inhibitor capable of inhibiting the activity of at least one PI3K pathway kinase and at least one Src family kinase. In some embodiments, the kinase inhibitor can be a dual kinase inhibitor, e.g. a single molecule that can inhibit the activity of at least one PI3K pathway kinase and at least one Src family kinase. In some embodiments, the dual kinase inhibitor can be, e.g. dasatinib. In some embodiments, the kinase inhibitor can comprise a mixture of at least two different kinase inhibitors, e.g. a Src kinase inhibitor and a separate BCR-Abl kinase inhibitor. In some embodiments, one of the kinase inhibitors in a mixture of at least two different kinase inhibitors can be a dual kinase inhibitor. In some embodiments, the composition can further comprise an EGFR inhibitor.

In one aspect, the technology described herein relates to a composition comprising a binding reagent specific for a transiently tolerant cancer cell and/or a cancer stem cell, an EGFR inhibitor, and a kinase inhibitor capable of inhibiting a Src family kinase.

The binding reagent specific for a transiently tolerant cancer cell and/or a cancer stem cell can target the kinase inhibitor (e.g. dual kinase inhibitor) to the cancer cells which are in need of inhibition of chemoresistance, reduce the effective dose, and/or reduce off-target effects.

As used herein, a "binding reagent specific for" a given entity is an agent that can bind specifically to that entity. As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. In some embodiments, "selectively binds" or "specifically binds" can refer to the ability of a binding reagent described herein to bind to a target, such as a molecule present on the cell-surface, with a $K_D$ of $10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less. Specific binding can be influenced by, for example, the affinity and avidity of the binding agent and the concentration of binding agent. The person of ordinary skill in the art can determine appropriate conditions under which the binding agents described herein selectively bind the targets using any suitable methods, such as titration of a binding agent in a suitable binding assay.

A binding reagent specific for a transiently tolerant cancer cell and/or a cancer stem cell can bind one or more markers (e.g. cell surface protein) which are markers of a transiently tolerant cancer cell and/or cancer stem cell phenotype. Methods for identifying such markers are known in the art, e.g. by subtractive hybridization. Examples of markers of transiently tolerant cancer cell or cancer stem cell phenotypes are known in the art and described herein. Non-limiting examples of markers of transiently tolerant cancer cells and/or cancer stem cells can include CD44 and isoforms thereof; cluster of differentiation protein family polypeptides; CD24; EpCAM; CD133; ganglioside GD2; epithelial specific antigen (ESA); Pgp; BCRP; MDR; ABC transport protein family polypeptides; EGFR; HER-2; ER; PR; IGF1R; insulin receptor; and EGFR-IGFR heterodimers. The sequences of such marker polypeptides are known in the art, e.g. human CD44 (NCBI Gene ID No: 960; SEQ ID NO: 37; NCBI Ref Seq: NP_000601). As described herein, the transiently tolerant cancer cell phenotype mimics, in many respects, the cancer stem cell phenotype. Accordingly, as demonstrated herein, makers of the cancer stem cell phenotype can also be markers of the transiently tolerant cancer cell phenotype, e.g. CD44.

In some embodiments, a binding reagent can be an antibody reagent, e.g. an antibody, a monoclonal antibody, or antigen-binding fragments and/or portions thereof. Antibody reagents specific for markers of transiently tolerant cancer cells and/or cancer stem cells are readily generated by one of skill in the art, as described below herein and are available commercially, e.g. anti-CD44 antibody (Cat. No. 1998-1; Abcam; Cambridge, Mass.), anti-CD24 antibody (Cat. No. ab77219; Abcam; Cambridge, Mass.), anti-EpCAM antibody (Cat. No. ab20160; Abcam; Cambridge, Mass.), anti-CD133 antibody (Cat No. MAB4310; Millipore, Billerica, Mass.), anti-ESA antibody (Cat. No. ab73988; Abcam; Cambridge, Mass.), anti-BCRP antibody (Cat. No. ab24114; Abcam; Cambridge, Mass.), anti-MDR antibody (Cat No. P7965; Sigma-Aldrich, St. Louis, Mo.), anti-EGFR antibody (Cat. No. 1727-1; Abcam; Cambridge, Mass.), anti-HER-2 antibody (Cat. No. 2064-1; Abcam; Cambridge, Mass.), anti-ER antibody (Cat. No. ab2746; Abcam; Cambridge, Mass.), anti-PR antibody (Cat. No. ab2764; Abcam; Cambridge, Mass.), and anti-IGF1R antibody (Cat. No. ab16890; Abcam; Cambridge, Mass.).

In some embodiments, a binding reagent can be an aptamer. Aptamers are short synthetic single-stranded oligonucleotides that specifically bind to various molecular targets such as small molecules, proteins, nucleic acids, and even cells and tissues. These small nucleic acid molecules can form secondary and tertiary structures capable of specifically binding proteins or other cellular targets, and are essentially a chemical equivalent of antibodies. Aptamers are highly specific, relatively small in size, and non-immunogenic. Aptamers are generally selected from a biopanning method known as SELEX (Systematic Evolution of Ligands by Exponential enrichment) (Ellington et al. Nature. 1990; 346(6287):818-822; Tuerk et al., Science. 1990; 249(4968): 505-510; Ni et al., Curr Med Chem. 2011; 18(27):4206-14; which are incorporated by reference herein in their entireties). Methods of generating an apatmer for any given target are well known in the art. Preclinical studies using, e.g. aptamer-siRNA chimeras and aptamer targeted nanoparticle therapeutics have been very successful in mouse models of cancer and HIV (Ni et al., Curr Med Chem. 2011; 18(27): 4206-14).

In some embodiments of multiple aspects described herein, the PI3K pathway kinase can be BCR-Abl and the Src family kinase can be Src. In some embodiments, the dual kinase inhibitor is dasatinib (also known as BMS-354825 and SPRYCEL™), e.g. an inhibitor of BCR-Abl and Src having the structure of Formula III. In one aspect, the technology described herein relates to a composition comprising a binding reagent specific for a transiently tolerant cancer cell and/or a cancer stem cell; and dasatinib.

In some embodiments, the composition described herein can have a structure selected from Formula I and Formula II, wherein the structure of Formula I or II is conjugated to a binding reagent molecule specific for a transiently tolerant cancer cell and/or a cancer stem cell. In some embodiments, the binding reagent specific for a transiently tolerant cancer cell and/or a cancer stem cell can be an antibody specific for a transiently tolerant cancer cell and/or cancer stem cell marker, e.g. CD44. In some embodiments, the binding reagent can be bound to and/or conjugated to multiple inhibitor molecules. In some embodiments, multiple molecules having a structure of Formula I or II can be conjugated to the binding reagent. In some embodiments, the ratio of a given inhibitor molecule (e.g. dasatinib) to the binding reagent molecule can be from about 1:1 to about 1,000:1, e.g. a single binding reagent molecule can be linked to, conjugated to, etc. from about 1 to about 1,000 individual inhibitor molecules. In some embodiments, the ratio of a given inhibitor molecule (e.g. dasatinib) to the binding reagent molecule can be from about 10:1 to about 500:1. In some embodiments, the ratio of a given inhibitor molecule (e.g. dasatinib) to the binding reagent molecule can be from about 40:1 to about 200:1.

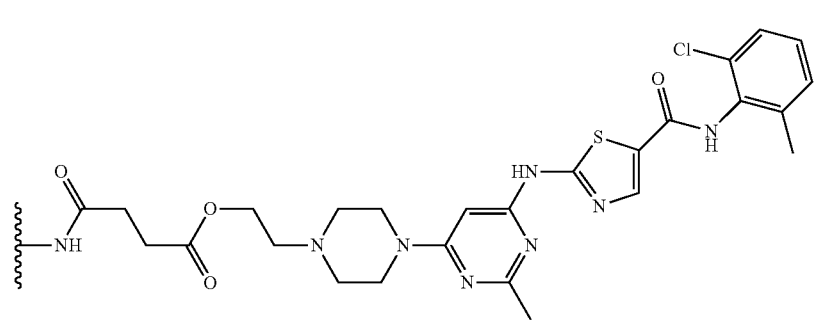

Formula I

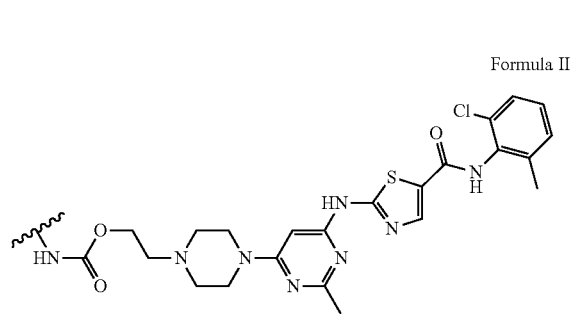 [SMILES: *NC(=O)OCCN1CCN(c2cc(Nc3ncc(C(=O)Nc4c(C)cccc4Cl)s3)nc(C)n2)CC1]

Formula II

The components of a composition described herein (e.g. a binding reagent and a kinase inhibitor and/or EGFR inhibitor) can be individually physically associated with the composition and/or physically associated with each other, e.g. the components can be bound to each other and/or conjugated to each other. In some embodiments, binding can be non-covalent, e.g., by hydrogen, electrostatic, or van der waals interactions, however, binding may also be covalent. By "conjugated" is meant the covalent linkage of at least two molecules. In some embodiments, the composition can be an antibody-drug conjugate.

In some embodiments, a scaffold material can comprise the plurality of components described herein. Scaffold materials suitable for use in therapeutic compositions are known in the art and can include, but are not limited to, a nanoparticle; a matrix; a hydrogel; and a biomaterial, biocompatible, and/or biodegradable scaffold material. As used herein, the term "nanoparticle" refers to particles that are on the order of about $10^{-9}$ or one billionth of a meter. The term "nanoparticle" includes nanospheres; nanorods; nanoshells; and nanoprisms; and these nanoparticles may be part of a nanonetwork.

The term "nanoparticles" also encompasses liposomes and lipid particles having the size of a nanoparticle. As used

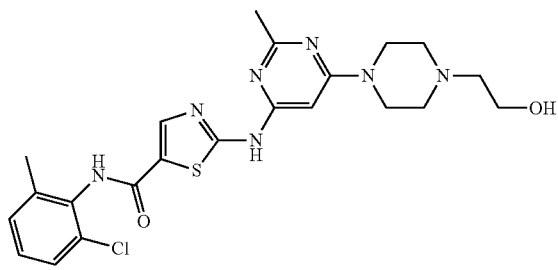

Formula III herein, the term "matrix" refers to a 3-dimensional structure comprising the components of a composition described herein (e.g. a binding reagent, kinase inhibitor, and/or EGFR inhibitor). Non-limiting examples of matrix structures include foams; hydrogels; electrospun fibers; gels; fiber mats; sponges; 3-dimensional scaffolds; non-woven mats; woven materials; knit materials; fiber bundles; and fibers and other material formats (See, e.g. Rockwood et al. Nature Protocols 2011 6:1612-1631 and US Patent Publications 2011/0167602; 2011/0009960; 2012/0296352; and U.S. Pat. No. 8,172,901; each of which is incorporated by reference herein in its entirety). The structure of the matrix can be selected by one of skill in the art depending upon the intended application of the composition, e.g. electrospun matrices can have greater surface area than foams.

In some embodiments, the scaffold is a hydrogel. As used herein, the term "hydrogel" refers to a three-dimensional polymeric structure that is insoluble in water but which is capable of absorbing and retaining large quantities of water to form a stable, often soft and pliable, structure. In some embodiments, water can penetrate in between the polymer chains of the polymer network, subsequently causing swelling and the formation of a hydrogel. In general, hydrogels are superabsorbent. Hydrogels have many desirable properties for biomedical applications. For example, they can be made nontoxic and compatible with tissue, and they are highly permeable to water, ions, and small molecules. Hydrogels are super-absorbent (they can contain over 99% water) and can be comprised of natural (e.g., silk) or synthetic polymers, e.g., PEG.

As used herein, "biomaterial" refers to a material that is biocompatible and biodegradable. As used herein, the term "biocompatible" refers to substances that are not toxic to cells. In some embodiments, a substance is considered to be "biocompatible" if its addition to cells in vitro results in less than or equal to approximately 20% cell death. In some embodiments, a substance is considered to be "biocompatible" if its addition to cells in vivo does not induce inflammation and/or other adverse effects in vivo. As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

In some embodiments, the scaffold can be a nanoparticle. In some embodiments, a nanoparticle can comprise dasatinib and PI103. In an exemplary embodiment, nanoparticles as described herein can be made as follows: 10 mg of L-α-phosphatidylcholine, 2 mg PI103-cholesterol conjugate, 2 mg of Dasatinib and 22 mg of 1,2-Distearoyl-sn-Glycero-3-Phosphoethanolamine-N-[Amino(Polythylene Glycol)2000](DSPE-PEG) are dissolved in 1.0 mL DCM and 0.5 mL of methanol. Solvent is evaporated into a thin and uniform lipid-drug film using a rotary evaporator. The lipid-drug film is then hydrated with 2.0 mL $H_2O$ for 1 h at 60° C. The mixtures can be passed though Sephadex G-25 column and extruded at 65° C. to obtain sub 200 nm particles. In some embodiments, the nanoparticle can further comprise a binding reagent specific for transiently tolerant cells.

In one aspect, described herein is a method of treatment comprising administering a cytotoxic chemotherapy to a subject in need of treatment for cancer and administering dasatinib and/or a composition as described herein. In some embodiments, the composition and/or dasatinib can be administered concomitantly and/or after the cytotoxic chemotherapy. In some embodiments, the composition and/or dasatinib can be administered after the cytotoxic chemotherapy.

In some embodiments, dasatinib and/or the composition as described herein can be administered during a period in which at least a subpopulation of cancer cells in the subject display increased levels of CD44 on the cell surface. In some embodiments, dasatinib and/or the composition as described herein can be administered during a period in which tumor growth plateaus. Methods of measuring the expression of a marker on a cell and/or measuring cell growth are well known in the art. By way of non-limiting example, CD44 expression can be measured by FACS analysis as described in the Examples herein, e.g. by contacting cells with a detectably labeled anti-CD44 antibody and detecting the amount of label bound to each cell via FACS.

In some embodiments, dasatinib and/or the composition as described herein can be administered at least 4 hours after the administration of the cytotoxic chemotherapy. In some embodiments, dasatinib and/or the composition as described herein can be administered no more than about 216 hours after the administration of the cytotoxic chemotherapy. In some embodiments, dasatinib and/or the composition as described herein can be administered from about 4 hours to about 216 hours after the administration of the cytotoxic chemotherapy. In some embodiments, dasatinib and/or the composition as described herein can be administered from about 4 hours to about 96 hours after the administration of the cytotoxic chemotherapy. In some embodiments, dasatinib and/or the composition as described herein can be administered from about 12 hours to about 96 hours after the administration of the cytotoxic chemotherapy. In some embodiments, dasatinib and/or the composition as described herein can be administered about 72 hours after the administration of the cytotoxic chemotherapy. In some embodiments, dasatinib and/or the composition as described herein can be administered within about 10 days of the administration of the cytotoxic chemotherapy, e.g. no later than about 10 days, no later than about 9 days, no later than about 8 days, no later than about 7 days, no later than about 6 days, no later than about 5 days, no later than about 4 days, no later than about 3 days, no later than about 2 days, no later than about 1 day, or on the same day as the administration of the cytotoxic chemotherapy. In some embodiments, dasatinib and/or the composition as described herein can be administered within about 7 days of the administration of the cytotoxic chemotherapy.

In some embodiments, the subject can be further administered an EGFR inhibitor, e.g. at the same time as the administration of the dasatinib and/or composition as described herein or at a different time.

As used herein, a "cytoxic chemotherapy" refers a substance that inhibits or prevents the function of cells and/or causes destruction of cells. Non-limiting examples of cytotoxic chemotherapies can include taxanes (e.g. paclitaxel (TAXOL™), cabazitaxel, and docetaxel); cytotoxic antibiotics such as anthracyclines (e.g. doxorubicin, daunorubicin, valrubicin, idarubicin, and epirubicin), actinomycin, bleomycin, plicamycin, and mitomycin; vinca alkaloids (e.g. vincristine, vinblastine, vinorelbine, and vindesine); and anti-tubulin chemotherapies. Cytotoxic chemotherapies can include toxins, such as small molecule toxins or enzymatically active toxins of bacterial, fungal, plant or animal origin, including fragments and/or variants thereof as well as radiation therapies.

As described herein, the inventors have characterized transiently tolerant cancer cells. The inventors have found that the phosphorylation levels of at least PRAS40, Src, and Hck, as well as the expression level of CD44 can vary between chemoresistant and chemosensitive cells. Accordingly, in one aspect, the technology described herein relates to a method of identifying a chemotherapy tolerant cancer cell and/or a cell likely to develop tolerance to chemotherapy, the method comprising detecting, in a cancer cell, the phosphorylation level of at least one gene selected from the group consisting of PRAS40, Src and Hck wherein increased phosphorylation of the Y411 residue of Hck, decreased phosphorylation of the Tyr527 residue of Src; or increased phosphorylation of T246 residue of PRAS40 indicates the cancer cell is a chemotherapy tolerant cancer cell, and/or is likely to develop tolerance to chemotherapy. In some embodiments, the method can further comprise detecting the expression level of CD44, wherein increased expression of CD44 indicates the cancer cell is a chemotherapy tolerant cancer cell and/or is likely to develop tolerance to chemotherapy.

In one aspect, described herein, is a method of treatment comprising detecting, in a cancer cell obtained from a subject, the phosphorylation level of at least one gene selected from the group consisting of PRAS40, Src and Hck; and administering a treatment as described above herein if increased phosphorylation of the Y411 residue of Hck, decreased phosphorylation of the Tyr527 residue of Src; or increased phosphorylation of T246 residue of PRAS40 is detected. In some embodiments, the method further comprises detecting the expression level of CD44, wherein increased expression of CD44 indicates the subject is a candidate for treatment.

In one aspect, described herein, is a method of determining if a subject is in need of a treatment as described herein, the method comprising detecting, in a cancer cell obtained from the subject, the phosphorylation level of at least one gene selected from the group consisting of PRAS40, Src and Hck; wherein if increased phosphorylation of the Y411 residue of Hck, decreased phosphorylation of the Tyr527 residue of Src; or increased phosphorylation of T246 residue of PRAS40 is detected, the subject is in need of treatment as described herein. In some embodiments, the method further comprises detecting the expression level of CD44, wherein increased expression of CD44 indicates the subject is a candidate for treatment.

Detection of the level of phosphorylation of PRAS40, Src and/or Hck and/or the expression level of CD44 can be according to any method known in the art Immunological methods to detect protein levels and/or phosphorylated proteins in accordance with the present technology include, but are not limited to antibody techniques such as immunohistochemistry, immunocytochemistry, flow cytometry, fluorescent-activated cell sorting (FACS), immunoblotting, radioimmunoassays, western blotting, immunoprecipitation, enzyme-linked immunosorbant assays (ELISA), and derivative techniques that make use of antibody reagents as described herein. Antibody reagents specific for each of the markers described herein can be made by methods known to one of skill in the art or obtained commercially, e.g. anti-Hck(phosphoY411 (Cat. No. 61055; Abcam; Cambridge, Mass.)), anti-Src(phosphoTyr527) (Cat. No. 2105; Cell Signaling Technology; Danvers, Mass.), anti-PRAS40(T246) (Cat. No. 5401-1; Abcam; Cambridge, Mass.), and anti-CD44 (Cat. No. 1998-1; Abcam; Cambridge, Mass.).

Immunochemistry is a family of techniques based on the use of a specific antibody, wherein antibodies are used to specifically target molecules inside or on the surface of cells. In some embodiments, immunohistochemistry ("IHC") and immunocytochemistry ("ICC") techniques can be used to detect or measure the levels of platelet-adherent leukocytes. IHC is the application of immunochemistry to tissue sections, whereas ICC is the application of immunochemistry to cells or tissue imprints after they have undergone specific cytological preparations such as, for example, liquid-based preparations. In some instances, signal amplification may be integrated into the particular protocol, wherein a secondary antibody, that includes a label, follows the application of an antibody reagent specific for platelets or leukocytes. Typically, for immunohistochemistry, tissue obtained from a subject and fixed by a suitable fixing agent such as alcohol, acetone, and paraformaldehyde, is sectioned and reacted with an antibody. Conventional methods for immunohistochemistry are described in Buchwalow and Bocker (Eds) "Immunohistochemistry: Basics and Methods" Springer (2010): Lin and Prichard "Handbook of Practical Immunohistochemistry" Springer (2011); which are incorporated by reference herein in their entireties. In some embodiments, immunocytochemistry may be utilized where, in general, tissue or cells are obtained from a subject are fixed by a suitable fixing agent such as alcohol, acetone, and paraformaldehyde, to which is reacted an antibody. Methods of immunocytological staining of human samples is known to those of skill in the art and described, for example, in Burry. "Immunocytochemistry: A Practical Guide for Biomedical Research" Springer (2009); which is incorporated by reference herein in its entirety.

In one embodiment, an assay, method, and/or system as described herein can comprise an ELISA. In an exemplary embodiment, a first antibody reagent can be immobilized on a solid support (usually a polystyrene micro titer plate). The solid support can be contacted with a sample obtained from a subject, and the antibody reagent will bind ("capture") cells for which it is specific (e.g. phosphoisoforms of PRAS40, Src and/or Hck and/or CD44). The solid support can then be contacted with a second labeled antibody reagent (e.g. a detection antibody reagent). The detection antibody reagent can, e.g. comprise a detectable signal, be covalently linked to an enzyme, or can itself be detected by a secondary antibody which is linked to an enzyme through bio-conjugation. The presence of a signal indicates that both the first antibody reagent immobilized on the support and the second "detection" antibody reagent have bound to a cell, i.e. the presence of a signal indicates the presence of cell expressing a detectable level of a marker described herein. Between each step the plate is typically washed with a mild detergent solution to remove any proteins or antibodies that are not specifically bound. After the final wash step the plate is developed by adding an enzymatic substrate to produce a visible signal, which indicates the quantity of transiently tolerant cancer cell markers in the sample. Older ELISAs utilize chromogenic substrates, though newer assays employ fluorogenic substrates with much higher sensitivity. There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem. 22:895-904. These references are hereby incorporated by reference in their entirety.

In one embodiment, the assays, systems, and methods described herein can comprise a lateral flow immunoassay test (LFIA), also known as the immunochromatographic assay, or strip test to measure or determine the level of phosphorylation of PRAS40, Src and/or Hck and/or the expression level of CD44 in a sample. LFIAs are a simple device intended to detect the presence (or absence) of a marker in a sample. There are currently many LFIA tests are used for medical diagnostics either for home testing, point of care testing, or laboratory use. LFIA tests are a form of immunoassay in which the test sample flows along a solid substrate via capillary action. After the sample is applied to the test it encounters a colored antibody reagent which mixes with the sample, and if bound to a portion of the sample, transits the substrate encountering lines or zones which have been pretreated with a second antibody reagent. Depending upon the level of maker present in the sample the colored antibody reagent can become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as blood, water samples etc. Strip tests are also known as dip stick test, the name bearing from the literal action of "dipping" the test strip into a fluid sample to be tested. LFIA strip test are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibody reagents specific for a target (e.g. a CD44-specific antibody reagent). The test line will also contain antibody reagents. The test line will show as a colored band in positive samples. In some embodiments, the lateral flow immunoassay can be a double antibody sandwich assay, a competitive assay, a quantitative assay or variations thereof. There are a number of variations on lateral flow technology. It is also possible to apply multiple capture zones to create a multiplex test.

A typical test strip consists of the following components: (1) sample application area comprising an absorbent pad (i. e. the matrix or material) onto which the test sample is applied; (2) conjugate or reagent pad—this contains antibody reagent(s) specific to the target which can be conjugated to colored particles (usually colloidal gold particles, or latex microspheres); (3) test results area comprising a reaction membrane—typically a hydrophobic nitrocellulose or cellulose acetate membrane onto which antibody reagents are immobilized in a line across the membrane as a capture zone or test line (a control zone may also be present, containing antibodies specific for the antibody reagents conjugated to the particles or microspheres); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line which contains an antibody that picks up free latex/gold in order to confirm the test has operated correctly.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622, 871; 6,565,808, U.S. patent applications Ser. No. 10/278, 676; U.S. Ser. No. 09/579,673 and U.S. Ser. No. 10/717,082, which are incorporated herein by reference in their entirety, are non-limiting examples of such lateral flow test devices.

Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teaching of these "dip stick" technology for the detection of the level of phosphorylation of PRAS40, Src and/or Hck and/or the expression level of CD44.

In some embodiments, detection of phosphorylation of PRAS40, Src and/or Hck and/or the expression level of CD44 can be performed using flow cytometry. In some embodiments, detection of phosphorylation of PRAS40, Src and/or Hck and/or the expression level of CD44 can be performed using immunocytological methods, e.g. FACS.

Flow cytometry is a well-known technique for analyzing and sorting cells (or other small particles) suspended in a fluid stream. This technique allows simultaneous analysis of the physical and/or chemical characteristics of single cells flowing through an optical, electronic, or magnetic detection apparatus. As applied to FACS, the flow cytometer consists of a flow cell which carries the cells in a fluid stream in single file through a light source with excites the fluorescently labeled detection marker(s) (for example, antibody reagents) and measures the fluorescent character of the cell. The fluid stream is then ejected through a nozzle and a charging ring, under pressure, which breaks the fluid into droplets. The flow cell device and fluid stream is calibrated such that there is a relatively large distance between individual cells, resulting in a low probability that any droplet contains more than a single cell or bound group of cells. The charging ring charges the droplets based on the fluorescence characteristic of the cell which is contained therein. The charged droplets are then deflected by an electrostatically-charged deflection system which diverts the droplets into various containers based upon their charge (related to the fluorescence intensity of the cell). A FACS system (e.g. the FACSARIA™ flow cytometer (BD Biosciences) and FLOWJO™ Version 7.6.4 (TreeStar)) can detect and record the number of total cells as well as the number of cells which display one or more fluorescent characteristics, e.g. (a) the total number of cells in a sample and (b) the number of cells with an antibody reagent specifically bound to them. In some embodiments, the level of transiently tolerant cancer cells and/or cells likely to become chemoresistant can be determined using high-throughput FACS (see, e.g. US Patent Publication 2009/0239235 describing a technology commercially available as FACSCANTO™ from BD Biosciences and which is incorporated by reference herein in its entirety).

In some embodiments, one or more of the antibody reagents described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into an antibody reagent are well known in the art.

In some embodiments, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the antibody reagent. Alternatively, a detectable label can be linked such as by directly labeling a molecule that achieves binding, to the antibody reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection antibody is label with a fluorescent compound. When the fluorescently labeled antibody is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA. CyDyes™, 6-carboxyfhiorescein (commonly known by the abbreviations FAM and F), 6-carboxy-2',4', 7',4,7-hexachlorofluorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g. umbelliferone, benzimide dyes, e.g. Hoechst 33258: phenanthridine dyes, e.g. Texas Red; ethidium dyes; acridine dyes; carbazole dyes; phenoxazine dyes: porphyrin dyes; polymethine dyes, e.g. cyanine dyes such as Cy3, Cy5, etc; BODIPY dyes and quinoline dyes.

In some embodiments, a detectable label can be a radiolabel including, but not limited to $^{3}$H, $^{125}$I, $^{35}$S, $^{14}$C, $^{32}$P, and $^{33}$P.

In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

In some embodiments, a detectable label is a chemiluminescent label, including, but not limited to lucigenin, luminol, luciferin, isoluminol, theromatic acridinium ester, imidazole, acridinium salt and oxalate ester.

In some embodiments, a detectable label can be a spectral colorimetric label including, but not limited to colloidal gold or colored glass or plastic (e.g., polystyrene. polypropylene, and latex) beads.

In some embodiments, antibodies can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif.

An antibody reagent can also be detectably labeled using fluorescence emitting metals such as $^{152}$Eu, or others of the lanthanide series. These metals can be attached to the antibody reagent using such metal chelating groups as diethylenetriaminepentaacetic acid (DTPA) or ethylenediaminetetraacetic acid (EDTA).

In some embodiments, the level of CD44 can be detected by detecting the level of mRNA encoding CD44. Such molecules can be isolated, derived, or amplified from a biological sample, such as a biopsy or blood sample. Assays for detecting mRNA transcripts are well known in the art and include, but are not limited to, PCR procedures, RT-PCR, Northern blot analysis, RNAse protection assay, microarray analysis, hybridization methods etc. In some embodiments, mRNA transcript expression product levels are assayed using reverse transcription polymerase chain reaction (RT-PCR).

The nucleic acid sequences of, e.g. CD44 have been assigned NCBI accession numbers for different species such as human, mouse and rat. In particular, the NCBI accession number for the nucleic acid sequences of the human CD44 expression product is included herein. Accordingly, a skilled artisan can design appropriate primers based on the known sequence for determining the mRNA level of CD44. In some embodiments, the RNA transcript level can be measured using reverse transcription polymerase chain reaction (RT-PCR).

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; and proteinase K extraction can be used to obtain nucleic acid from blood (Roiff, A et al. PCR: Clinical Diagnostics and Research, Springer (1994)).

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments, the methods described herein relate to treating a subject having or diagnosed as having cancer. Subjects having, e.g. cancer can be identified by a physician using current methods of diagnosing cancer. Symptoms and/or complications of cancer which characterize these conditions and aid in diagnosis are well known in the art and include but are not limited to, growth of a tumor, impaired function of the organ or tissue harboring cancer cells, etc. Tests that may aid in a diagnosis of, e.g. cancer include, but are not limited to, tissue biopsies and histological examination. A family history of cancer or exposure to risk factors for cancer (e.g. smoking or radiation) can also aid in determining if a subject is likely to have cancer or in making a diagnosis of cancer.

The compositions and methods described herein can be administered to a subject having or diagnosed as having cancer. In some embodiments, the methods described herein comprise administering an effective amount of compositions described herein to a subject in order to alleviate a symptom of a cancer. As used herein, "alleviating a symptom of a cancer" is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular anti-tumor effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a composition described herein, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for the presence of chemoresistant cells and/or tumor size, among others. The dosage can be determined by a physician and adjusted, as necessary, to suit observed effects of the treatment.

In some embodiments, the dosage of an inhibitor as described herein (e.g. a kinase inhibitor or EGFR inhibitor) is less than a cytotoxic dose of that inhibitor. In some embodiments, the dosage of an inhibitor as described herein is 50% or less of a cytotoxic dose of that inhibitor, e.g. 50% or less, 40% or less, 30% or less, 20% or less, or 10% or less. In some embodiments, the dosage of an inhibitor as described herein is 40% or less of a cytotoxic dose of that inhibitor. In some embodiments, the dosage of an inhibitor as described herein is 30% or less of a cytotoxic dose of that inhibitor. In some embodiments, the dosage of an inhibitor as described herein is 20% or less of a cytotoxic dose of that inhibitor. In some embodiments, the dosage of an inhibitor as described herein is 10% or less of a cytotoxic dose of that inhibitor.

In some embodiments, the technology described herein relates to a composition as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. a composition as described herein.

In some embodiments, the pharmaceutical composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a composition as disclosed herein can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering an additional agent and/or treatment to the subject, e.g. as part of a combinatorial therapy. Non-limiting examples of an additional agent and/or treatment can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1 I and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN@ doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb™); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. In addition, the methods of treatment can further include the use of radiation or radiation therapy. Further, the methods of treatment can further include the use of surgical treatments.

In certain embodiments, an effective dose of a composition as described herein can be administered to a patient once. In certain embodiments, an effective dose of a composition can be administered to a patient repeatedly. For systemic administration, subjects can be administered a therapeutic amount of a composition, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. tumor size and/or rate of growth by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to a composition. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

The dosage ranges for the administration of a composition as described herein, according to the methods described herein depend upon, for example, the form of a composition, its potency, and the extent to which symptoms, markers, or indicators of a condition described herein are desired to be reduced, for example the percentage reduction desired for, e.g. tumor size and/or rate of growth. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a composition in, e.g. the treatment of a condition described herein, or to induce a response as described herein (e.g. reduction in tumor size) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. tumor size. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. tumor size). It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g. tumor size.

In vitro and animal model assays are provided herein which allow the assessment of a given dose of a composition. By way of non-limiting example, the effects of a dose of a composition as described herein can be assessed by determining cell viability. A non-limiting example of a protocol for such an assay is as follows: Cells (e.g. tumor cells) can be grown to semi-confluence and treated with a chemotherapeutic (e.g. cytotoxic) agent and/or the compositions described herein in serum containing medium. Following incubation, cells can be washed and recovered in serum and phenol red-free RPMI or DMEM and treated with MTS ONE solution (Promega) as described previously (Chaudhuri et al., 2009).

The efficacy of a given dosage combination can also be assessed in an animal model, e.g. a mouse model of cancer. For example, MDA-MB-231 cells suspended in 100 µL PBS can be injected into the flank of 5-6 week old Nu/Nu Crl:NU-Foxn1$^{nu}$ nude mice. Once tumors became palpable, day 0 (approximately 3 weeks after implant) a chemotherapeutic (e.g. cytotoxic) agent and/or the compositions described herein can be administered, e.g. intraperitoneally. Tumors can be harvested, e.g. on day 6 and tumor volume determined.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulfide-linked scfv, diabody), whether derived from any species that naturally produces an antibody, or created by recombinant DNA technology; whether isolated from serum, B-cells, hybridomas, transfectomas, yeast or bacteria.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883. Antibody fragments can be obtained using any appropriate technique including conventional techniques known to those of skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

A further kind of antibody reagent is an intrabody i.e. an intracellular antibody (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). Intrabodies work within the cell and bind intracellular protein. Intrabodies can include whole antibodies or antibody binding fragments thereof, e.g. single Fv, Fab and F(ab)'2, etc. Methods for intrabody production are well known to those of skill in the art, e.g. as described in WO 2002/086096. Antibodies will usually bind with at least a KD of about 1 mM, more usually at least about 300 µM, typically at least about 10 µM, more typically at least about 30 µM, preferably at least about 10 µM, and more preferably at least about 3 µM or better.).

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives to hybridoma-based production systems. The main advantages of transgenic animals are potential high yields from renewable sources.

As used herein, an "epitope" can be formed both from contiguous amino acids, or noncontiguous amino acids juxtaposed by folding of a protein. Epitopes formed from contiguous amino acids are typically retained on exposure to denaturing solvents, whereas epitopes formed by folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein.

Nucleic acid molecules encoding amino acid sequence variants of antibodies are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, antigen-binding portion thereof, or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, N Y, 1982 and 1989), and Ausubel, 1987, 1993, and can be used to construct nucleic acid sequences which encode a monoclonal antibody molecule or antigen binding region thereof. A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art. See, e.g., Sambrook et al., 1989; Ausubel et al., 1987-1993.

Accordingly, the expression of an antibody or antigen-binding portion thereof as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or portion thereof as described herein with a specified amino terminus sequence. Moreover, problems associated with retention of initiation codon-derived methionine residues in direct yeast (or bacterial) expression may be avoided. Sabin et al., 7 Bio/Technol. 705 (1989); Miller et al., 7 Bio/Technol. 698 (1989). Any of a series of yeast gene expression systems incorporating promoter and termination elements from the actively expressed genes coding for glycolytic enzymes produced in large quantities when yeast are grown in media rich in glucose can be utilized to obtain recombinant antibodies or antigen-binding portions thereof. Known glycolytic genes can also provide very efficient transcriptional control signals. For example, the promoter and terminator signals of the phosphoglycerate kinase gene can be utilized.

Production of antibodies or antigen-binding portions thereof as described herein can be achieved in insects, for example, by infecting the insect host with a baculovirus engineered to express a transmembrane polypeptide by methods known to those of skill in the art. See Ausubel et al., 1987, 1993.

In some embodiments, the introduced nucleotide sequence is incorporated into a plasmid or viral vector capable of autonomous replication in the recipient host. Any of a wide variety of vectors can be employed for this purpose and are known and available to those of ordinary skill in the art. See, e.g., Ausubel et al., 1987, 1993. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli.*, for example. Other gene expression elements useful for the expression of cDNA encoding antibodies or antigen-binding portions thereof include, but are not limited to (a) viral transcription promoters and their enhancer elements, such as the SV40 early promoter (Okayama et al., 3 Mol. Cell. Biol. 280 (1983)), Rous sarcoma virus LTR (Gorman et al., 79 PNAS 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983) Immunoglobulin cDNA genes can be expressed as described by Liu et al., infra, and Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric immunoglobulin chain gene product are then transfected singly with an antibody, antigen-binding portion thereof, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In some embodiments, the fused genes encoding the antibody, antigen-binding fragment thereof, or chimeric H and L chains, or portions thereof are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes. Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the fused genes encoding chimeric H and L chains can be assembled on the same expression vector.

For transfection of the expression vectors and production of the chimeric, humanized, or composite human antibodies described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a chimeric, humanized, or composite human antibody construct, antibody, or antigen-binding portion thereof as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988), as known to one of ordinary skill in the art.

Yeast provides certain advantages over bacteria for the production of immunoglobulin H and L chains. Yeasts carry out post-translational peptide modifications including glycosylation. A number of recombinant DNA strategies exist that utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Intl. Conf. Yeast, Genetics & Molec. Biol. (Montpelier, France, 1982).

Yeast gene expression systems can be routinely evaluated for the levels of production, secretion and the stability of antibodies, and assembled chimeric, humanized, or composite human antibodies, portions and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See II DNA Cloning 45, (Glover, ed., IRL Press, 1985) and e.g., U.S. Publication No. US 2006/0270045 A1.

Bacterial strains can also be utilized as hosts for the production of the antibody molecules or peptides described herein, E. coli K12 strains such as E. coli W3110 (ATCC 27325), Bacillus species, enterobacteria such as Salmonella typhimurium or Serratia marcescens, and various Pseudomonas species can be used. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of chimeric, humanized, or composite humanized antibodies and fragments thereof encoded by the cloned immunoglobulin cDNAs or CDRs in bacteria (see Glover, 1985; Ausubel, 1987, 1993; Sambrook, 1989; Colligan, 1992-1996).

Host mammalian cells can be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

In some embodiments, one or more antibodies or antibody reagents thereof as described herein can be produced in vivo in an animal that has been engineered or transfected with one or more nucleic acid molecules encoding the polypeptides, according to any suitable method.

In some embodiments, an antibody or antibody reagent as described herein is produced in a cell-free system. Nonlimiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

Many vector systems are available for the expression of cloned H and L chain genes in mammalian cells (see Glover, 1985). Different approaches can be followed to obtain complete $H_2L_2$ antibodies. As discussed above, it is possible to co-express H and L chains in the same cells to achieve intracellular association and linkage of H and L chains into complete tetrameric $H_2L_2$ antibodies or antigen-binding portions thereof. The co-expression can occur by using either the same or different plasmids in the same host. Genes for both H and L chains or portions thereof can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing antibodies, antigen-binding portions thereof and/or $H_2L_2$ molecules via either route could be transfected with plasmids encoding additional copies of peptides, H, L, or H plus L chains in conjunction with additional selectable markers to generate cell lines with enhanced properties, such as higher production of assembled $H_2L_2$ antibody molecules or enhanced stability of the transfected cell lines.

Additionally, plants have emerged as a convenient, safe and economical alternative main-stream expression systems for recombinant antibody production, which are based on large scale culture of microbes or animal cells. Antibodies can be expressed in plant cell culture, or plants grown conventionally. The expression in plants may be systemic, limited to susb-cellular plastids, or limited to seeds (endosperms). See, e.g., U.S. Patent Pub. No. 2003/0167531; U.S. Pat. No. 6,080,560; U.S. Pat. No. 6,512,162; WO 0129242. Several plant-derived antibodies have reached advanced stages of development, including clinical trials (see, e.g., Biolex, NC).

In some aspects, provided herein are methods and systems for the production of a humanized antibody, which is prepared by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors can be the same vector. Also provided herein are DNA sequences encoding the light chain or the heavy chain of the humanized antibody; an expression vector which incorporates a said DNA sequence; and a host transformed with a said expression vector.

Generating a humanized antibody from the sequences and information provided herein can be practiced by those of ordinary skill in the art without undue experimentation. In one approach, there are four general steps employed to humanize a monoclonal antibody, see, e.g., U.S. Pat. No. 5,585,089; U.S. Pat. No. 6,835,823; U.S. Pat. No. 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. Although not usually desirable, it is sometimes possible to make one or more conservative amino acid substitutions of CDR residues without appreciably affecting the binding affinity of the resulting humanized immunoglobulin or human antibody variant. Occasionally, substitutions of CDR regions can enhance binding affinity.

In addition, techniques developed for the production of "chimeric antibodies" (see Morrison et al., Proc. Natl. Acad. Sci. 81:851-855 (1984); Neuberger et al., Nature 312:604-608 (1984); Takeda et al., Nature 314:452-454 (1985); which are incorporated by reference herein in their entireties) by splicing genes from a mouse, or other species, antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region, e.g., humanized antibodies. The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells (WO 87/02671; which is incorporated by reference herein in its entirety). The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Alternatively, techniques described for the production of single chain antibodies (see, e.g. U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989); which are incorporated by reference herein in their entireties) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* can also be used (see, e.g. Skerra et al., Science 242:1038-1041 (1988); which is incorporated by reference herein in its entirety).

Chimeric, humanized and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the cross-reacting antibodies. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. *E. coli* is one prokaryotic host particularly useful for cloning the DNA sequences. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization. Mammalian cells are a preferred host for expressing nucleotide segments encoding immunoglobulins or fragments thereof. See Winnacker, From Genes to Clones, (VCH Publishers, N Y, 1987), which is incorporated herein by reference in its entirety. A number of suitable host cell lines capable of secreting intact heterologous proteins have been developed in the art, and include CHO cell lines, various COS cell lines, HeLa cells, L cells and multiple myeloma cell lines. Expression vectors for these cells can include expression control sequences, such as an origin of replication, a promoter, an enhancer (Queen et al., "Cell-type Specific Regulation of a Kappa Immunoglobulin Gene by Promoter and Enhancer Elements," *Immunol Rev* 89:49 (1986), incorporated herein by reference in its entirety), and necessary processing information sites, such as ribosome binding sites, RNA splice sites, polyadenylation sites, and transcriptional terminator sequences. Preferred expression control sequences are promoters substantially similar to a region of the endogenous genes, cytomegalovirus, SV40, adenovirus, bovine papillomavirus, and the like. See Co et al., "Chimeric and Humanized Antibodies with Specificity for the CD33 Antigen," *J Immunol* 148:1149 (1992), which is incorporated herein by reference in its entirety. Alternatively, antibody coding sequences can be incorporated in transgenes for introduction into the genome of a transgenic animal and subsequent expression in the milk of the transgenic animal (e.g., according to methods described in U.S. Pat. No. 5,741,957, U.S. Pat. No. 5,304,489, U.S. Pat. No. 5,849,992, all incorporated by reference herein in their entireties). Suitable transgenes include coding sequences for light and/or heavy chains in operable linkage with a promoter and enhancer from a mammary gland specific gene, such as casein or beta lactoglobulin. The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra, which is herein incorporated by reference in is entirety). For production of transgenic animals, transgenes can be microinjected into fertilized oocytes, or can be incorporated into the genome of embryonic stem cells, and the nuclei of such cells transferred into enucleated oocytes. Once expressed, antibodies can be purified according to standard procedures of the art, including HPLC purification, column chromatography, gel electrophoresis and the like (see generally, Scopes, Protein Purification (Springer-Verlag, NY, 1982), which is incorporated herein by reference in its entirety).

Once expressed, the whole antibodies, their dimers, individual light and heavy chains, or other immunoglobulin forms of the present invention can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROTEIN PURIF. (Springer-Verlag, N Y, 1982). Substantially pure immunoglobulins of at least about 90% to 95% homogeneity are advantageous, as are those with 98% to 99% or more homogeneity, particularly for pharmaceutical uses. Once purified, partially or to homogeneity as desired, a humanized or composite human antibody can then be used therapeutically or in developing and performing assay procedures, immunofluorescent stainings, and the like. See generally, Vols. I & II Immunol Meth. (Lefkovits & Pernis, eds., Acad. Press, N Y, 1979 and 1981).

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to a cancer cell marker.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, a "portion" refers to a part or fraction of a whole, e.g. a part or fraction of a molecule and/or compound.

The term "stem cell" as used herein, as used in the context of or with reference to a "cancer stem cell" refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "cancer stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell can derive from a multipotent cell which itself is derived from a multipotent cell, and so on. While each of these multipotent cells can be considered stem cells, the range of cell types each can give rise to can vary considerably. Some differentiated cells also have the capacity to give rise to cells of greater developmental potential. Such capacity can be natural or can be induced artificially upon treatment with various factors. In many biological instances, stem cells are also "multipotent" because they can produce progeny of more than one distinct cell type, but this is not required for "sternness." Self-renewal is the other classical part of the stem cell definition, and it is essential as used in this document. In theory, self-renewal can occur by either of two major mechanisms. Stem cells can divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation". Cancer stem cells have the ability for self-renewal, multipotent differentiation and vigorous proliferative capacity. In some embodiments, cancer stem cells or cells having a cancer stem cell-like phenotype are chemoresistant.

As used herein, the term "chemoresistant" refers to tumor cells which show little or no significant detectable response to an agent used in chemotherapy. As used herein, the term "chemosensitive" refers to tumor cells which show a detectable response to an agent used in chemotherapy. Chemoresistance and/or chemosensitivity can be in reference to one or more agents, e.g. a cell can be chemoresistant or chemosensitive to one agent, to two agents, to three agents or more agents. Chemoresistance and/or chemosensitivity can vary with time for any given cell and/or tumor.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A composition comprising a combination of
   a binding reagent specific for a transiently tolerant cancer cell and/or a cancer stem cell; and
   a kinase inhibitor, capable of inhibiting the activity of at least one PI3K pathway kinase and at least one Src family kinase.
2. The composition of paragraph 1, wherein the PI3K pathway kinase is selected from the group consisting of Akt; BCR-Abl; PRAS40; mTOR; S6K; Rsk1; Rsk2; and Rsk3.
3. The composition of any of paragraphs 1-2, wherein the PI3K pathway kinase is BCR-Abl.
4. The composition of any of paragraphs 1-3, wherein the kinase inhibitor comprises a dual kinase inhibitor.
5. The composition of paragraph 4, wherein the dual kinase inhibitor is dasatinib.
6. The compositions of any of paragraphs 1-5, wherein the kinase inhibitor comprises a mixture of at least two kinase inhibitors.
7. A composition comprising a combination of
   a binding reagent specific for a transiently tolerant cancer cell and/or a cancer stem cell;
   a kinase inhibitor capable of inhibiting the activity at least one Src family kinase;
   and an EGFR inhibitor.
8. The composition of any of paragraphs 1-7, wherein the Src family kinase is selected from the group consisting of Src; Yes; Fyn; Fgr; Lck; Hck; Blk; Lyn; and Frk.
9. The composition of any of paragraphs 1-8, wherein the Src family kinase is selected from the group consisting of Src; Yes; Fyn; and Fgr.
10. The composition of any of paragraphs 1-9, wherein the Src family kinase is Src.
11. A composition comprising
    a binding reagent specific for a transiently tolerant cancer cell and/or a cancer stem cell; and
    dasatinib.
12. The composition of any of paragraphs 1-11, wherein the binding reagent specific for a transiently tolerant cancer cell and/or a cancer stem cell is an antibody or antigen-binding portion of an antibody.
13. The composition of any of paragraphs 1-11, wherein the binding reagent specific for a transiently tolerant cancer cell and/or a cancer stem cell is an aptamer.
14. The composition of paragraph 12, wherein the binding reagent is conjugated to the dual kinase inhibitor.
15. The composition of paragraph 14, wherein the dual kinase inhibitor is selected from Formula I and Formula II,

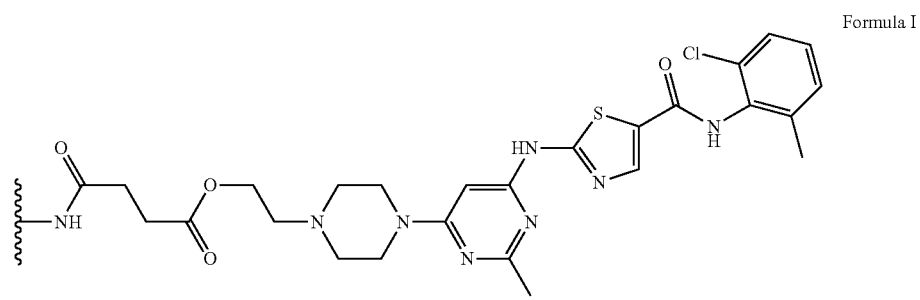

Formula I

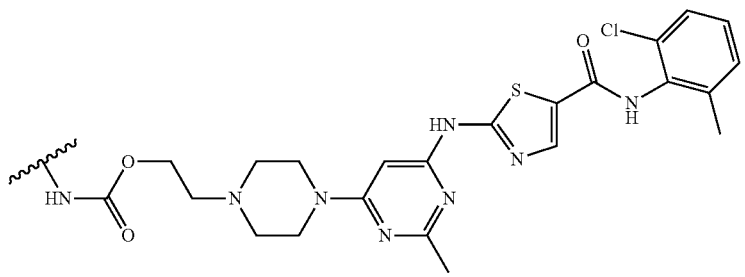

Formula II wherein the structure of Formula I or Formula II is conjugated to a binding reagent specific for a transiently tolerant cancer cell and/or a cancer stem cell.
16. The composition of any of paragraphs 1-15, wherein the binding reagent specific for a transiently tolerant cancer cell and/or a cancer stem cell binds specifically to a cell surface protein selected from the group consisting of:
CD44; and isoforms thereof; cluster of differentiation protein family polypeptides; CD24; EpCAM; CD133; ganglioside GD2; epithelial specific antigen (ESA); Pgp; BCRP; MDR; ABC transport protein family polypeptides; EGFR; HER-2; ER; PR; IGF1R; insulin receptor; and EGFR-IGFR heterodimers.
17. The composition of any of paragraphs 1-16, further comprising a scaffold material.
18. The composition of paragraph 17, wherein the scaffold material is selected from the group consisting of: a nanoparticle; a matrix; a hydrogel; and a biodegradable scaffold material.
19. The composition of any of paragraphs 1-18, further comprising an EGFR inhibitor.
20. The composition of any of paragraphs 1-19, wherein the EGFR inhibitor is selected from the group consisting of:
erlotinib; cetuximab; gefitinib; panitumumab; zaltuumumab; nimotuzmab; matuzaumab; and lapatinib.
21. The composition of paragraph 20, wherein the EGFR inhibitor is erlotinib.
22. The composition of any of paragraphs 1-21, further comprising a pharmaceutically acceptable carrier.
23. A method for treating cancer in a subject in need thereof comprising administering to the subject in need of treatment for cancer a combination of a cytotoxic chemotherapy agent and dasatinib or a composition of any of paragraphs 1-22.
24. The method of paragraph 23, wherein the cytotoxic chemotherapy agent is selected from the group consisting of: doxorubicin; taxanes; cabazitaxel; vincristine; anti-tubulin chemotherapies; and vinblastine.
25. The method of any of paragraphs 23-24, wherein the composition of any of paragraphs 1-22 is administered after the administration of the cytotoxic chemotherapy agent.
26. The method of any of paragraphs 23-25, wherein the composition of any of paragraphs 1-22 is administered during a period in which at least a subpopulation of cancer cells in the subject display increased levels of CD44 on the cell surface.
27. The method of paragraph 23-26, wherein the composition of any of paragraphs 1-22 is administered during a period in which tumor growth plateaus.
28. The method of paragraph 23-26, wherein the composition of any of paragraphs 1-22 is administered at least 4 hours after the administration of the cytotoxic chemotherapy agent.
29. The method of paragraph 23-26, wherein the composition of any of paragraphs 1-22 is administered no more than about 216 hours after the administration of the cytotoxic chemotherapy agent.
30. The method of paragraph 23-26, wherein the composition of any of paragraphs 1-22 is administered from about 4 hours to about 216 hours after the administration of the cytotoxic chemotherapy agent.
31. The method of paragraph 23-26, wherein the composition of any of paragraphs 1-22 is administered from about 4 hours to about 96 hours after the administration of the cytotoxic chemotherapy agent.
32. The method of paragraph 23-26, wherein the composition of any of paragraphs 1-22 is administered from about 12 hours to about 96 hours after the administration of the cytotoxic chemotherapy.
33. The method of paragraph 23-26, wherein the composition of any of paragraphs 1-22 is administered about 72 hours after the administration of the cytotoxic chemotherapy.
34. The method of paragraph 23-26, wherein the composition of any of paragraphs 1-22 is administered within 10 days after the administration of the cytotoxic chemotherapy.
35. The method of paragraph 23-26, wherein the composition of any of paragraphs 1-22 is administered within 7 days after the administration of the cytotoxic chemotherapy.
36. The method of any of paragraphs 23-35, wherein the subject is further administered an EGFR inhibitor.
37. The method of paragraph 36, wherein the EGFR inhibitor is selected from the group consisting of:
erlotinib; cetuximab; gefitinib; panitumumab; zaltuumumab; nimotuzmab; matuzaumab; and lapatinib.
38. The method of paragraph 37, wherein the EGFR inhibitor is erlotinib.
39. A method of identifying a chemotherapy tolerant cancer cell, the method comprising;
detecting, in a cancer cell, the phosphorylation level of at least one gene selected from the group consisting of:
PRAS40, Src and Hck;
wherein increased phosphorylation of the Y411 residue of Hck, decreased phosphorylation of the Tyr527 residue of Src; or increased phosphorylation of T246 residue of PRAS40 indicates the cancer cell is a chemotherapy tolerant cancer cell.

40. The method of paragraph 39, further comprising detecting the expression level of CD44, wherein increased expression of CD44 indicates the cancer cell is a chemotherapy tolerant cancer cell.
41. A method of treatment of a cancer in a subject in need thereof comprising;
    detecting, in a cancer cell, the phosphorylation level of at least one gene selected from the group consisting of:
        PRAS40, Src and Hck; and
    administering a composition of paragraphs 1-22 to the subject when increased phosphorylation of the Y411 residue of Hck, decreased phosphorylation of the Tyr527 residue of Src; or increased phosphorylation of T246 residue of PRAS40 is detected.
42. The method of paragraph 41, further comprising detecting the expression level of CD44, and administering the composition of paragraphs 1-22 to the subject when increased expression of CD44 is detected.

EXAMPLES

Example 1

Temporal Tumor Cell Switching to Stem-Like Phenocopies Predipsoses a Vulnerable Chemoresistant Transition Acquired resistance to chemotherapy is a key obstacle to successful cancer treatment. A number of reports have implicated the existence of inalterable cancer stem cells (CSC) capable of inherently overcoming chemotherapy and re-populating a viable tumor. However, intratumoral heterogeneity, intrinsic plasticity and fundamental Darwinian dynamics challenge this static CSC paradigm. Described herein is a transitional state of chemoresistance conferred by the induced, ephemeral emergence of stemlike phenocopies mimicking a subset of inherently chemoresistant cells and predisposing therapeutic vulnerability. It is demonstrated herein that transitory induction of a CSC biomarker (CD44) functionally engages receptor tyrosine kinases to re-organize a cortex network and trigger survival via phosphatidylinositol-3-OH kinase (PI(3)K) and Src-Family Kinase (SFK) signaling-redundancy. Utilizing dasatinib in sequence with docetaxel during a temporally-dependent window of therapeutic opportunity, significant tumor regression is observed in a highly aggressive in-vivo cancer model. These findings reveal novel insight into the CSC hypothesis and non-genetic mechanisms of chemoresistance, invoking temporality and Darwinian dynamics to address the global role of heterogeneity. Furthermore, the results conclude on the importance of kinase redundancies, drug combination and schedule-dependency, impacting immediately the clinical management of cancer.

The inability of chemotherapy to completely ablate tumor cells and the resulting relapse remains a vital obstacle in the clinical management of cancer. The conventional model for the development of resistance to chemotherapy is built on the stochastic acquisition of resistance-favored mutations (Cairns, 1975). However, this antiquated paradigm ignores the emergence of competing phenotypic variants as a consequence of the non-genetic heterogeneity of cancer (Marusyk et al., 2012). For example, chronic myeloid leukemia (CML) cells in patients treated with the drug imatinib, will survive an immediate blast phase, even re-growing during treatment despite an absence of genetic alterations which confer imatinib-resistance (Okabe et al., 2008; Talpaz et al., 2002). Similarly in other tumors, resistance to cytotoxic antitubulin chemotherapy can occur independent of mutation status (Berrieman et al., 2004). Such phenomena are commonly associated with non-genetic alterations such as enhancement of redundant signaling circuitry (Logue and Morrison, 2012). Indeed, Darwinian dynamics suggest that adaptive responses to microenvironmental stressors such as cytotoxic and targeted chemotherapies may precede mutations and therefore serve as substrates for the somatic evolution of cancer (Gillies et al., 2012). Therefore, understanding non-genetic mechanisms of adaptive chemoresistance becomes a key challenge in the development of successful therapeutic interventions.

As a prominent theory of intrinsic chemoresistance, researchers have evolved a cancer stem cell (CSC) model which underscores a static population of cells capable of exerting phenotypic advantages to overcome chemotherapy and re-produce a viable tumor (Dean et al., 2005). Indeed, the CSC model has served as the central paradigm by which researchers describe the non-genetic basis of chemoresistance (Shackleton et al., 2009). However, the CSC model does not incorporate mechanisms of adaptive, rather than inherent resistance. Indeed, the central dogma of the CSC hypothesis posits an inherent inalterability, thus ignoring intrinsic parameters of plasticity; a potential and fundamental flaw of this model. For example, recent experimental evidence demonstrates that cancer cells exert stochastic state-transitions and phenotypic variations giving rise to CSC characteristics from non-stem-like cells, subsequently returning to phenotypic equilibrium (Gupta et al., 2011). Alternatively, microenvironmental cues, such as exogenous stressors, are integral to the maintenance of tumorigenic populations including putative CSC (Bissell and Labarge, 2005). Such hypotheses indicate that beyond stochastic flux, deterministic acquisition of phenotypic, stem-like properties may be invoked to overcome exogenous stimuli and potentially occurring as a transitory property. Indeed, identifying and exploiting temporality during drug treatment may optimize the efficacy of available therapeutics (Gillies et al., 2012), yet no studies have identified a mechanistic basis or validated this contention particularly as it relates to the CSC model.

Although CSCs have emerged as critical constituents in tumorigenicity, there remains a poor understanding for the mechanisms and cellular determinants which drive acquired and adaptive resistance. The results described herein provide for unification of the CSC theory with non-genetic mechanisms of adaptive resistance, invoking the elegant principles of Darwinian dynamics to describe a transitory property of cancer cell behavior. Identified herein are tumor cells that are induced to temporally switch to phenocopies which mimic inherent chemoresistance. Through acquisition of stemlike properties, induction and functional engagement of a CSC biomarker, cancer cells confer a transient ability to reorganize a redundant kinase-signaling network to persist and re-emerge from cytotoxic stress. This temporal plasticity can be exploited by a schedule-dependent combination of cytotoxic chemotherapy and a rationally derived kinase inhibitor as provided herein Enhancing this effect, chimeric-nanoformulations limit toxicity and provide a spatial advantage over free-drugs. The findings presented here elucidate novel biological principles of cancer progression and chemoresistance, impacting directly the method of cancer treatment.

Development of resistance to chemotherapy is a key obstacle in successful cancer treatment. While the underlying dogma of chemoresistance was built on heritable mutations and selection under pressure, emerging evidence indicates that distinct epigenetic mechanisms or cellular heterogeneity can drive therapeutic resistance. Described herein is a novel phenomenon, which is termed cancer stem cell (CSC) 'mimicry', where tumor cells can transiently acquire morphological and phenotypic characteristics mimicking stem-like cells as a consequence of chemotherapeutic stress. Using taxane-resistant human breast cancer explants and by inducing chemotherapeutic stress in cancer cell lines, the transient acquisition of the CSC biomarker (CD44) is demonstrated in a small population of reversibly chemotolerant cells, which functionally engages and re-organizes a cortex network of tyrosine kinases triggering survival via phosphatidylinositol-3-OH kinase (PI3K) and Src-Family Kinase (SFK) signaling, and permitting re-growth of a heterogeneous population. The disruption of this semistable state of CSC mimicry can be achieved using PI3K inhibitors, and dasatinib, a Src kinase inhibitor in vitro and in vivo, but only within a temporal constraint. Combinations of a PI3K inhibitor and dasatinib in a multifunctional nanoparticle exhibited synergistic tumor inhibition in sequence with docetaxel. These results suggest that temporal combinations of taxanes with PI3K- and SFK-inhibitors can emerge as therapeutic strategies for the management of taxane-refractory breast cancer. The current study supports the emerging paradigm that cancer cells can exist in a continuum of distinct phenotypic states, unifying the divergent theories of cancer stem cells and cell signaling-driven adaptive resistance underlying chemotherapy failure The inability of chemotherapy to completely ablate tumor cells and the resulting relapse remains a vital obstacle in the treatment of cancer. The central model for the development of resistance to chemotherapy is built on a somatic version of Darwinian evolution, where the stochastic acquisition of resistance-favored mutations that are selected under chemotherapy pressure (Cairns, 1975). However, this dogma is increasingly being challenged by the emerging evidence of non-genetic mechanisms driving chemotherapy tolerance (Marusyk et al., 2012). For example, chronic myeloid leukemia (CML) cells in patients treated with the drug imatinib can survive an immediate blast phase, and can even grow during treatment, despite an absence of genetic alterations which confer imatinib-resistance (Okabe et al., 2008; Talpaz et al., 2002). Similarly, resistance to cytotoxic antitubulin chemotherapy can arise independent of mutation status (Berrieman et al., 2004). Furthermore, in a recent study, Kreso et al demonstrated that variability in chemotherapy tolerance could exist within lineages from a single clone in colorectal cancer (Kreso et al., 2013). Indeed, in a perspective, Brock et al argued that non-genetic individuality among clonal cells may also serve as a substrate for somatic Darwinian evolution (Brock et al., 2009). However, the mechanisms contributing to these phenomena remain poorly understood.

Two divergent theories have emerged to explain the non-genetic basis of chemoresistance. The first relies on a hierarchical model, where minor, static populations of cancer stem cells (CSCs) that are tumorigenic are also the ones that are inherently resistant to chemotherapy (Shackleton et al., 2009). CSCs are thought to exploit drug-efflux proteins, relative dormancy or epigenetic switches to overcome chemotherapeutic stress (Vincent and Van Seuningen, 2012). However, the true contribution of cancer stem cells in the development of therapeutic resistance remains debatable (Marusyk and Polyak, 2013). The recent results of Kreso et al lend credence to the argument that alternative mechanisms besides CSCs may be involved in mediating non-genetic origins of resistance (Kreso et al., 2013). Indeed, another emerging theory of 'adaptive chemoresistance' addresses the evidence for phenotypic heterogeneity arising from stochasticity in gene expression and activation of survival pathways. For example, dysregulation and feedback activation of cortex signaling kinases leads to the resistance against promising targeted therapeutics such as dual Akt/mTOR inhibitors in malignant breast cancer models (Muranen et al., 2012). Similarly in other solid malignancies, the engagement of a receptor tyrosine kinase (RTK) and altered chromatin state have been implicated in downstream epigenetic alterations conferring adaptive resistance to cytotoxic chemotherapy (Sharma et al., 2010). Indeed, uncontrolled activation of kinase circuitry is regarded as a major constituent of acquired chemoresistance (Huang and Hung, 2009) which can be further enhanced through complex signaling redundancy (Logue and Morrison, 2012).

It is demonstrated herein that cancer cells can potentially exist in a continuum in-between stem-like and non-stem cell states tending towards the former under chemotherapeutic pressure. These imperfect mimics of cancer stem-like cells over-express the CSC-biomarker, CD44, which acts as a scaffold to transiently reorganize a redundant kinase-signaling network to persist, re-emerge from cytotoxic stress and re-equilibrate a heterogeneous phenotype. Interestingly, a therapeutic vulnerability emerges from this transiently-induced plasticity, which can be exploited by the temporally rational combination of kinase inhibitors with chemotherapy. The findings presented here elucidate novel biological principles potentially unifying the divergent theories of chemotherapy tolerance, directly impacting the clinical management of cancer.

Results

Atypical Cancer Stem-Like Cell Descriptors are Induced within a Chemoresistant State.

Figure 1A:
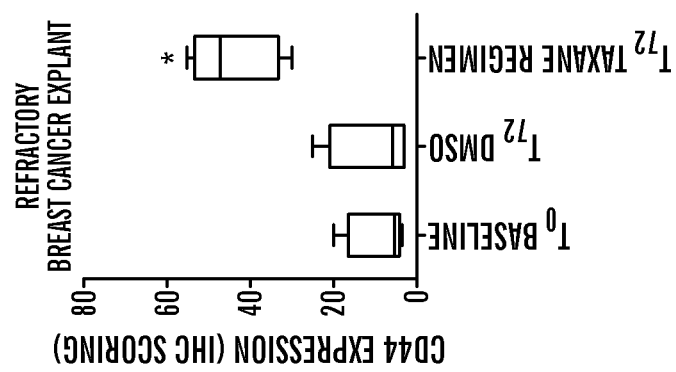
FIGS. 1A-1N demonstrate the CSC properties induced in a subset of chemotherapy-tolerant cancer cells.
Figure 10A:
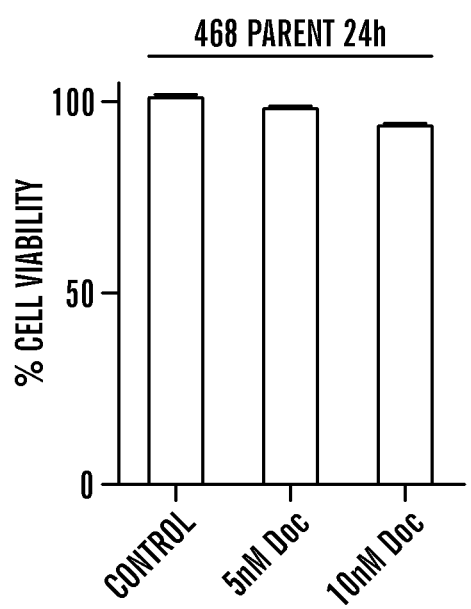
FIGS. 10A-10F demonstrate the characterization of chemotherapy-tolerant cells.
Figure 10B:
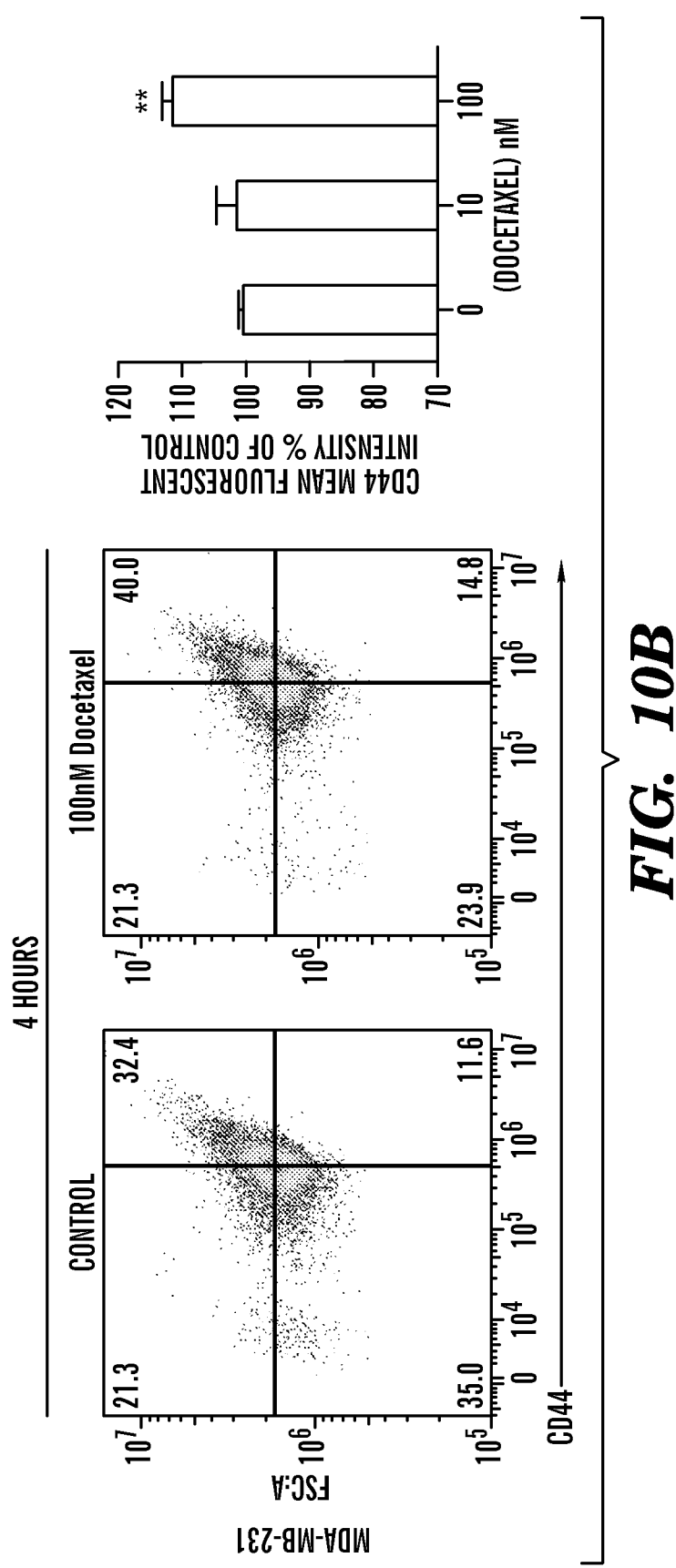
Figure 10C:
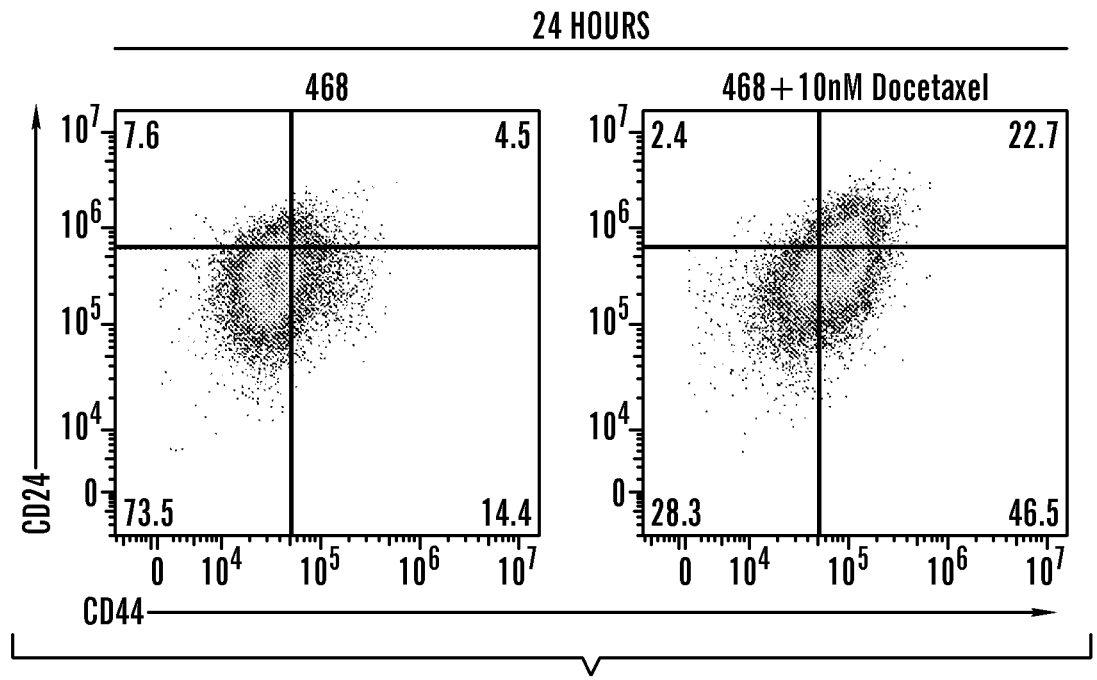
Figure 10D:
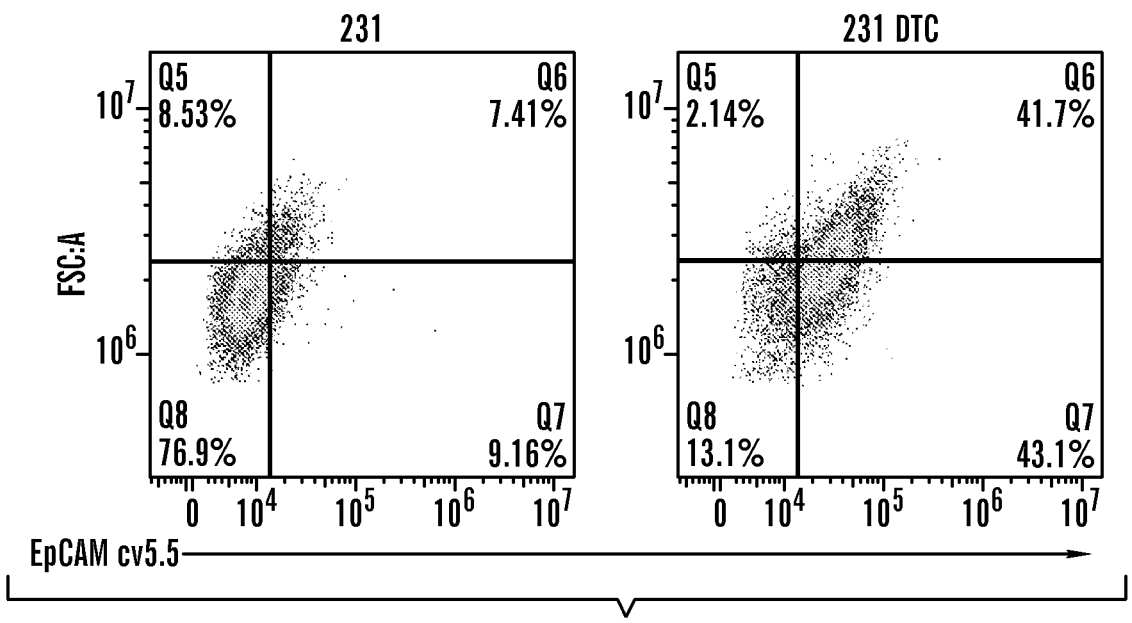

Chemotherapy is the treatment of choice for patients with metastatic breast cancer that is hormone resistant or estrogen/progesterone receptor negative or for patients who experience rapid progression. While anthracyclines are used as the first-line chemotherapy in adjuvant or metastatic setting, taxanes are the standard of care in the case of subsequent disease progression (Pal et al., 2011). To study the mechanisms which contribute to adaptive chemoresistance under conditions that closely mimic the clinical pathology, explant cultures were generated from tumor biopsy of seven taxane-refractory breast cancer patients cultured in autologous serum (See FIG. 9 for patient history). The explants were then incubated ex vivo with docetaxel (DTX) for 72 h. Interestingly, as shown in FIG. 1A, immunohistochemistry profiling revealed that treatment with a taxane-containing regimen induced the over-expression of CD44 (FIGS. 1A-1B), which correlated with reduced apoptosis (decreased expression of cleaved caspase-3) and a reduced proliferative capacity indicated by Ki-67 staining (FIG. 1B). A similar observation was made in the case of explants treated with a liposomal formulation of doxorubicin (Doxil), indicating that this phenomenon was not restricted to taxanes. In contrast to the notion that CSCs are enriched in response to chemotherapy, these data indicated that a putative stem-like quiescent state is inducible in response to chemotherapy. This observation was validated using the triple negative breast cancer (TNBC) MDA-MB-468 (468) cell line. Consistent with the ex vivo results, induction of CD44 was observed following 24 hour incubation with docetaxel (DTX) chemotherapy without selecting for viable subsets (FIGS. 1C and 1OA), an effect observed in a dose-dependent manner in another TNBC cell line, MDA-MB- 231 (231) as early as 4 hours post treatment (FIG. 10B). Surprisingly, in contrast to the classic definition of a breast CSC as exhibiting a CD44$^{HI}$, CD24$^{-/low}$ signature (Al-Hajj et al., 2003), which is predicted to be the chemoresistant CSC population selected under chemotherapeutic pressure (Dean et al., 2005), docetaxel chemotherapy induced a CD44$^{HI}$, CD24$^{+/HI}$ signature (FIG. 10C), indicative of the induction of an atypical or 'imperfect' subset of CSCs in response to chemotherapeutic pressure.

Figure 1D:
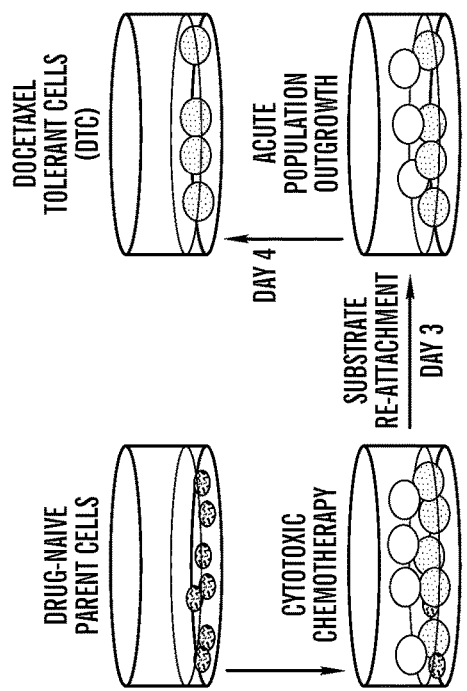
FIG. 1D depicts a schematic for the generation of a DTX tolerant cell (DTC) subpopulation. Following DTX treatment in parent cells (48 h) cells were washed and selected based on substrate re-attachment and acute population outgrowth (24 h) ('DTC' were exposed to 100 nM DTX).
Figure 1F:
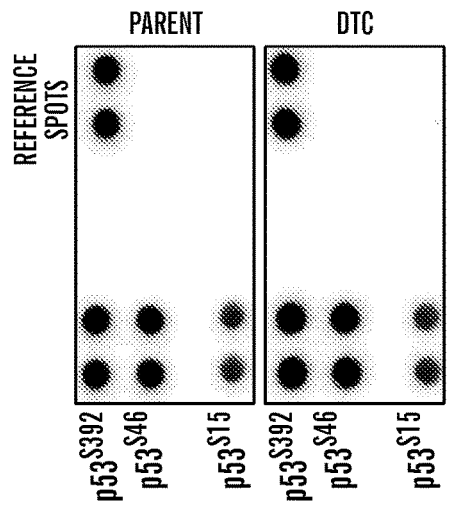
FIG. 1F depicts images of membranes from a phosphorylation assay. Equal concentration of cell extract from parent 231 or a subset of DTC were analyzed by a p53 phosphorylation array; no change between arrays indicate parental toxic burden in the DTC subset, reference spots normalize membranes.
Figure 1C:
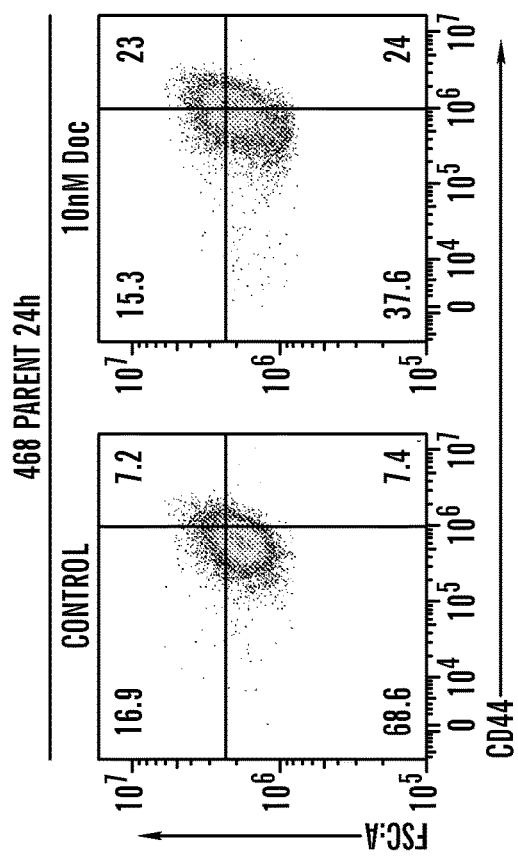
FIG. 1C depicts graphs of FACS analysis. 468 cells were incubated with 10 nM DTX (24) and labeled with fluorescently conjugated antibody detecting CD44 analyzed by FACS. Note induction of CD44 surface expression in response to sub-lethal dose of chemotherapy.
Figure 1E:
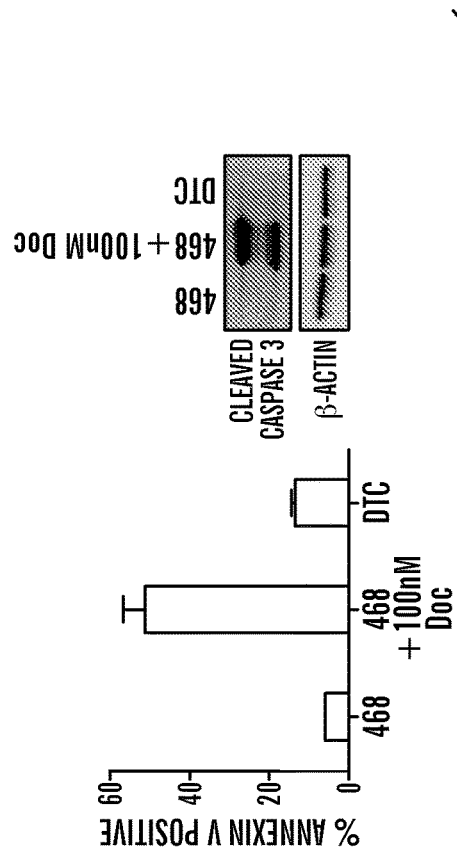
FIG. 1E depicts a graph of apoptosis. Parent 468 cells were untreated, treated with 100 nM DTX (48 h) or DTC were generated as described. Floating and attached cells were collected and active apoptosis was quantified by annexin V/Propidium iodide (PI) by FACS (left panel, error bars indicate SEM from 3 samples) or applied to western blot to detect activated (cleaved) caspase-3 (right panel).
Figure 1H:
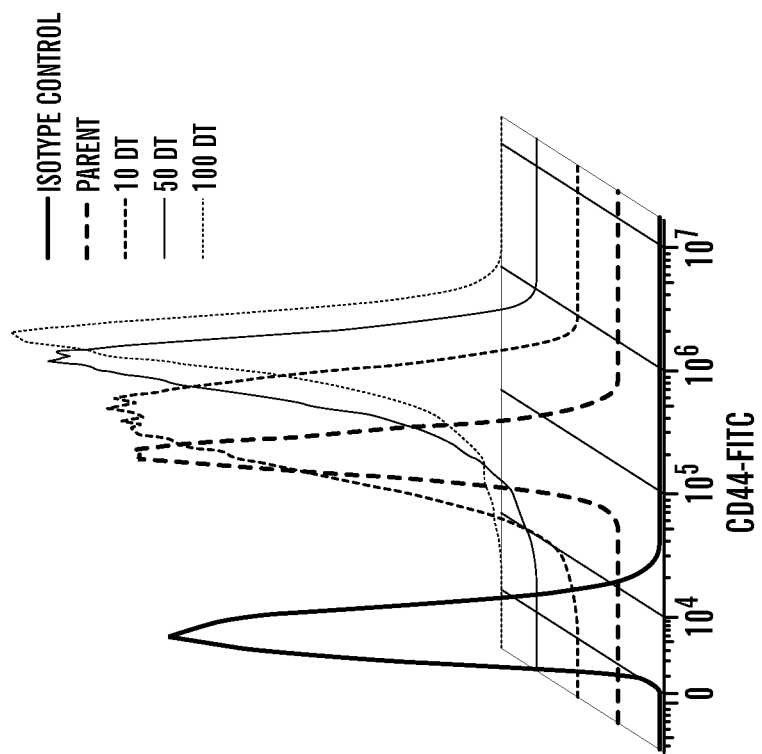
FIG. 1H depicts a graph. A subset of 468 cells were isolated by the schematic depicted in FIG. 1D utilizing the following concentrations of DTX: 10 nM (10DT), 50 nM (50DT) or 100 nM (100DT), following incubation with fluorescently-conjugated CD44 antibody, cells were analyzed by FACS. Histogram represents quantitative analysis of mean fluorescence performed from duplicate plates (Error bars indicate SEM).
Figure 1G:
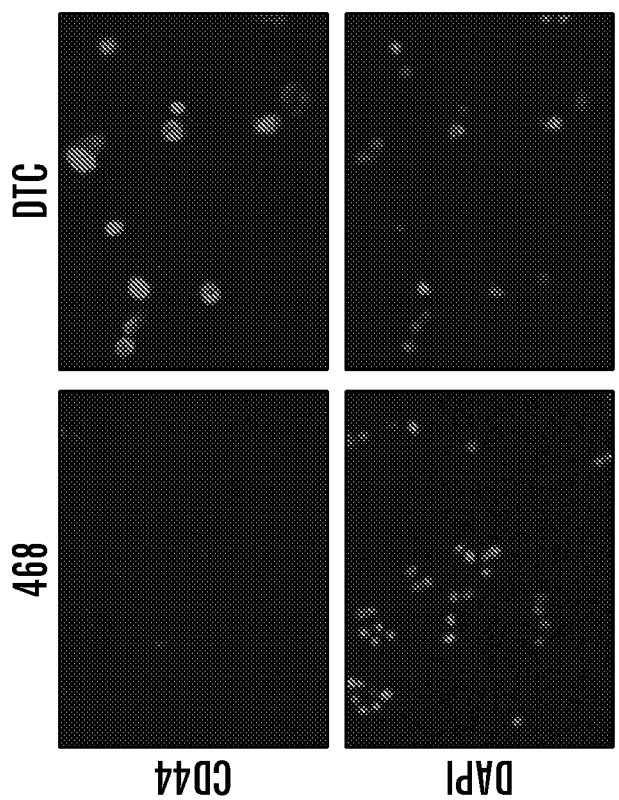
FIG. 1G depicts fluorescence microscopy images. 468 Parent cells or a subset of DTC were labeled with fluorescent CD44 antibody and analyzed by fluorescent microscopy; DAPI nuclear counterstain.
Figure 1I:
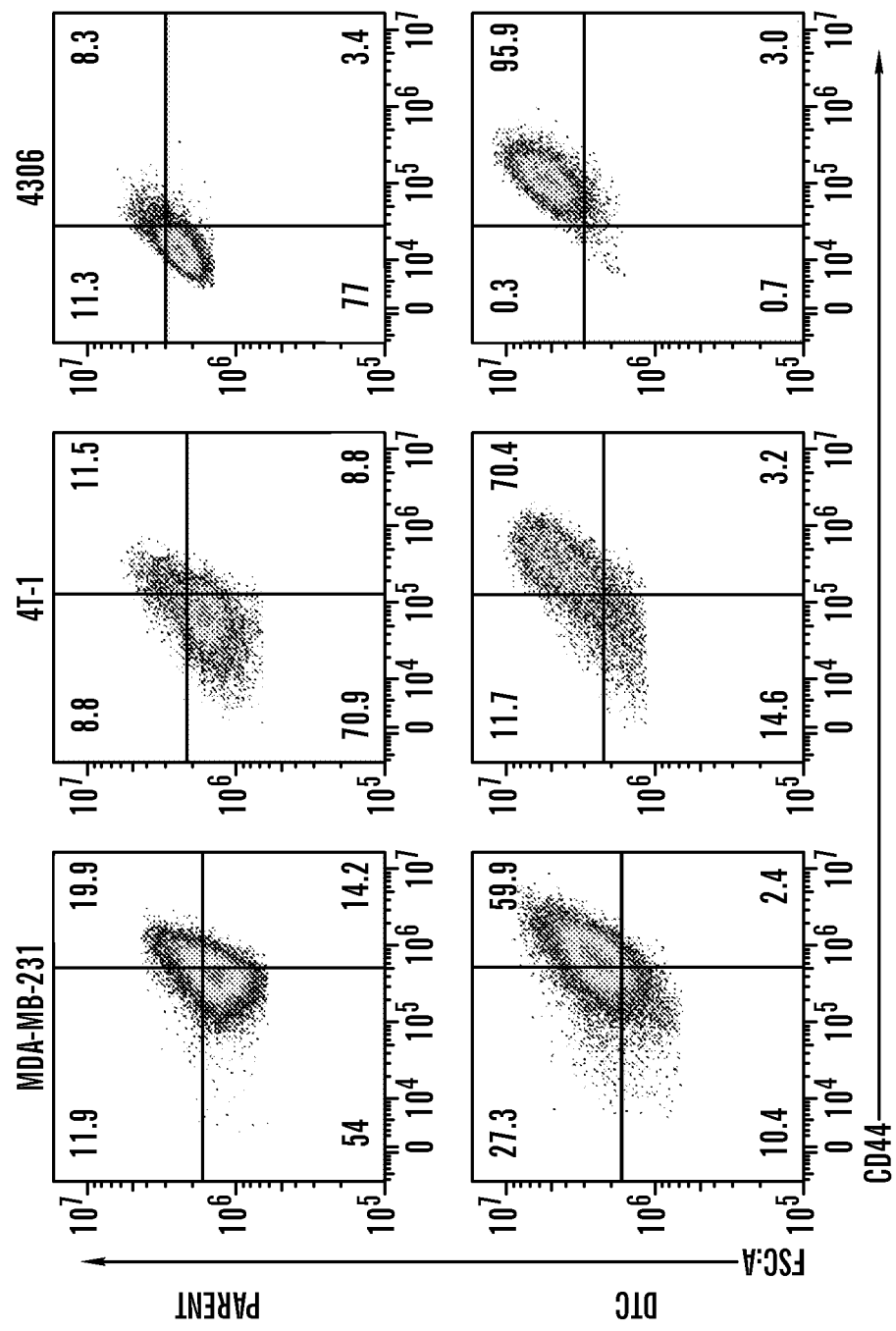
FIG. 1I depicts FAC analysis results. Parent cells or a subset of DTC were generated from the indicated cell lines. Cells were incubated with fluorescently conjugated CD44 and analyzed by FACS, note increase of CD44 in DTC subset.
Figure 1J:
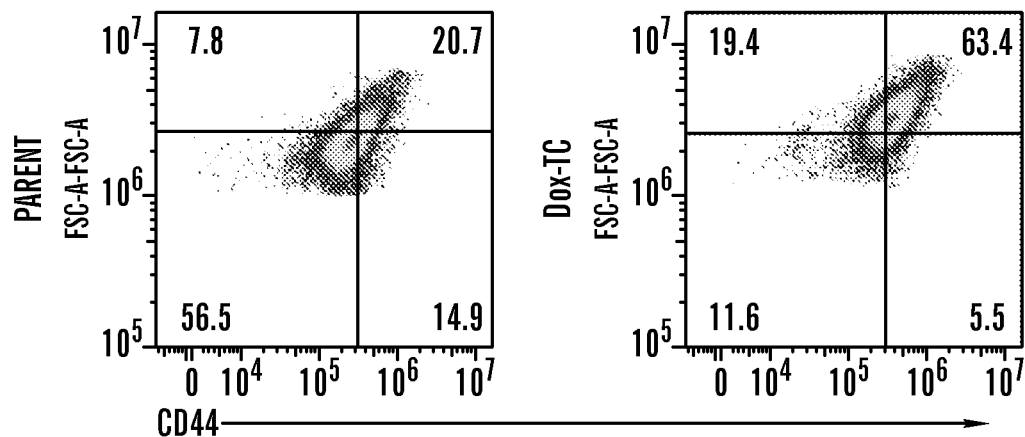
FIG. 1J depicts FAC analysis results. Surviving 231 cells were isolated following 500 nM doxorubicin by the treatment-scheme outlined in FIG. 1D and defined as 'Dox-TC'. Subsequently, cells were stained with fluorescently conjugated CD44 antibody and analyzed by FACS.
Figure 1K:
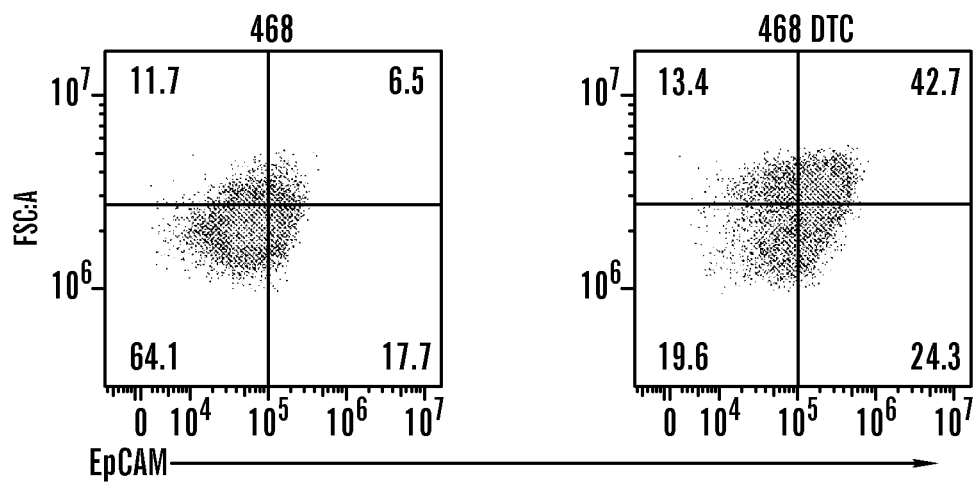
FIG. 1L depicts FAC analysis results. 468 Parent cells or a subset of DTC were labeled with CD44-APC and CD24-PE antibodies and analyzed by FACS; DAPI nuclear counterstain.
FIG. 1M depicts the survival curve of 468 parent cells and a subset of DTC following 48 h exposure to indicated chemotherapy. Data points indicate values from 3 separate samples. Similar results identified from other cell lines (data not shown).
Figure 10E:
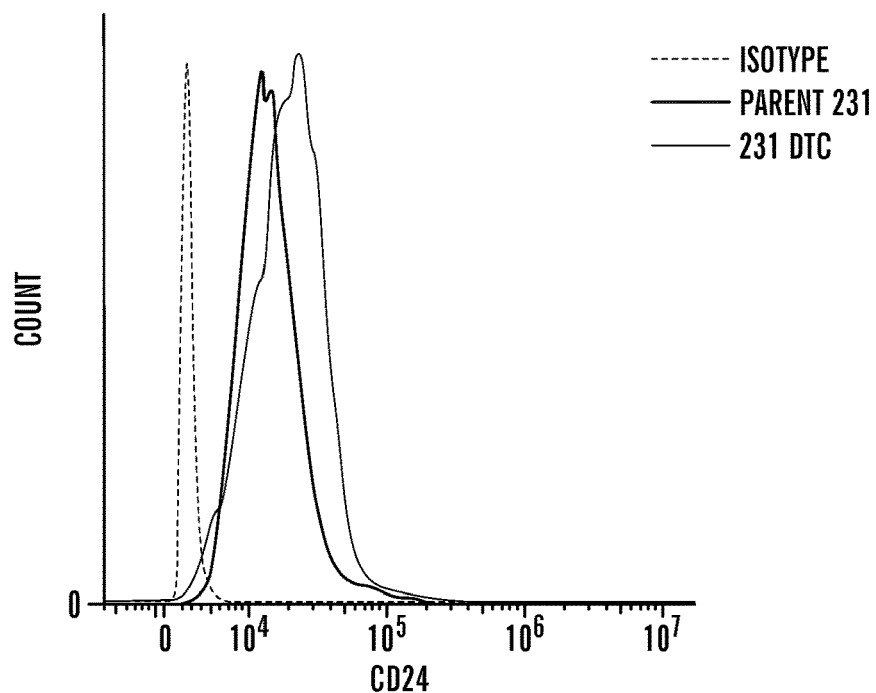
Figure 10F:
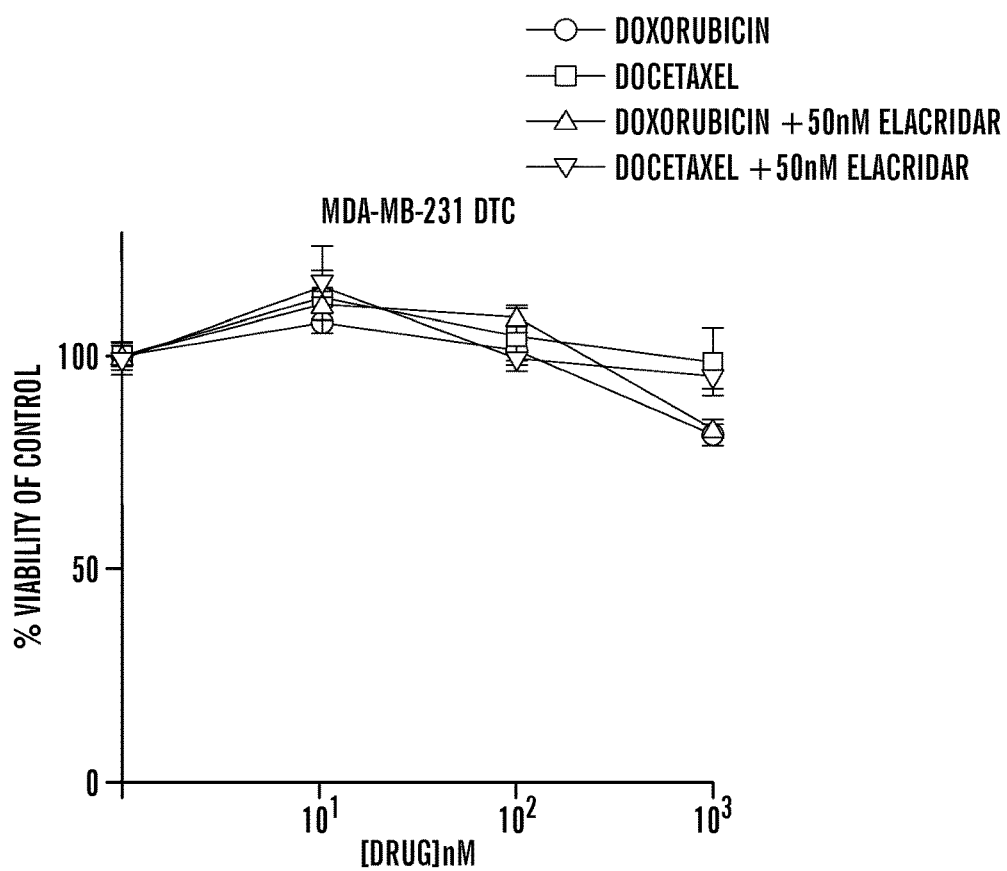

To test whether chemotherapy-induced CD44 expression correlates with survival, a subset of cells was isolated which could overcome an extended (48 hr) DTX insult at a lethal concentration greater than 20 times published $_{IC50}$ values (Watters et al., 2004). The cells were further selected for viability and chemoresistance based on the capacity for substrate reattachment (Matrone et al., 2010) and a subsequent acute population-outgrowth, terming this subpopulation 'DTX tolerant cells' (DTC) (FIG. 1D). In contrast to chemotherapy-treated parent 468, DTC displayed low Annexin V positivity (FIG. 1E, left panel), caspase-3 activity (FIG. 1E, right panel) and elicited a parental toxic-burden indicated by p53 phosphorylation (FIG. 1F)(MacLaine and Hupp, 2011). Importantly, a chemotherapy-induced CD44 signature was identified (FIG. 1G), an effect which directly correlated to dose-dependent tolerance to DTX (DT) (FIG. 1H). Additionally, the enhanced CD44 expression was identified in DTCs generated from the human TNBC cell line MDA-MB-231 (231), non-TNBC murine mammary carcinoma 4T-1 and KRas/PTEN 4306 murine ovarian cancer cells (FIG. 1I). Interestingly, the cells found tolerant to doxorubicin (Dox-TC) also demonstrated a robust expression of CD44, suggesting a broad, non-cytotoxic-selective response consistent with the explant data (FIG. 1J). Furthermore, as shown in FIGS. 1K and 1 OD, the DTCs were also found to upregulate EpCAM, a TNBC CSC surface marker (Stratford et al., 2010) associated with negative clinical prognosis (Schmidt et al., 2008). Consistent with the imperfectly-induced subset of CSC from above with a CD24 enhanced profile, selection under chemotherapeutic pressure showed preservation of this acquired phenotypic alteration (FIGS. 1L and 10E). Finally, the susceptibility of DTC to chemotherapy was tested, and an acquired resistance to multiple classes of taxanes (FIG. 1M) as well as the anthracycline, doxorubicin was found, suggesting a more universal resistance to cytotoxic chemotherapy compared to parent cell (FIG. 1N). It was significant to note that the DTCs were insensitive to cabazitaxel, a novel taxane that does not act as a PgP substrate (Bouchet and Galmarini, 2010). Furthermore, treatment with the PgP transport inhibitor, elacridar, could not augment cytotoxic sensitivity (FIG. 1 OF), indicating drug efflux, which has been implicated in mediating resistance to chemotherapy in classical CSCs, does not support adaptive resistance observed in the current study.

Induced Cellular Mimicry of a Stem-Like Population.

Figure 2A:
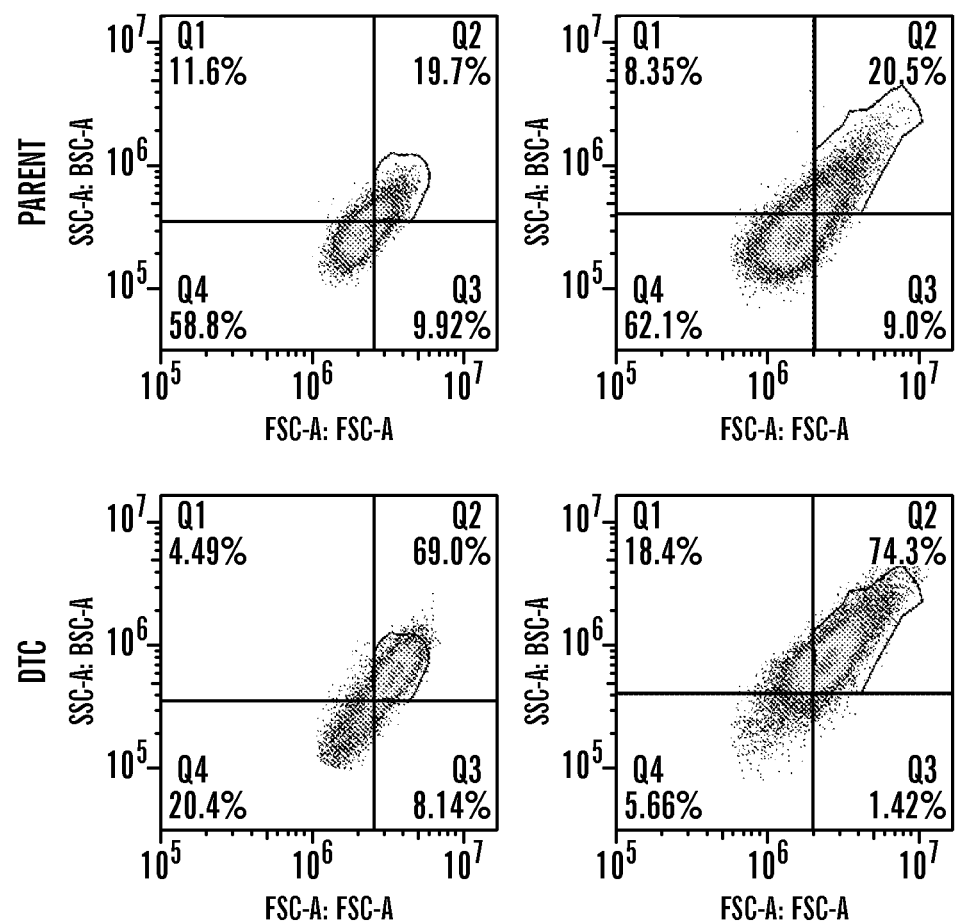
FIGS. 2A-2I demonstrate cancer stem cell mimicry involved in adaptive chemoresistance.
Figure 2B:
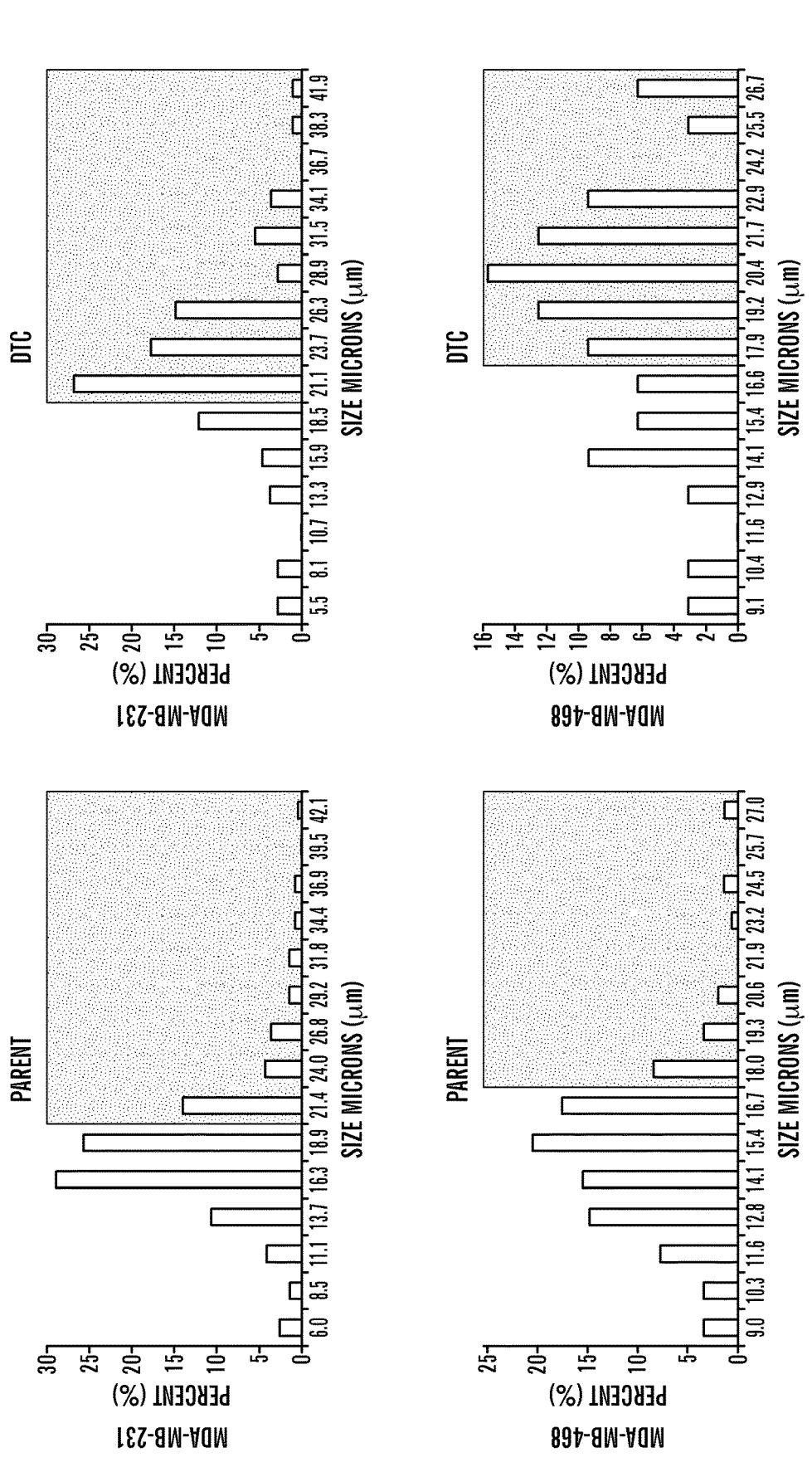
Figure 2C:
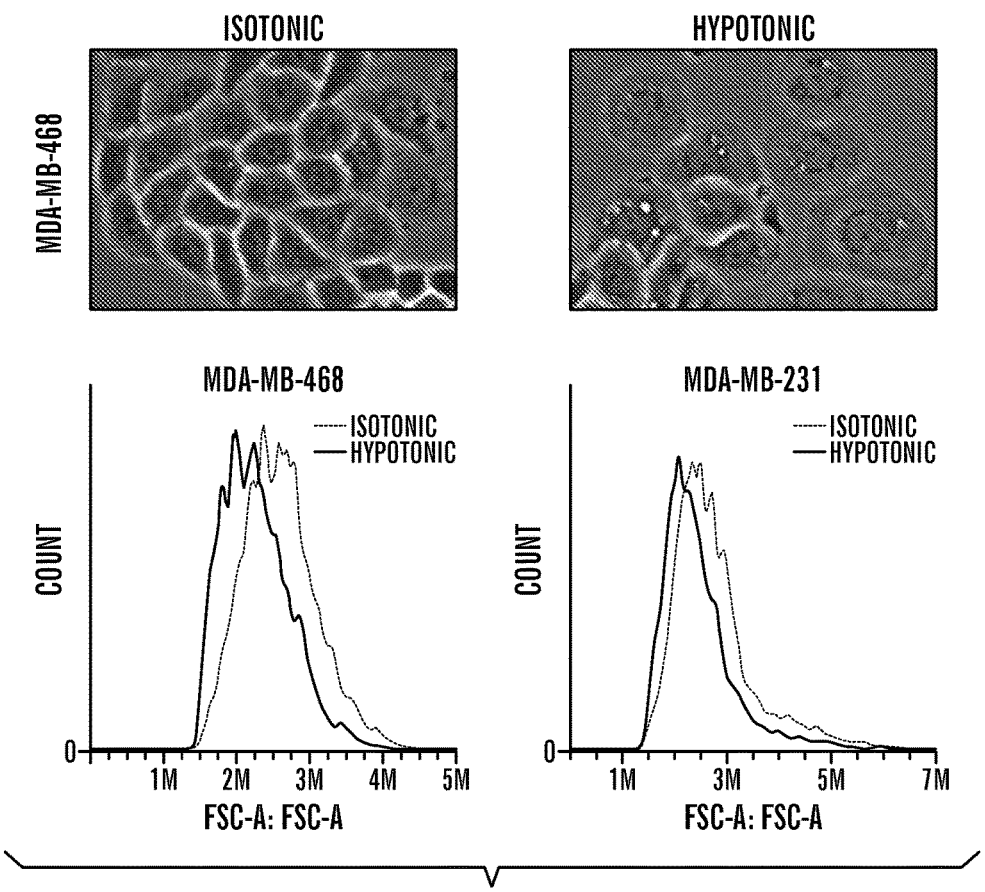
Figure 2D:
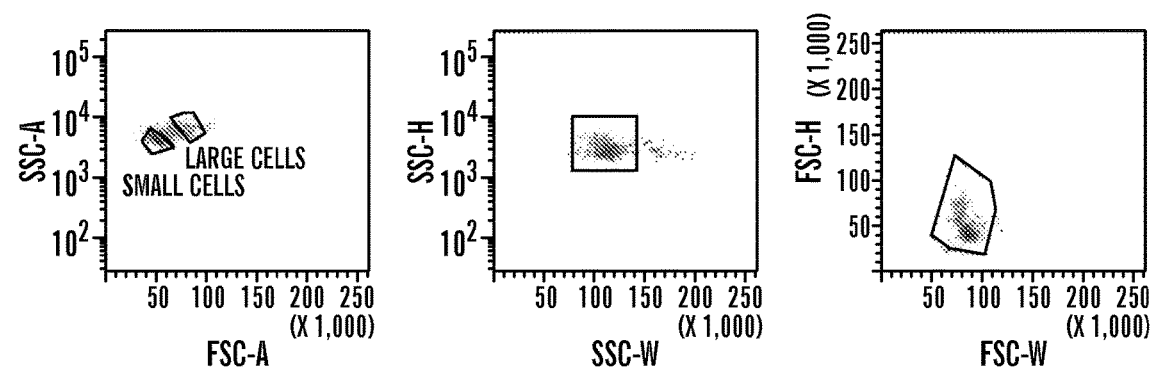
Figure 2E:
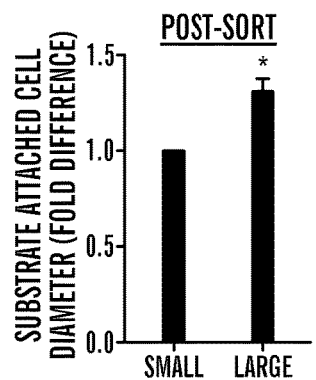
Figure 2F:
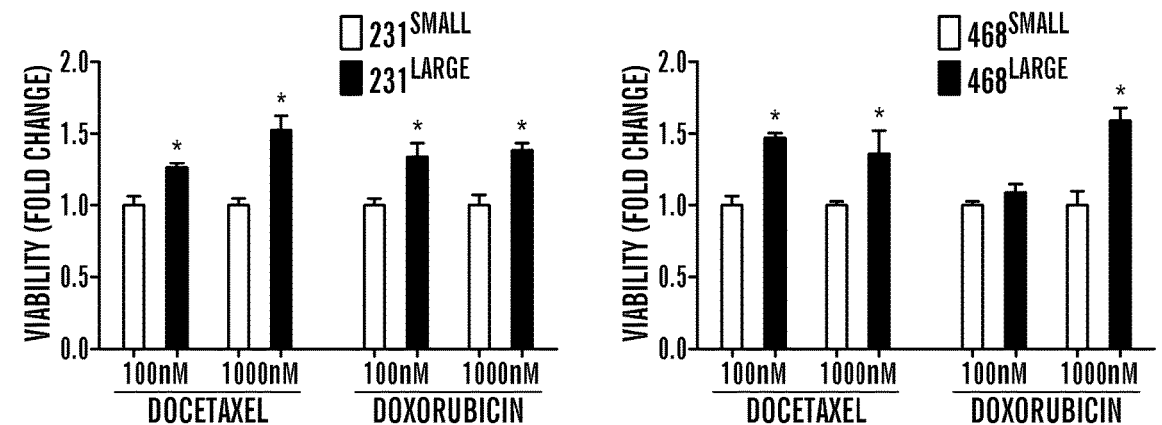
Figure 11A:
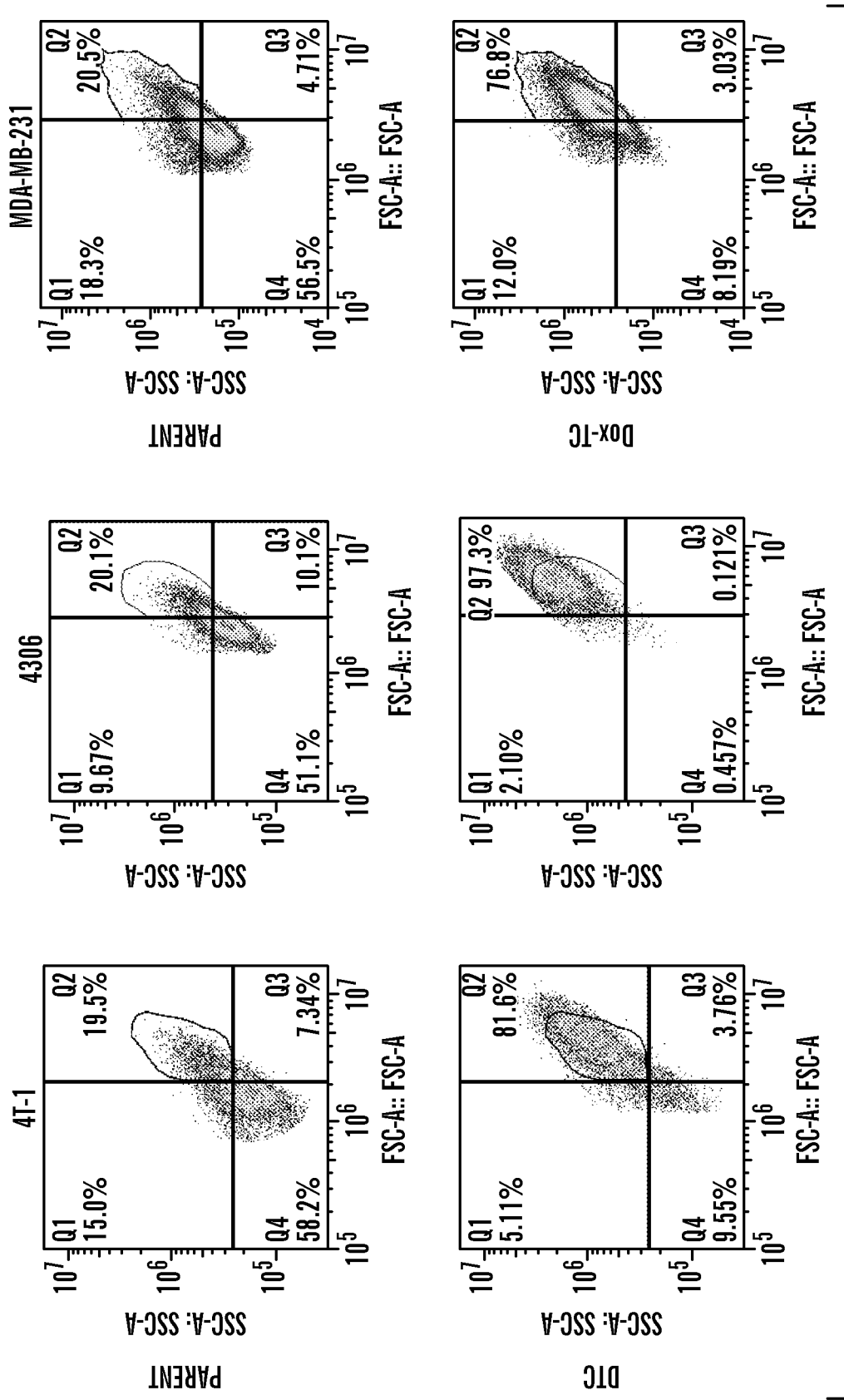
FIG. 11A shows similar analysis performed in parental and DTC cells obtained from multiple cell lines.
Figure 11B:
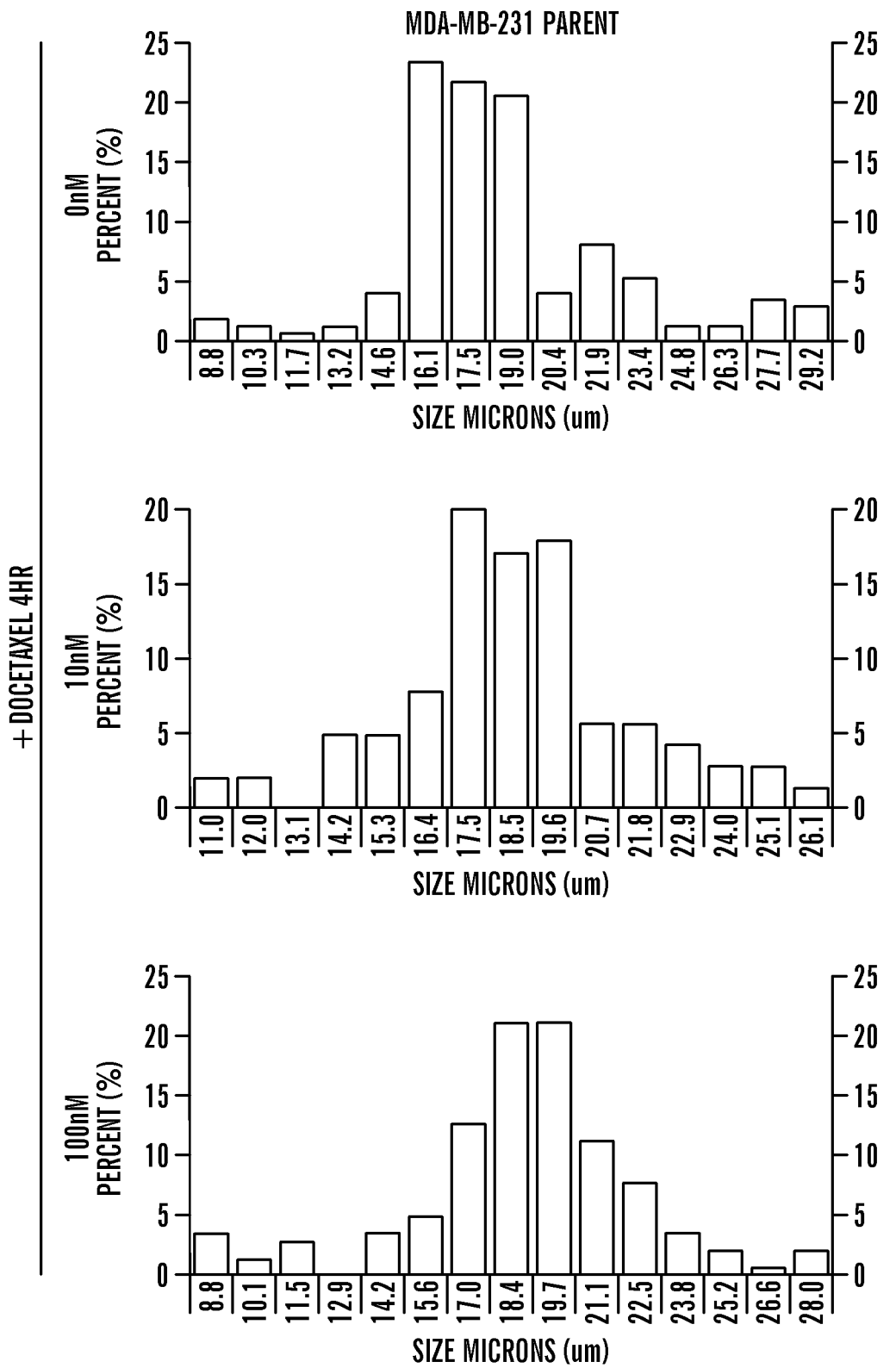
FIG. 11B shows similar analysis performed in cells following 4 hours treatment with increasing concentrations of DTX.
Figure 11C:
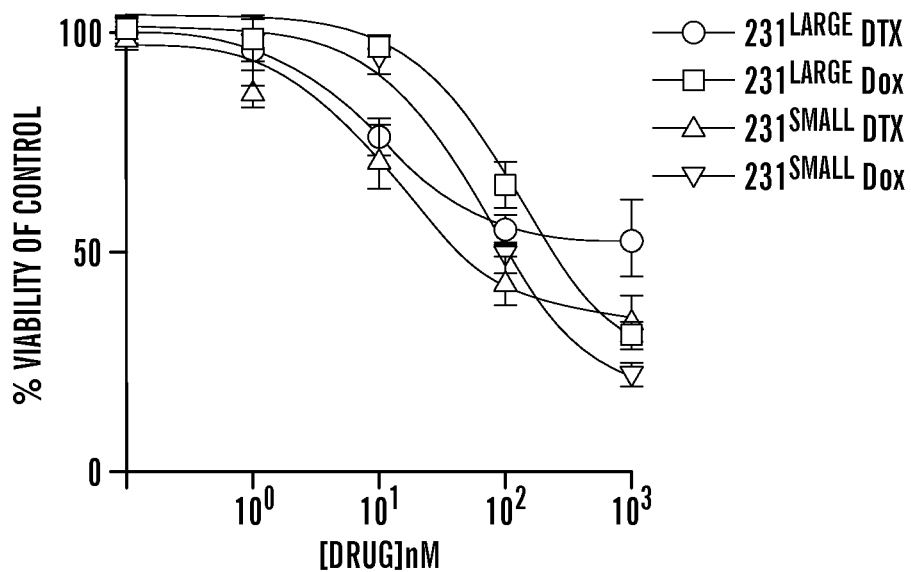
FIG. 11C depicts microscopy images and graphs. 231 and 468 parent cells were treated with an isotonic solution (1×PBS) or hypotonic solution (PBS+Sterile H2O; 2:1) for 15 minutes. Upper panels show representative bright field microscopy (20×), note the visual increase of size as a result of swelling in hypotonic solution. Lower panels show histogram analysis of forward scatter (FSC:A) parameter during FACS. Note the decrease of FSC:A as a consequence of osmosis-dependent cell swelling.

While CSCs have been considered a subset of parental cells with inherent chemoresistance, biomarker identification alone is an imperfect way to designate this population (Zapperi and La Porta, 2012). Therefore morphological and phenotypic similarities between DTC and a subset of parental cells with an inherent capacity to overcome chemotherapy were investigated. One of the most striking alterations of the DTC subset was a systematized change in size firmly correlating to the largest 20% of the parent population (FIGS. 2A, 2B, and 11A), an induced effect confirmed as early as 4 hours following exposure to chemotherapy (FIG. 11B). Indeed, cell size has emerged as a robust determinant of cellular identity, indicative of signaling processes, growth states and homeostasis (Jorgensen and Tyers, 2004). Incubation in hypotonic saline solution for 15 min altered the visually perceived size of parent cells yet resulted in reduction of the forward scatter parameter during flow cytometry (FIG. 2C) confirming the assertion that DTC are not merely osmotically swollen. Utilizing cell sorting strategy based on three-dimensional light scattering parameters, the 20% largest and 20% smallest cells were isolated from the parent population (FIG. 2D), achieving enrichment of approximately 60-70% (data not shown) which was confirmed by measuring cell diameter following substrate re-attachment (FIG. 2E). Cytotoxicity analysis indicated MDA-MB-231 $^{Large}$ and MDA-MB-468$^{Large}$ subsets resisted high dose chemotherapy compared to their smaller counterparts by augmenting their viability 1.2 to 1.5 fold in response to high doses (FIGS. 2F and 11C).

Figure 2G:
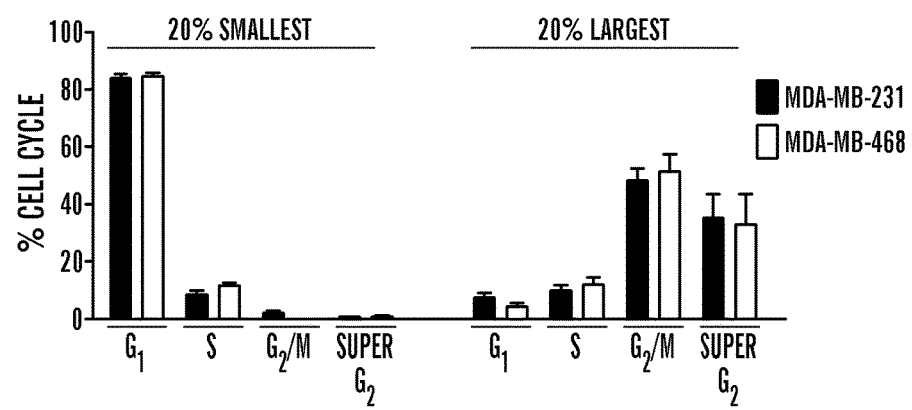
Figure 2H:
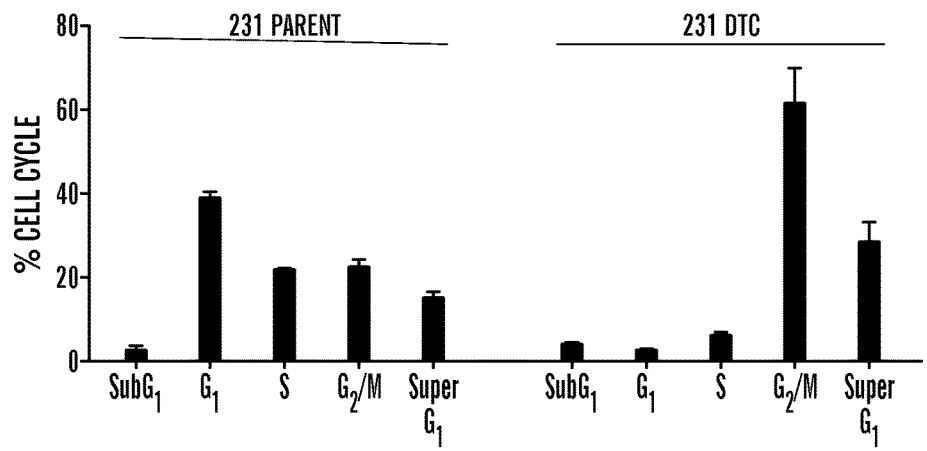
Figure 11D:
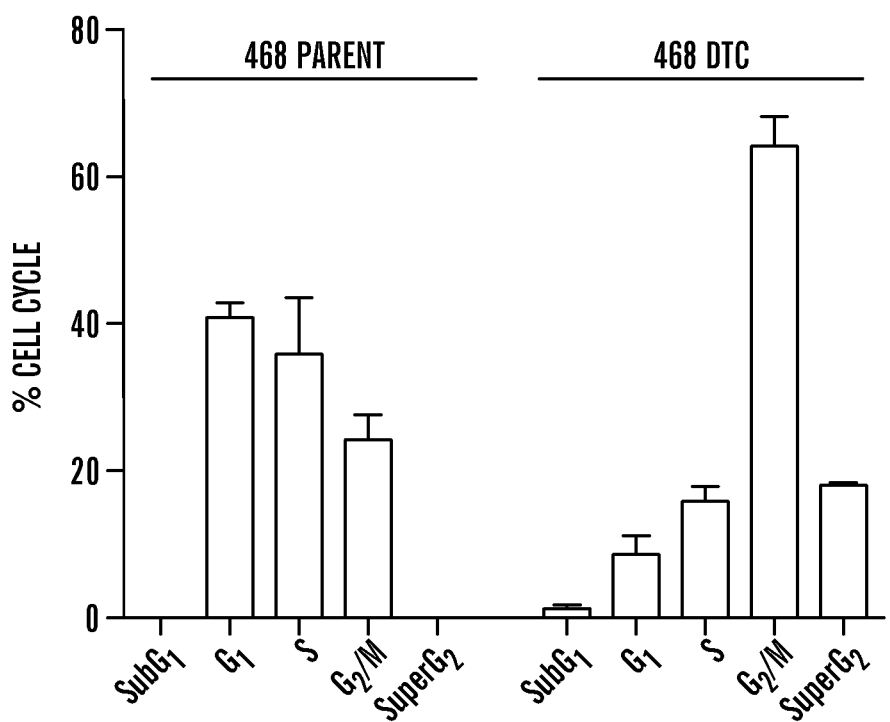

It was next investigated whether other phenotypic properties correlate with CSC characteristics. Recent evidence obtained through evaluation of human solid malignancies suggests a G2/M 'lock', or extended cell cycle, is a common feature of CSC populations and serves a putative chemoresistant role (Harper et al., 2010). Population gating for the largest 20% of parent cells during FACS analysis correlated with a G2/M-polyploidy-heavy cell cycle status. In contrast, the smallest 20% subset presented a G1,S-heavy cell cycle status (FIG. 2G). Similar to parental 'large cells', the DTC subset demonstrated a major shift to G2/M and enhanced polyploidization compared to parent cells (FIGS. 2H and 11D). These results suggest that in contrast to a cell cycle lock as a pre-catastrophic phase, this signature may confer a cytoprotective mechanism.

Figure 2I:
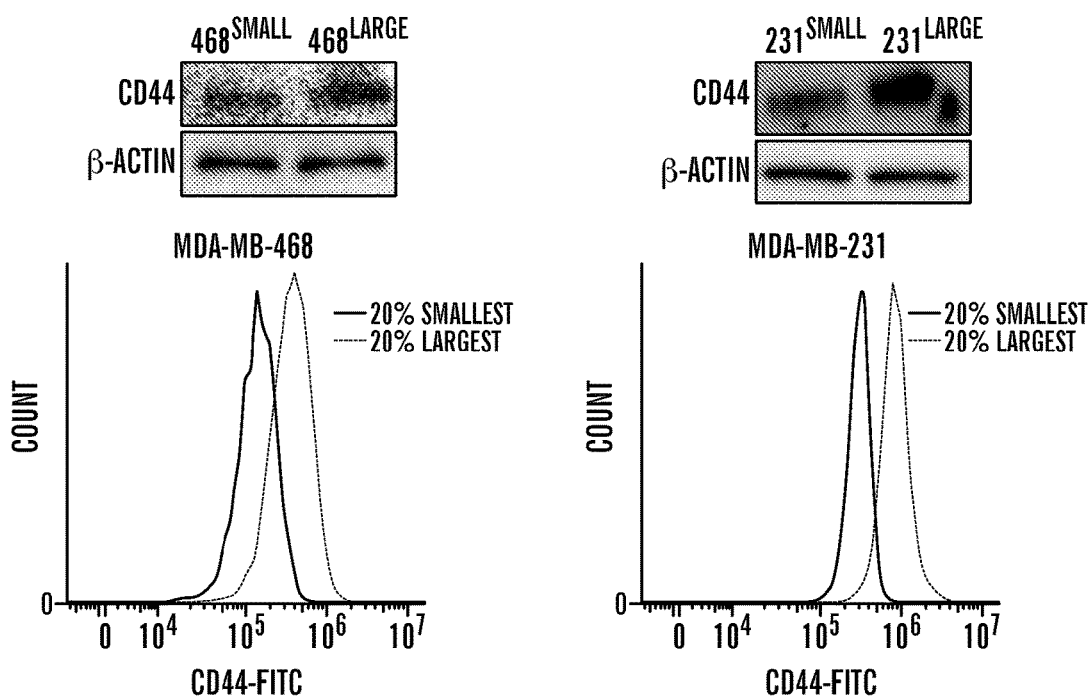
Figure 11E:
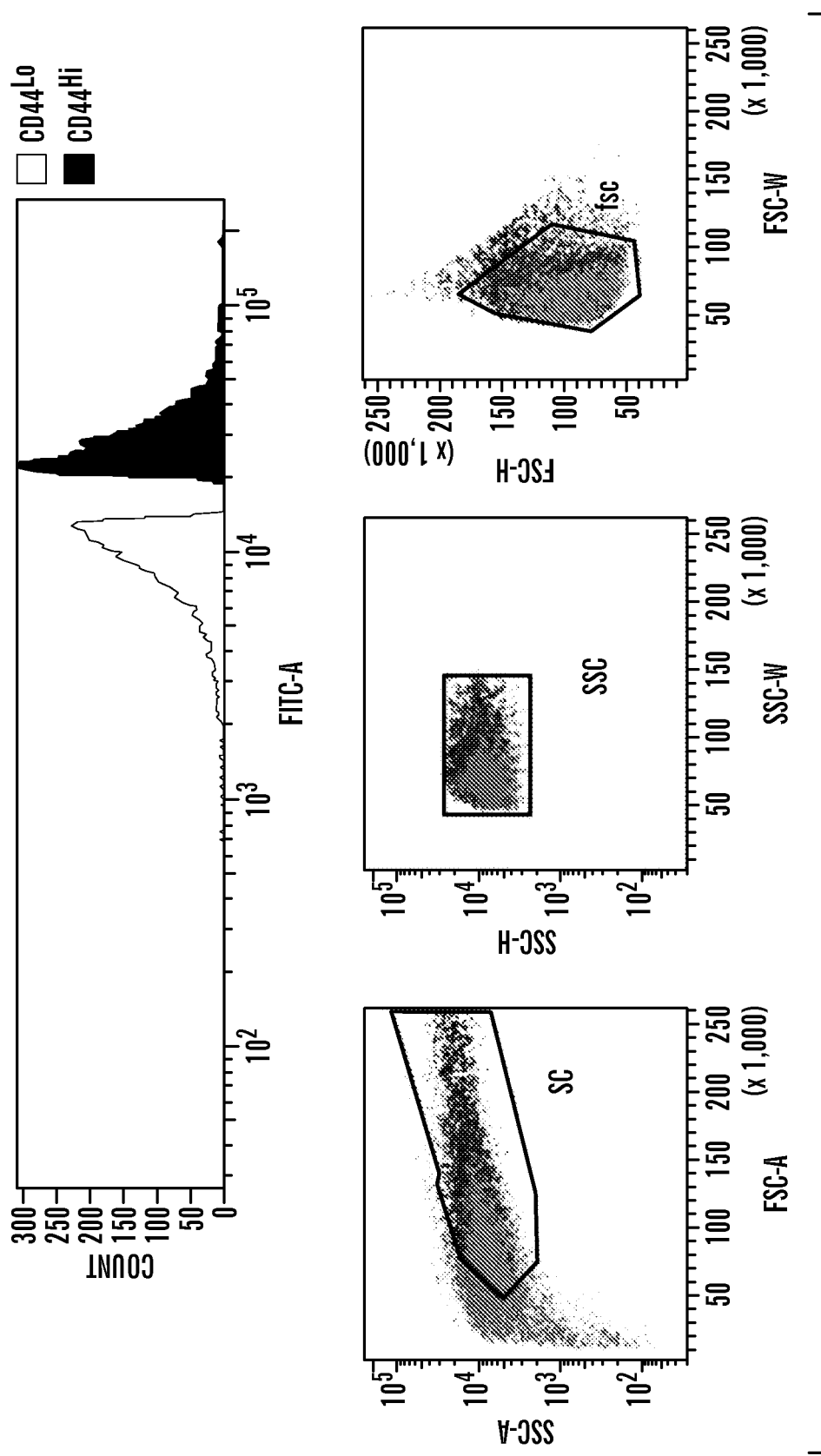

Since CD44 expression was notably increased in the DTCs, it was sought to identify whether 'large' parental cells displayed a similar, relative enhancement of CD44. Utilizing fluorescence activated cell sorting (FACS) isolated CD44$^{Hi}$ cells correlated to the largest population determined by three-dimensional light scattering (FIG. 11E). Similarly, population gating during FACS confirmed enhanced expression of CD44 in the 20% largest cells compared to the 20% smallest, which was validated by western blot (FIG. 2I).

Induced CSC-Mimicry is Capable of Re-Equilibrating a Heterogeneous Landscape.

Figure 3A:
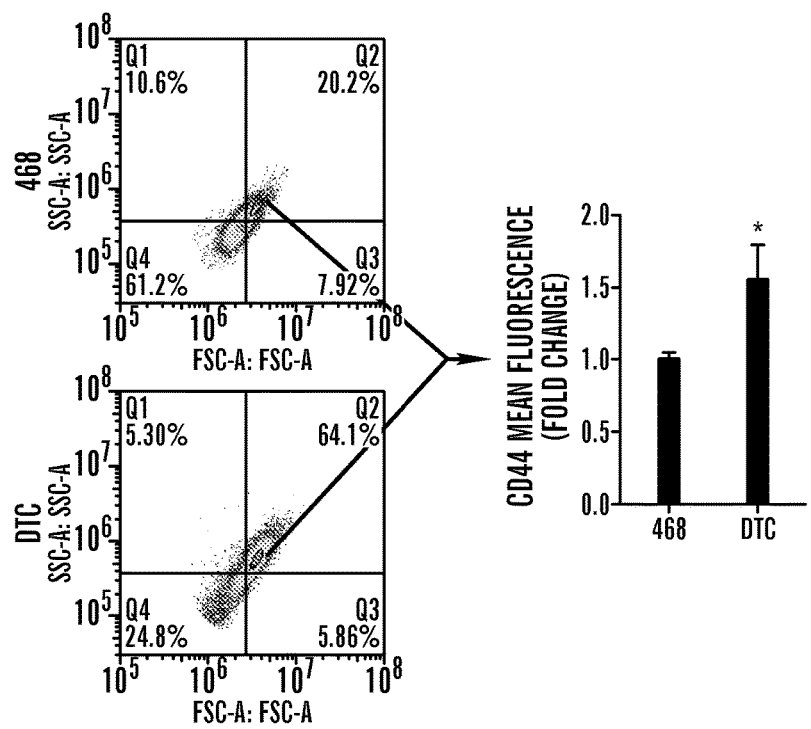
FIGS. 3A-3G demonstrate that Cancer Stem Cell mimicry and adaptive chemoresistance is transient.
Figure 3B:
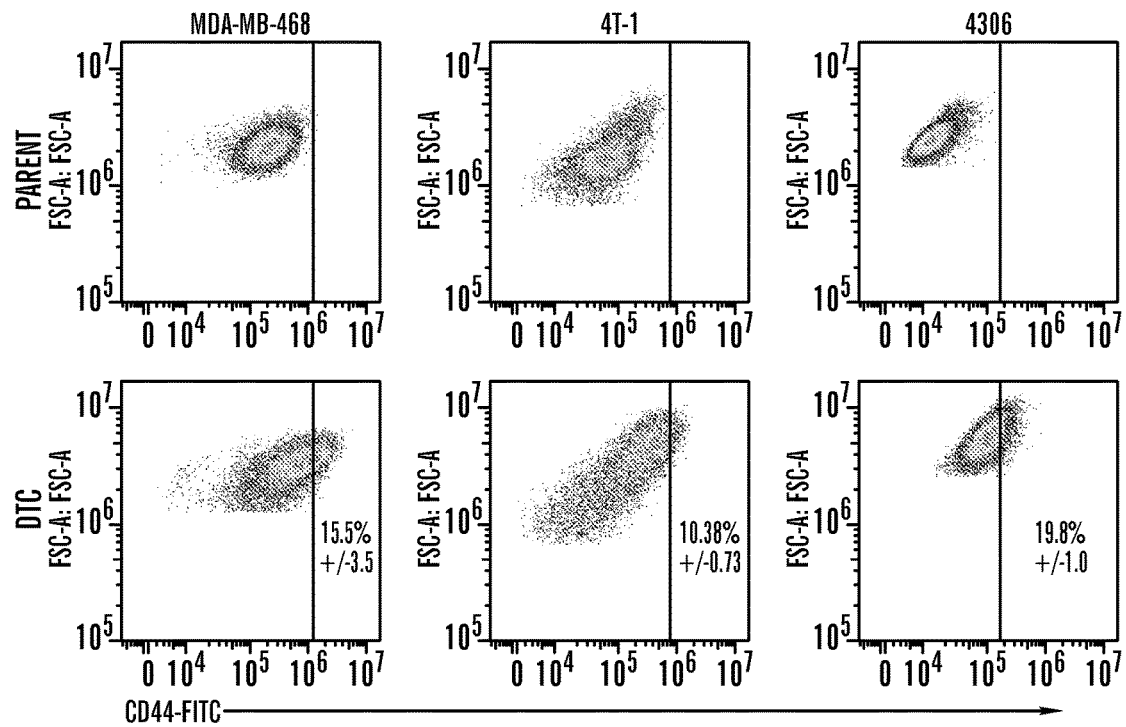
Figure 3C:
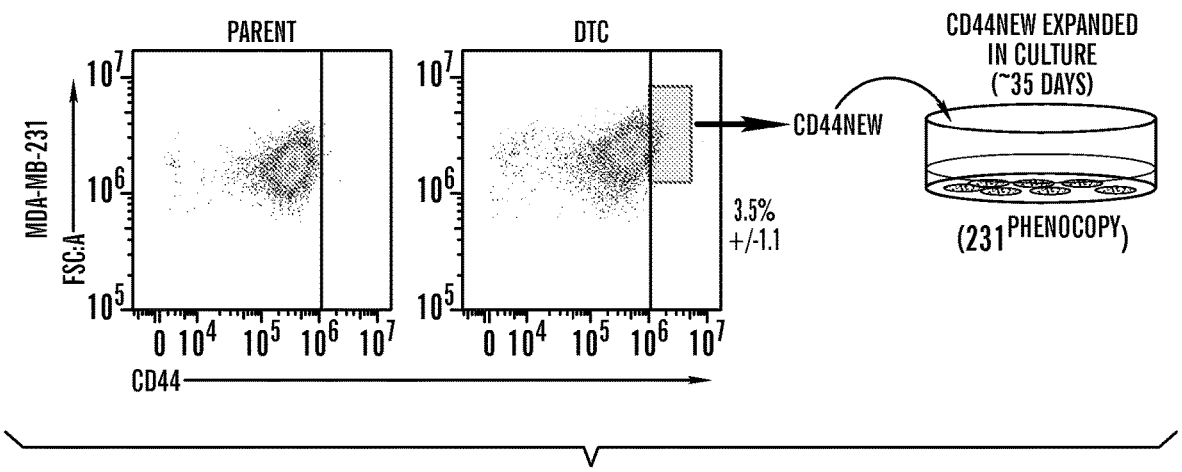
Figure 3D:
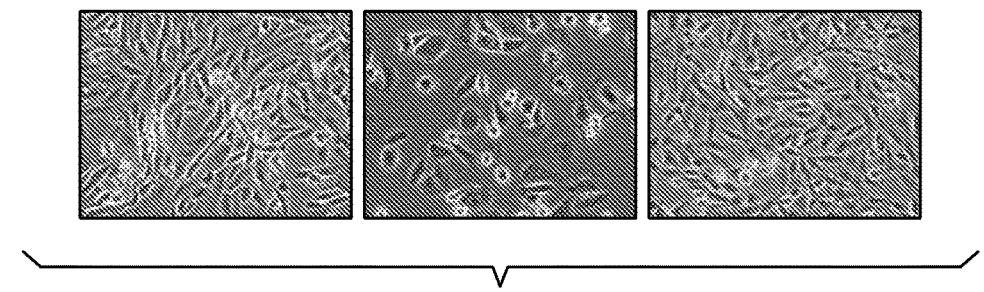
Figure 3E:
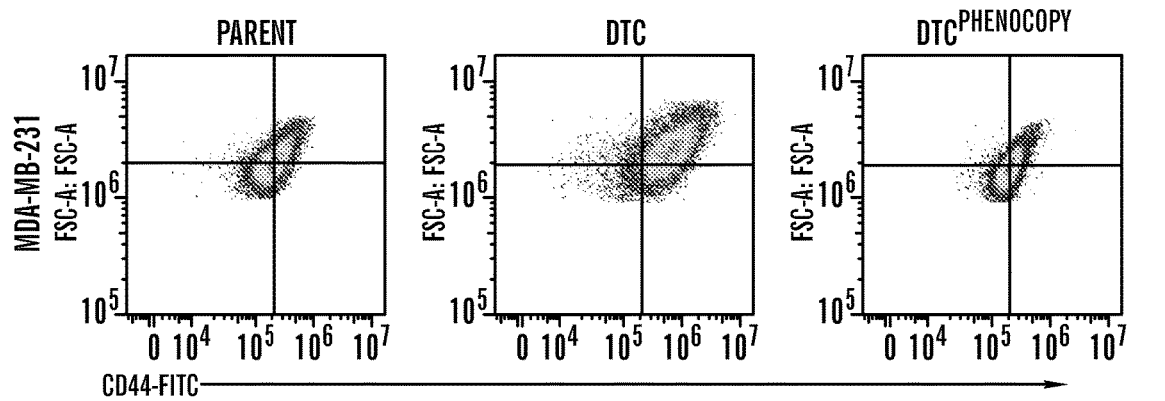

To confirm whether DTCs comprised of a homogenous set of only large inherently chemoresistant CD44$^{Hi}$ cells described above, 'similar sized' populations using side and forward scatter were selected from both parent and DTC cells. Analysis of the mean fluorescent intensity (fluorescence per cell) of CD44 revealed that the parent cells, of equal size to DTC, express less CD44 than DTC cells (FIG. 3A), indicating that DTC population represent a heterogeneous mixture of inherently resistant cancer cells and 'induced', imperfect stem-like cells. Significantly, we identified a population of cells within the DTC which exerted enhanced CD44 expression beyond that of any parental cell (Cells observed to the right of the red gate in the DTC subset). This subset of cells was termed 'CD44$^{New}$' (FIG. 3B). Utilizing FACS, the CD44$^{New}$ population was isolated and readapted into culture until they regained a proliferative capacity, defining the resulting expanded population as $^{231Phenocopy}$ (FIG. 3C). CD44$^{New}$ remained quiescent for a period of approximately 23 days, and full repopulation occurs by approximately 35 days, an observation consistent between cell lines. Characterization of the $^{231Phenocopy}$ revealed a heterogeneous morphology similar to parent cells (FIG. 3D), including CD44 expression (FIG. 3E) indicating achievement of a phenotypic equilibrium; an effect previously predicted through stochasticity (Gupta et al., 2011).

Figure 3F:
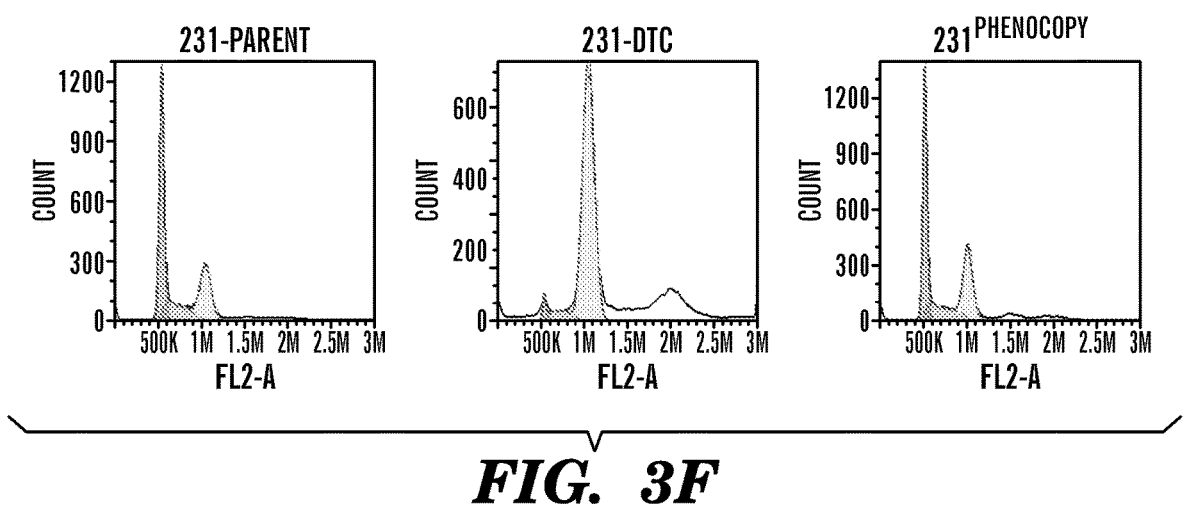
Figure 3G:
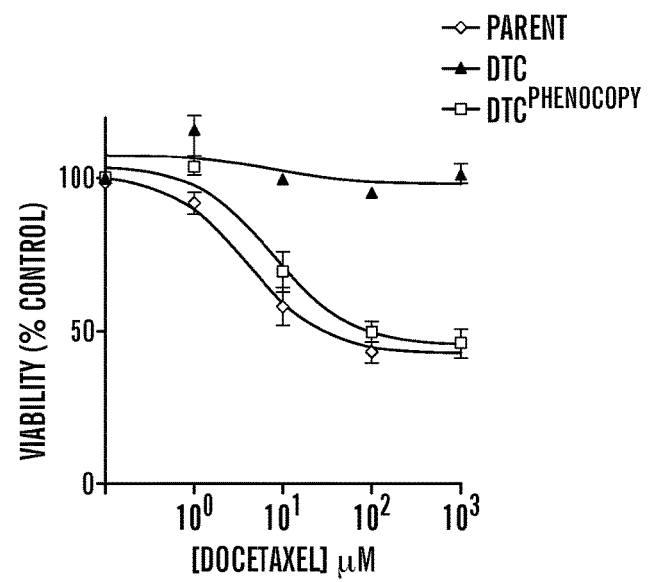

Concurrently, cell cycle (FIG. 3F) and response to chemotherapy were found to re-equilibrate to parental status (FIG. 3G).

Chemotherapy-Induced CD44 Engages a Scaffold-Kinase Interaction with EGFR to Elicit Akt Survival Signaling.

Figure 4B:
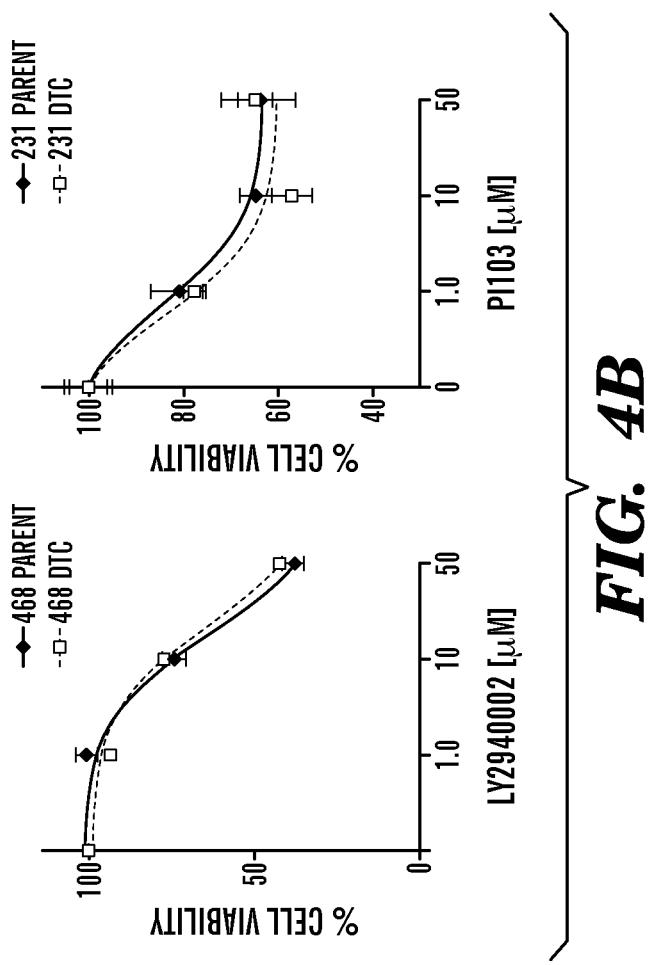
FIGS. 4A-4I demonstrate that chemotherapy-induced CD44 functionally engages EGFR to promote survival of DTCs.
Figure 4A:
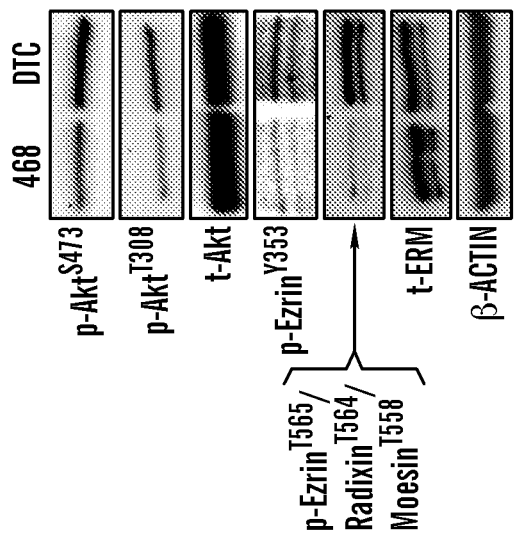

It was next explored if the induction of CD44 has a functional implication. Since CD44 expression could be induced with short burst chemotherapy treatment (described above), this incubation period was utilized to dissect a mechanism involving CD44 over-expression. Interestingly, CD44 has been reported to function in membrane-recruitment of ezrin, a known adaptor of AKT (Gautreau et al., 1999) that has recently been shown to correlate with invasiveness of breast cancer (Sarrio et al., 2006), and the cortex complex with Radixin and Moesin (ERM) (Mori et al., 2008). Indeed, western blotting indicated activation of these cortex proteins are enhanced in the DTC subset compared to parent (FIG. 4A). Importantly, PI3K/AKT is one of the most abundantly dysregulated oncogenic drivers in a large fraction of cancers, particularly TNBC (Di Cosimo and Baselga, 2010), yet mechanisms implicating this pathway in adaptive resistance remain poorly understood (Huang and Hung, 2009). Finally, that inhibition of AKT pathway-activation using multiple small molecule inhibitors of PI3Kinase resulted in similar decrease in cell viability in both parental and DTCs (FIG. 4B) suggesting AKT is a critical component of survival for the DTC subset.

Figure 4D:
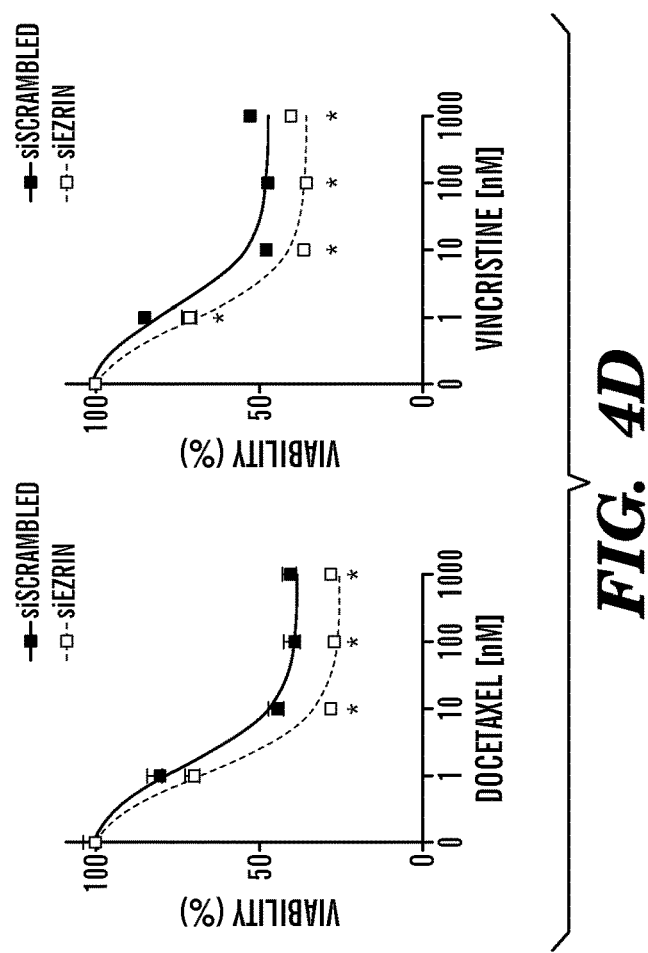
Figure 4C:
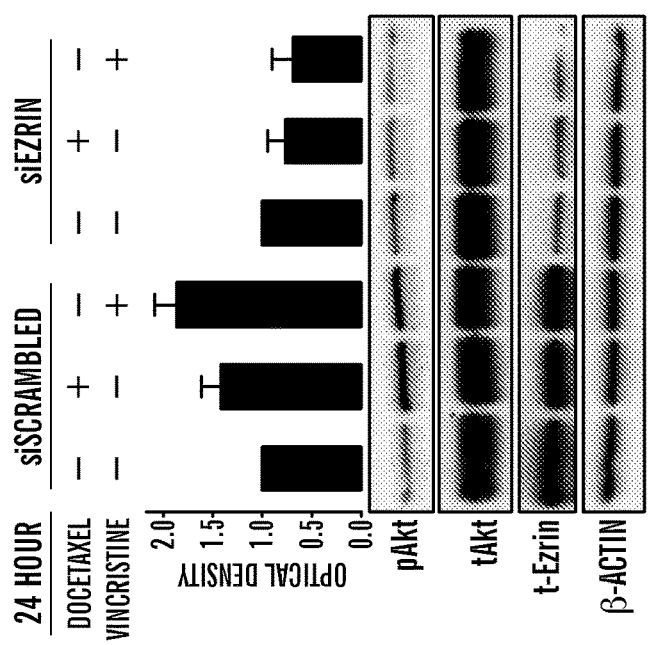
Figure 4E:
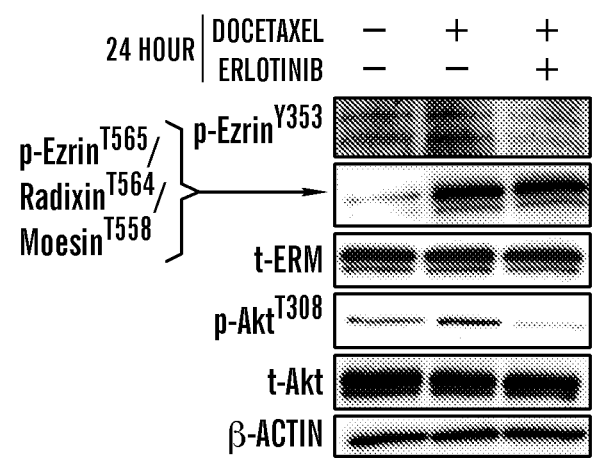
Figure 4F:
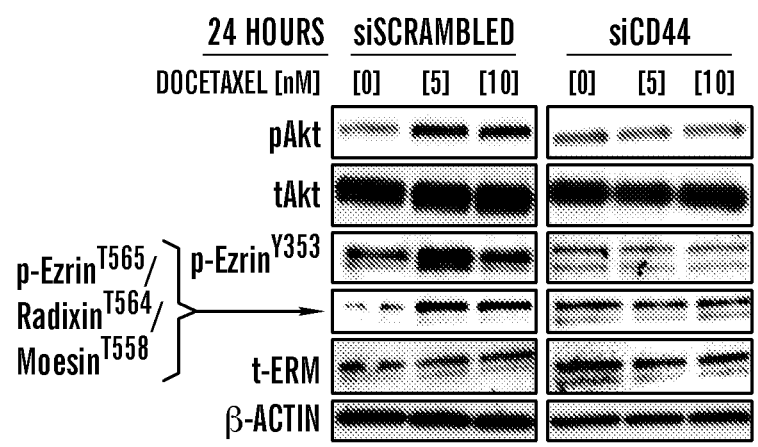
Figure 4G:
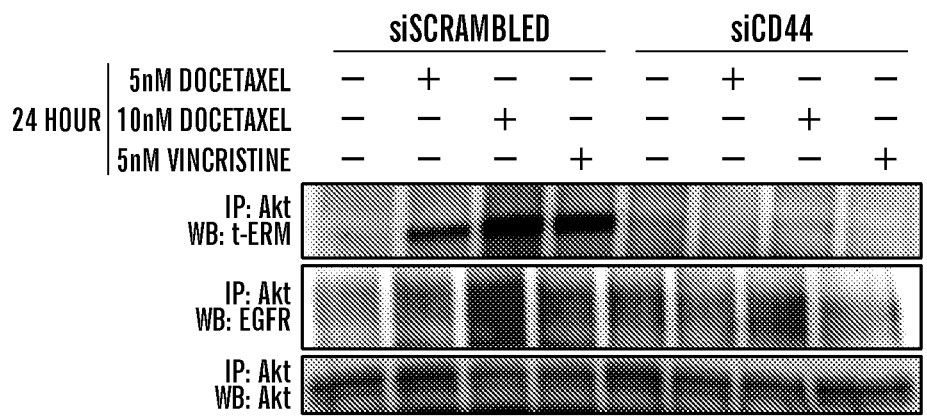
Figure 4H:
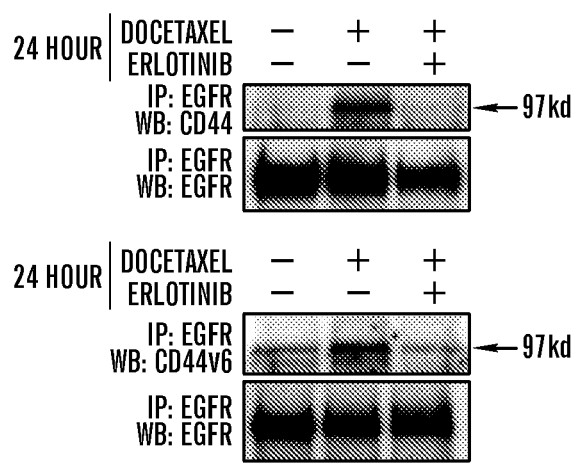
Figure 4I:
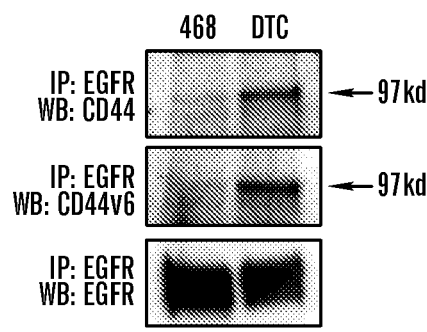
Figure 12A:
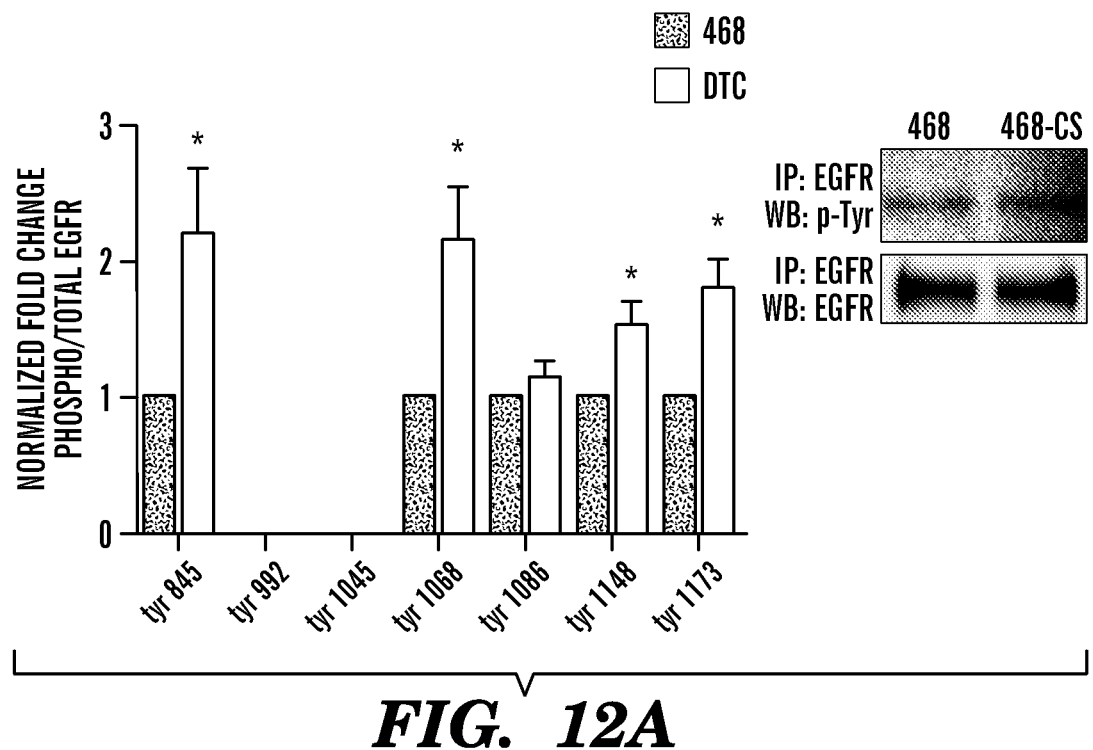
FIGS. 12A-12D demonstrate the elucidation of the functional implication of CD44 induction in CSC mimicry.
Figure 12B:
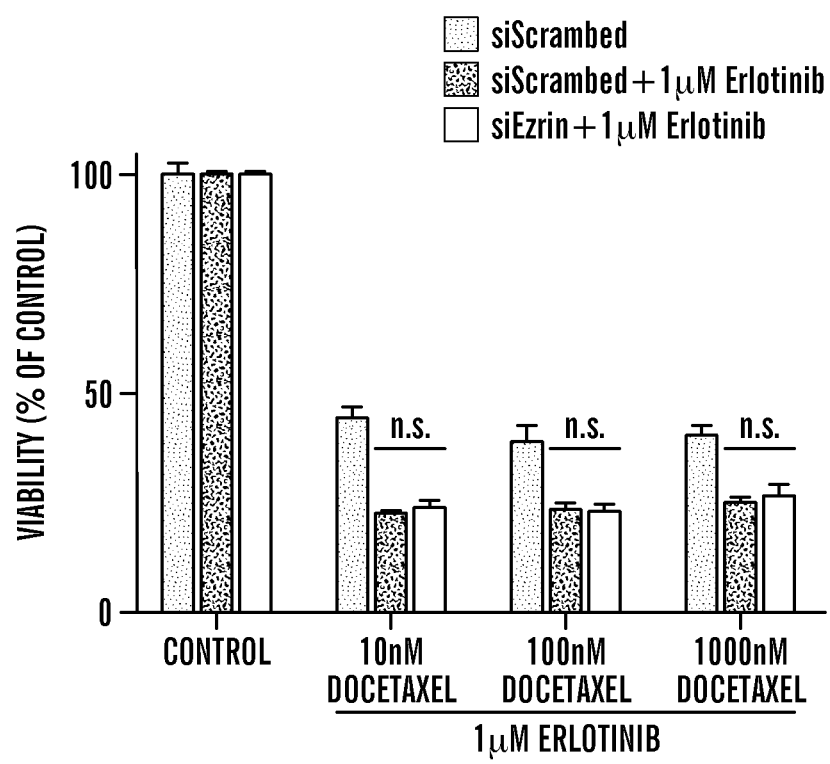
Figure 12C:
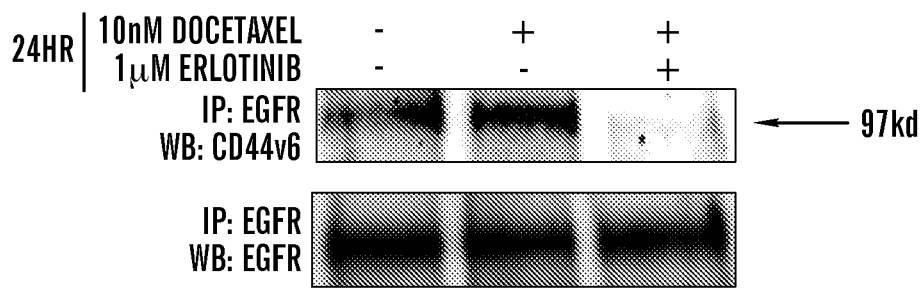
Figure 12D:
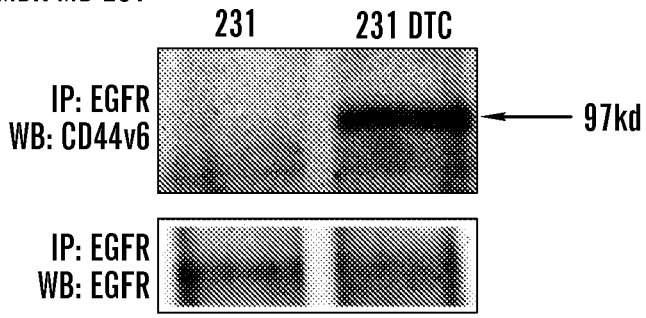

Since total AKT and ERM protein levels appeared constant between parent and DTC, the findings indicated a re-wiring of the kinase network. Therefore, it was desired to identify a mechanism underlying chemotherapy-induced AKT signaling as an early event to predispose the DTC subset. Using small interfering RNA (siRNA) gene knockdown, it was confirmed that ezrin lies upstream of AKT activated in response to chemotherapy (FIG. 4C). Furthermore, silencing ezrin augmented sensitivity to antitubulins (FIG. 4D). In agreement with a phosphorylation array performed in the DTC subset (FIG. 12A) and consistent with previous speculation that the epidermal growth factor receptor (EGFR) activates AKT in response to chemotherapy (Huang and Hung, 2009), the EGFR-selective inhibitor, erlotinib, prevented induction of AKT and ezrin signaling (FIGS. 4E and 12B). However ERM-complex signaling remained intact (FIG. 4E) suggesting that CD44 could act as a scaffolding partner to support this cortex signaling event. Indeed, siRNA-mediated gene-knockdown of CD44 attenuated ezrin, AKT and ERM-complex signaling in response to acute treatment with chemotherapy (FIG. 4F). Furthermore, immunoprecipitation revealed CD44 expression was critical to engage the complexation of EGFR, AKT and ERM cortex-signaling components (FIG. 4G). These findings suggested CD44 and EGFR cooperate in a scaffold-kinase fashion to recruit and subsequently activate AKT in response to chemotherapy. Immunoprecipitation of EGFR confirmed an enhanced, physical association with CD44 is elicited in response to DTX; inhibiting the kinase activity of EGFR was found to modulate this interaction (FIG. 4H, upper panel). A variant of CD44 (CD44v6) was identified as the putative isoform which interacts with EGFR (FIG. 4H, lower panel and FIG. 12C). Importantly, this enhanced scaffolding effect was preserved in the basal state of the DTC subset (FIGS. 4I and 12D). Taken together, these are the first evidence that induction and functional engagement of a CSC biomarker with RTKs to re-organize a kinase signaling network confers a chemoresistant advantage through an adaptive response. This finding is in contrast to the paradigm that CSC biomarkers serve as innocuous gauges of differentiation.

Dasatinib Attenuates a Rewired Kinase Network in DTCs.

Although inhibition of the AKT pathway resulted in reduced DTC viability, the sensitivity of DTCs to the PI3K inhibitor, PI103, was similar to the sensitivity of the parent population, with a subset in both cell populations escaping PI103-induced cell death. Therefore, a drug screen was performed with a library of single and dual kinase inhibitors which exert nanomolar affinity, identifying dasatinib, a dual Src Family kinase (SFK), BCR-Abl inhibitor, as the only candidate drug which exerted greater sensitivity in the DTC than the parental cell line (Sensitivity index >1, FIG. 5A). This enhanced dasatinib sensitivity-index was consistent in additional DTC subsets derived from multiple cancer types (FIG. 5B). Interestingly, the 231Phenocopy regained parental sensitivity to dasatinib (FIG. 5C) suggesting temporality is a parameter in susceptibility of the cells to dasatinib. Since dasatinib is a dual kinase inhibitor, targeting both SFK and BCR-Abl, we tested whether both targets were required to sensitize the DTC subset. Cell viability analysis utilizing the SFK-selective inhibitor, PP2, and BCR-Abl-selective inhibitor, imatinib, separately and in combination indicated that dual inhibition does not further augment the sensitivity of the DTC population, effectively eliminating the BCR-Abl pathway as a key component for DTC survival (FIG. 5D).

Figure 5F:
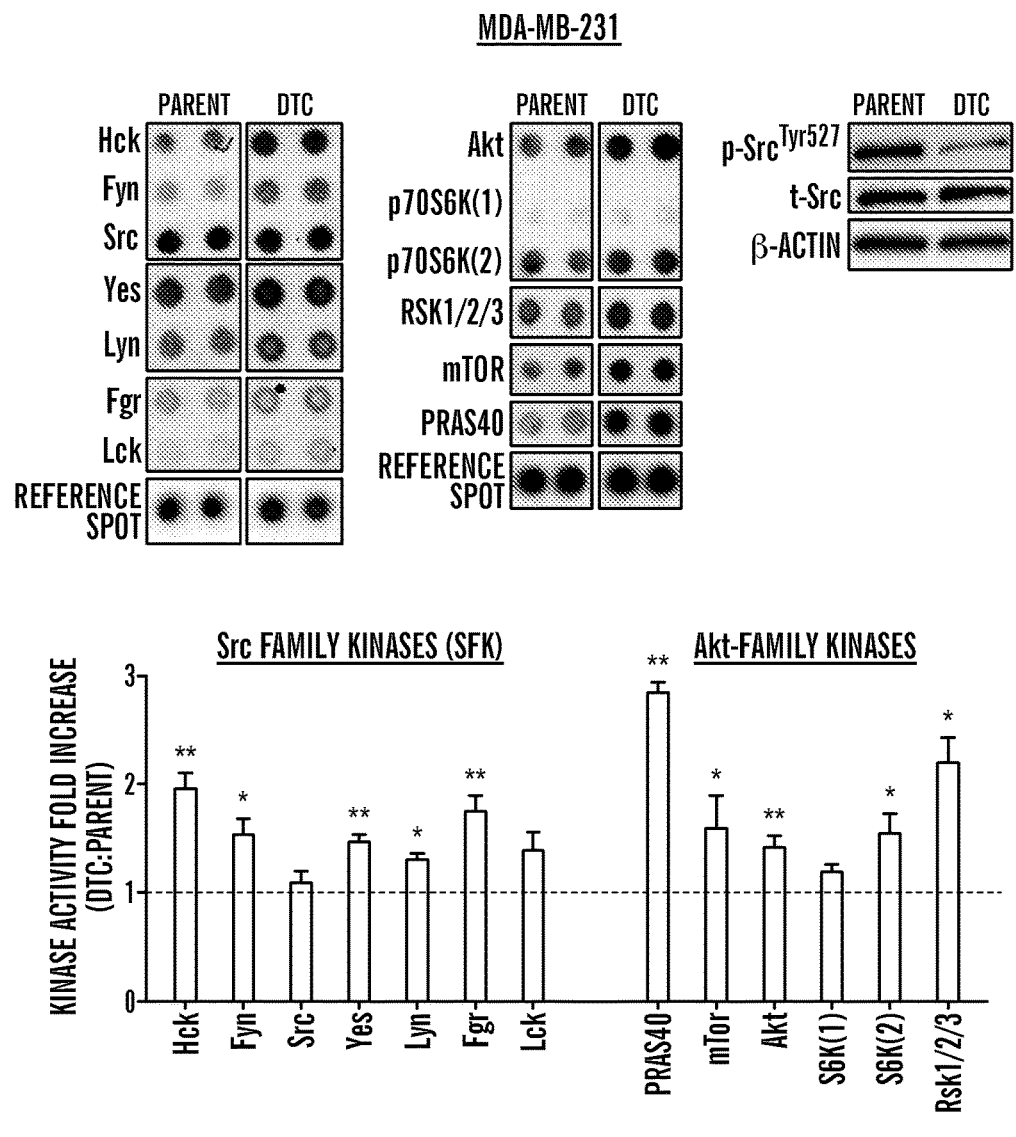
Figure 5G:
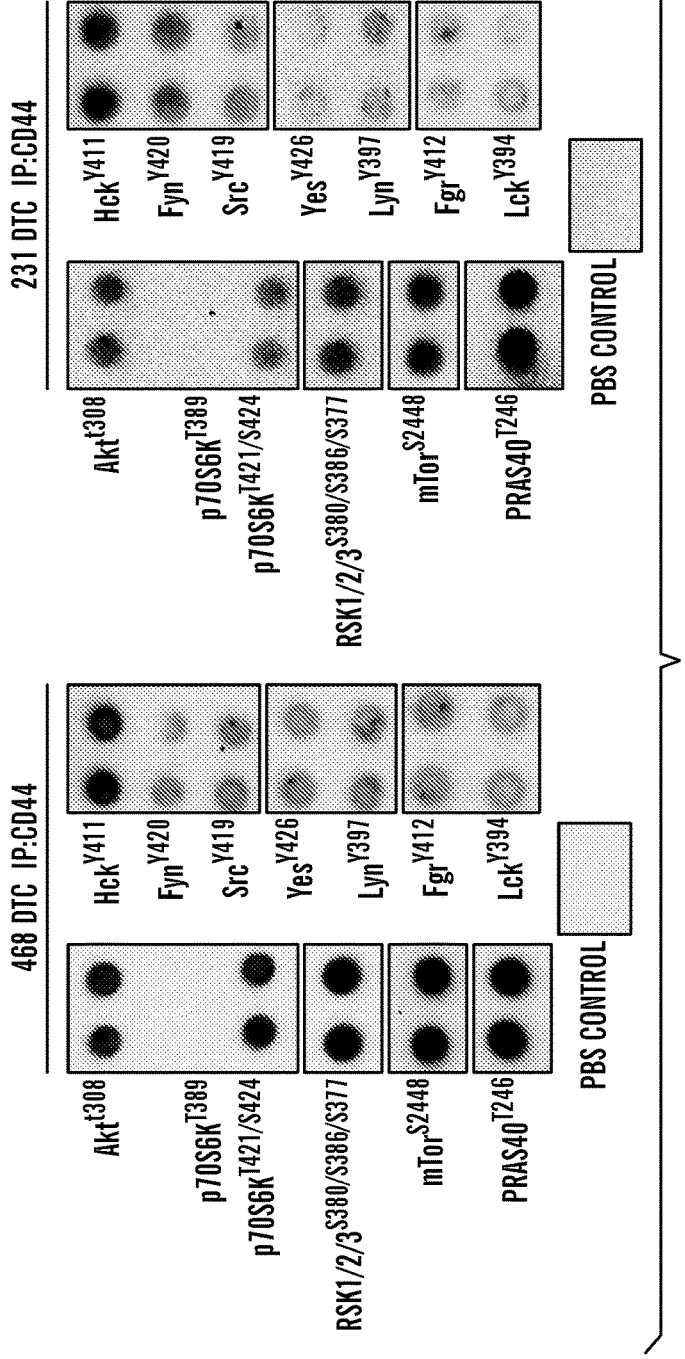
Figure 5H:
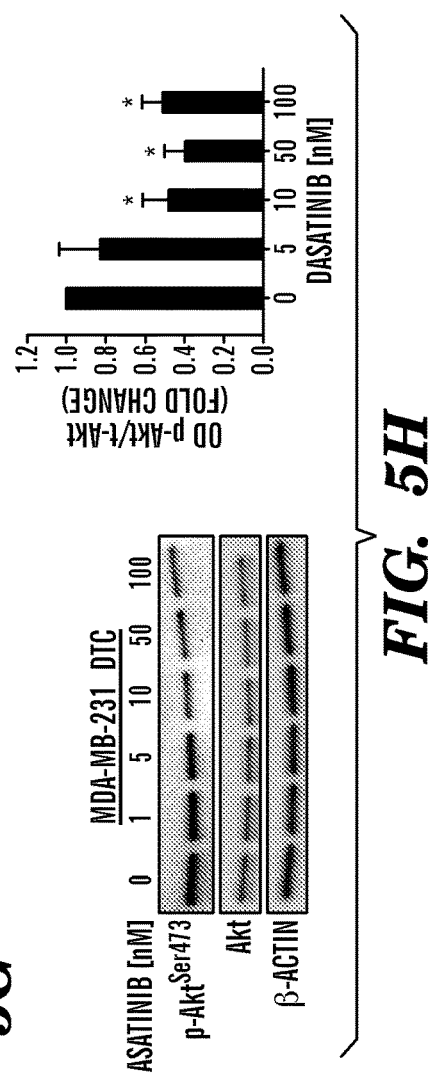

A phosphorylation array was used to analyze specific AKT-family and SFK residues enhanced in the DTC subset (FIG. 5E). A significant increase in the phosphorylation status of multiple residues implicated within these pathways was quantified by optical density (FIG. 5F). Interestingly, the activating residue of Src (Y416) was unchanged between parent and DTC, yet Src inactivation (Y527) diminished nearly completely (FIG. 5F western blot). Most significant activation was observed in the SFK protein Hck, as well as a robust activation of PRAS40, a novel substrate of AKT which relieves inhibition of mTOR to promote activation of key survival signaling pathways (Vander Haar et al., 2007). To investigate a functional involvement of CD44, a phosphorylation array was performed in the DTC subset following immunoprecipitation. The results indicated that key residues shown to be over-activated in the DTC subset physically associated with CD44 (FIG. 5G). These findings implicate CD44 as a robust scaffolding support for multiple AKT and SFK proteins. Indeed, a potential involvement of other RTKs is likely enhanced, similar to the effects observed between EGFR. Interestingly, western blots indicated that increasing doses of dasatinib reduced, to a minor degree, AKT signaling in the DTC subset (FIG. 5H) suggesting the existence of a cross-talk signaling-component between these critical survival kinases in the DTC subset and explains, in part, the potent effect of dasatinib.

Transient Expression of CD44 Physically Activates an Oncogenic Kinase Signature, In Vivo.

Figure 6E:
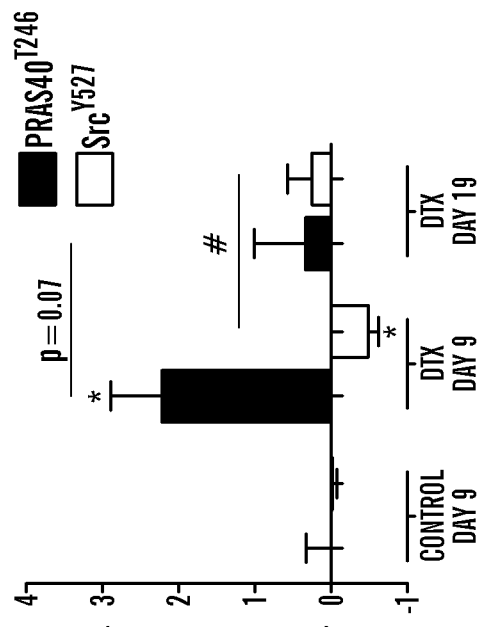
Figure 6D:
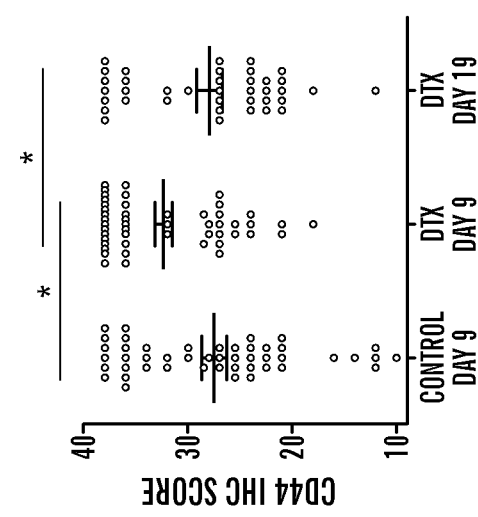
Figure 6F:
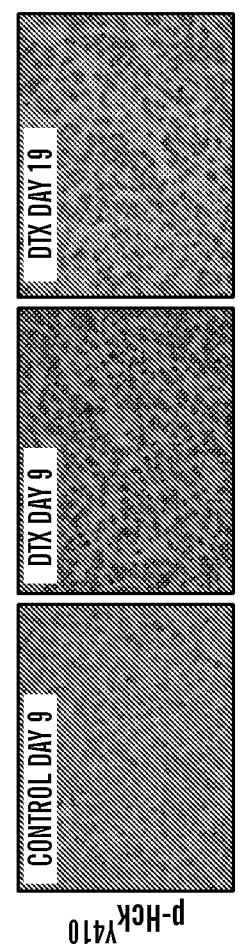
Figure 13A:
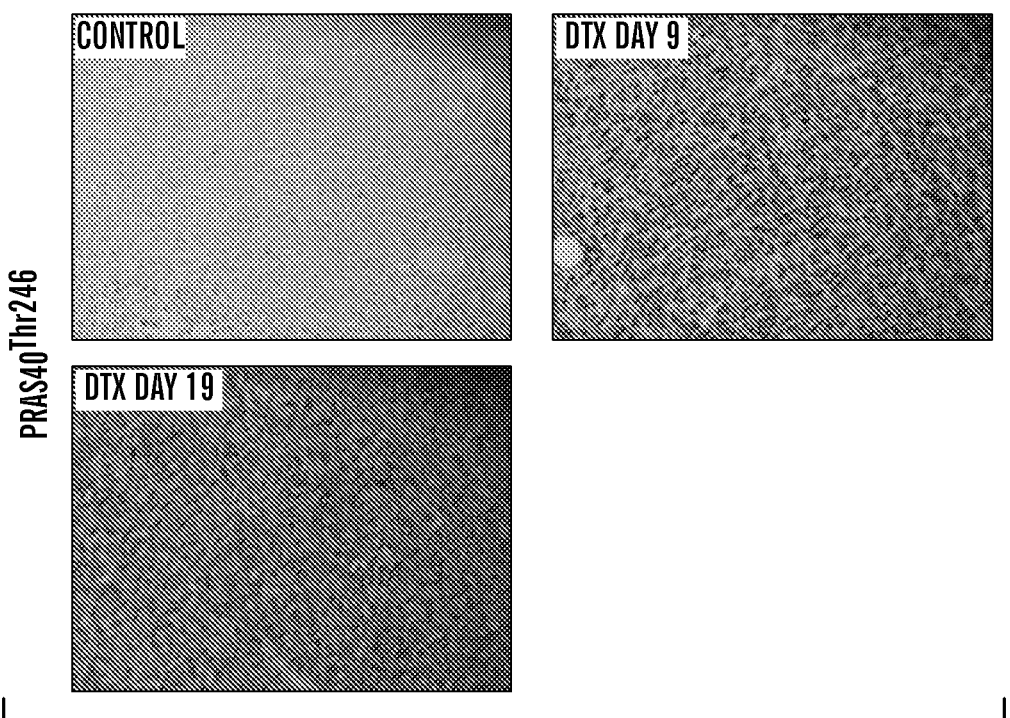
FIGS. 13A-13B demonstrate targeting signaling redundancies evoked in CSC mimicry.

To validate the above mechanistic observations in vivo, 4T1 breast tumor-bearing mice were treated with DTX at the maximum tolerated doses (MTD). As shown in FIG. 6A, treatment with DTX inhibited tumor growth as compared with vehicle-treated tumors as evident by the separation of growth rates within 48 hours of administration of the first dose, but the tumor re-emerged robustly by day 19. Western blot analysis of tumor tissue harvested from control Day 9 and DTX-treated day 9 revealed significantly enhanced CD44 expression following DTX treatment, a transient effect that was found diminished by day 19 (FIG. 6B). To validate this analysis, immunohistochemistry (IHC)

revealed transient expression of CD44 exclusively in the cell membrane (FIG. 6C) as quantified for intensity of staining and percent of cells stained in a blinded fashion (FIG. 6D). It was next investigated whether a transient kinase signature encompassing key oncogenic residues which correlated to the in vitro studies could be detected. Reduction of the inhibitory residue of Src (Y527) and enhancement of activated PRAS40$^{T246}$ occurred in DTX day 9 samples compared to control, an effect which diminished by day 19 as quantified by Western blot (FIG. 6E). In addition, IHC analysis revealed that Hck phosphorylation was markedly enhanced in DTX day 9 tissue compared to control which, again, was diminished by day 19 (FIG. 6F). Interestingly, although active Hck and PRAS40 (FIG. 13A) predominantly localized to the nucleus, immunoprecipitation from tumor lysate revealed that enhanced membrane-cortex interactions with CD44 were robust in DTX day 9 samples compared to control, an effect reduced in DTX day 19 samples (FIG. 6G). These findings indicate that CD44 functionally scaffolds key oncogenic kinases which, subsequent to activation, localize to the nucleus where their pro-survival effects are greatest (Paliwal et al., 2007; Saito et al., 2004).

Exploiting Temporality in Drug-Schedule In Vivo Targets the Emergence of CSC Mimicry and Re-Sensitizes Refractory Tumors.

Since these data suggested stem-like mimicry arises in a transient manner in response to chemotherapy, the efficacy of a temporally-constrained application of DTX and dasatinib in vivo was investigated. To address this question, dasatinib was administered in two phases; 1. 'Early Dasatinib', given 72 hours following DTX when tumor growth plateaued and a putative population of stem-like cells with an oncogenic signature arise, or 2. 'Late Dasatinib', administered 216 hours following administration of DTX when tumor burden and growth had significantly re-emerged, suggestive of stem-like diminishment. 'Early' administration of dasatinib significantly augmented the reversal of tumor growth rate, while 'late' administration was ineffective (FIG. 6H). Indeed, tumor regression could be achieved by this regimen in the early treatment group (FIG. 6I, left panel) compared to late treatment which showed no difference over a matched vehicle control (FIG. 6I right panel).

Figure 7A:
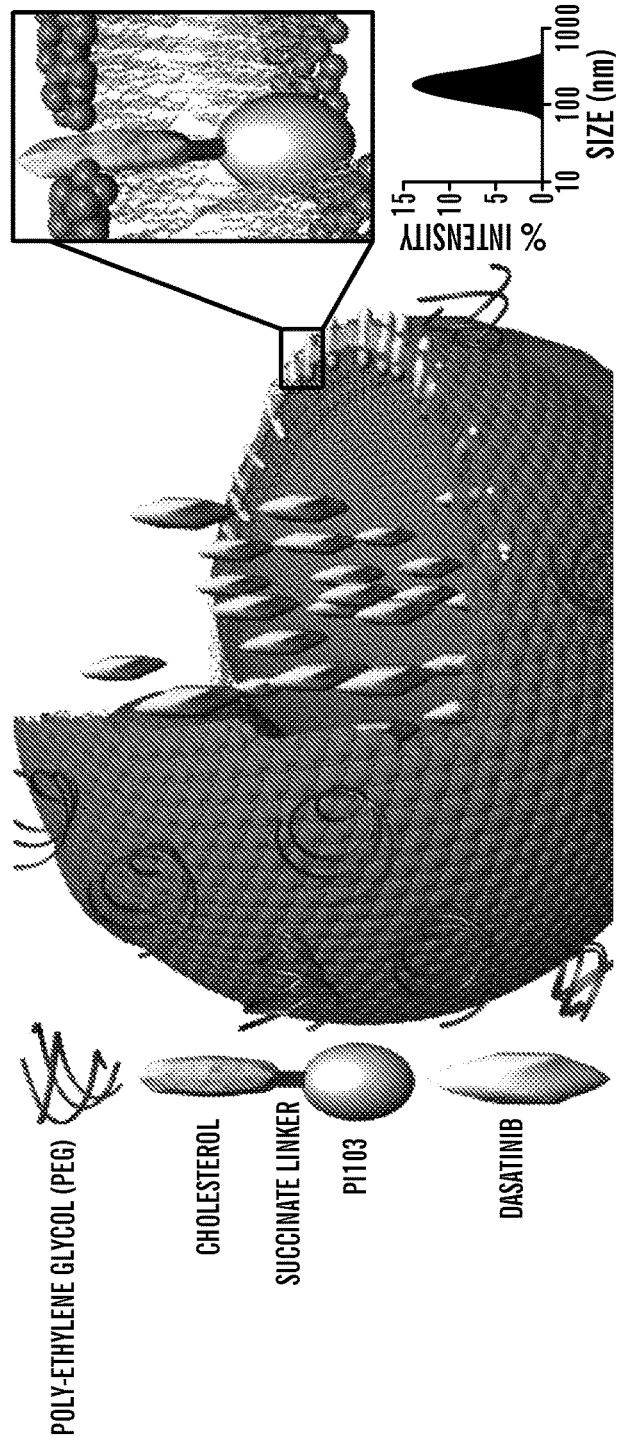
FIGS. 7A-7H demonstrate temporal targeting of redundant signaling cascades in vivo and re-sensitizing refractory human tumor tissue with appropriate dasatinib drug-schedule.
Figure 7B:
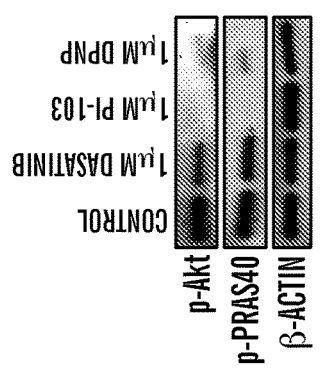
Figure 7C:
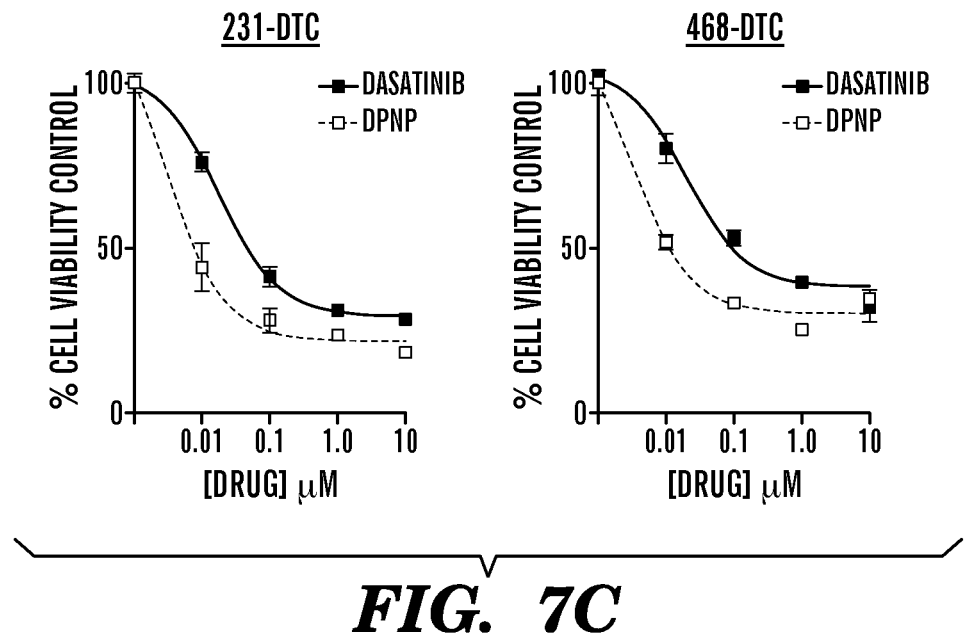
Figure 7D:
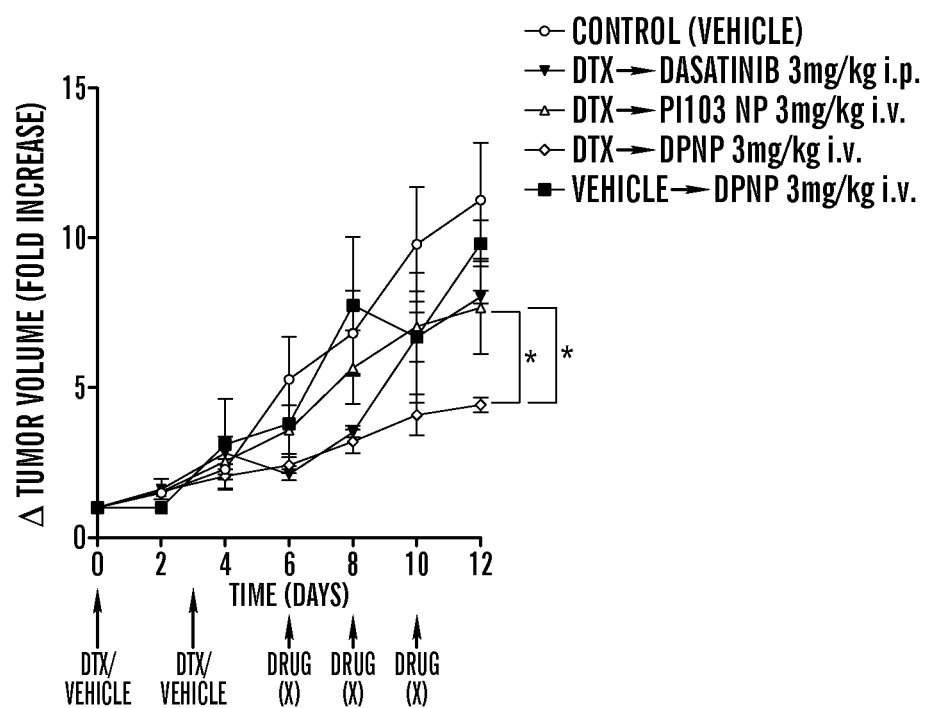
Figure 13B:
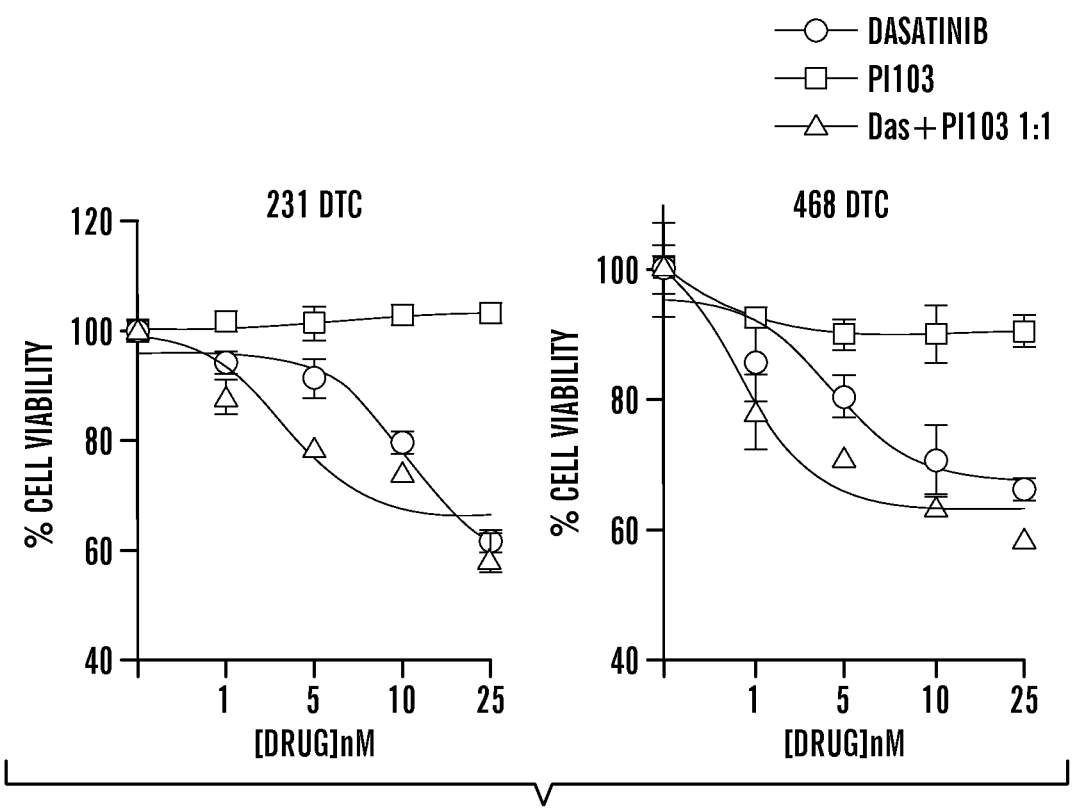

It was determined whether a combination of dasatinib with a PI3K/mTOR inhibitor could ablate signaling-redundancy and exert a synergistic outcome. Low doses of the PI3K/mTOR inhibitor, PI103, and dasatinib were used in combination to dissect a synergistic effect of these inhibitors in the DTC subsets (FIG. 13B). However, while dasatinib exerted a significant toxic burden in clinical trials (Herold et al., 2011), experience with PI3K inhibitors suggest a requirement for sustained inhibition of the pathway in the tumors (Courtney et al., 2010). It was rationalized that these challenges can be addressed using a multifunctional nanoparticle that can deliver both drugs. Nanoparticles harness the leaky vasculature of tumors and the 'EPR (enhanced permeability and retention) effect, which enable preferential accumulation in the tumor (Maeda et al., 2013). To enable self-assembly into a nanostructure, we tethered PI103 to cholesterol derivative via the phenolic hydroxyl group of PI103, which further facilitated the entrapment of dasatinib by increasing membrane integrity (FIG. 7A) (attempts at entrapment of dasatinib in lipidic nanoparticles in the absence of the PI103-cholesterol conjugate resulted in unstable structures). As shown in FIG. 7B, the dasatinib-PI103 multifunctional nanoparticle (DPNP) inhibited redundant signaling compared with dasatinib alone, resulting in decreased cell viability (FIG. 7C). The multifunctional nanoparticles were tested in vivo, where the treatments were administered during an optimally-derived temporal window created by the administration of DTX. As shown in FIG. 7D, the treatment with DPNP post-treatment with DTX was significantly more effective than any single drug combination with DTX. Importantly, DPNP as a single agent was ineffective, thus supporting the importance of DTX schedule-dependency and the generation of vulnerable stem-like mimicry.

Figure 7E:
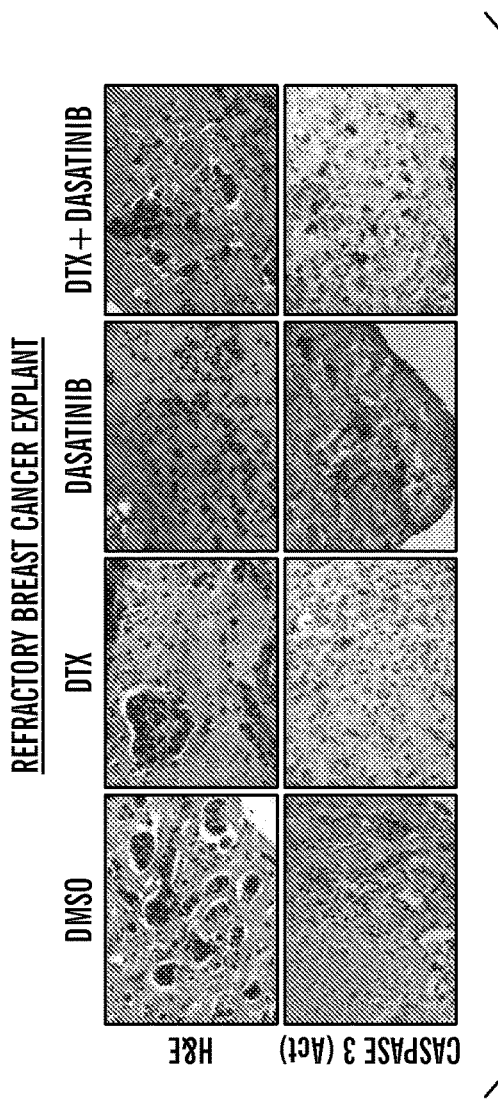
Figure 7F:
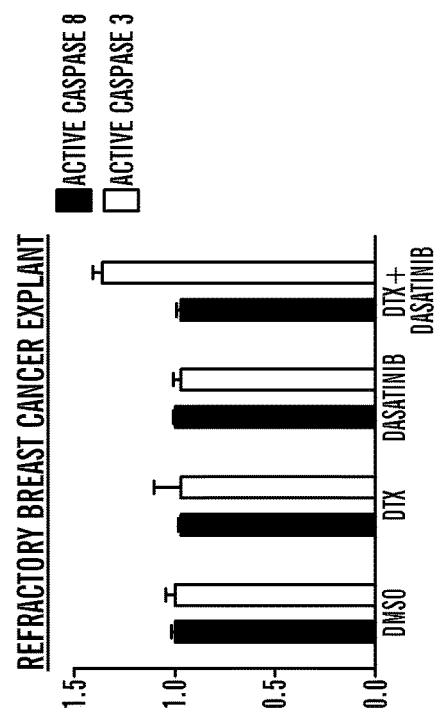

Finally, in a very preliminary study to explore potential clinical implications of the above results, the efficacy of DTX-dasatinib treatment in an explant derived from the biopsy of a clinically confirmed case of invasive carcinoma obtained from a stage IV, metastatic breast cancer patient who had relapsed from taxane chemotherapy was investigated. The explant was treated for 48 h with DMSO (vehicle), DTX, Dasatinib, or a combination of DTX and dasatinib. Strikingly, we observed that the combination of dasatinib with DTX could re-sensitize the refractory cancer tissue to chemotherapy as indicated by IHC of cleaved caspase 3 (FIG. 7E). Interestingly, quantification of caspase activity revealed this apoptotic response was specific to an intrinsic caspase-3 response as no change was observed in the caspase 8 levels (FIG. 7F). These results provide insight into the biological complexity of adaptive chemoresistance through the transient emergence of CSC mimicry. Additionally, therapeutic intervention that can target CSC mimicry can result in enhanced antitumor outcomes.

Discussion

While the emerging paradigm of chemotherapy failure is one built on inherent heterogeneity of the tumor (beyond the Darwinian principles of acquisition of mutations and selection pressure), the exact nature and diversity of heterogeneity is not fully defined. Heterogeneity contributing to chemotherapy failure could arise from distinct cell differentiation hierarchy, where non-stem cells are susceptible to chemotherapy while stem-like or cancer stem cells are inherently tolerant to cytotoxics (Shackleton et al., 2009). Similarly, phenotypic heterogeneity arising from stochasticity in activation of cell signaling/survival pathways can confer chemotherapy failure in subsets of cells (Brock et al., 2009). It is demonstrated herein that chemoresistance could additionally arise from a more dynamic heterogeneity, where cancer cells can exist in a continuum of phenotypic states tending, under chemotherapy pressure, to mimic a stem-like cell. In this state, cells exploit phenotypic advantages of stem-like properties to transiently rewire a distinct signaling network via CD44, EGFR, PI3K/AKT and SFK and evoke a survival response.

Figure 14:
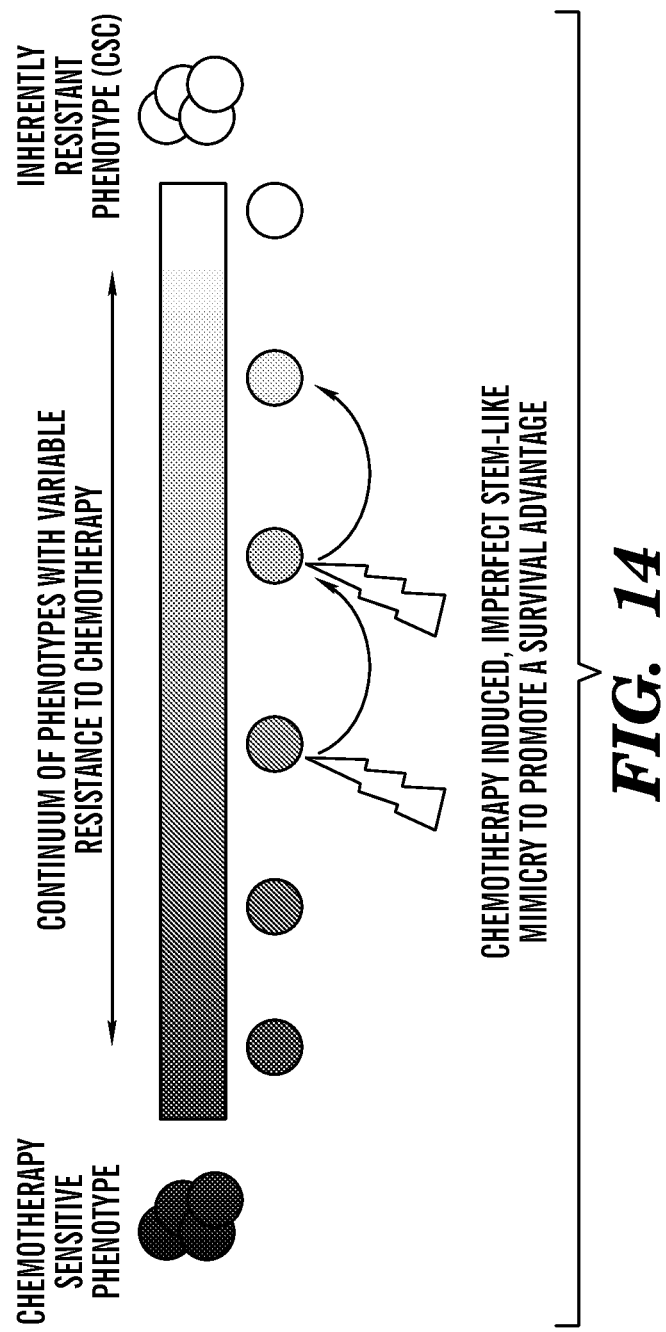
FIG. 14 depicts a schematic hypothetical model for the continuum of phenotypes and the emergence of CSC mimicry. Without wishing to be bound by theory, cells can be considered as either chemotherapy sensitive (left-hand extreme) or inherently chemotherapy resistant (right-hand extreme, also denoted as putative population of CSC). Between these two phenotypic extremes lie a continuum of phenotypes which shuttle variably through these states of chemo-resistant and chemo-sensitive. Introduction of chemotherapy (lightning bolts) can deterministically alter the phenotype of cancer cells existing within the continuum by shuttling them to more closely, yet imperfectly mimic the most inherently resistant subset of cells (CSC mimicry). Utilizing adaptive mechanisms obtained by this transition, cells can overcome chemotherapy and re-emerge.
Figure 15:
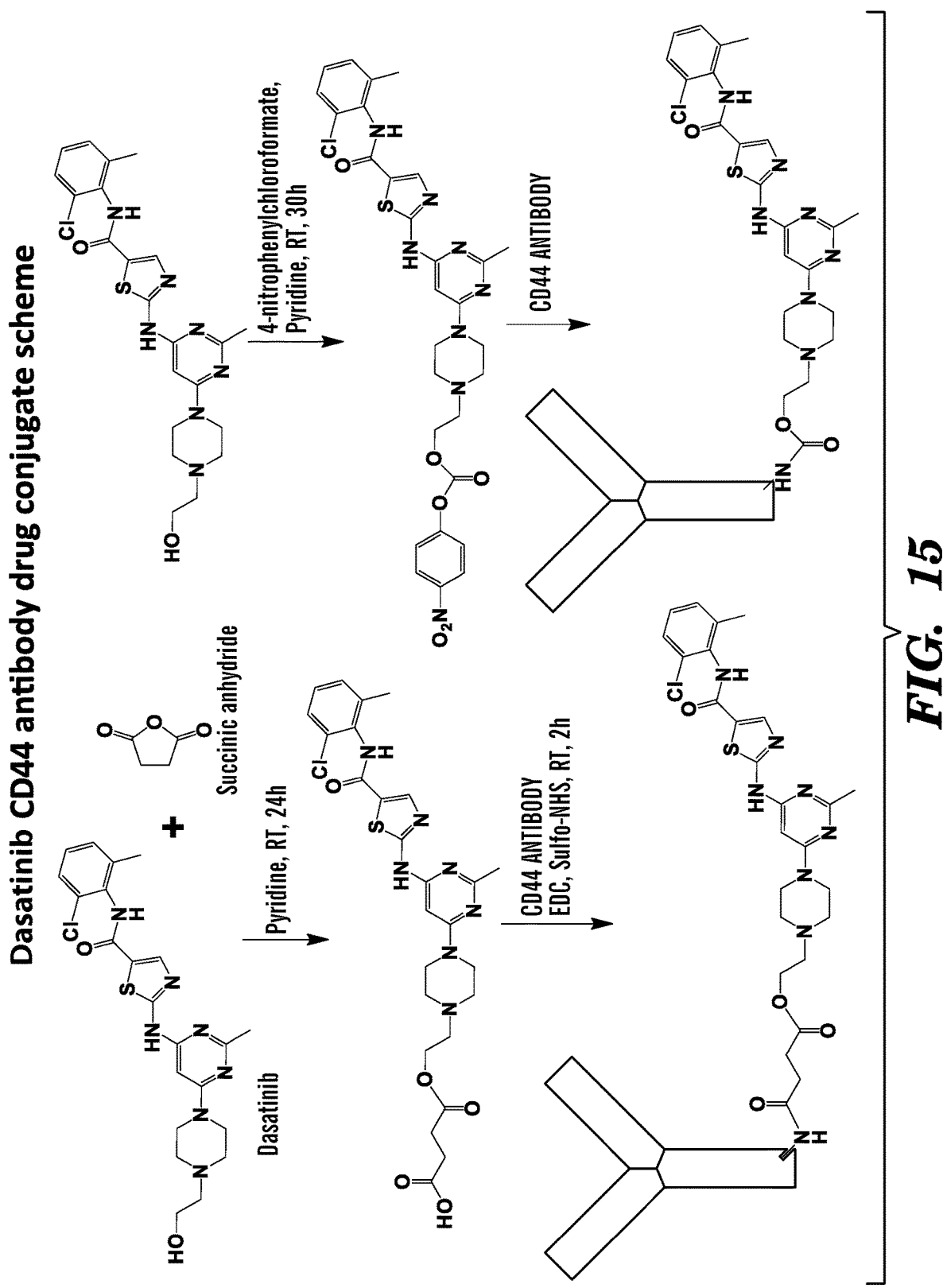
FIG. 15 depicts a schematic of the synthesis of some embodiments of the antibody-drug conjugates described herein.
Figure 16A:
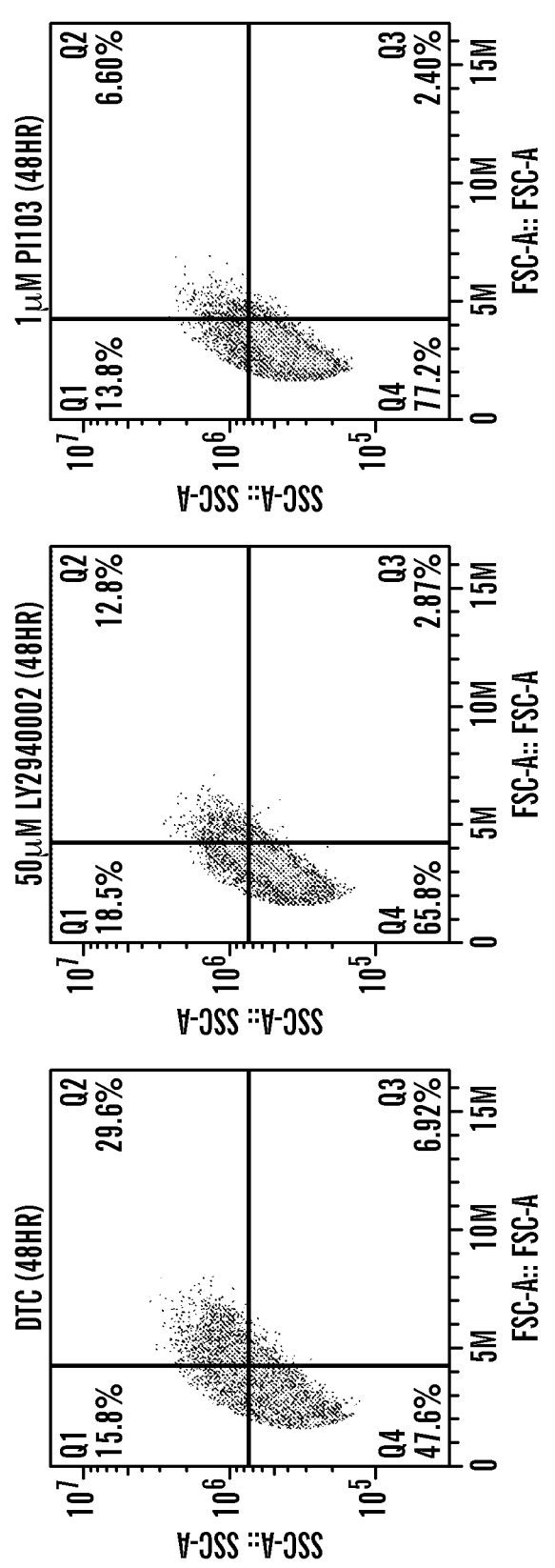
FIGS. 16A-16B demonstrate that inhibiting mimicy ablates acquired chemoresistant cancer cells.
Figure 16B:
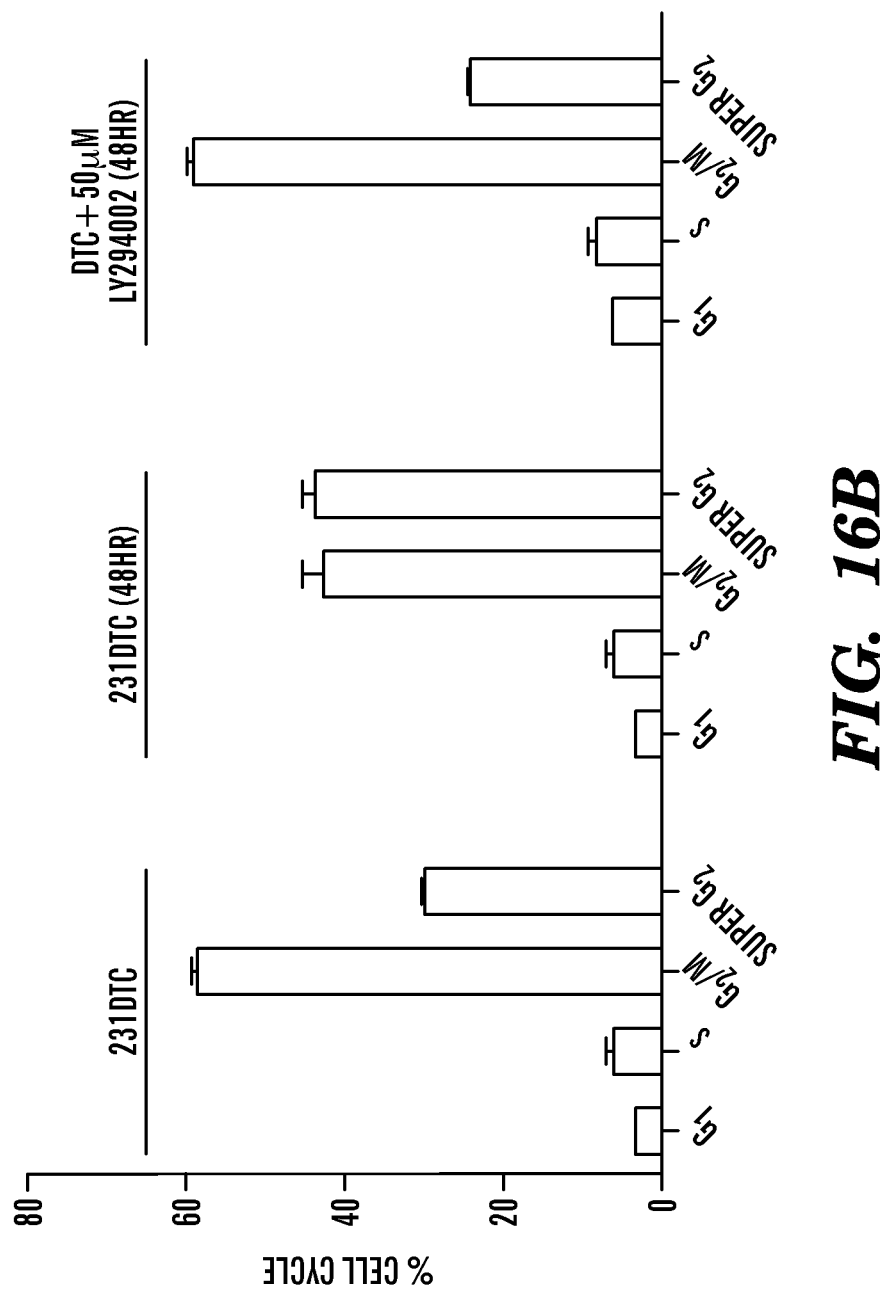

While the cancer stem-like cell conferring chemotherapy resistance/tolerance is an attractive hypothesis, clinical observations and mathematical analysis highlight the inconsistencies in the theory (Kern and Shibata, 2007). Indeed, recent evidence indicates that cancer stem-like cells can spontaneously arise de novo from non-stem like cells, supporting a more flexible model than the current differentiation hierarchy model (Gupta et al., 2011). The results described herein indicate that in addition to the inherently-resistant cells that exist in the parent population, an additional subset of cells can transiently acquire a state of imperfect 'mimicry' of a cancer stem cell in response to chemotherapy. While these cells exhibited enhanced size related to enrichment of DNA content >2N, a quiescent phase, re-population of a heterogeneous landscape, and the induction of CD44$^{Hi}$ consistent with a cancer stem cell identity, they were CD24$^{+/Hi}$ and inhibition of drug efflux had no impact on efficacy, suggesting that the newly generated cells were not true cancer stem cells but imperfect mimics. The imperfect mimicry supports the hypothesis that cells could exist in a continuum between non-stem cell and stem cell phenotypes, tending but not completely switching to the latter state under chemotherapy pressure (FIG. 14). Interestingly, this is synonymous to Batesian mimicry, where the mimic can acquire a degree of protection from predation (death) and environmental challenges (chemotherapy pressure) by exerting the phenotype of a dominant species (CSCs) (Johnstone, 2002). However, in contrast to an inheritable phenotypic alteration, presented herein is a context of 'adaptive mimicry'. In the clinical translation of this phenomenon, repeated generation of CSC mimicry and enhancement of polyploidization may lead to generation of aneuploidy and accelerate a malignant conversion over time (Storchova and Pellman, 2004) and thus serving as a substrate for the somatic mutational evolution of cancer. Additionally, a transient drug-tolerant state can also confer the tumor the ability to survive long enough under chemotherapy insult to establish heritable and stable mechanisms of resistance. Similar behavior has been reported in bacterial cell populations, where a subset of cells can stochastically assume a distinct phenotype that confers tolerance to antibiotics not caused by genetic mutation or acquisition of plasmids but by reduced proliferation rates (Dawson et al., 2011). Indeed, the collective findings of Sharma et al and Kreso et al, highlight the analogy between the bacterial and the chemotherapy-tolerant cancer cells (Kreso et al., 2013; Sharma et al., 2010), and are consistent with the observation made herein that the induced multidrug tolerance does not involve drug efflux, and give rise to parental phenocopies on removal of chemotherapy pressure.

While CSCs have been explored more extensively as a driver for chemotherapy tolerance, emerging studies have implicated multiple mechanisms in driving an adaptive state of chemotherapy tolerance (Marusyk et al., 2012). Without wishing to be bound by theory, the data described herein indicates that the acquisition of CD44 enabled the tumor cells to scaffold and activate two critical signaling pathways, the PI3K-AKT and SFK families, which are pervasively implicated in pro-survival signaling. The combination of PI103 and dasatinib resulted in the synergistic induction of cell death in the DTC subset, indicating that while the two pathways can cross-talk, they may regulate disparate survival functions within a 'stressed' cancer cell. For example, AKT has been implicated in regulation of the cell cycle (Chang et al., 2003), and may thus serve to prevent mitotic catastrophe, a function not connected to SFK proteins. Therefore, the choice of kinase inhibitors in combinatorial regimens for the clinical management of cancer should be considered carefully as to disrupt unique survival components that confer resistance to cytotoxic agents.

The analysis presented herein challenges the classical notion of CSC biomarkers, such as CD44, as merely innocuous designations of differentiation and posits a functional role for the emergence of stem-like proteins in adaptive chemoresistance. Without wishing to be bound by theory, for example, EpCAM, a biomarker over expressed in the stem-like mimics, has been shown to coordinate functional activity of the AP-1 protein transcription factor (Sankpal et al., 2011). Similarly, other CSC surface markers and their supporting roles within the cortex may contribute important tumorigenic advantages. Indeed, among the plethora of cancer types which can arise from all tissue within the body, there is an equally diverse signature of stem-cell designations (Jaggupilli and Elkord, 2012). It may be the case that different tumors respond to chemotherapy by exerting a distinct signature of stem-like descriptors corresponding to unique oncogenic profile, thus asserting the rationale for tailored combinations of drugs to target these emergent populations.

A number of single-agent kinase inhibitors have been discarded in clinic due to the endpoint failure, never to emerge again for the treatment of particular cancer subtypes. For example, dasatinib had previously failed as a single-agent in the clinical management of TNBC (Finn et al., 2011), however the data presented herein indicates that dasatinib could emerge as an attractive therapeutic agent for TNBC primed with a taxane therapy. Indeed, these findings emphasize the importance of temporality in combining cytotoxics and targeted therapeutics; perhaps even warranting the re-examination of kinase inhibitors previously considered ineffective.

Figure 7G:
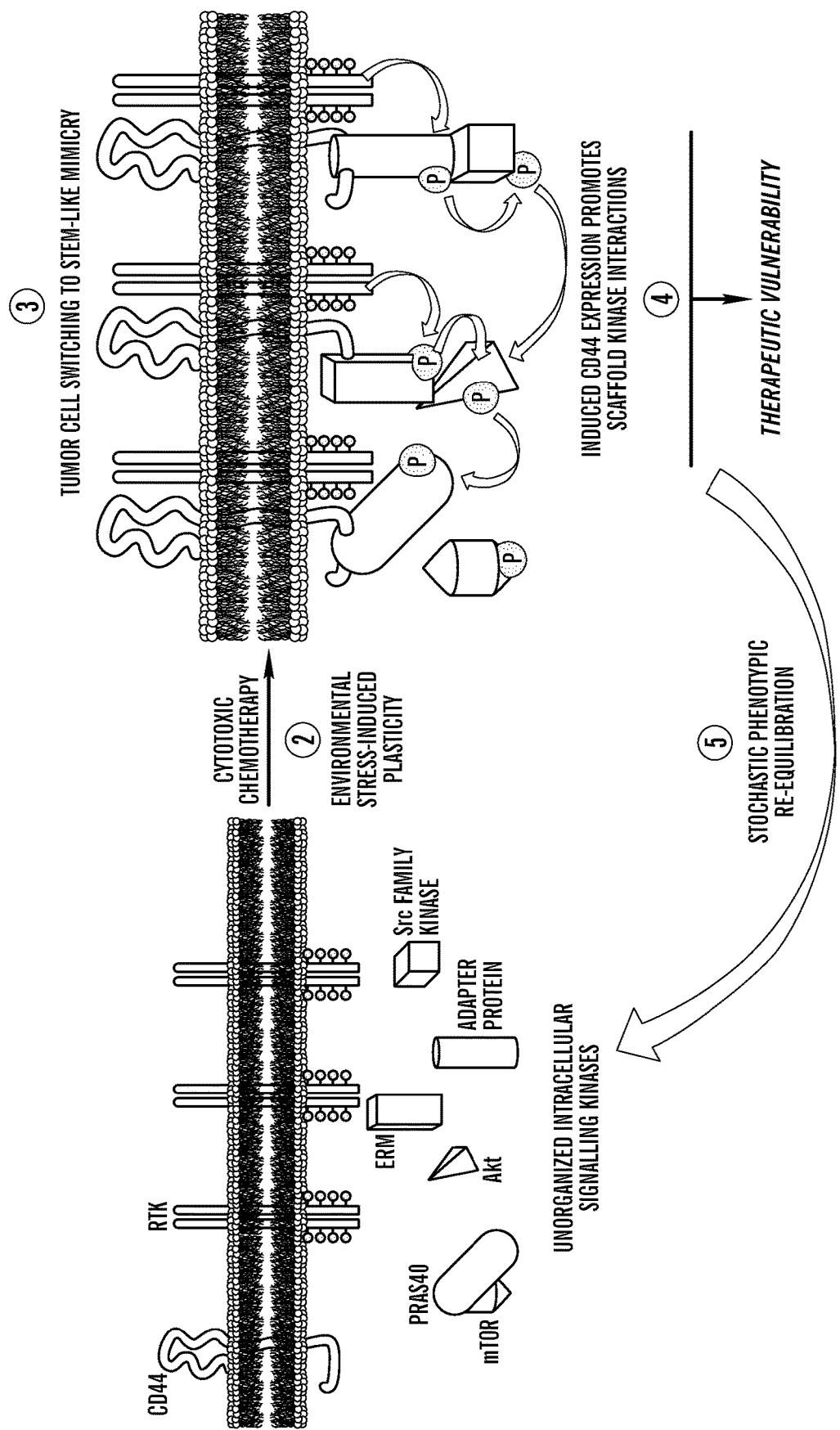
Figure 7H:
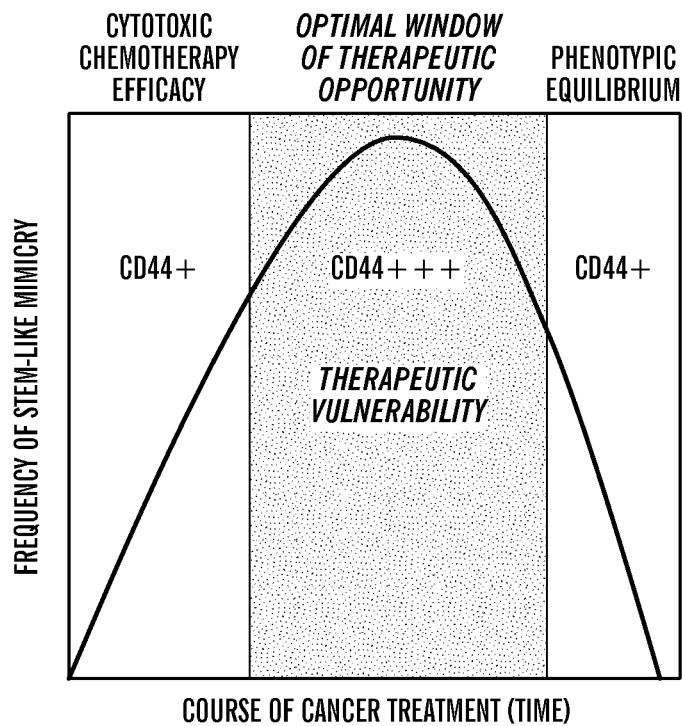
Figure 8A:
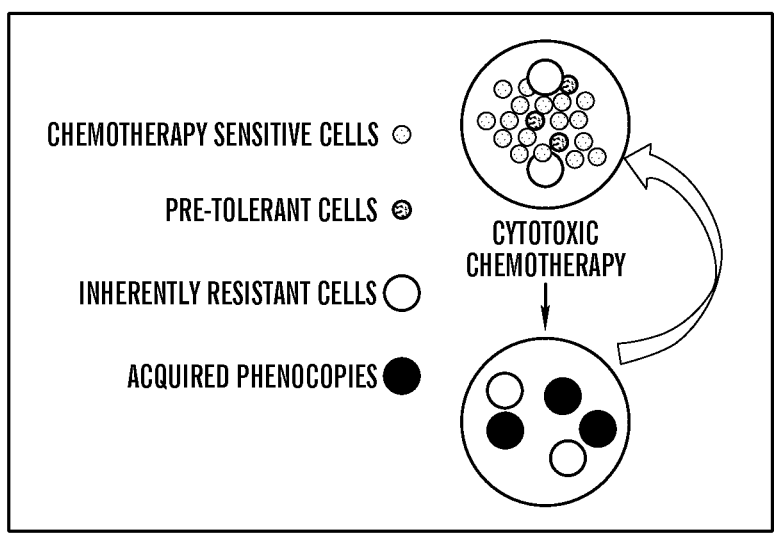
FIG. 8A depicts a schematic of the transition of cancer cell phenotypes.
Figure 8B:
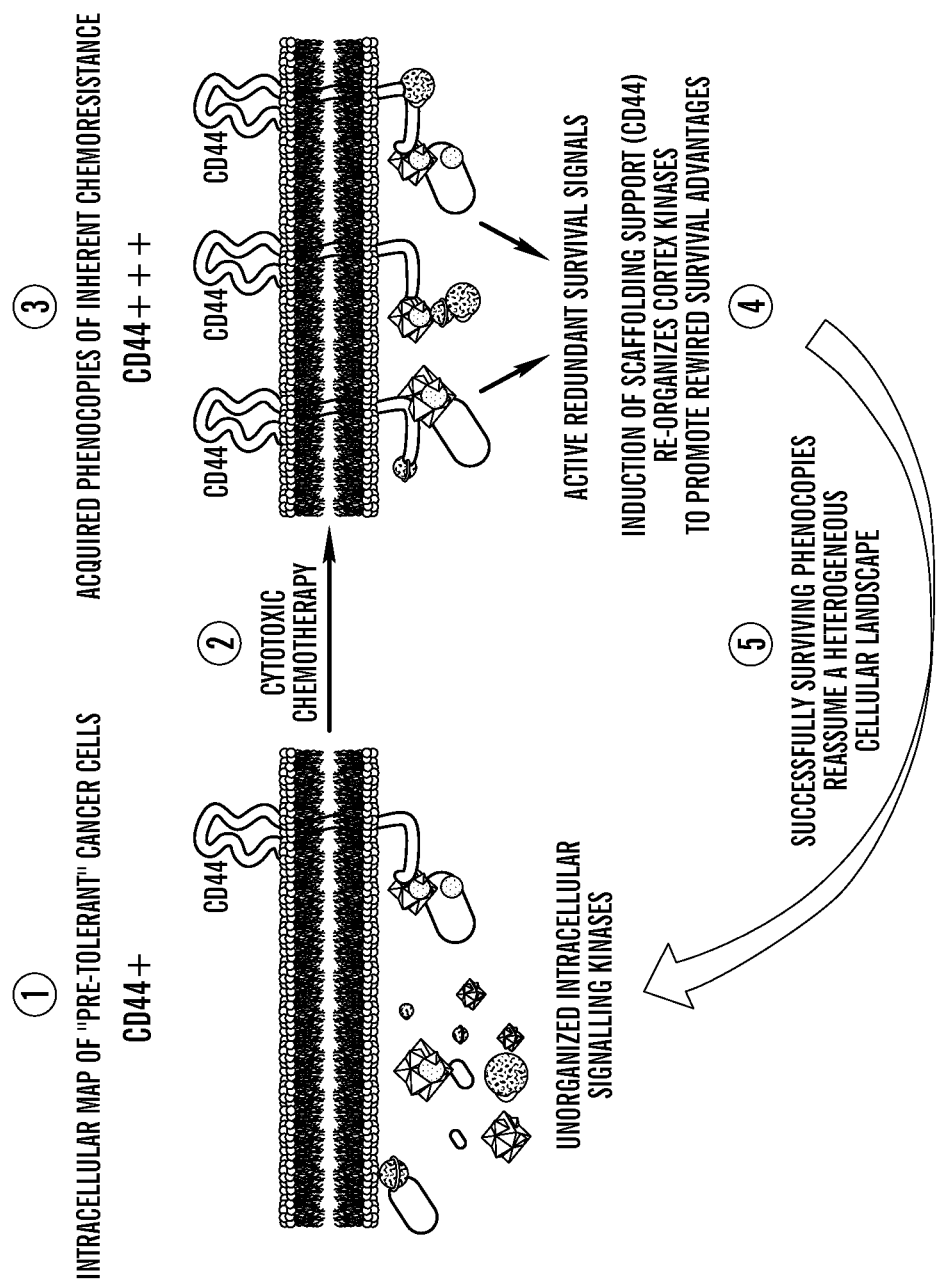
FIG. 8B depicts a schematic model of the signaling pathways involved in control of the transiently tolerant phenotype.

The upregulation of CD44 and the resultant rewiring of the intracellular signaling network via PI3K/AKT pathway and Src family kinases open up the possibility of overcoming adaptive resistance to taxanes with a combination of appropriate inhibitors (FIG. 7G). Interestingly, this window of therapeutic opportunity for using the kinase inhibitors such as dasatinib arises when the cells shuttle to the transient phenotype characterized by the rewired network state, and is lost when the tumor re-equilibrates to the parental phenocopy state (FIG. 7H). Indeed, these results highlight the emerging understanding of the importance of temporality or sequencing in the design of rational combinations for the treatment of cancer (Lee et al., 2012). Interestingly, the results with the multifunctional nanoparticles indicate that such mechanistically-inspired nanomedicines can address these developing needs. The key observation is the evolving convergence between the hierarchical (Dean et al., 2005) and the mechanism-driven phenotypic heterogeneity models (Meads et al., 2009) during the induction of adaptive resistance to chemotherapy. The full acquisition of a CSC phenotype is not necessary; instead even imperfect mimics can potentially mount a survival response. Indeed, Marusyk and Polyak recently articulated that 'refraining from mapping the differences in cancer cell phenotypes into differentiation hierarchies would lead to more accurate scientific interpretation of the data, which is critical for clinical translation' (Marusyk and Polyak, 2013). The current study highlights the potential complexities that might exist, where instead of simplistic static pools of CSCs and non-CSCs, tumor cells can exist in a dynamic equilibrium between the two states that can shift in the presence or absence of a catalyst, for example under chemotherapy pressure towards the CSC phenotype.

Experimental Procedures

Cell Culture and Generating a Subpopulation of Chemotherapy-Tolerant Breast Cancer Cells (DTC)

MDA-MB-231, MDA-MB-468 were purchased from ATCC. For acute treatments, cells were plated at a density of $0.5-1 \times 10^5$ cells/ml and allowed to adhere for 24-48 hr. when cells reached ~70% confluency they were treated with antitubulins at indicated concentrations for 4-24 hours and utilized for subsequent assays. To generate chemotherapy tolerant subset, cells were treated with indicated concentrations of chemotherapy (48). Following washes with PBS, adherent cells were trypsinized and re-plated at a density of $1.5-2 \times 10^5$ cells/ml and cultured in serum-containing medium. After 24 hours incubation, floating cells were removed and remaining cells were washed with 1×PBS and considered a subpopulation of chemotherapy-tolerant cells. A separate plate of control cells were maintained concurrently in serum containing medium and provided fresh media at every interval where DTC received fresh media.

In Vivo Experiments.

4-6 week old Balb/C mice (Charles River, Cambridge Mass.) were inoculated with $10^6$ 4 T-1 mouse mammary carcinoma cells in the left flank (Charles River, Cambridge Mass.). Mice identified with tumors were treated with docetaxel (DTX) or vehicle twice at 72 hour intervals at 10 mg/kg i.v. or 15 mg/kg i.p. and subsequently treated with dasatinib i.p. or nanoparticles i.v. 72 hours following the final DTX dose. Tumors were harvested at indicated time points and evaluated for protein phosphorylation and expression. Experimental detail provided in supplemental data.

Human Refractory Breast Cancer Explant.

Anonymous human breast cancer tissues (N=7) from patients refractory to taxane-containing regimens were incubated ex vivo in autologous patient serum in the presence or absence of taxane-containing or liposomal doxorubicin (Doxil) regimens for 72 hours. Following fixation in formalin and paraffin embedding, tissue was processed by H&E to identify tumor cells and immunohistochemistry (IHC) was performed to identify protein expression. IHC scores were determined in a third party blinded fashion by multiplying the intensity of staining at the cellular level with the percentage of cells stained per field of view.

Cytotoxicity Analysis and Calculation of Drug Sensitivity Index.

Following viability analyses conducted as described in supplemental data, drug sensitivity index (SI) was determined as follows: Cell viability was determined as % of control for treatment conditions of 10 nM, 100 nM 1000 nM and 10 µM to generate an average cell viability across these 4 drug concentrations. SI was calculated as a ratio of parent:DTC or parent:parent$^{phenocopy}$. SI=1 correlates to parental sensitivity, SI<1 correlates to resistance compared to parent cell line and SI>1 correlates to enhanced sensitivity to the indicated drug compared to the parent cell line at the same concentration average.

FACS Analyses.

Following formalin fixation (4% in PBS) cells were blocked with 10% goat serum in 1×PBS and incubated with antibodies overnight at 4° C. Cells were processed by flow cytometry (Accuri C6, BD Ann Arbor, Mich.).

Synthesis of Chimeric Nanoparticles.

Dasatinib was encapsulated within a cholesterol-conjugated PI-103 lipid nanoparticle decorated with polyethylene glycol (PEG). Unreacted drug was removed by Spehadex-G25 column and nanoparticles sized by lipid extrusion confirmed by dynamic light scattering (DLS). Loading of PI103-Dasatinib nanoparticle was determined in DMF by measuring absorbance at 270 and 285 nm respectively using UV-Vis spectrophotometry (Shimadzu 2450). Full nanoparticle formulation can be found in supplemental data.

Statistics.

Statistical analysis was carried out with Prism software (Graphpad, LaJolla Calif.) experimental data is expressed as mean±SEM and analyzed by student's T-test. Unless noted otherwise all p-values were obtained at the two-sided level of significance, p-values *<0.05, <0.01, *<0.001. The data are expressed as a mean±SEM.

Antibodies and Reagents.

CD44 (Clone IM7 from eBioScience) conjugated to FITC (AnaSpec, Freemont Calif.), CD44 (clone ABIN135065, Antibodies Online, Atlanta Ga.) conjugated to Biotin (Thermo Fischer, Waltham, Mass.), epCAM-Cy5.5, CD24-PE and CD44-APC (BD biosciences, San Jose, Calif.) anti-Ezrin, ERM, p-ERM, IP-Specific EGFR, anti-Akt antibodies, cleaved caspase-3 and β-Actin were purchased from cell signaling technology (Cambridge, Mass.). Total EGFR polyclonal antibody specific for the cytoplasmic domain (clone 1005) was purchased from Santa Cruz Biotechnology (Santa Cruz, Calif.). Monoclonal, neutralizing antibodies against EGFR (Clone LA1) and CD44v6 (clone VFF18) were purchased from Millipore (Billerica, Mass.), CD44v6 (Clone 2F10) was purchased from R&D systems (Minneapolis, Minn.). Unless noted otherwise, all reagents, small molecule inhibitors and chemotherapies were of the highest grade purchased from Sigma-Aldrich (St. Louis, Mo.). Vincristine was purchased from Tocris biosciences (Minneapolis, Minn.). Cabazitaxel, PI103, Dasatinib, Doxorubicin, LY294002 and Erlotinib were purchased from LC Labs (Woburn, Mass.). All chemotherapeutics and small molecule inhibitors were dissolved in DMSO to a stock concentration of 10 mM and kept frozen.

Cell Culture and Gene Knockdown with siRNA.

MDA-MB-231 (ATCC) were cultured in DMEM containing 10% Fetal Bovine Serum (FBS), MDA-MB-468 MDA-MB-435 and 4T-1 mammary carcinoma cells (ATCC) were cultured in RPMI containing 10% FBS (Invitrogen, Carlsbad Calif.) at 37 C and 5% $CO_2$. During treatments with chemotherapeutics, cells were grown to semi-confluence and treated with indicated concentrations of chemotherapy in serum-containing medium for indicated time points. When small molecule inhibitors were included in treatments, they were added simultaneously with chemotherapy. For siRNA gene knockdown, cells were plated at a concentration of $5 \times 10^4$ cells/ml. Pre-validated Silencer Select siRNA targeting pan-CD44 (5'UAUUCCACGUGGA-GAAAAAtt3') (SEQ ID NO: 38) or Ezrin (5'CGUGGGAUGCUCAAAGAUAtt3') (SEQ ID NO: 39) were purchased from Ambion (Invitrogen, Grand Island, N.Y.). siRNA plasmids were transfected using lipofectamine 2000 (Invitrogen, Carlsbad Calif.) following manufacturer protocol and cultured for 72 hours prior to treatment. Scrambled siRNA was used as a control.

Generating a Subpopulation of Chemotherapy-Tolerant Breast Cancer Cells (DTC) and Expanded (DTCE).

Cells were plated in 100 mm Plates at a density of $1 \times 10^6$ cells/ml and cultured for 48 hours. Cells were then treated with indicated concentrations of chemotherapy and cultured for 48 hours, docetaxel tolerant cells (DTC) were treated with 100 nM docetaxel which is a concentration >20 times the IC50. After 48 hours of treatment floating cells were washed with PBS, adherent cells were trypsinized and re-plated at a density of $1 \times 10^5$ cells/ml and cultured in serum-containing medium. After 24 hours incubation, floating cells were removed and remaining cells were washed with 1×PBS. The remaining adherent cells are considered a subpopulation of chemotherapy-tolerant cells. A separate plate of control cells were maintained concurrently in serum containing medium, at every interval where DTC received fresh media, parent cells were given fresh media as well and harvested at the same time as DTC. A schematic can be found in FIG. 1D. An expanded population of DTC (DTCE) were cultured in drug free media for an additional 23 days beyond DTC.

In Vivo Experiments.

1 million 4T-1 mouse mammary carcinoma cells suspended in 100 □L PBS were injected per left flank of 5-6 week old Balb/C (Charles River, Wilmington Mass.). DTX was dissolved in pure Ethanol at a concentration of 50 mg/ml mixed 1:1 with Polysorbate 80 (Tween 80) and brought to a final working concentration with 5% glucose in PBS. Once Tumors became palpable (~100 mm$^3$), DTX or vehicle treatments were administered at 100 µL volumes. Dasatinib was dissolved in DMSO to working concentration and delivered as 50 µL injections on indicated days, 50 µL DMSO used as a control in these studies. Tumor volumes were measured by a third party unaware of treatment conditions using digital calipers (Starlett, Athol, Mass.), volumes were assessed by the following formula: (Width× Width×length)/2 and expressed as relative volume increase from day 1. Tumor homogenate was prepared by homogenization of equal weight tissue sections incubated in 3×RIPA buffer containing 2× protease/phosphatase inhibitor cocktail (Thermo Fisher, Waltham, Mass.).

Human Explant Studies.

Anonymous human breast cancer tissues (N=7) from patients refractory to taxane-containing regimens and varying stages of disease (FIG. 9 shows patient history) were obtained from Mitra Biotech collected under IRB approval from HCG Bangalore Institute of Oncology with due consent. Fresh tumor tissues were collected from breast cancer patients immediately after surgical resection at HCG cancer hospital, Bangalore, India. The tumor samples were transported to the laboratory at 4° C., in appropriate transport buffer within 60 minutes post-resection, for ex-vivo studies and molecular and pathological evaluation. Tissues were cut into thin sections and cultured in 96 well plate using optimized conditions (Radhakrishnan et al., 2013). Tumors were treated with a taxane-containing regimen (Docetaxel+ Doxorubicin+Cyclophosphamide) or other drugs as indicated. DMSO was used as a vehicle control. After 48 hrs of treatment, tumor cell viability was measured and release of soluble cleaved caspase-3 and caspase-8 were determined.

Cytotoxicity and Cell Viability Assays and Calculation of Drug Sensitivity Index.

Parent cells DTC or Parent$^{Phenocopy}$ were generated as described and plated at a concentration of $1.5 \times 10^5$ in a clear bottom 96-well plate. Cells were exposed to indicated treatments (100 mL) for 48 hours in serum containing medium. Following incubation, cells were washed 1 time with PBS and recovered in serum and phenol red-free RPMI or DMEM and subsequently treated with MTS following manufacturer protocol (Promega, Madison, Wis.). Drug sensitivity index (SI) was determined as follows: Cell viability was determined as % of control for treatment conditions of 10 nM, 100 nM 1000 nM and 10 µM to generate an average cell viability across these 4 drug concentrations. SI was calculated as a ratio of parent:DTC or parent:parent$^{phenocopy}$. SI=1 correlates to parental sensitivity, SI<1 correlates to resistance compared to parent cell line and SI>1 correlates to enhanced sensitivity to the indicated drug compared to the parent cell line at the same concentration average.

Phosphorylation Arrays.

EGFR phosphorylation array was performed following manufacturer protocol (Raybiotech Inc. Norcross, Ga.). Values were determined by phosphorylated residue/Total EGFR and expressed as relative increase in DTC compared to parental control. The Proteome Profiler™ (R&D systems, Minneapolis Minn.) was used to identify phosphorylated residues correlating to p53, Akt and SFK-associated proteins. Following the Bradford protein analysis assay to normalize total protein content, cell lysate was applied to the phosphorylation membranes following manufacturer protocol. Western blot of total Actin was used to confirm equal loading of lysate. Membranes were visualized by chemiluminescence (Syngene, Cambridge UK). Optical densities were determined by Image J™ software and Adobe CS5™. Reference spots were used to normalize between array membranes.

FACS Analyses.

Cells were cultured as indicated and fixed with 4% paraformaldehyde in PBS for 30 min at RT and blocked in 10% goat serum (v/v). Following PBS washes, cells were incubated with indicated antibodies for 60 minutes at room temperature or overnight at 4 C and analyzed by FACS (Accuri cyomteters Inc. Ann Arbor, Mich.). Cell cycle analyzed in propidium iodide solution following incubation in 70% Ethanol overnight at 4 C and following manufacturer protocol (Genscript USA Inc. Piscataway, N.J.). AnnexinV/ PI was analyzed FACS following manufacturer protocol (BD, Ann Arbor Mich.). All FACS results were analyzed by FlowJo™ software following a rigorous doublet discrimination based on FSC:A vs. width as well as FSC:A vs. height (Tree Star Inc., Ashland Oreg.). Analyses were also performed through Accuri cFlow™ plus software to obtain and confirm mean fluorescent intensity. Cell Sorting: Cell sorting was performed on live cells. Briefly, cells were incubated with fluorescent antibody for 20 minutes at room temperature in PBS. Following washes, cells were sorted by FACS (BD FACS Aria HU Special Order, Ann Arbor Mich.). Isolation based on size in the FSC:A vs. SSC:A parameters determined after exclusion of doublets based on width and height vs. FSC:A or SSC:A scattering parameters (visual can be found in FIG. 2D). Validation was confirmed by re-analysis and in some instances were enriched twice or more.

Immunohistochemistry.

Human Tumor tissues were fixed in Phos stop (Roche) containing 4% buffered formalin and embedded in paraffin. Prior to immunohistochemical staining of target proteins 4-µm-thick tissue sections mounted in poly L lysine coated glass slides were deparaffinized and rehydrated. Heat induced antigen retrieval was achieved using citrate buffer (pH7.8). The sections were soaked in Antigen Unmasking Solution (Vector Burlingame, Calif.) for 10 minutes followed by retrieval using a microwave for 25 minutes. Endogenous hydrogen peroxidase was blocked by incubating the sections with 3% $H_2O_2$ (Merck) for 15 minutes and washed in running tap water for 3 minutes followed by a wash in 1×TBS for 7 minutes. After initial blocking of the slides in 10% normal goat serum (Vector Laboratory) for one hour at room temperature tissue sections were incubated with primary antibodies for additional 1 hour at room temperature. Following primary antibodies were used: anti human Ki-67 (rabbit polyclonal from Vector Laboratory, 1:600 dilution), anti human cleaved caspase3 (rabbit polyclonal, clone D175, from Cell Signaling Technology, Cambridge, Mass., 1:600 dilution). Anti human CD44 (Clone IM7) P-HckY410 (Cell Signaling tech.) p-PRAS40T246 (Cell Signaling Tech.) Secondary antibody (Signal Stain Boost IHC Detection Reagent, HRP, Rabbit, Cell Signaling Technology) was added to the sections and incubated for 45 minutes at room temperature and washed four times in 1×PBS for 3 minutes each. Appropriate Isotype matched IgG controls were included for each secondary antibody. Chromogenic development was done by exposure of tissues to DAB substrate (DAB Peroxidase Substrate Kit; Vector Labs). Images of immunostained sections were visualized by Leica DM4000 microscope at 200× or 400× magnifications and images were acquired. Immunoreactivity was scored by intensity of staining (0, no staining, 1 weak; 2 moderate; 3 strong) and percentage of positive cells. By multiplying both values, a final score was calculated. Scoring was performed in a blinded fashion by two experienced pathologists Cells were generated as described above and plated in 4 chamber glass slides (BD Biosciences, San Jose Calif.) at a concentration of 100,000 cells/ml. Following treatments, cells were washed in PBS and fixed in 4% Paraformaldehyde for 30 minutes. Permeabilization, when necessary, was achieved with 10% (v/v) Goat serum (Vector Laboratories, Burlingame Calif.) and 0.05% Saponin (w/v) in PBS for 90 minutes. Blocking was performed in 10% (v/v) Goat serum in PBS. The cells were labeled with the indicated primary antibodies at 1:100 and tagged with FITC or unconjugated followed by a secondary antibody conjugated with Alexa Fluor 488 or Alexa Fluor 594 (Invitrogen Carlsbad Calif.) at 1:250 were added 24 hours later and incubated for 90 minutes at room temperature in blocking buffer and masked with DAPI-containing hard-set mounting medium (Vector Laboratories, Burlingame Calif.). Bright field and fluorescent images were obtained using three channels on a NIKON Eclipse TI-U microscope with a 20×ELDW, 10× or 40× Plan-Apo objective lens (Nikon, Melville N.Y.). NIS Elements Viewer version 3.22 (Nikon, Melville N.Y.) software was used to capture the images to file. For histological quantification, IHC were scored blindly by a clinical pathologist based on number of cells which stain for the target protein (1-4) and multiplied by the intensity of staining as a subjective percentile. This value was expressed as IHC score to quantify the level of staining.

Immunoprecipitation and Immunoblotting.

Laemli sample buffer was prepared as a 5× solution containing β-mercaptoethanol as a reducing agent. Immunoprecipitaion was performed using both classic and direct IP kits purchased from Pierce following manufacturer protocols (Thermo Fisher inc. Rockford, Ill.). Briefly, cell lysates were prepared using IP/Lysis Buffer (Thermo Fisher inc. Rockford, Ill.) in the presence of 2×HALT protease/phosphatase inhibitor cocktail (Thermo Fisher inc. Rockford, Ill.). For classic Immunoprecipitation, lysates were combined with indicated antibodies for 48 hours at 4 C and combined with protein A/G agarose beads for 4 hours prior to elution with 2× Laemli Buffer at 100 C. Direct immunoprecipitation was performed following manufacturer protocol. Briefly, antibodies were covalently attached to agarose beads, lysate was combined with antibody-agarose bead conjugates for 24 hours prior to washes and elution with provided Elution Buffer. Protein samples were resolved by SDS-PAGE and transferred to PVDF membranes prior to incubation at 4 C with indicated primary antibodies. PVDF membranes with primary antibody were incubated at room temperature with HRP conjugated secondary antibodies (BD Ann Arbor, Mich.) and resolved by chemiluminescence using the G-Box and Syngene software (Syngene Cambridge, UK). When possible, blots were stripped (Thermo Fischer, Rockford Ill.) and re-probed with a second primary antibody. Optical densities of western blots were measured using ImageJ™ open source software (National Institutes of Health) and validated using Adobe CS5™.

All chemical reagents were of analytical grade, used as supplied without further purification unless indicated. All reactions were performed under inert conditions unless otherwise indicated. Dichloromethane (DCM), anhydrous DCM, Methanol, Cholesterol, Dimethylamino Pyridine (DMAP), Succinic Anhydride, Sodium Sulfate, Pyridine, 1-Ethyl-3-(3-dimethylaminopropyl)carbodiimide (EDC), L-α-phosphatidylcholine and Sephadex G-25 were purchased from Sigma-Aldrich. PI-103 was purchased from Selleckchem and PI828 was purchased from Tocris Biosciences. 1,2-Distearoyl-sn-Glycero-3-Phosphoethanolamine-N-[Amino(Polyethylene Glycol)2000] and the mini handheld Extruder kit (including 0.2 μm Whatman Nucleopore Track-Etch Membrane, Whatman filter supports and 1.0 mL Hamiltonian syringes) were bought from Avanti Polar Lipids Inc. Analytical thin-layer chromatography (TLC) was performed using precoated silica gel Aluminium sheets 60 $_{F254}$ bought from EMD Laboratories. Spots on the TLC plates were visualized under UV light, and/or by treatment with alkaline permanganate solution followed by heating. Column chromatography was conducted using silica gel (230-400 mesh) from Qualigens. $^1$H spectra were recorded on Bruker DPX 400 MHz spectrometer. Chemical shifts are reported in δ (ppm) units using residual $^1$H signals from deuterated solvents as references. Spectra were analyzed with Mest-Re-C Lite (Mestrelab Research) and/or XWinPlot (Bruker Biospin). Electrospray ionization mass spectra were recorded on a Micromass Q Tof 2 (Waters) and data were analyzed with MassLynx 4.0 (Waters) software.

Figure 17:
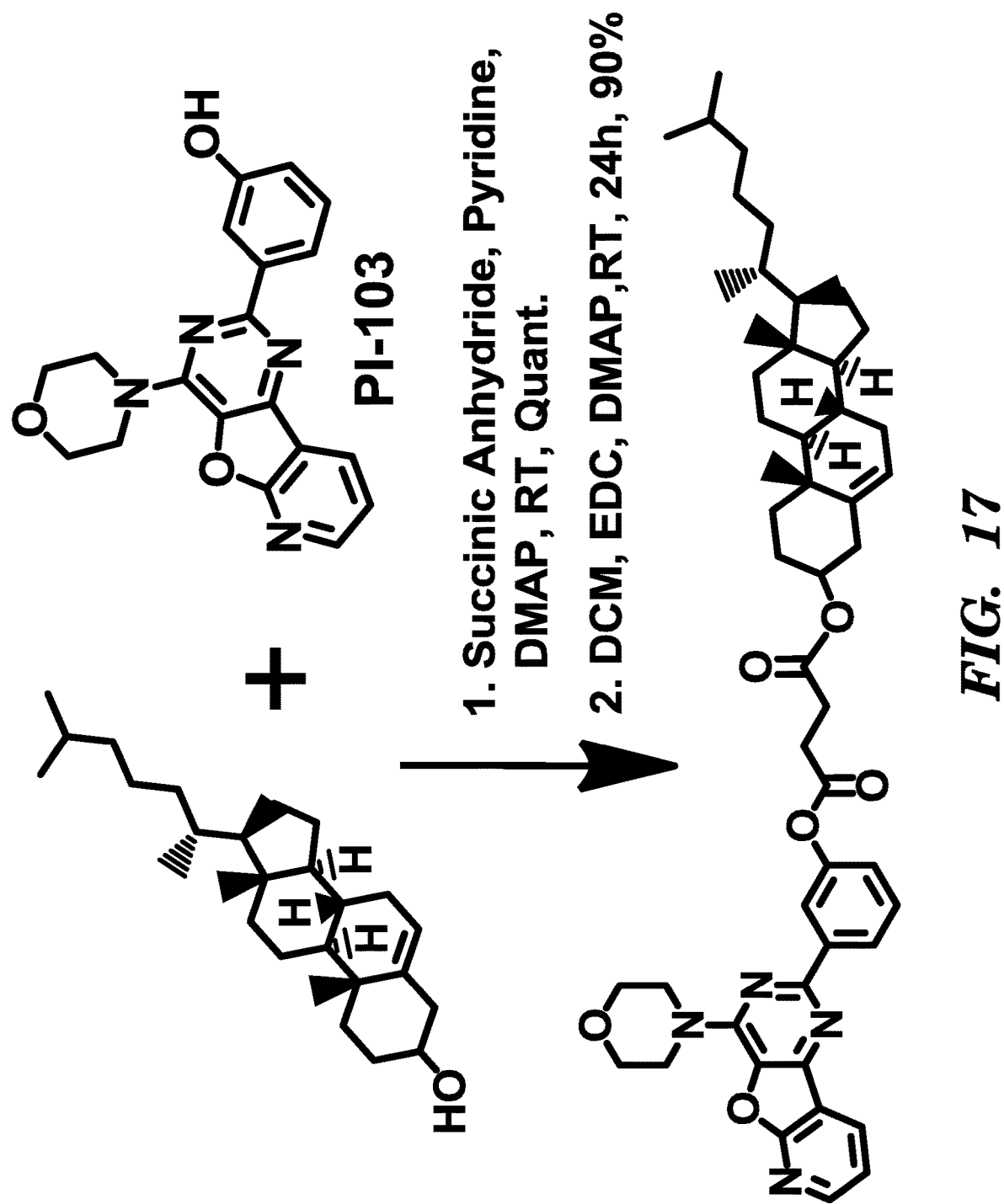
FIG. 17 depicts a schematic of PI103-cholesterol conjugatesynthesis.

Synthesis of PI103-Cholesterol Conjugate:

Cholesterol (500 mg, 1.29 mmol) was dissolved in 5 ml of anhydrous pyridine. Succinic anhydride (645 mg, 6.45 mmol) and catalytic amount of DMAP was added to the reaction mixture to form clear solution. The reaction mixture was flushed with argon and allowed to stir under argon atmosphere for 12 h. Then, pyridine was removed under vacuum and the crude residue was diluted in 30 ml DCM. It was washed with 1N HCl (30 ml) and water (30 ml). The organic layer was separated and dried over anhydrous sodium sulfate, filtered and concentrated in vacuo (FIG. 17). Completion of the reaction was confirmed by performing a TLC in 1:99 Methanol:DCM solvent mixture. The product was used for next step without further purification. PI-103 (25 mg, 0.072 mmol) was dissolved in 3 ml anhydrous DCM followed by addition of cholesterol-succinic acid (0.216 mmol, 105 mg), EDC (0.216 mmol, 41.4 mg) and DMAP (0.216, 26 mg). The reaction mixture was stirred at rt for 12 h under argon. Upon completion of reaction as monitored by TLC, the reaction mixture was diluted with 10 ml DCM and washed with dilute HCl and water. The organic layers were separated, combined and dried over anhydrous sodium sulfate. The solvent was evaporated under vacuum and the crude product was purified by using column chromatography, eluting with methanol:methylene chloride gradient, to give the PI-103 cholesterol conjugate as a light yellow solid (52 mg, 90%). $^{1H}$ NMR (CDCl3, 400 MHz): δ 8.65-8.53 (m, 1H), 8.36 (d, J=8.3 Hz, 1H), 8.19 (d, J=1.7 Hz, 1H), 7.56-7.41 (m, 1H), 5.29 (s, 1H), 4.28-4.15 (m, 2H), 3.97-3.86 (m, 2H), 3.64 (s, 1H), 2.93 (d, J=7.0 Hz, 1H), 2.76 (d, J=7.0 Hz, 1H), 2.35 (s, 1H), 2.17 (s, 1H), 1.59 (s, 4H), 1.29 (d, J=34.2 Hz, 3H), 1.25-1.23 (m, 6H), 1.13-0.80 (m, 13H), 0.66 (s, 2H), 0.03 (m, 12H). HRMS Calculated for [C50H64N4O6+H]$^+$:817.4899 Found: 817.4883.

Dasatinib Chimeric Nanoparticle:

10 mg of L-α-phosphatidylcholine, 2 mg PI103-cholesterol conjugate (Described above), 2 mg of Dasatinib and 22 mg of 1,2-Distearoyl-sn-Glycero-3-Phosphoethanolamine-N-[Amino(Polythylene Glycol)2000](DSPE-PEG) were dissolved in 1.0 mL DCM and 0.5 mL of methanol. Solvent was evaporated into a thin and uniform lipid-drug film using a rotary evaporator. The lipid-drug film was then hydrated with 2.0 mL H$_2$O for 1 h at 60° C. The hydrated nanoparticles looked light yellow to white with little viscous texture. It was passed though Sephadex G-25 column and extruded at 65° C. to obtain sub 200 nm particles.

Loading of Drug from Nanoparticle:

A standard curve of PI103-Cholesterol conjugate and Dasatinib in DMF was generated by measuring absorbance at 270 and 285 nm respectively using UV-Vis spectrophotometry (Shimadzu 2450). A known concentration of nanoparticle was dissolved in DMF and the absorbance value at 270 and 285 nm was used to calculate the loading from standard curve.

Nanoparticle Characterization and Stability Studies:

The mean particle size of the nanoparticles was measured by Dynamic Light Scattering method using Zetasizer Nano ZS90 (Malvern, UK). 10 µL of nanoparticles solution was diluted to 1 ml using DI water and 3 sets of 10 measurements each were performed at 90 degree scattering angle to get the average particle size. The zeta potential was measured using a Zetasizer ZS90 with the nanoparticles diluted in water for measurement according to the manufacturer's manual.

3Dimensional Illustration.

3D rendering was performed using the 3D Studio Max Software (Autodesk).

REFERENCES

Berrieman, H. K., Lind, M. J., and Cawkwell, L. (2004). Do beta-tubulin mutations have a role in resistance to chemotherapy? The lancet oncology 5, 158-164.

Bissell, M. J., and Labarge, M. A. (2005). Context, tissue plasticity, and cancer: are tumor stem cells also regulated by the microenvironment? Cancer cell 7, 17-23.

Bouchet, B. P., and Galmarini, C. M. (2010). Cabazitaxel, a new taxane with favorable properties. Drugs Today (Barc) 46, 735-742.

Brennan, M., Davison, P. F., and Paulus, H. (1985). Preparation of bispecific antibodies by chemical recombination of monoclonal immunoglobulin G1 fragments. Science 229, 81-83.

Cairns, J. (1975). Mutation selection and the natural history of cancer. Nature 255, 197-200.

Chaudhuri, P., Paraskar, A., Soni, S., Mashelkar, R. A., and Sengupta, S. (2009). Fullerenol-cytotoxic conjugates for cancer chemotherapy. ACS nano 3, 2505-2514.

Dean, M., Fojo, T., and Bates, S. (2005). Tumour stem cells and drug resistance. Nature reviews Cancer 5, 275-284.

Di Cosimo, S., and Baselga, J. (2010). Management of breast cancer with targeted agents: importance of heterogeneity. [corrected]. Nature reviews Clinical oncology 7, 139-147.

Dylla, S. J., Beviglia, L., Park, I. K., Chartier, C., Raval, J., Ngan, L., Pickell, K., Aguilar, J., Lazetic, S., Smith-Berdan, S., et al. (2008). Colorectal cancer stem cells are enriched in xenogeneic tumors following chemotherapy. PloS one 3, e2428.

Finn, R. S., Bengala, C., Ibrahim, N., Roche, H., Sparano, J., Strauss, L. C., Fairchild, J., Sy, O., and Goldstein, L. J. (2011). Dasatinib as a single agent in triple-negative breast cancer: results of an open-label phase 2 study. Clinical cancer research: an official journal of the American Association for Cancer Research 17, 6905-6913.

Gautreau, A., Poullet, P., Louvard, D., and Arpin, M. (1999). Ezrin, a plasma membrane-microfilament linker, signals cell survival through the phosphatidylinositol 3-kinase/Akt pathway. Proceedings of the National Academy of Sciences of the United States of America 96, 7300-7305.

Gillies, R. J., Verduzco, D., and Gatenby, R. A. (2012). Evolutionary dynamics of carcinogenesis and why targeted therapy does not work. Nature reviews Cancer 12, 487-493.

Gupta, P. B., Fillmore, C. M., Jiang, G., Shapira, S. D., Tao, K., Kuperwasser, C., and Lander, E. S. (2011). Stochastic state transitions give rise to phenotypic equilibrium in populations of cancer cells. Cell 146, 633-644.

Harper, L. J., Costea, D. E., Gammon, L., Fazil, B., Biddle, A., and Mackenzie, I. C. (2010). Normal and malignant epithelial cells with stem-like properties have an extended G2 cell cycle phase that is associated with apoptotic resistance. BMC cancer 10, 166.

Huang, W. C., and Hung, M. C. (2009). Induction of Akt activity by chemotherapy confers acquired resistance. J Formos Med Assoc 108, 180-194.

Idowu, M. O., Kmieciak, M., Dumur, C., Burton, R. S., Grimes, M. M., Powers, C. N., and Manjili, M. H. (2012). CD44(+)/CD24(-/low) cancer stem/progenitor cells are more abundant in triple-negative invasive breast carcinoma phenotype and are associated with poor outcome. Human pathology 43, 364-373.

Johnstone, R. A. (2002). The evolution of inaccurate mimics Nature 418, 524-526.

Jorgensen, P., and Tyers, M. (2004). How cells coordinate growth and division. Current biology: CB 14, R1014-1027.

Logue, J. S., and Morrison, D. K. (2012). Complexity in the signaling network: insights from the use of targeted inhibitors in cancer therapy. Genes & development 26, 641-650.

MacLaine, N. J., and Hupp, T. R. (2011). How phosphorylation controls p53. Cell Cycle 10, 916-921.

Marusyk, A., Almendro, V., and Polyak, K. (2012). Intratumour heterogeneity: a looking glass for cancer? Nature reviews Cancer 12, 323-334.

Matrone, M. A., Whipple, R. A., Thompson, K., Cho, E. H., Vitolo, M. I., Balzer, E. M., Yoon, J. R., Ioffe, O. B., Tuttle, K. C., Tan, M., and Martin, S. S. (2010). Metastatic breast tumors express increased tau, which promotes microtentacle formation and the reattachment of detached breast tumor cells. Oncogene 29, 3217-3227.

Mori, T., Kitano, K., Terawaki, S., Maesaki, R., Fukami, Y., and Hakoshima, T. (2008). Structural basis for CD44 recognition by ERM proteins. The Journal of biological chemistry 283, 29602-29612.

Okabe, S., Tauchi, T., and Ohyashiki, K. (2008). Characteristics of dasatinib- and imatinib-resistant chronic myelogenous leukemia cells. Clinical cancer research: an official journal of the American Association for Cancer Research 14, 6181-6186.

Pal, S. K., Childs, B. H., and Pegram, M. (2011). Triple negative breast cancer: unmet medical needs. Breast cancer research and treatment 125, 627-636.

Park, S. Y., Lee, H. E., Li, H., Shipitsin, M., Gelman, R., and Polyak, K. (2010). Heterogeneity for stem cell-related markers according to tumor subtype and histologic stage in breast cancer. Clinical cancer research: an official journal of the American Association for Cancer Research 16, 876-887.

Sarrio, D., Rodriguez-Pinilla, S. M., Dotor, A., Calero, F., Hardisson, D., and Palacios, J. (2006). Abnormal ezrin localization is associated with clinicopathological features in invasive breast carcinomas. Breast cancer research and treatment 98, 71-79.

Shackleton, M., Quintana, E., Fearon, E. R., and Morrison, S. J. (2009). Heterogeneity in cancer: cancer stem cells versus clonal evolution. Cell 138, 822-829.

Talpaz, M., Silver, R. T., Druker, B. J., Goldman, J. M., Gambacorti-Passerini, C., Guilhot, F., Schiffer, C. A., Fischer, T., Deininger, M. W., Lennard, A. L., et al. (2002). Imatinib induces durable hematologic and cytogenetic responses in patients with accelerated phase chronic myeloid leukemia: results of a phase 2 study. Blood 99, 1928-1937.

Turner, N. C., and Reis-Filho, J. S. (2012). Genetic heterogeneity and cancer drug resistance. The lancet oncology 13, e178-185.

Vander Haar, E., Lee, S. I., Bandhakavi, S., Griffin, T. J., and Kim, D. H. (2007). Insulin signalling to mTOR mediated by the Akt/PKB substrate PRAS40. Nature cell biology 9, 316-323.

Watters, J. W., Kraja, A., Meucci, M. A., Province, M. A., and McLeod, H. L. (2004). Genome-wide discovery of loci influencing chemotherapy cytotoxicity. Proceedings of the National Academy of Sciences of the United States of America 101, 11809-11814.

What is claimed is:

1. A method for treating breast cancer in a subject in need thereof comprising administering to the subject in need of treatment for breast cancer a combination of:
   a. a cytotoxic taxane chemotherapy agent; and
   b. a kinase inhibitor which inhibits the activity of at least Hck kinase, wherein the kinase inhibitor is A 419259.

2. The method of claim 1, wherein the subject is further administered an EGFR inhibitor.

3. The method of claim 1, wherein the kinase inhibitor is administered after the administration of the cytotoxic chemotherapy agent.

4. The method of claim 1, wherein the combination of the cytotoxic chemotherapy agent and the kinase inhibitor is administered during a period in which at least a subpopulation of cancer cells in the subject display increased levels of CD44 on the cell surface.

5. The method of claim 1, wherein the combination of the cytotoxic chemotherapy agent and the kinase inhibitor is administered during a period in which tumor growth plateaus.

6. The method of claim 1, wherein the combination of the cytotoxic chemotherapy agent and the kinase inhibitor is administered at least 4 hours after the administration of the cytotoxic chemotherapy agent.

7. The method of claim 1, wherein the combination of the cytotoxic chemotherapy agent and the kinase inhibitor is administered no more than about 216 hours after the administration of the cytotoxic chemotherapy agent.

8. The method of claim 1, wherein the combination of the cytotoxic chemotherapy agent and the kinase inhibitor is administered from about 4 hours to about 216 hours after the administration of the cytotoxic chemotherapy agent.

9. The method of claim 1, wherein the combination of the cytotoxic chemotherapy agent and the kinase inhibitor is administered about 72 hours after the administration of the cytotoxic chemotherapy.

10. The method of claim 1, wherein the combination of the cytotoxic chemotherapy agent and the kinase inhibitor is administered within 10 days after the administration of the cytotoxic chemotherapy.

11. A method for treating breast cancer in a subject in need thereof comprising administering to the subject in need of treatment for breast cancer a combination of:
    a. a cytotoxic taxane chemotherapy agent, wherein the taxane is docetaxel; and
    b. a kinase inhibitor which inhibits the activity of at least Hck kinase.

12. The method of claim 11, wherein the subject is further administered an EGFR inhibitor.

13. The method of claim 11, wherein the kinase inhibitor is dasatinib.

14. The method of claim 11, wherein the kinase inhibitor is administered after the administration of the cytotoxic chemotherapy agent.

15. The method of claim 11, wherein the combination of the cytotoxic chemotherapy agent and the kinase inhibitor is administered during a period in which at least a subpopulation of cancer cells in the subject display increased levels of CD44 on the cell surface.

16. The method of claim 11, wherein the combination of the cytotoxic chemotherapy agent and the kinase inhibitor is administered during a period in which tumor growth plateaus.

17. The method of claim 11, wherein the combination of the cytotoxic chemotherapy agent and the kinase inhibitor is administered at least 4 hours after the administration of the cytotoxic chemotherapy agent.

18. The method of claim 11, wherein the combination of the cytotoxic chemotherapy agent and the kinase inhibitor is administered no more than about 216 hours after the administration of the cytotoxic chemotherapy agent.

19. The method of claim 11, wherein the combination of the cytotoxic chemotherapy agent and the kinase inhibitor is administered from about 4 hours to about 216 hours after the administration of the cytotoxic chemotherapy agent.

20. The method of claim 11, wherein the combination of the cytotoxic chemotherapy agent and the kinase inhibitor is administered about 72 hours after the administration of the cytotoxic chemotherapy.

21. The method of claim 11, wherein the combination of the cytotoxic chemotherapy agent and the kinase inhibitor is administered within 10 days after the administration of the cytotoxic chemotherapy.

\* \* \* \* \*

UNITED STATES PATENT AND TRADEMARK OFFICE
CERTIFICATE OF CORRECTION

| | |
|---|---|
| PATENT NO. | : 10,813,931 B2 |
| APPLICATION NO. | : 14/768230 |
| DATED | : October 27, 2020 |
| INVENTOR(S) | : Goldman et al. |

It is certified that error appears in the above-identified patent and that said Letters Patent is hereby corrected as shown below:

In the Specification

At Column 1, Lines 17-22:
"This invention was made with federal funding under Grant No. IRO1CA135242-01A2 awarded by the National Institutes of Health and Grant Nos. W81XWH-07-1-0482 and W81XWH-09-1-0700 awarded by the Department of Defense. The U.S. government has certain rights in the invention." should be replaced with -- This invention was made with government support under W81XWH-07-1-0482, and W81XWH-09-1-0070 awarded by the Medical Research and Development Command, and CA135242 awarded by the National Institutes of Health. The government has certain rights in the invention. --

Signed and Sealed this
Second Day of May, 2023

Katherine Kelly Vidal
*Director of the United States Patent and Trademark Office*